United States Patent
Berdini et al.

(10) Patent No.: US 7,977,477 B2
(45) Date of Patent: Jul. 12, 2011

(54) BENZIMIDAZOLE DERIVATIVES AND THEIR USE AS PROTEIN KINASE INHIBITORS

(75) Inventors: Valerio Berdini, Cambridge (GB); Michael Alistair O'Brien, Cambridge (GB); Maria Grazia Carr, Cambridge (GB); Theresa Rachel Early, Cambridge (GB); Eva Figueroa Navarro, Cambridge (GB); Adrian Liam Gill, Cambridge (GB); Steven Howard, Cambridge (GB); Gary Trewartha, Cambridge (GB); Alison Jo-Anne Woolford, Cambridge (GB); Andrew James Woodhead, Cambridge (GB); Paul Wyatt, Cambridge (GB)

(73) Assignee: Astex Therapeutics, Limited, Cambridge (GB)

( * ) Notice: Subject to any disclaimer, the term of this patent is extended or adjusted under 35 U.S.C. 154(b) by 1338 days.

(21) Appl. No.: 10/564,166

(22) PCT Filed: Jul. 5, 2004

(86) PCT No.: PCT/GB2004/002824
§ 371 (c)(1),
(2), (4) Date: Aug. 7, 2006

(87) PCT Pub. No.: WO2005/002552
PCT Pub. Date: Jan. 13, 2005

(65) Prior Publication Data
US 2007/0135477 A1  Jun. 14, 2007

Related U.S. Application Data

(60) Provisional application No. 60/484,685, filed on Jul. 3, 2003, provisional application No. 60/514,374, filed on Oct. 24, 2003.

(30) Foreign Application Priority Data

Jul. 3, 2003  (GB) .................................. 0315657.7
Oct. 24, 2003  (GB) .................................. 0324919.0

(51) Int. Cl.
*A61K 31/5377* (2006.01)
*A61K 31/4184* (2006.01)
*C07D 413/14* (2006.01)

(52) U.S. Cl. ................... 544/140; 548/306.1; 514/234.5; 514/394

(58) Field of Classification Search ............... 548/306.1; 544/140
See application file for complete search history.

(56) References Cited

U.S. PATENT DOCUMENTS

| | | |
|---|---|---|
| 5,952,368 A | 9/1999 | Kertesz et al. |
| 6,350,746 B1 | 2/2002 | Buckman et al. |
| 6,358,978 B1 | 3/2002 | Ritzeler et al. |
| 6,696,437 B1 | 2/2004 | Lubisch et al. |
| 7,087,616 B2 | 8/2006 | Fischer et al. |
| 2003/0207883 A1 | 11/2003 | Renhowe et al. |
| 2004/0048868 A1 | 3/2004 | Edwards et al. |
| 2004/0082798 A1 | 4/2004 | Alonso-Alija et al. |
| 2004/0214814 A1 | 10/2004 | Bebbington et al. |
| 2004/0242559 A1 | 12/2004 | Ugolini et al. |
| 2005/0009894 A1 | 1/2005 | Babin et al. |
| 2007/0021472 A1 | 1/2007 | Zhu et al. |
| 2007/0105900 A1 | 5/2007 | Berdini et al. |
| 2007/0208007 A1 | 9/2007 | Saitou et al. |
| 2008/0132495 A1 | 6/2008 | Berdini et al. |
| 2008/0312223 A1 | 12/2008 | Berdini et al. |

FOREIGN PATENT DOCUMENTS

| | | |
|---|---|---|
| EP | 0169051 A2 | 1/1986 |
| EP | 711768 A1 | 5/1996 |
| EP | 1264820 | 12/2002 |
| EP | WO 03/004488 | 1/2003 |
| EP | WO 03/035065 | 5/2003 |
| EP | 1460067 | 9/2004 |
| WO | 94/14435 A1 | 7/1994 |
| WO | 94/29300 A1 | 12/1994 |
| WO | 96/00218 A1 | 1/1996 |
| WO | 97/12615 A1 | 4/1997 |
| WO | 97/36585 A1 | 10/1997 |
| WO | 99/46244 A1 | 9/1999 |
| WO | 99/61426 A1 | 12/1999 |
| WO | 00/39108 A1 | 7/2000 |
| WO | 00/43384 A1 | 7/2000 |
| WO | 00/59902 A2 | 10/2000 |
| WO | 00/64888 A1 | 11/2000 |
| WO | 01/02385 A1 | 1/2001 |

(Continued)

OTHER PUBLICATIONS

CA Registry No. 518987-01-4, entered in the Registry file on STN CAS Online May 22, 2003.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*

(Continued)

*Primary Examiner* — Laura L. Stockton
(74) *Attorney, Agent, or Firm* — Heslin Rothenberg Farley & Mesiti P.C.

(57) ABSTRACT

The invention provides compounds of the formula (I):

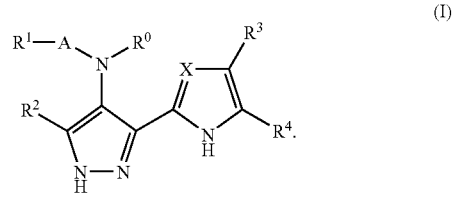

The compounds have activity against cyclin dependent kinases, glycogen synthase kinase and Auroa kinases and are therefore useful to treat cancer and viral diseases.

23 Claims, No Drawings

FOREIGN PATENT DOCUMENTS

| | | | |
|---|---|---|---|
| WO | 01/19788 | A2 | 3/2001 |
| WO | 01/19798 | A2 | 3/2001 |
| WO | 01/57022 | A2 | 8/2001 |
| WO | 01/64642 | A2 | 9/2001 |
| WO | 01/64643 | A2 | 9/2001 |
| WO | 01/79198 | A1 | 10/2001 |
| WO | 02/00647 | A1 | 1/2002 |
| WO | 02/00651 | A2 | 1/2002 |
| WO | 02/00655 | A1 | 1/2002 |
| WO | WO-02/059111 | A2 * | 8/2002 |
| WO | 02/72549 | A1 | 9/2002 |
| WO | 02/096426 | A1 | 12/2002 |
| WO | 03/002566 | A1 | 1/2003 |
| WO | 03/004488 | A1 | 1/2003 |
| WO | 03/006465 | A1 | 1/2003 |
| WO | 03/035065 | A1 | 5/2003 |
| WO | 03/044014 | A1 | 5/2003 |
| WO | 03/053941 | A2 | 7/2003 |
| WO | 03/066629 | A2 | 8/2003 |
| WO | 2004/041277 | A1 | 5/2004 |
| WO | 2004/050636 | A2 | 6/2004 |
| WO | 2004/052370 | A1 | 6/2004 |
| WO | 2004/054515 | A2 | 7/2004 |
| WO | 2004/056815 | A1 | 7/2004 |
| WO | 2005/002576 | A2 | 1/2005 |
| WO | 2005/005414 | A2 | 1/2005 |
| WO | 2005/028624 | A2 | 3/2005 |
| WO | 2005/047266 | A1 | 5/2005 |
| WO | 2007/077435 | A1 | 7/2007 |
| WO | 2008/001101 | A2 | 1/2008 |
| WO | 2008/001115 | A2 | 1/2008 |

OTHER PUBLICATIONS

Essassi et al.: Synthese et Hererocyclisation Des (Pyrazolyl-3-(5))-2 Benzimidazoles en Catalyse Par Transfert de Phase, *Bull. Soc. Chim. Belg.* vol. 96, pp. 63-67, 1987.

International Search Report for WO 2005/002552 (PCT/GB2004/002824 filed Jul. 5, 2004).

Blankley et al.: Antihypertensive Activity of 6-Arylpyrido[2,3-d] Pyrimidim-7-Amine Derivatives. 2. 7-Acyl Amide Analogues, *Journal of Medicinal Chemistry*, vol. 26, No. 3, Mar. 1, 1983, pp. 403-411.

Abd El-Wareth A O Sarhan et al.: Synthesis, Characterization and Reactions of 2-Deoxo-5-Deazaalloxazines, *Bioorganic & Medicinal Chemistry*, vol. 9, Jan. 1, 2001, pp. 2993-2998.

Mesguiche et al.: 4-Alkoxy-2,6-Diaminopyrimidine Derivatives: Inhibitors of Cyclin Dependent Kinases 1 and 2, *Bioorganic & Medicinal Chemistry Letters*, vol. 13, Jan. 1, 2003, pp. 217-222.

GB search report GB 0315657.7 filed Jul. 3, 2003.

GB search report GB 0324919.0 filed Oct. 24, 2003.

European Supplementary Search report EP Application No. 04 743 172.1, Sep. 19, 2008.

GB search report GB 0428552.4 filed Dec. 30, 2004.

GB search report GB 0428554.0 filed Dec. 30, 2004.

International Search Report PCT/GB2005/005097 filed Mar. 28, 2006.

GB search report GB 0526607.7 filed Dec. 30, 2005.

International Search Report PCT/GB2006/004954 filed May 14, 2007.

Essassi E M et al., "Synthese Et Hererocyclisation Des (Pyrazolyl-3(5))-2 Benzimidazoles En Catalyse Par Transfert De Phase" Bulletin Des Societes Chimiques Belges, 96(1), 63-67 (1987).

International Search Report from priority application WO 2005/002552 published Jan. 13, 2005.

Morissette et al., "High-throughput crystallization: polymorphs, salts, co-crytsals and solvates of pharmaceutical solids", Advanced Drug Delivery Reviews, 2004, 56, 275-300.

Souillac et al., "Characterization of Delivery Systems, Differential Scanning Calorimetry", Encyclopedia of Controlled Drug Delivery, Wiley, 1999, 212-227.

Vippagunta et al., "Crystalline solids", Advanced Drug Delivery Reviews, 2001, 48, 3-26.

* cited by examiner

BENZIMIDAZOLE DERIVATIVES AND THEIR USE AS PROTEIN KINASE INHIBITORS

CROSS REFERENCE TO RELATED APPLICATIONS

This application is a 371 filing of PCT International application no. PCT/GB2004/002824 filed Jul. 5, 2004, published in English as WO 2005/002552 on Jan. 13, 2005. PCT/GB2004/002824 claims the priority of GB Application No. 0315657.7 filed Jul. 3, 2003; GB Application No. 0324919.0 filed Oct. 24, 2003; U.S. Provisional Application No. 60/484,685 filed Jul. 3, 2003 and U.S. Provisional Application No. 60/514,374 filed Oct. 24, 2003.

FIELD OF THE INVENTION

This invention relates to pyrazole compounds that inhibit or modulate the activity of Cyclin Dependent Kinases (CDK), Glycogen Synthase Kinases (GSK) and Aurora kinases to the use of the compounds in the treatment or prophylaxis of disease states or conditions mediated by the kinases, and to novel compounds having kinase inhibitory or modulating activity. Also provided are pharmaceutical compositions containing the compounds and novel chemical intermediates.

BACKGROUND OF THE INVENTION

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Cyclin Dependent Kinases

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (cdks) and a diverse set of their cognate protein partners termed cyclins. Cdks are cdc2 (also known as cdk1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific cdk partner proteins.

Modulation of the expression levels, degradation rates, and activation levels of various cdks and cyclins throughout the cell cycle leads to the cyclical formation of a series of cdk/cyclin complexes, in which the cdks are enzymatically active. The formation of these complexes controls passage through discrete cell cycle checkpoints and thereby enables the process of cell division to continue. Failure to satisfy the prerequisite biochemical criteria at a given cell cycle checkpoint, i.e. failure to form a required cdk/cyclin complex, can lead to cell cycle arrest and/or cellular apoptosis. Aberrant cellular proliferation, as manifested in cancer, can often be attributed to loss of correct cell cycle control. Inhibition of cdk enzymatic activity therefore provides a means by which abnormally dividing cells can have their division arrested and/or be killed. The diversity of cdks, and cdk complexes, and their critical roles in mediating the cell cycle, provides a broad spectrum of potential therapeutic targets selected on the basis of a defined biochemical rationale.

Progression from the G1 phase to the S phase of the cell cycle is primarily regulated by cdk2, cdk3, cdk4 and cdk6 via association with members of the D and E type cyclins. The D-type cyclins appear instrumental in enabling passage beyond the G1 restriction point, where as the cdk2/cyclin E complex is key to the transition from the G1 to S phase. Subsequent progression through S phase and entry into G2 is thought to require the cdk2/cyclin A complex. Both mitosis, and the G2 to M phase transition which triggers it, are regulated by complexes of cdk1 and the A and B type cyclins.

During G1 phase Retinoblastoma protein (Rb), and related pocket proteins such as p130, are substrates for cdk(2, 4, & 6)/cyclin complexes. Progression through G1 is in part facilitated by hyperphosphorylation, and thus inactivation, of Rb and p130 by the cdk(4/6)/cyclin-D complexes. Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the cdk2/cyclin E complex which amplifies, or maintains, E2F levels via further phosphorylation of Rb. The cdk2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the cdk2/cyclin E pathway. Cdk2 is also connected to the p53 mediated DNA damage response pathway via p53 regulation of p21 levels. p21 is a protein inhibitor of cdk2/cyclin E and is thus capable of blocking, or delaying, the G1/S transition. The cdk2/cyclin E complex may thus represent a point at which biochemical stimuli from the Rb, Myc and p53 pathways are to some degree integrated. Cdk2 and/or the cdk2/cyclin E complex therefore represent good targets for therapeutics designed at arresting, or recovering control of, the cell cycle in aberrantly dividing cells.

The exact role of cdk3 in the cell cycle is not clear. As yet no cognate cyclin partner has been identified, but a dominant negative form of cdk3 delayed cells in G1, thereby suggesting that cdk3 has a role in regulating the G1/S transition.

Although most cdks have been implicated in regulation of the cell cycle there is evidence that certain members of the cdk family are involved in other biochemical processes. This is exemplified by cdk5 which is necessary for correct neuronal development and which has also been implicated in the phosphorylation of several neuronal proteins such as Tau, NUDE-1, synapsin1, DARPP32 and the Munc18/Syntaxin1A complex. Neuronal cdk5 is conventionally activated by binding to the p35/p39 proteins. Cdk5 activity can, however, be deregulated by the binding of p25, a truncated version of p35. Conversion of p35 to p25, and subsequent deregulation of cdk5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

Cdk7 is a nuclear protein that has cdc2 CAK activity and binds to cyclin H. Cdk7 has been identified as component of the TFIIH transcriptional complex which has RNA polymerase II C-terminal domain (CTD) activity. This has been associated with the regulation of HIV-1 transcription via a Tat-mediated biochemical pathway. Cdk8 binds cyclin C and has been implicated in the phosphorylation of the CTD of RNA polymerase II. Similarly the cdk9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. Cdk7, cdk8, cdk9 and the P-TEFb complex are therefore potential targets for anti-viral therapeutics.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as wee1, Myt1 and Mik1. Dephosphorylation is performed by phosphatases such as cdc25(a & c), pp2a, or KAP.

Cdk/cyclin complex activity may be further regulated by two families of endogenous cellular proteinaceous inhibitors: the Kip/Cip family, or the INK family. The INK proteins specifically bind cdk4 and cdk6. $p16^{ink4}$ (also known as MTS1) is a potential tumour suppressor gene that is mutated, or deleted, in a large number of primary cancers. The Kip/Cip family contains proteins such as $p21^{CiP1,Waf1}$, $p27^{Kip1}$ and $p57^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumor agents as they would not directly interact with DNA and should therefore reduce the risk of secondary tumour development.

Aurora Kinases

Relatively recently, a new family of serine/threonine kinases known as the Aurora kinases has been discovered that are involved in the G2 and M phases of the cell cycle, and which are important regulators of mitosis.

The precise role of Aurora kinases has yet to be elucidated but that they play a part in mitotic checkpoint control, chromosome dynamics and cytokinesis (Adams et al., *Trends Cell Biol.*, 11: 49-54 (2001). Aurora kinases are located at the centrosomes of interphase cells, at the poles of the bipolar spindle and in the mid-body of the mitotic apparatus.

Three members of the Aurora kinase family have been found in mammals so far (E. A. Nigg, *Nat. Rev. Mol. Cell. Biol.* 2: 21-32, (2001)). These are:
Aurora A (also referred to in the literature as Aurora 2);
Aurora B (also referred to in the literature as Aurora 1); and
Aurora C (also referred to in the literature as Aurora 3).

The Aurora kinases have highly homologous catalytic domains but differ considerably in their N-terminal portions (Katayama H, Brinkley W R, Sen S.; The Aurora kinases: role in cell transformation and tumorigenesis; Cancer Metastasis Rev. 2003 December; 22(4):451-64).

The substrates of the Aurora kinases A and B have been identified as including a kinesin-like motor protein, spindle apparatus proteins, histone H3 protein, kinetochore protein and the tumour suppressor protein p53.

Aurora A kinases are believed to be involved in spindle formation and become localised on the centrosome during the early G2 phase where they phosphorylate spindle-associated proteins (Prigent et al., *Cell*, 114: 531-535 (2003). Hirota et al, *Cell*, 114:585-598, (2003) found that cells depleted of Aurora A protein kinase were unable to enter mitosis. Furthermore, it has been found (Adams, 2001) that mutation or disruption of the Aurora A gene in various species leads to mitotic abnormalities, including centrosome separation and maturation defects, spindle aberrations and chromosome segregation defects.

The Aurora kinases are generally expressed at a low level in the majority of normal tissues, the exceptions being tissues with a high proportion of dividing cells such as the thymus and testis. However, elevated levels of Aurora kinases have been found in many human cancers (Giet et al., *J. Cell. Sci.* 112: 3591-361, (1999) and Katayama (2003). Furthermore, Aurora A kinase maps to the chromosome 20q 13 region that has frequently been found to be amplified in many human cancers.

Thus, for example, significant Aurora A over-expression has been detected in human breast, ovarian and pancreatic cancers (see Zhou et al., *Nat. Genet.* 20: 189-193, (1998), Tanaka et al., *Cancer Res.*, 59: 2041-2044, (1999) and Han et al., *cancer Res.*, 62: 2890-2896, (2002).

Moreover, Isola, *American Journal of Pathology* 147, 905-911 (1995) has reported that amplification of the Aurora A locus (20q13) correlates with poor prognosis for patients with node-negative breast cancer.

Amplification and/or over-expression of Aurora-A is observed in human bladder cancers and amplification of Aurora-A is associated with aneuploidy and aggressive clinical behaviour, see Sen et al., *J. Natl. Cancer Inst,* 94: 1320-1329 (2002).

Elevated expression of Aurora-A has been detected in over 50% of colorectal cancers, (see Bischoff et al., *EMBO J.,* 17: 3052-3065, (1998) and Takahashi et al., *Jpn. J. Cancer Res.,* 91: 1007-1014 (2000)) ovarian cancers (see Gritsko et al. *Clin. Cancer Res.,* 9: 1420-1426 (2003), and gastric tumours Sakakura et al., *British Journal of Cancer,* 84: 824-831 (2001).

Tanaka et al. *Cancer Research,* 59: 2041-2044 (1999) found evidence of over-expression of Aurora A in 94% of invasive duct adenocarcinomas of the breast.

High levels of Aurora A kinase have also been found in renal, cervical, neuroblastoma, melanoma, lymphoma, pancreatic and prostate tumour cell lines Bischoff et al. (1998), EMBO J., 17: 3052-3065 (1998); Kimura et al. J. Biol. Chem., 274: 7334-7340 (1999); Zhou et al., Nature Genetics, 20: 189-193 (1998); Li et al., Clin Cancer Res. 9 (3): 991-7 (2003)].

Aurora-B is highly expressed in multiple human tumour cell lines, including leukemic cells [Katayama et al., Gene 244: 1-7)]. Levels of this enzyme increase as a function of Duke's stage in primary colorectal cancers [Katayama et al., J. Natl Cancer Inst., 91: 1160-1162 (1999)].

High levels of Aurora-3 (Aurora-C) have been detected in several tumour cell lines, even though this kinase tends to be restricted to germ cells in normal tissues (see Kimura et al. *Journal of Biological Chemistry,* 274: 7334-7340 (1999)). Over-expression of Aurora-3 in approximately 50% of colorectal cancers has also been reported in the article by Takahashi et al., *Jpn J Cancer Res.* 91: 1007-1014 (2001)].

Other reports of the role of Aurora kinases in proliferative disorders may be found in Bischoff et al., *Trends in Cell Biology* 9: 454-459 (1999); Giet et al. *Journal of Cell Science,* 112: 3591-3601 (1999) and Dutertre, et al. *Oncogene,* 21: 6175-6183 (2002).

Royce et al report that the expression of the Aurora 2 gene (known as STK15 or BTAK) has been noted in approximately one-fourth of primary breast tumours. (Royce M E, Xia W, Sahin A A, Katayama H, Johnston D A, Hortobagyi G, Sen S, Hung M C; STK15/Aurora-A expression in primary breast tumours is correlated with nuclear grade but not with prognosis; *Cancer.* 2004 Jan. 1; 100(1): 12-9).

Endometrial carcinoma (EC) comprises at least two types of cancer: endometrioid carcinomas (EECS) are estrogen-related tumours, which are frequently euploid and have a good prognosis. Nonendometrioid carcinomas (NEECs; serous and clear cell forms) are not estrogen related, are frequently aneuploid, and are clinically aggressive. It has also been found that Aurora was amplified in 55.5% of NEECs but not in any EECs (P<or =0.001) (Moreno-Bueno G, Sanchez-Estevez C, Cassia R, Rodriguez-Perales S, Diaz-Uriarte R, Dominguez O, Hardisson D, Andujar M, Prat J, Matias-Guiu X, Cigudosa J C, Palacios *J Cancer Res.* 2003 Sep. 15; 63(18):5697-702).

Reichardt et al (*Oncol Rep.* 2003 September-October; 10(5):1275-9) have reported that quantitative DNA analysis by PCR to search for Aurora amplification in gliomas revealed that five out of 16 tumours (31%) of different WHO grade (1× grade II, 1× grade III, 3× grade IV) showed DNA amplification of the Aurora 2 gene. It was hypothesized that amplification of the Aurora 2 gene may be a non-random genetic alteration in human gliomas playing a role in the genetic pathways of tumourigenesis.

Results by Hamada et al (*Br. J. Haematol.* 2003 May; 121(3):439-47) also suggest that Aurora 2 is an effective candidate to indicate not only disease activity but also tumourigenesis of non-Hodgkin's lymphoma. Retardation of tumour cell growth resulting from the restriction of this gene's functions could be a therapeutic approach for non-Hodgkin's lymphoma.

In a study by Gritsko et al (*Clin Cancer Res.* 2003 April; 9(4):1420-6)), the kinase activity and protein levels of Aurora A were examined in 92 patients with primary ovarian tumours. In vitro kinase analyses revealed elevated Aurora A kinase activity in 44 cases (48%). Increased Aurora A protein levels were detected in 52 (57%) specimens. High protein levels of Aurora A correlated well with elevated kinase activity.

Results obtained by Li et al (*Clin. Cancer Res.* 2003 March; 9(3):991-7) showed that the Aurora A gene is over-expressed in pancreatic tumours and carcinoma cell lines and suggest that overexpression of Aurora A may play a role in pancreatic carcinogenesis.

Similarly, it has been shown that Aurora A gene amplification and associated increased expression of the mitotic kinase it encodes are associated with aneuploidy and aggressive clinical behaviour in human bladder cancer. (*J. Natl. Cancer Inst.* 2002 Sep. 4; 94(17):1320-9).

Investigation by several groups (Dutertre S, Prigent C., Aurora-A overexpression leads to override of the microtubule-kinetochore attachment checkpoint; *Mol. Interv.* 2003 May; 3(3):127-30 and Anand S, Penrhyn-Lowe S, Venkitaraman A R., Aurora-A amplification overrides the mitotic spindle assembly checkpoint, inducing resistance to Taxol, *Cancer Cell.* 2003 January; 3(1):51-62) suggests that over-expression of Aurora kinase activity is associated with resistance to some current cancer therapies. For example overexpression of Aurora A in mouse embryo fibroblasts can reduce the sensitivity of these cells to the cytotoxic effects of taxane derivatives. Therefore Aurora kinase inhibitors may find particular use in patients who have developed resistance to existing therapies.

On the basis of work carried out to date, it is envisaged that inhibition of Aurora kinases, particularly Aurora kinase A and Aurora kinase B, will prove an effective means of arresting tumour development.

Harrington et al (*Nat. Med.* 2004 March; 10(3):262-7) have demonstrated that an inhibitor of the Aurora kinases suppresses tumour growth and induces tumour regression in vivo. In the study, the Aurora kinase inhibitor blocked cancer cell proliferation, and also triggered cell death in a range of cancer cell lines including leukaemic, colorectal and breast cell lines.

Cancers which may be particularly amenable to Aurora inhibitors include breast, bladder, colorectal, pancreatic, ovarian, non-Hodgkin's lymphoma, gliomas and nonendometrioid endometrial carcinomas.

Glycogen Synthase Kinase

Glycogen Synthase Kinase-3 (GSK3) is a serine-threonine kinase that occurs as two ubiquitously expressed isoforms in humans (GSK3α & beta GSK3β). GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X-X-X-(pSer/pThr), where X is any amino acid (at positions (n+1), (n+2), (n+3)) and pSer and pThr are phospho-serine and phospho-threonine respectively (n+4). GSK3 phosphorylates the first serine, or threonine, at position (n). Phospho-serine, or phospho-threonine, at the (n+4) position appear necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3α and GSKβ may be subtly regulated by phosphorylation of tyrosines 279 and 216 respectively. Mutation of these residues to a Phe caused a reduction in in vivo kinase activity. The X-ray crystallographic structure of GSK3β has helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type II, or non-insulin-dependent diabetes mellitus (NIDDM): a condition in which body tissues become resistant to insulin stimulation. The cellular insulin response in liver, adipose, or muscle tissues, is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dependent protein kinase 1 (PDK1) and protein kinase B (PKB or Akt) to the membrane, where PDK1 activates PKB. PKB is able to phosphorylate, and thereby inhibit, GSK3α and/or GSKβ through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycin" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimuli.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimuli. This can lead to the dephosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein a (C/EBPα), c-Myc and/or other substrates such as Nuclear Factor of Activated T-cells (NFATc), Heat Shock Factor-1 (HSF-1) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyperphosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation, through inhibition of GSK3, may thus provide a means of limiting and/or preventing neurodegenerative effects.

WO 02/34721 from Du Pont discloses a class of indeno[1,2-c]pyrazol-4-ones as inhibitors of cyclin dependent kinases.

WO 01/81348 from Bristol Myers Squibb describes the use of 5-thio-, sulphinyl- and sulphonylpyrazolo[3,4-b]-pyridines as cyclin dependent kinase inhibitors.

WO 00/62778 also from Bristol Myers Squibb discloses a class of protein tyrosine kinase inhibitors.

WO 01/72745A1 from Cyclacel describes 2-substituted 4-heteroaryl-pyrimidines and their preparation, pharmaceutical compositions containing them and their use as inhibitors of cyclin-dependant kinases (cdks) and hence their use in the treatment of proliferative disorders such as cancer, leukaemia, psoriasis and the like.

WO 99/21845 from Agouron describes 4-aminothiazole derivatives for inhibiting cyclin-dependent kinases (cdks), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

WO 01/53274 from Agouron discloses as CDK kinase inhibitors a class of compounds which can comprise an amide-substituted benzene ring linked to an N-containing heterocyclic group. Although indazole compounds are not mentioned generically, one of the exemplified compounds comprises an indazole 3-carboxylic acid anilide moiety linked via a methylsulphanyl group to a pyrazolopyrimidine.

WO 01/98290 (Pharmacia & Upjohn) discloses a class of 3-aminocarbonyl-2-carboxamido thiophene derivatives as protein kinase inhibitors. The compounds are stated to have multiple protein kinase activity.

WO 01/53268 and WO 01/02369 from Agouron disclose compounds that mediate or inhibit cell proliferation through the inhibition of protein kinases such as cyclin dependent kinase or tyrosine kinase. The Agouron compounds have an aryl or heteroaryl ring attached directly or though a CH═CH or CH═N group to the 3-position of an indazole ring.

WO 00/39108 and WO 02/00651 (both to Du Pont Pharmaceuticals) describe broad classes of heterocyclic compounds that are inhibitors of trypsin-like serine protease enzymes, especially factor Xa and thrombin. The compounds are stated to be useful as anticoagulants or for the prevention of thromboembolic disorders.

Heterocyclic compounds that have activity against factor Xa are also disclosed in WO 01/1978 Cor Therapeutics) and US 2002/0091116 (Zhu et al.).

WO 03/035065 (Aventis) discloses a broad class of benzimidazole derivatives as protein kinase inhibitors but does not disclose activity against CDK kinases or GSK kinases.

WO 97/36585 and U.S. Pat. No. 5,874,452 (both to Merck) disclose biheteroaryl compounds that are inhibitors of farnesyl transferase.

WO 03/066629 (Vertex) discloses benzimidazolylpyrazole amines as GSK-3 inhibitors.

WO 97/12615 (Warner Lambert) discloses benzimidazoles as 15-lipoxygenase inhibitors.

SUMMARY OF THE INVENTION

The invention provides compounds that have cyclin dependent kinase inhibiting or modulating activity and glycogen synthase kinase-3 (GSK3) inhibiting or modulating activity, and/or Aurora kinase inhibiting or modulating activity, and which it is envisaged will be useful in preventing or treating disease states or conditions mediated by the kinases.

Thus, for example, it is envisaged that the compounds of the invention will be useful in alleviating or reducing the incidence of cancer.

Accordingly, the invention provides inter alia:

The use of a compound of the formula (I) as defined herein for the manufacture of a medicament for the prophylaxis or treatment of a disease state or condition mediated by a cyclin dependent kinase or glycogen synthase kinase-3.

A method for the prophylaxis or treatment of a disease state or condition mediated by a cyclin dependent kinase or glycogen synthase kinase-3, which method comprises administering to a subject in need thereof a compound of the formula (I) as defined herein.

A method for alleviating or reducing the incidence of a disease state or condition mediated by a cyclin dependent kinase or glycogen synthase kinase-3, which method comprises administering to a subject in need thereof a compound of the formula (I) as defined herein.

A method for treating a disease or condition comprising or arising from abnormal cell growth in a mammal, which method comprises administering to the mammal a compound of the formula (I) as defined herein in an amount effective in inhibiting abnormal cell growth.

A method for alleviating or reducing the incidence of a disease or condition comprising or arising from abnormal cell growth in a mammal, which method comprises administering to the mammal a compound of the formula (I) as defined herein in an amount effective in inhibiting abnormal cell growth.

A method for treating a disease or condition comprising or arising from abnormal cell growth in a mammal, the method comprising administering to the mammal a compound of the formula (I) as defined herein in an amount effective to inhibit a cdk kinase (such as cdk1 or cdk2) or glycogen synthase kinase-3 activity.

A method for alleviating or reducing the incidence of a disease or condition comprising or arising from abnormal cell growth in a mammal, the method comprising administering to the mammal a compound of the formula (I) as defined herein in an amount effective to inhibit a cdk kinase (such as cdk1 or cdk2) or glycogen synthase kinase-3 activity.

A method of inhibiting a cyclin dependent kinase or glycogen synthase kinase-3, which method comprises contacting the kinase with a kinase-inhibiting compound of the formula (I) as defined herein.

A method of modulating a cellular process (for example cell division) by inhibiting the activity of a cyclin dependent kinase or glycogen synthase kinase-3 using a compound of the formula (I) as defined herein.

The use of a compound of the formula (I) as defined herein for the manufacture of a medicament for prophylaxis or treatment of a disease or condition characterised by up-regulation of an Aurora kinase (e.g. Aurora A kinase or Aurora B kinase).

The use of a compound of the formula (I) as defined herein for the manufacture of a medicament for the prophylaxis or treatment of a cancer, the cancer being one which is characterised by up-regulation of an Aurora kinase (e.g. Aurora A kinase or Aurora B kinase).

The use of a compound of the formula (I) as defined herein for the manufacture of a medicament for the prophylaxis or treatment of cancer in a patient selected from a sub-population possessing the Ile31 variant of the Aurora A gene.

The use of a compound of the formula (I) as defined herein for the manufacture of a medicament for the prophylaxis or treatment of cancer in a patient who has been diagnosed as forming part of a sub-population possessing the Ile31 variant of the Aurora A gene.

A method for the prophylaxis or treatment of a disease or condition characterised by up-regulation of an Aurora kinase (e.g. Aurora A kinase or Aurora B kinase), the method comprising administering a compound of the formula (I) as defined herein.

A method for alleviating or reducing the incidence of a disease or condition characterised by up-regulation of an Aurora kinase (e.g. Aurora A kinase or Aurora B kinase), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses the Ile31 variant of the Aurora A gene; and (ii) where the patient does possess the said variant, thereafter administering to the patient a compound of the formula (I) as defined herein having Aurora kinase inhibiting activity.

A method for the prophylaxis or treatment of (or alleviating or reducing the incidence of) a disease state or condition characterised by up-regulation of an Aurora kinase (e.g. Aurora A kinase or Aurora B kinase); which method comprises (i) subjecting a patient to a diagnostic test to detect a marker characteristic of up-regulation of the Aurora kinase and (ii) where the diagnostic test is indicative of up-regulation of Aurora kinase, thereafter administering to the patient a compound of the formula (I) as defined herein having Aurora kinase inhibiting activity.

The compounds of the invention are compounds of the general formula (I):

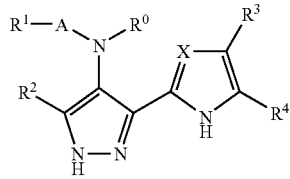

wherein
X is $CR^5$ or N;
A is a bond or $-(CH_2)_m-(B)_n-$;

B is C=O, NR$^g$(C=O) or O(C=O) wherein R$^g$ is hydrogen or C$_{1-4}$ hydrocarbyl optionally substituted by hydroxy or C$_{1-4}$ alkoxy;

m is 0, 1 or 2;

n is 0 or 1;

R$^0$ is hydrogen or, together with NR$^g$ when present, forms a group —(CH$_2$)$_p$— wherein p is 2 to 4;

R$^1$ is hydrogen, a carbocyclic or heterocyclic group having from 3 to 12 ring members, or an optionally substituted C$_{1-8}$ hydrocarbyl group;

R$^2$ is hydrogen, halogen, methoxy, or a C$_{1-4}$ hydrocarbyl group optionally substituted by halogen, hydroxyl or methoxy;

R$^3$ and R$^4$ together with the carbon atoms to which they are attached form an optionally substituted fused carbocyclic or heterocyclic ring having from 5 to 7 ring members of which up to 3 can be heteroatoms selected from N, O and S; and R$^5$ is hydrogen, a group R$^2$ or a group R$^{10}$ wherein R$^{10}$ is selected from halogen, hydroxy, trifluoromethyl, cyano, nitro, carboxy, amino, mono- or di-C$_{1-4}$ hydrocarbylamino, carbocyclic and heterocyclic groups having from 3 to 12 ring members; a group R$^a$-R$^b$ wherein R$^a$ is a bond, O, CO, X$^1$C(X$^2$), C(X$^2$)X$^1$, X$^1$C(X$^2$)X$^1$, S, SO, SO$_2$, NR$^c$, SO$_2$NR$^c$ or NR$^c$SO$_2$; and R$^b$ is selected from hydrogen, carbocyclic and heterocyclic groups having from 3 to 12 ring members, and a C$_{1-8}$ hydrocarbyl group optionally substituted by one or more substituents selected from hydroxy, oxo, halogen, cyano, nitro, carboxy, amino, mono- or di-C$_{1-4}$ hydrocarbylamino, carbocyclic and heterocyclic groups having from 3 to 12 ring members and wherein one or more carbon atoms of the C$_{1-8}$ hydrocarbyl group may optionally be replaced by O, S, SO, SO$_2$, NR$^c$, X$^1$C(X$^2$), C(X$^2$)X$^1$ or X$^1$C(X$^2$)X$^1$;

R$^c$ is selected from hydrogen and C$_{1-4}$ hydrocarbyl; and

X$^1$ is O, S or NR$^c$ and X$^2$ is =O, =S or =NR$^c$;

and salts, N-oxides and solvates thereof.

The aforementioned methods and uses, and any other therapeutic and diagnostic methods and uses, and methods of treating animals and plants defined herein, may also employ any sub-group, sub-genus, preference or example falling within formula (I), for example the compounds of formulae (II) to (IXa) and any sub-groups thereof, unless the context indicates otherwise.

GENERAL PREFERENCES AND DEFINITIONS

The following general preferences and definitions shall apply to each of the moieties R$^1$ to R$^{10}$, and their various sub-groups, sub-definitions, examples and embodiments unless the context indicates otherwise. In this specification, a superscript letter following the number of an R group indicates that the R group is a sub-group of the R group designated solely by the number. Thus, for example R$^{1a}$, R$^{1b}$ and R$^{1c}$ are all sub groups of R$^1$, and, analogously, R$^{9a}$ and R$^{9b}$ are subgroups of R$^9$. Thus, unless indicated otherwise, the general preferences, definitions and examples set out for, e.g. R$^1$ apply also to its sub-groups R$^{1a}$, R$^{1b}$ R$^{1c}$ etcetera, and similarly with the other R groups.

Any references to formula (I) herein shall also be taken to refer to formulae (II) to (VIII) and any other sub-group of compounds within formula (I) unless the context requires otherwise.

The term upregulation of Aurora kinase as used herein is defined as including elevated expression or over-expression of Aurora kinase, including gene amplification (i.e. multiple gene copies) and increased expression by a transcriptional effect, and hyperactivity and activation of Aurora kinase, including activation by mutations.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups R$^{10}$ as defined herein.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cyclohexenyl, cycloheptenyl and cyclooctenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) an imidazole ring fused to a 5- or 6-membered ring containing 1 or 2 ring heteroatoms;
g) an oxazole ring fused to a 5- or 6-membered ring containing 1 or 2 ring heteroatoms;
h) an isoxazole ring fused to a 5- or 6-membered ring containing 1 or 2 ring heteroatoms;
i) a thiazole ring fused to a 5- or 6-membered ring containing 1 or 2 ring heteroatoms;
j) an isothiazole ring fused to a 5- or 6-membered ring containing 1 or 2 ring heteroatoms;
k) a thiophene ring fused to a 5- or 6-membered ring containing 1, 2 or 3 ring heteroatoms;
l) a furan ring fused to a 5- or 6-membered ring containing 1, 2 or 3 ring heteroatoms;
m) an oxazole ring fused to a 5- or 6-membered ring containing 1 or 2 ring heteroatoms;
n) an isoxazole ring fused to a 5- or 6-membered ring containing 1 or 2 ring heteroatoms;
o) a cyclohexyl ring fused to a 5- or 6-membered ring containing 1, 2 or 3 ring heteroatoms; and
p) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole). Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocylic groups can contain, for example, cyclic ether moieties (e.g. as in tetrahydrofuran and dioxane), cyclic thio-ether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclic groups include saturated groups such as piperidine, pyrrolidine, azetidine, morpholine, piperazine and N-alkyl piperazines.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; or two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S;

$R^c$ is selected from hydrogen and $C_{1-4}$ hydrocarbyl; and
$X^1$ is O, S or $NR^c$ and $X^2$ is $=$O, $=$S or $=NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 11, or 10, or 9, or 8, or 7, or 6, or 5 non-hydrogen atoms.

Where the carbocyclic and heterocyclic groups have a pair of substituents on adjacent ring atoms, the two substituents may be linked so as to form a cyclic group. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group. Examples of such linked substituent groups include:

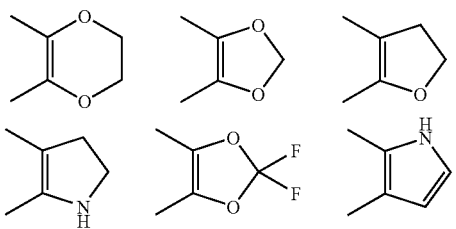

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone, except where otherwise stated. In certain cases, as defined herein, one or more of the carbon atoms making up the carbon backbone may be replaced by a specified atom or group of atoms. Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

Preferred non-aromatic hydrocarbyl groups are saturated groups such as alkyl and cycloalkyl groups.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl(vinyl), 1-propenyl, 2-propenyl(allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members, more usually 3, 4, 5 or 6 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$), and ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members.

The definition "$R^a$-$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), NR$^c$(O), OC(S), SC(S), NR$^c$C(S), OC(NR$^c$), SC(NR$^c$), NR$^c$C(NR$^c$), C(O)O, C(O)S, C(O)NR$^c$, C(S)O, C(S)S, C(S)NR$^c$, C(NR$^c$)O, C(NR$^c$)S, C(NR$^c$)NR$^c$, OC(O)O, SC(O)O, NR$^c$C(O)O, OC(S)O, SC(S)O, NR$^c$C(S)O, OC(NR$^c$)O, SC(NR$^c$)O, NR$^c$C(NR$^c$)O, OC(O)S, SC(O)S, NR$^c$C(O)S, OC(S)S, SC(S)S, NR$^c$C(S)S, OC(NR$^c$)S, SC(NR$^c$)S, NR$^c$C(NR$^c$)S, OC(O)NR$^c$, SC(O)NR$^c$, NR$^c$C(O)NR$^c$, OC(S)NR$^c$, SC(S)NR$^c$, NR$^c$C(S)NR$^c$, OC(NR$^c$)NR$^c$, SC(NR$^c$)NR$^c$, NR$^c$C(NR$^c$NR$^c$, S, SO, SO$_2$ NR$^c$, SO$_2$NR$^c$ and NR$^c$SO$_2$ wherein $R^c$ is hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups substituted by a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy— as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When $R^a$ is SO$_2$NR$^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is SO$_2$NR$^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is SO$_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is NR$^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is NR$^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for $R^0$ to $R^{10}$ and X

In formula (I), X can be CR$^5$ or N. In one particular embodiment, X is N. In another particular embodiment, X is CH. Preferably X is N.

$R^0$ can be hydrogen or, together with the group R$^g$ when present, can form a bridging group —(CH$_2$)$_p$— wherein p is 2 to 4, more usually 2-3, e.g. 2. Preferably $R^0$ is hydrogen.

When $R^0$ and the group R$^g$ form a bridging group —(CH$_2$)$_p$—, the entity —(CH$_2$)$_m$—(B)$_n$—NR$^0$— can be represented thus:

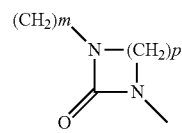

When A is a bond or a group —(CH$_2$)$_m$—(B)$_n$— wherein n is 0, X can be N or CR$^5$ wherein R$^5$ is hydrogen or a group R$^{10}$. More preferably, X is N.

When A is a bond or a group —(CH$_2$)$_m$—(B)$_n$— wherein n is 1, it is preferred that X is N or CR$^5$ wherein R$^5$ is hydrogen or a group R$^2$. More preferably, X is N.

Where R$^5$ is other than hydrogen, more particularly when n is 1, it is preferably a small substituent containing no more than 14 atoms, for example a $C_{1-4}$ alkyl or $C_{3-6}$ cycloalkyl group such as methyl, ethyl, propyl and butyl, or cyclopropyl and cyclobutyl.

A is a bond or —(CH$_2$)$_m$—(B)$_n$— wherein B is C=O, NR$^g$(C=O) or O(C=O), m is 0, 1 or 2; and n is 0 or 1. In one preferred group of compounds of the invention, m is 0 or 1, n is 1 and B is C=O or NR$^g$(C=O), preferably C=O. More preferably, m is 0, n is 1 and B is C=O. It is presently preferred that when B is NR$^g$(C=O), R$^g$ is hydrogen.

It will be appreciated that the moiety R$^1$-A-NH linked to the 4-position of the pyrazole ring can take the form of an amine R$^1$—(CH$_2$)$_m$—NH, an amide R$^1$—(CH$_2$)$_m$—C(=O)NH, a urea R$^1$—(CH$_2$)$_m$—NHC(=O)NH or a carbamate R$^1$—(CH$_2$)$_m$—OC(=O)NH wherein in each case m is 0, 1 or 2, preferably 0 or 1 and most preferably 0.

R$^1$ is hydrogen, a carbocyclic or heterocyclic group having from 3 to 12 ring members, or an optionally substituted C$_{1-8}$ hydrocarbyl group as hereinbefore defined. Examples of carbocyclic and heterocyclic, and optionally substituted hydrocarbyl groups are as set out above.

For example, R$^1$ can be a monocyclic or bicyclic group having from 3 to 10 ring members.

Where R$^1$ is a monocyclic group, typically it has 3 to 7 ring members, more usually 3 to 6 ring members, for example, 3, 4, 5 or 6.

When the monocyclic group R$^1$ is an aryl group, it will have 6 ring members and will be an unsubstituted or substituted phenyl ring.

When the monocyclic group R$^1$ is a non-aromatic carbocyclic group, it can have from 3 to 7 ring members, more usually 3 to 6 ring members, for example, 3, or 4, or 5, or 6 ring members. The non-aromatic carbocyclic group may be saturated or partially unsaturated but preferably it is saturated, i.e. R$^1$ is a cycloalkyl group.

When the monocyclic group R$^1$ is a heteroaryl group, it will have 5 or 6 ring members. Examples of heteroaryl groups having 5 and 6 ring members are set out above, and particular examples are described below.

In one sub-group of compounds, the heteroaryl group has 5 ring members.

In another sub-group of compounds, the heteroaryl group has 6 ring members.

The monocyclic heteroaryl groups R$^1$ typically have up to 4 ring heteroatoms selected from N, O and S, and more typically up to 3 ring heteroatoms, for example 1, or 2, or 3 ring heteroatoms.

When R$^1$ is a non-aromatic monocyclic heterocyclic group, it may be any one of the groups listed hereinabove or hereinafter. Such groups typically have from 4 to 7 ring members and more preferably 5 or 6 ring members. The non-aromatic monocyclic heterocyclic groups typically contain up to 3 ring heteroatoms, more usually 1 or 2 ring heteroatoms, selected from N, S and O. The heterocyclic group may be saturated or partially unsaturated, but preferably it is saturated. Particular examples of non-aromatic monocyclic heterocyclic groups are the particular and preferred examples defined in the "General Preferences and Definitions" section above, and as set out in the tables and examples below.

Where R$^1$ is a bicyclic group, typically it has 8 to 10 ring members, for example 8, or 9, or 10 ring members. The bicyclic group can be an aryl or heteroaryl group and examples of such groups include groups comprising a 5-membered ring fused to another 5-membered ring; a 5-membered ring fused to a 6-membered ring; and a 6-membered ring fused to another 6-membered ring. Examples of groups in each of these categories are set out above in the "General Preferences and Definitions" section.

A bicyclic aryl or heteroaryl group can comprise two aromatic or unsaturated rings, or one aromatic and one non-aromatic (e.g. partially saturated) ring.

Bicyclic heteroaryl groups typically contain up to 4 heteroatom ring members selected from N, S and O. Thus, for example, they may contain 1, or 2, or 3, or 4 heteroatom ring members.

In the monocyclic and bicyclic heterocyclic groups R$^1$, examples of combinations of heteroatom ring members include N; NN; NNN; NNNN; NO; NNO; NS; NNS, O, S, OO and SS.

Particular examples of R$^1$ include optionally substituted or unsubstituted heteroaryl groups selected from pyrazolo[1,5-a]pyridinyl (e.g. pyrazolo[1,5-a]pyridin-3-yl), furanyl (e.g. 2-furanyl and 3-furanyl), indolyl (e.g. 3-indolyl, 4-indolyl and 7-indolyl), oxazolyl, thiazolyl (e.g. thiazol-2-yl and thiazol-5-yl), isoxazolyl (e.g. isoxazol-3-yl and isoxazol-4-yl), pyrrolyl (e.g. 3-pyrrolyl), pyridyl (e.g. 2-pyridyl), quinolinyl (e.g. quinolin-8-yl), 2,3-dihydro-benzo[1,4]dioxine (e.g. 2,3-dihydro-benzo[1,4]dioxin-5-yl), benzo[1,3]dioxole (e.g. benzo[1,3]dioxol-4-yl), 2,3-dihydrobenzofuranyl (e.g. 2,3-dihydrobenzofuran-7-yl), imidazolyl and thiophenyl (e.g. 3-thiophenyl).

Other examples of R$^1$ include substituted or unsubstituted heteroaryl groups selected from pyrazolo[1,5-a]pyrimidine, isobenzofuran, [1,2,4]triazolo[1,5-a]pyrimidine, tetrazolyl, tetrahydroisoquinolinyl (e.g. 1,2,3,4-tetrahydroisoquinolin-7-yl), pyrimidinyl, pyrazolyl, triazolyl, 4,5,6,7-tetrahydro-benzo[d]isoxazole, phthalazine, 2H-phthalazin-1-one, benzoxazole, cinnoline, quinoxaline, naphthalene, benzo[c]isoxazole, imidazo[2,1-b]thiazole, pyridone, tetrahydroquinolinyl (e.g. 1,2,3,4-tetrahydroquinolin-6-yl), and 4,5,6,7-tetrahydro-benzofuran groups.

Preferred R$^1$ heteroaryl groups include pyrazolo[1,5-a]pyridinyl, furanyl, 2,3-dihydrobenzofuranyl, thiophenyl, indolyl, thiazolyl, isoxazolyl and 2,3-dihydro-benzo[1,4]dioxine groups.

Preferred aryl groups R$^1$ are optionally substituted phenyl groups.

Examples of non-aromatic groups R$^1$ include monocyclic cycloalkyl and azacycloalkyl groups such as cyclohexyl, cyclopentyl and piperidinyl, particularly cyclohexyl and 4-piperidinyl groups. Other examples of non-aromatic groups R$^1$ include monocyclic oxacycloalkyl groups such as tetrahydropyranyl and aza-oxa cycloalkyl groups such as morpholino (e.g. 2-morpholino and 4-morpholino).

Preferred substituted and unsubstituted C$_{1-8}$ hydrocarbyl groups include trifluoromethyl and tertiary butyl groups.

One sub-set of preferred R$^1$ groups includes phenyl, pyrazolo[1,5-a]pyridinyl and 2,3-dihydro-benzo[1,4]dioxine groups.

Another sub-set of preferred R$^1$ groups includes unsubstituted and substituted phenyl, pyrazolo[1,5-a]pyridinyl, 2,3-dihydro-benzo[1,4]dioxine, indol-4-yl, 2,3-dihydrobenzofuranyl, tert-butyl, furanyl, pyrazolo[1,5-a]pyridin-3-yl, pyrazolo[1,5-a]pyrimidin-3-yl, oxazolyl, isoxazolyl, benzoxazol-2-yl, 2H-tetrazol-5-yl, pyrazin-2-yl, pyrazolyl, benzyl, α,α-dimethylbenzyl, α-aminobenzyl, α-methylaminobenzyl, 4,5,6,7-tetrahydro-benzo[d]isoxazol-3-yl, 2H-phthalazin-1-one-4-yl, benzoxazol-7-yl, quinazolinyl, 2-naphthyl, cyclopropyl, benzo[c]isoxazol-3-yl, 4-piperidinyl, 5-thiazolyl, 2-pyridyl, 3-pyridyl, 3-pyrrolyl, isoxazolyl, imidazo[2,1-b]thiazolyl, 4-pyrimidinyl, cyclohexyl, tetrahydropyran-4-yl, tetrahydroquinolinyl, 4,5,6,7-tetrahydro-benzofuranyl and morpholinyl groups.

The group R$^1$ can be an unsubstituted or substituted carbocyclic or heterocyclic group in which one or more substituents can be selected from the group R$^{10}$ as hereinbefore defined. In one embodiment, the substituents on R$^1$ may be selected from the group R$^{10a}$ consisting of halogen, hydroxy, trifluoromethyl, cyano, nitro, carboxy, heterocyclic groups having 5 or 6 ring members and up to 2 heteroatoms selected from O, N and S, a group $R^a$-$R^b$ wherein $R^a$ is a bond, O, CO, $X^3C(X^4)$, $C(X^4)X^3$, $X^3C(X^4)X^3$, S, SO, or $SO_2$, and $R^b$ is selected from hydrogen, heterocyclic groups having 5 or 6 ring members and up to 2 heteroatoms selected from O, N and S, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having 5 or 6 ring members and up to 2 heteroatoms selected from O, N and S; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is =O or =S.

In a further embodiment, the substituents on $R^1$ may be selected from the group $R^{10b}$ consisting of halogen, hydroxy, trifluoromethyl, cyano, nitro, carboxy, a group $R^a$-$R^b$ wherein $R^a$ is a bond, O, CO, $X^3C(X^4)$, $C(X^4)X^3$, $X^3C(X^4)X^3$, S, SO, or $SO_2$, and $R^b$ is selected from hydrogen and a $C_{1-8}$ hydrocarbyl group optionally substituted by one or more substituents selected from hydroxy, oxo, halogen, cyano, nitro, carboxy; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is =O or =S.

In another embodiment, the substituents on $R^1$ may be selected from halogen, hydroxy, trifluoromethyl, a group $R^a$-$R^b$ wherein $R^a$ is a bond or O, and $R^b$ is selected from hydrogen and a $C_{1-4}$ hydrocarbyl group optionally substituted by one or more substituents selected from hydroxyl and halogen.

One sub-set of substituents that may be present on a group $R^1$ (e.g. an aryl or heteroaryl group $R^1$) includes fluorine, chlorine, methoxy, methyl, oxazolyl, morpholino, trifluoromethyl, bromomethyl, chloroethyl, pyrrolidino, pyrrolidinylethoxy, pyrrolidinylmethyl, difluoromethoxy and morpholinomethyl.

Another sub-set of substituents that may be present on a group $R^1$ includes fluorine, chlorine, methoxy, ethoxy, methyl, ethyl, isopropyl, tert-butyl, amino, oxazolyl, morpholino, trifluoromethyl, bromomethyl, chloroethyl, pyrrolidino, pyrrolidinylethoxy, pyrrolidinylmethyl, difluoromethoxy, trifluoromethoxy, morpholino, N-methylpiperazino, piperazine, piperidino, pyrrolidino, and morpholinomethyl.

The moiety $R^1$ may be substituted by more than one substituent. Thus, for example, there may be 1 or 2 or 3 or 4 substituents, more typically 1, 2 or 3 substituents. In one embodiment, where $R^1$ is a six membered ring (e.g. a carbocyclic ring such as a phenyl ring), there may be a single substituent which may be located at any one of the 2-, 3- and 4-positions on the ring. In another embodiment, there may be two or three substituents and these may be located at the 2-, 3-, 4- or 6-positions around the ring. By way of example, a phenyl group $R^1$ may be 2,6-disubstituted, 2,3-disubstituted, 2,4-disubstituted 2,5-disubstituted, 2,3,6-trisubstituted or 2,4,6-trisubstituted.

In one embodiment, a phenyl group $R^1$ may be disubstituted at positions 2- and 6- with substituents selected from fluorine, chlorine and $R^a$-$R^b$, where $R^a$ is O and $R^b$ is $C_{1-4}$ alkyl, with fluorine being a particular substituent.

In one subgroup of compounds, the group $R^1$ is a five membered heteroaryl group containing 1 or 2 ring heteroatoms selected from O, N and S. Particular heteroaryl groups include furan, thiophene, pyrrole, oxazole, isoxazole and thiazole groups. The heteroaryl groups may be unsubstituted or substituted by one or more substituent groups as hereinbefore defined.

One preferred group of five membered heteroaryl groups consists of optionally substituted isoxazole and thiazole groups.

In another sub-group of compounds, $R^1$ is a pyrazolopyridine group, for example, a pyrazolo[1,5-a]pyridine group, such as a 3-pyrazolo[1,5-a]pyridinyl group.

Particular examples of groups $R^1$ include the groups A1 to A183 (e.g. A1 to A60) set out in Table 1 below.

TABLE 1

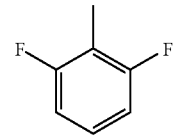

A1

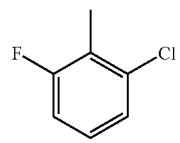

A2

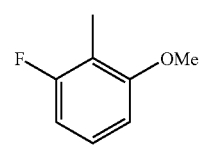

A3

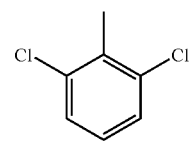

A4

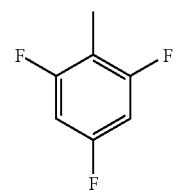

A5

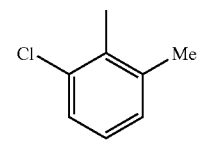

A6

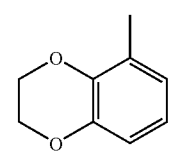

A7

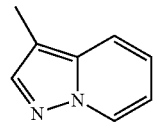

A8

TABLE 1-continued
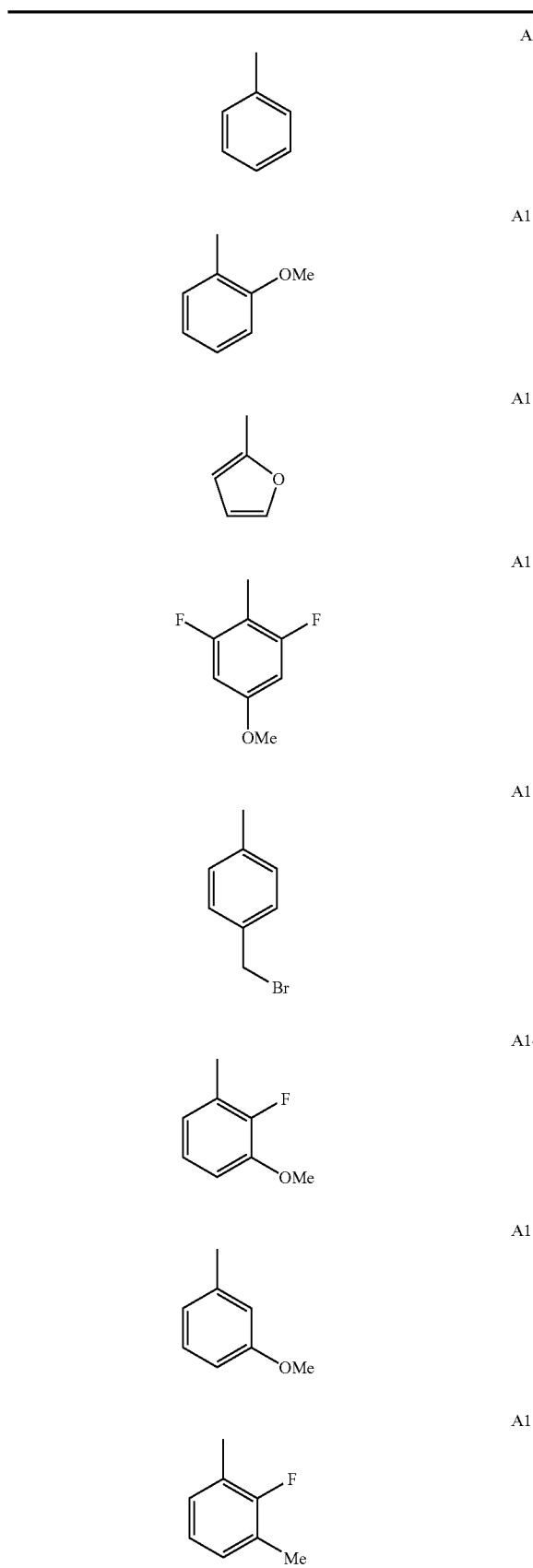
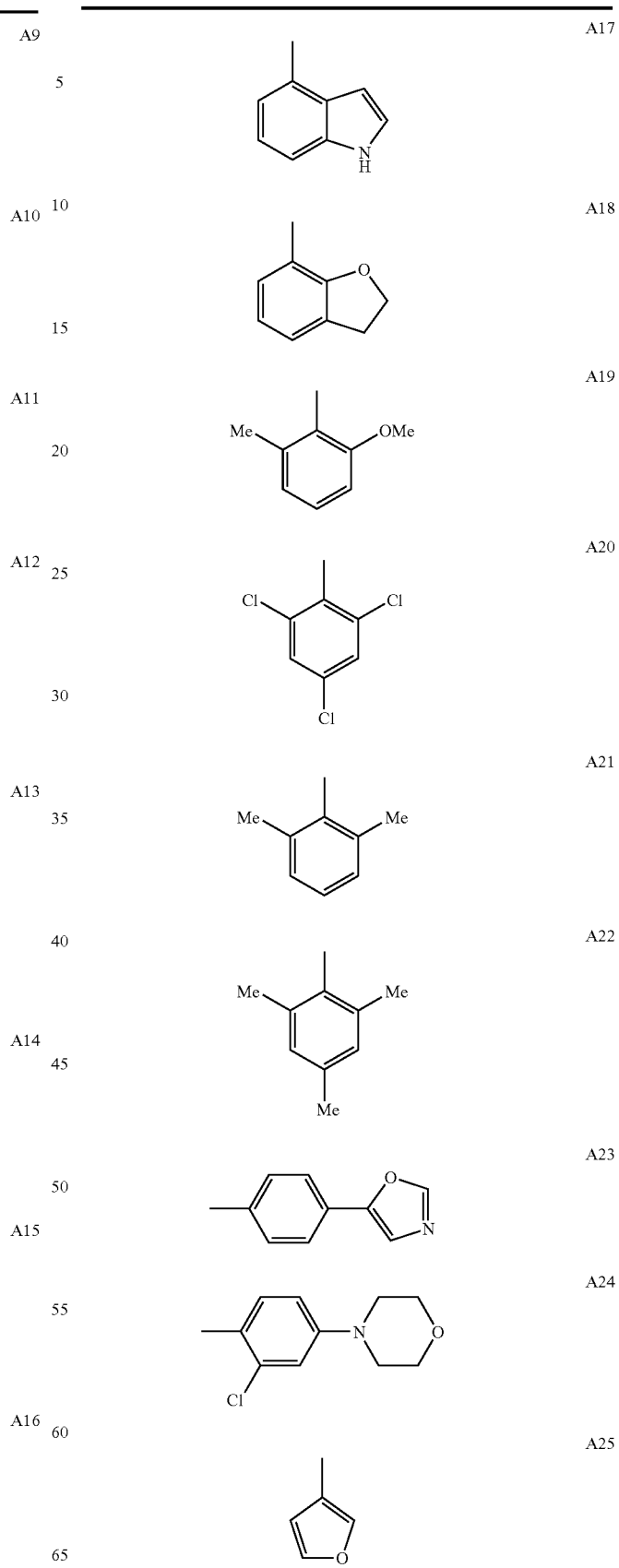

TABLE 1-continued

| | |
|---|---|
| A26 | A36 |
| A27 | A37 |
| A28 | A38 |
| A29 | A39 |
| A30 | A40 |
| A31 | A41 |
| A32 | A42 |
| A33 | A43 |
| A34 | A44 |
| A35 | |

TABLE 1-continued
| | |
|---|---|
| 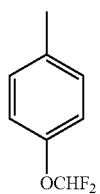 | A45 |
| 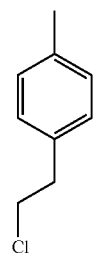 | A46 |
| 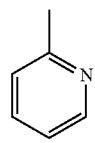 | A47 |
| 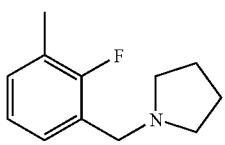 | A48 |
| 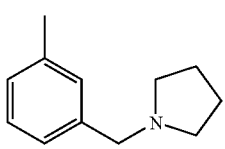 | A49 |
| 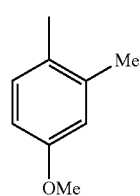 | A50 |
| 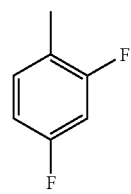 | A51 |
TABLE 1-continued
| | |
|---|---|
| 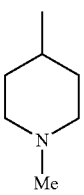 | A52 |
| 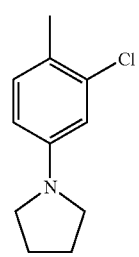 | A53 |
| 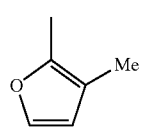 | A54 |
| 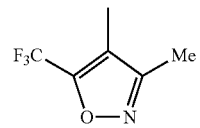 | A55 |
| 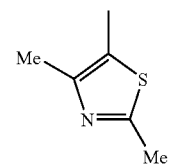 | A56 |
| 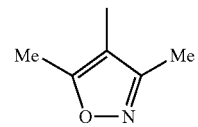 | A57 |
| 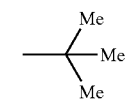 | A58 |
| 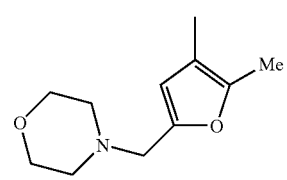 | A59 |

TABLE 1-continued
| | |
|---|---|
| 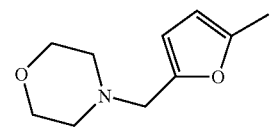 | A60 |
| 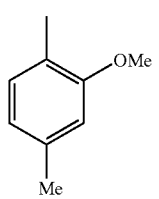 | A61 |
| 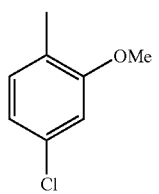 | A62 |
| 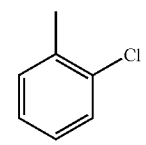 | A63 |
| 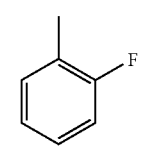 | A64 |
| 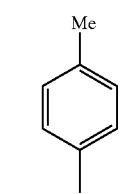 | A65 |
| 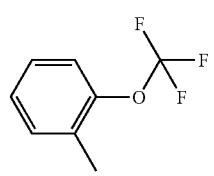 | A66 |
| 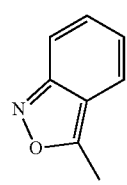 | A67 |
TABLE 1-continued
| | |
|---|---|
| 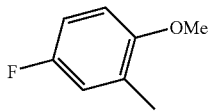 | A68 |
| 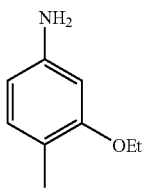 | A69 |
| 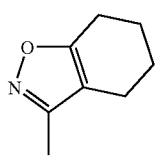 | A70 |
| 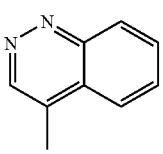 | A71 |
| 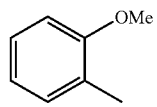 | A72 |
| 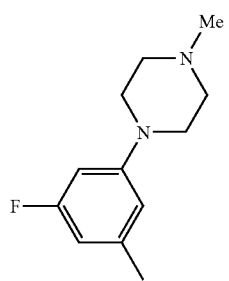 | A73 |
| 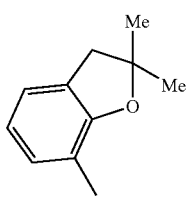 | A74 |
| 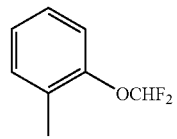 | A75 |

TABLE 1-continued
A76 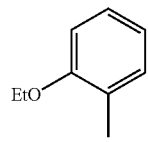
A77 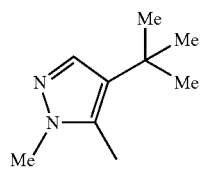
A78 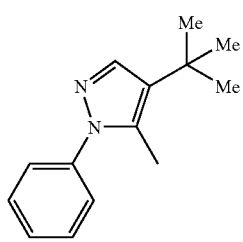
A79 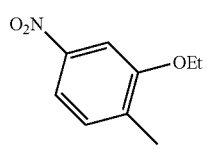
A80 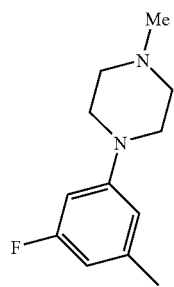
A81 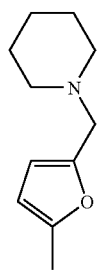
A82 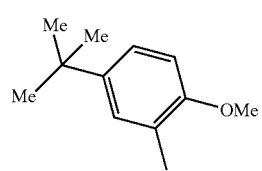
TABLE 1-continued
A83 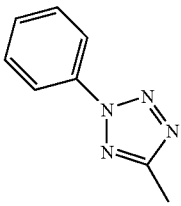
A84 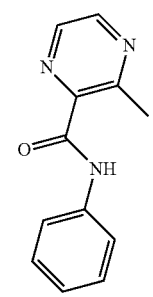
A85 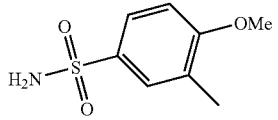
A86 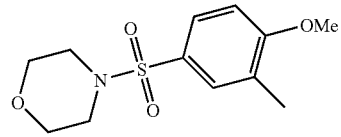
A87 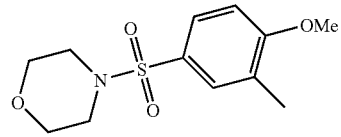
A88 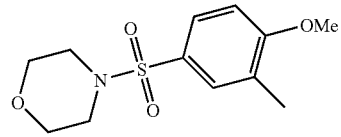

TABLE 1-continued
| | |
|---|---|
| 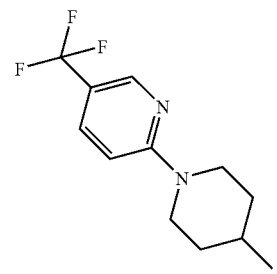 | A89 |
| 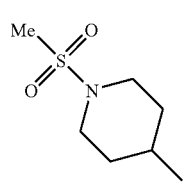 | A90 |
| 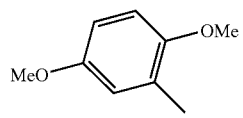 | A91 |
|  | A92 |
| 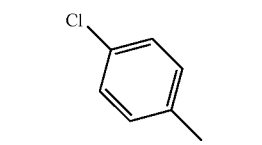 | A93 |
| 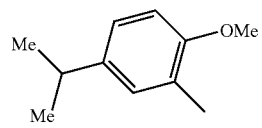 | A94 |
| 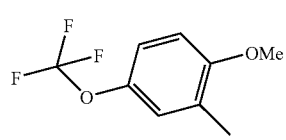 | A95 |
| 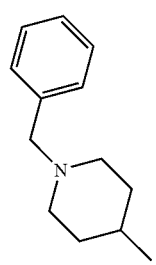 | A96 |
TABLE 1-continued
| | |
|---|---|
|  | A97 |
| 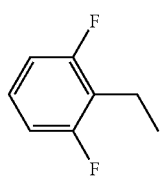 | A98 |
| 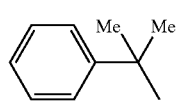 | A99 |
| 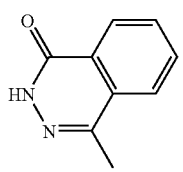 | A100 |
| 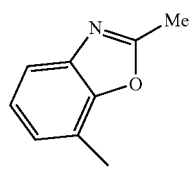 | A101 |
| 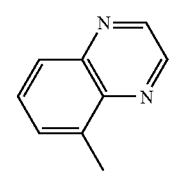 | A102 |
| 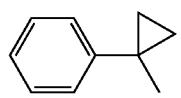 | A103 |
| 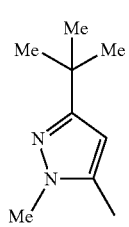 | A104 |

TABLE 1-continued
A105 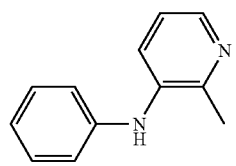
A106 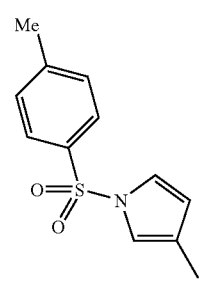
A107 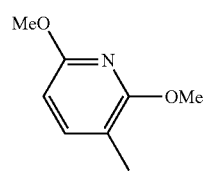
A108 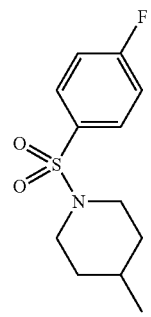
A109 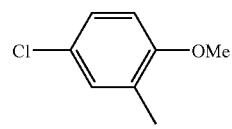
A110 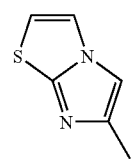
A111 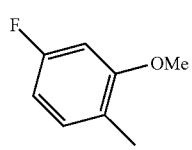
TABLE 1-continued
A112 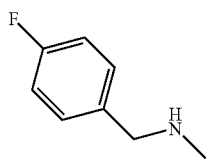
A113 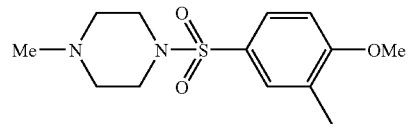
A114 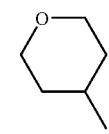
A115 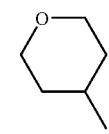
A116 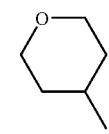
A117 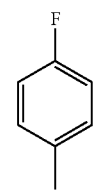
A118 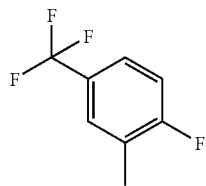

TABLE 1-continued
A119
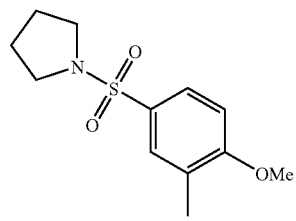
A120
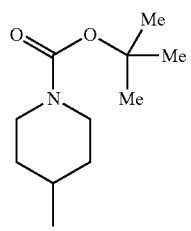
A121
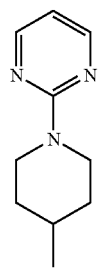
A122
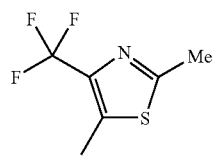
A123
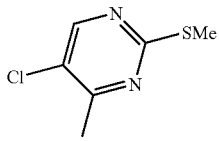
A124
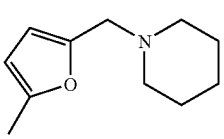
A125
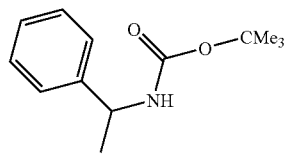
A126
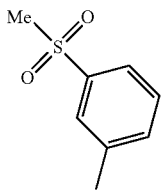
A127
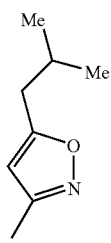
A128
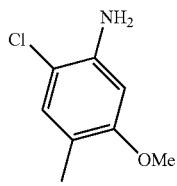
A129
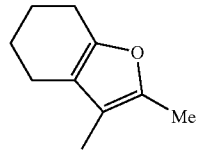
A130
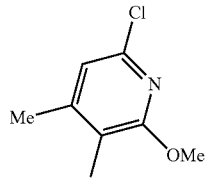
A131
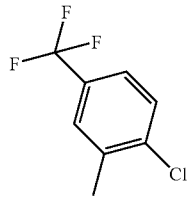
A132
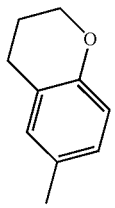

TABLE 1-continued
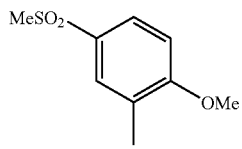 A133
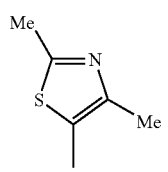 A134
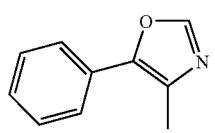 A135
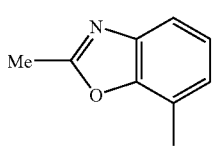 A136
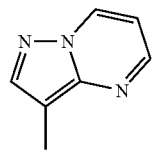 A137
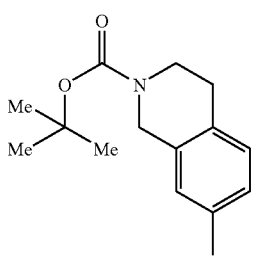 A138
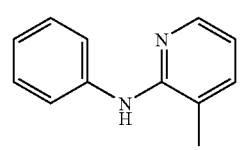 A139
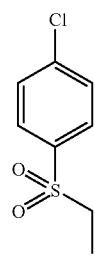 A140
TABLE 1-continued
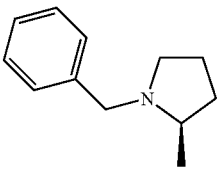 A141
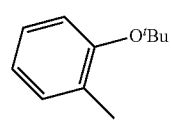 A142
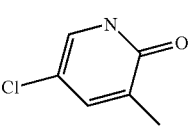 A143
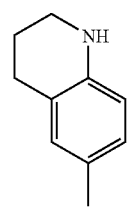 A144
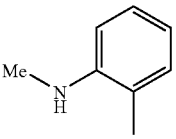 A145
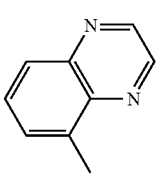 A146
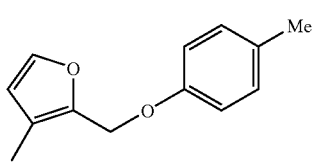 A147
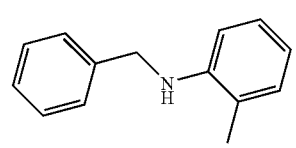 A148

TABLE 1-continued
A149
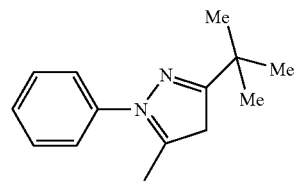
A150
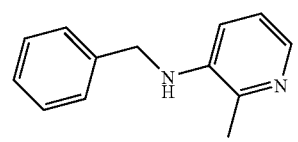
A151
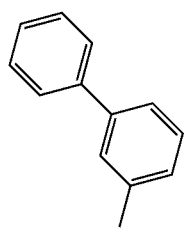
A152
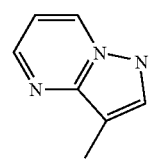
A153
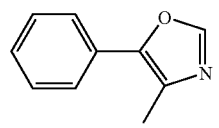
A154
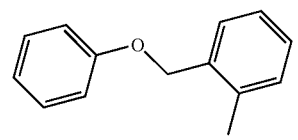
A155
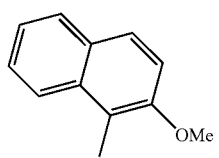
A156
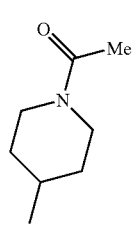
TABLE 1-continued
A157
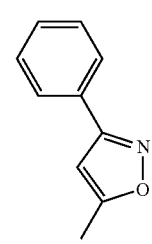
A158
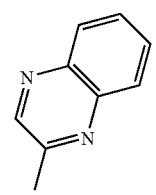
A159
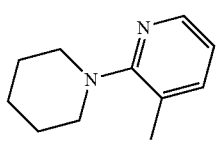
A160
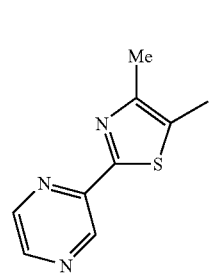
A161
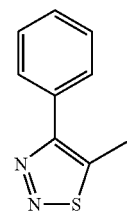
A162
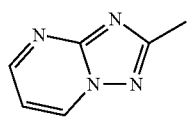
A163
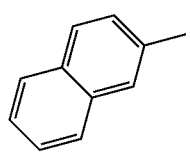

TABLE 1-continued
| | |
|---|---|
| 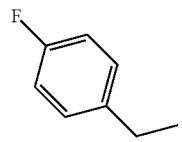 | A164 |
| 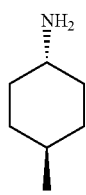 | A165 |
|  | A166 |
| 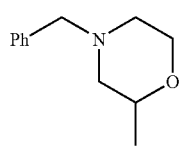 | A167 |
| 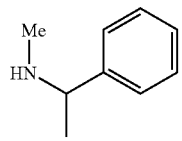 | A168 |
| 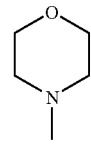 | A169 |
| 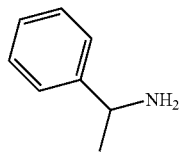 | A170 |
| 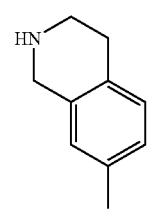 | A171 |
TABLE 1-continued
| | |
|---|---|
| 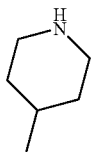 | A172 |
| 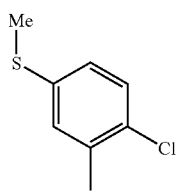 | A173 |
| 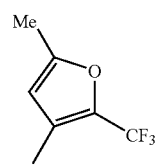 | A174 |
| 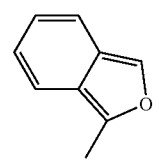 | A175 |
| 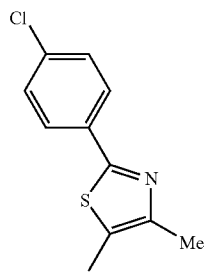 | A176 |
| 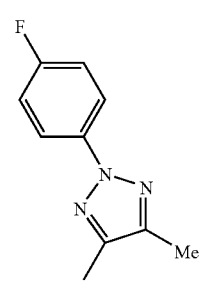 | A177 |
| 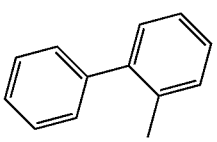 | A178 |

TABLE 1-continued

A179: 3,4,6-trimethyl-pyridin-2(1H)-one derivative (Me groups at 3,4,6 positions on pyridinone)

A180: 3-methyl-pyridin-2(1H)-one

A181: 3-(4-fluorophenyl)-4-methyl-5-methyl-isoxazole

A182: 2-(4-chlorophenylthio)-3-methylpyridine

A183: 4-(4-methoxy-3-methylphenyl)morpholine

One preferred sub-set of compounds of the invention is the sub-set wherein $R^1$ is a group selected from A1 to A34.

Another preferred sub-set of compounds of the invention is the sub-set wherein $R^1$ is a group selected from A1 to A24, A26 to A34, A38 to A46, A48 to A57, A59 to A64, A66 to A114, A116 to A165, A167 to A168 and A170 to A183.

One particularly preferred sub-set of groups $R^1$ includes 2,6-difluorophenyl, 2-chloro-6-fluorophenyl, 2-fluoro-6-methoxyphenyl, 2,6-dichlorophenyl, 2,4,6-trifluorophenyl, 2-chloro-6-methyl, 2,3-dihydro-benzo[1,4]dioxin-5-yl and pyrazolo[1,5-a]pyridin-3-yl. Compounds containing groups $R^1$ selected from this sub-set have particularly good cdk inhibitory activity.

Another particularly preferred sub-set of groups $R^1$ includes 2,6-difluorophenyl, 2-methoxyphenyl, 2,6-difluoro-4-methoxyphenyl, 2-fluoro-6-methoxyphenyl, 2-fluoro-5-methoxyphenyl, 2,6-dimethoxyphenyl, 2,4-dimethoxyphenyl, 2-chloro-6-fluorophenyl, 2,6-dichlorophenyl, 2,4,6-trifluorophenyl, 2-chloro-6-methyl, 2,3-dihydro-benzo[1,4]dioxin-5-yl and pyrazolo[1,5-a]pyridin-3-yl.

In the context of the inhibition of cdk kinases, one currently most preferred group $R^1$ is 2,6-difluorophenyl.

$R^2$ is hydrogen, halogen, methoxy, or a $C_{1-4}$ hydrocarbyl group optionally substituted by halogen, hydroxyl or methoxy. Preferably $R^2$ is hydrogen, chlorine or methyl, and most preferably $R^2$ is hydrogen.

In the compounds of the formula (I), $R^3$ and $R^4$, together with the carbon atoms to which they are attached, form a fused heterocyclic or carbocyclic group having from 5 to 7 ring members, of which up to 3 can be heteroatoms selected from N, O and S. The fused carbocyclic or heterocyclic ring can be optionally substituted by 0 to 4 groups $R^{10}$ as defined herein. The fused heterocyclic or carbocyclic group can be aromatic or non-aromatic but preferably is aromatic.

In one preferred group of compounds, $R^3$ and $R^4$ together with the carbon atoms to which they are attached form a fused carbocyclic group having from 5 to 7 ring members.

Fused five and six membered carbocyclic or heterocyclic groups are particularly preferred. Examples of fused heterocyclic rings include five and six membered rings such as thiazolo, isothiazolo, oxazolo, isoxazolo, pyrrolo, pyrido, thieno, furano, pyrimido, pyrazolo, pyrazino, tetrahydroazepinone and imidazolo fused rings. It is preferred that the fused heterocyclic group is selected from six membered ring groups, one particularly preferred group being the pyrido group.

Examples of fused carbocyclic rings include five and six membered rings such as benzo, dihydro or tetrahydro-benzo and cyclopenta-fused rings. Six membered rings are preferred. One particularly preferred group is the benzo group.

Particular examples of ring systems formed by the five membered ring and $R^3$ and $R^4$ are ring systems (i) to (iv) set out below. Ring system (i) is generally preferred.

(i) benzimidazole (ii) imidazo[4,5-c]pyridine (iii) imidazo[4,5-d]pyrimidine (purine-like)

(iv) imidazo-fused tetrahydroazepinone

The fused carbocyclic or heterocyclic group can be optionally substituted by one or more groups $R^{10}$ as hereinbefore defined.

In one embodiment, the substituents on the fused carbocyclic or heterocyclic group may be selected from halogen, hydroxy, trifluoromethyl, cyano, nitro, carboxy, amino, monocyclic carbocyclic and heterocyclic groups having from 3 to 7 (typically 5 or 6) ring members, a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, a carbocyclic or heterocyclic group with 3-7 ring members and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, a carbocyclic or heterocyclic group with 3-7 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; and $R^c$, $X^1$ and $X^2$ are as hereinbefore defined, or two adjacent groups $R^{10}$ together with the carbon atoms or heteroatoms to which they are attached may form a 5-membered heteroaryl ring or a 5- or 6-membered non-aromatic heterocyclic ring, wherein the said heteroaryl and heterocyclic groups contain up to 3 heteroatom ring members selected from N, O and S.

Preferred $R^{10}$ groups on the fused carbocyclic or heterocyclic group formed by $R^3$ and $R^4$ include halogen (e.g. fluorine and chlorine), a group $R^a$-$R^b$ wherein $R^a$ is a bond, O, CO, $C(X^2)X^1$, and $R^b$ is selected from hydrogen, heterocyclic groups having 3-7 ring members (preferably 5 or 6 ring members) and a $C_{1-4}$ hydrocarbyl group (e.g. a saturated hydrocarbyl group such as an alkyl or cycloalkyl group) optionally substituted by one or more substituents selected from hydroxy, carboxy, amino, mono- or di-$C_{1-4}$ hydrocarbylamino, and heterocyclic groups with 3-7 ring members (e.g. 5 or 6 ring members).

One preferred group of compounds of the invention is represented by the formula (II):

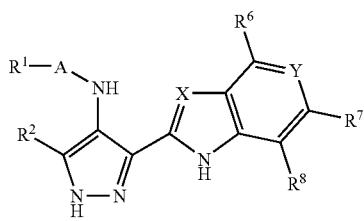

(II)

wherein $R^1$, $R^2$ and X are as defined herein;
Y is N or $CR^9$ wherein $R^9$ is hydrogen or a group $R^{10}$; and $R^6$, $R^7$ and $R^8$ are the same or different and each is hydrogen or a group $R^{10}$ as defined herein.

In one sub-group of compounds of the formula (II), X is N.
In another sub-group of compounds of the formula (II), Y is $CR^9$.

When Y is N, it is preferred that $R^6$ is other than amino.

In one embodiment, the compounds of the invention are represented by the formula (III):

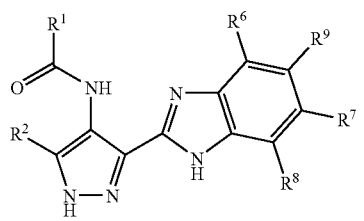

(III)

wherein $R^1$, $R^2$ and $R^6$ to $R^9$ are as defined herein.

Another embodiment of the invention can be represented by the formula (IIIa):

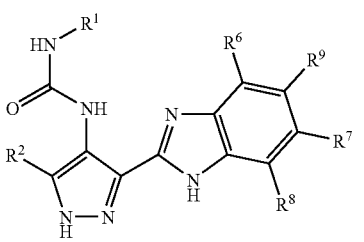

(IIIa)

Within formula (III) and formula (IIIa), it is preferred that $R^2$ is hydrogen or $C_{1-4}$ alkyl, and more typically $R^2$ is hydrogen.

Within the group of compounds defined by the formula (III), $R^1$ is preferably 2,3 disubstituted, 2,6 disubstituted or 2,4,6, trisubstituted phenyl or 2,3-dihydro-benzo[1,4]dioxine, where the substituents are selected from halogen and $C_{1-4}$ alkoxy.

More preferably $R^1$ is selected from 2,6-difluorophenyl, 2-fluoro-6-methoxyphenyl, 2-chloro-6-fluorophenyl, 2,6-dichlorophenyl, 2,4,6-trifluorophenyl, 2,6-difluoro-4-methoxyphenyl, and 2,3-dihydro-benzo[1,4]dioxine.

One particularly preferred group $R^1$ is 2,6-difluorophenyl.

The moieties $R^6$, $R^7$, $R^8$ and $R^9$ are typically selected from hydrogen, halogen, hydroxy, trifluoromethyl, cyano, nitro, carboxy, amino, monocyclic carbocyclic and heterocyclic groups having from 3 to 12 (preferably 3 to 7, and more typically 5 or 6) ring members, a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^1$ or $NR^cSO_2$; and $R^b$ is selected from hydrogen, a carbocyclic or heterocyclic group with 3-7 ring members and a $C_{1-8}$ hydrocarbyl group optionally substituted by one or more substituents selected from hydroxy, $C_{1-4}$ acyloxy, oxo, halogen, cyano, nitro, carboxy, amino, mono- or di-$C_{1-4}$ hydrocarbylamino, a carbocyclic or heterocyclic group with 3-7 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; and $R^c$, $X^1$ and $X^2$; or an adjacent pair of substituents selected from $R^6$, $R^7$, $R^8$ and $R^9$ together with the carbon atoms to which they are attached may form a non-aromatic five or six membered ring containing up to three heteroatoms selected from O, N and S.

In one embodiment, $R^6$ to $R^9$ are each hydrogen or are selected from halogen, cyano, hydroxy, trifluoromethyl, nitro, a group $R^a$-$R^b$ wherein $R^a$ is a bond, O, CO or $C(X^2)X^1$ and $R^b$ is selected from hydrogen, heterocyclic groups having from 3 to 12 ring members (preferably 4 to 7 ring members, e.g. 5 and 6 ring members), and a $C_{1-8}$ hydrocarbyl group (preferably a $C_{1-4}$ hydrocarbyl group, e.g. a saturated hydrocarbyl group such as alkyl or cyclopropyl), optionally substituted by one or more substituents selected from hydroxy, $C_{1-4}$ acyloxy, mono- or di-$C_{1-4}$ hydrocarbylamino (e.g. monoalkylamino and dialkylamino), heterocyclic groups having from 3 to 12 ring members, more preferably 4 to 7 ring members (e.g. 5 or 6 ring members); where $R^c$ is selected from hydrogen and $C_{1-4}$ hydrocarbyl (e.g. saturated hydrocarbyl such as alkyl and cycloalkyl), $X^1$ is O or $NR^c$ and $X^2$ is =O.

In another embodiment, $R^6$, $R^7$, $R^8$ and $R^9$ are selected from hydrogen, fluorine, chlorine, bromine, nitro, trifluoromethyl, carboxy, a group $R^a$-$R^b$ wherein $R^a$ is a bond, O, CO, $C(X^2)X^1$, and $R^b$ is selected from hydrogen, heterocyclic groups having 3-7 ring members (e.g. pyrrolidine, N-methyl piperazine or morpholine) and a $C_{1-4}$ hydrocarbyl group optionally substituted by one or more substituents selected from hydroxy, carboxy, $C_{1-4}$ acyloxy, amino, mono- or di-$C_{1-4}$ hydrocarbylamino, heterocyclic groups with 3-7 ring members (e.g. pyrrolidine, N-methyl piperazine or morpholine); or an adjacent pair of substituents selected from $R^6$, $R^7$, $R^8$ and $R^9$ together with the carbon atoms to which they are attached may form a non-aromatic five or six membered ring containing one or two oxygen atoms as ring members.

In a more preferred embodiment, $R^6$, $R^7$, $R^8$ and $R^9$ are selected from hydrogen, fluorine, chlorine, trifluoromethyl, a group $R^a$-$R^b$ wherein $R^a$ is a bond, O, CO, $C(X^2)X^1$, and $R^b$ is selected from hydrogen, saturated heterocyclic groups having 5-6 ring members and a $C_{1-2}$ hydrocarbyl group optionally substituted by one or more substituents selected from hydroxy, carboxy, $C_{1-2}$ acyloxy, amino, mono- or di-$C_{1-4}$ hydrocarbylamino, heterocyclic groups with 5-6 ring members; or an adjacent pair of substituents selected from $R^6$, $R^7$, $R^8$ and $R^9$ may form a methylenedioxy or ethylenedioxy group each optionally substituted by one or more fluorine atoms.

In another embodiment, particular substituent groups $R^6$ to $R^9$ include halogen, nitro, carboxy, a group $R^a$-$R^b$ wherein $R^a$ is a bond, O, CO, C(X$^2$)X$^1$, and $R^b$ is selected from hydrogen, heterocyclic group having 3-7 ring members and a $C_{1-4}$ hydrocarbyl group optionally substituted by one or more substituents selected from hydroxy, carboxy, amino, mono- or di-$C_{1-4}$ hydrocarbylamino, heterocyclic group with 3-7 ring members.

Whereas each of $R^6$ to $R^9$ can be hydrogen or a substituent as hereinbefore defined, it is preferred that at least one, more preferably at least two, of $R^6$ to $R^9$ are hydrogen.

In one particular embodiment, one of $R^6$ to $R^9$ is a substituent and the others each are hydrogen. For example, $R^6$ can be a substituent group and $R^7$ to $R^9$ can each be hydrogen, or $R^9$ can be a substituent and $R^6$, $R^7$ and $R^8$ can each be hydrogen.

In another particular embodiment, two of $R^6$ to $R^9$ are substituents and the other two are both hydrogen. For example, $R^6$ and $R^9$ can both be substituents when $R^7$ and $R^8$ are both hydrogen; or $R^6$ and $R^7$ can both be substituents when $R^8$ and $R^9$ are both hydrogen; or $R^7$ and $R^9$ can both be substituents when $R^6$ and $R^8$ are both hydrogen.

$R^6$ is preferably selected from:
hydrogen;
halogen (preferably fluorine or chlorine);
methyl optionally substituted by a substituent selected from hydroxy, halogen (e.g. fluorine, preferably difluoro or trifluoro, and more preferably trifluoro) and NR$^{11}$R$^{12}$; and
C(=O)NR$^{11}$R$^{12}$;
wherein $R^{11}$ and $R^{12}$ are the same or different and each is selected from hydrogen and $C_{1-4}$ alkyl or $R^{11}$ and $R^{12}$ together with the nitrogen atom form a five or six membered heterocyclic ring having 1 or 2 heteroatom ring members selected from O, N and S (preferably O and N).

$R^7$ is preferably selected from:
hydrogen;
halogen (preferably fluorine or chlorine);
$C_{1-4}$ alkoxy (for example methoxy);
methyl optionally substituted by a substituent selected from hydroxy, halogen (e.g. fluorine, preferably difluoro or trifluoro, and more preferably trifluoro) and NR$^{11}$R$^{12}$; and
C(=O)NR$^{11}$R$^{12}$;
wherein $R^{11}$ and $R^{12}$ are the same or different and each is selected from hydrogen and $C_{1-4}$ alkyl or $R^{11}$ and $R^{12}$ together with the nitrogen atom form a five or six membered heterocyclic ring having 1 or 2 heteroatom ring members selected from O, N and S (preferably O and N).

$R^8$ is preferably selected from hydrogen, fluorine and methyl, most preferably hydrogen.

$R^9$ is preferably selected from:
hydrogen;
halogen (preferably fluorine or chlorine);
$C_{1-4}$ alkoxy (for example methoxy);
methyl optionally substituted by a substituent selected from hydroxy, halogen (e.g. fluorine, preferably difluoro or trifluoro, and more preferably trifluoro) and NR$^{11}$R$^{12}$; and
C(=O)NR$^{11}$R$^{12}$;
wherein $R^{11}$ and $R^{12}$ are the same or different and each is selected from hydrogen and $C_{1-4}$ alkyl or $R^{11}$ and $R^{12}$ together with the nitrogen atom form a five or six membered heterocyclic ring having 1 or 2 heteroatom ring members selected from O, N and S (preferably O and N).

Alternatively, $R^6$ and $R^9$, or $R^7$ and $R^9$, together with the carbon atoms to which they are attached may form a cyclic group selected from:

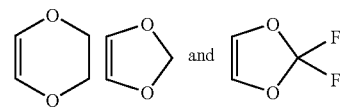

In the foregoing definitions, when $R^{11}$ and $R^{12}$ together with the nitrogen atom in the group NR$^{11}$R$^{12}$ form a five or six membered heterocyclic ring, the heteroatom ring members are preferably selected from O and N. The heterocyclic ring is typically non-aromatic and examples of such rings include morpholine, piperazine, N—$C_{1-4}$-alkylpiperazine, piperidine and pyrrolidine. Particular examples of N—$C_{1-4}$-alkylpiperazine groups include N-methylpiperazine and N-isopropylpiperazine.

Preferred groups $R^6$ to $R^9$ include those in which the benzimidazole group

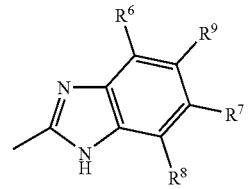

is as shown in Table 2 below.

TABLE 2

| | |
|---|---|
| 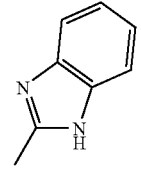 | B1 |
| 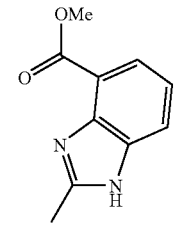 | B2 |
| 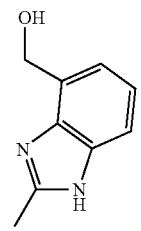 | B3 |
| 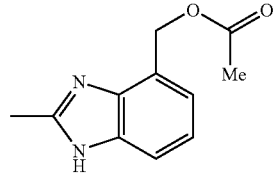 | B4 |

TABLE 2-continued
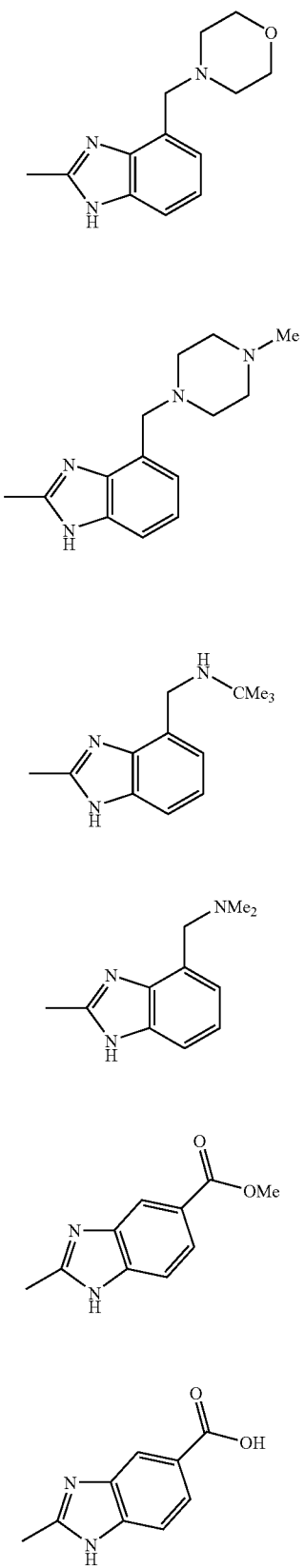
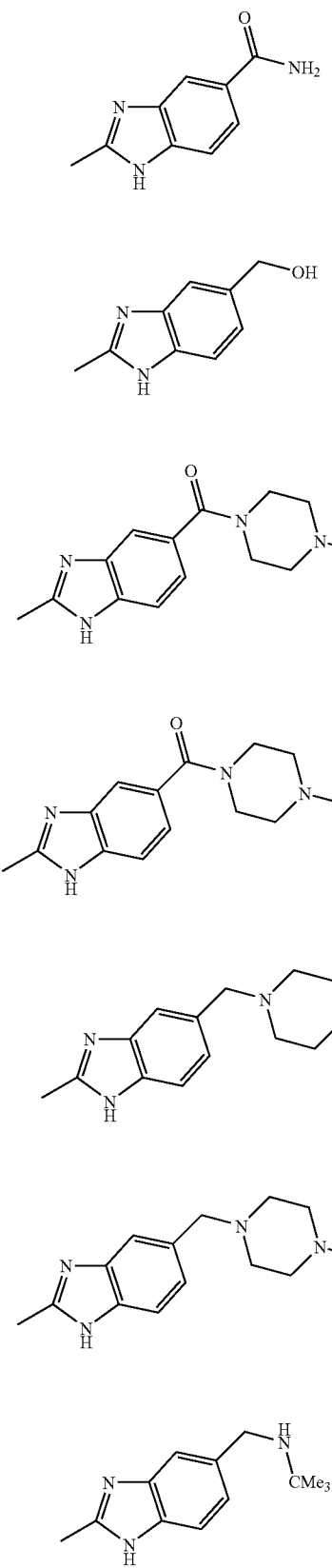

TABLE 2-continued
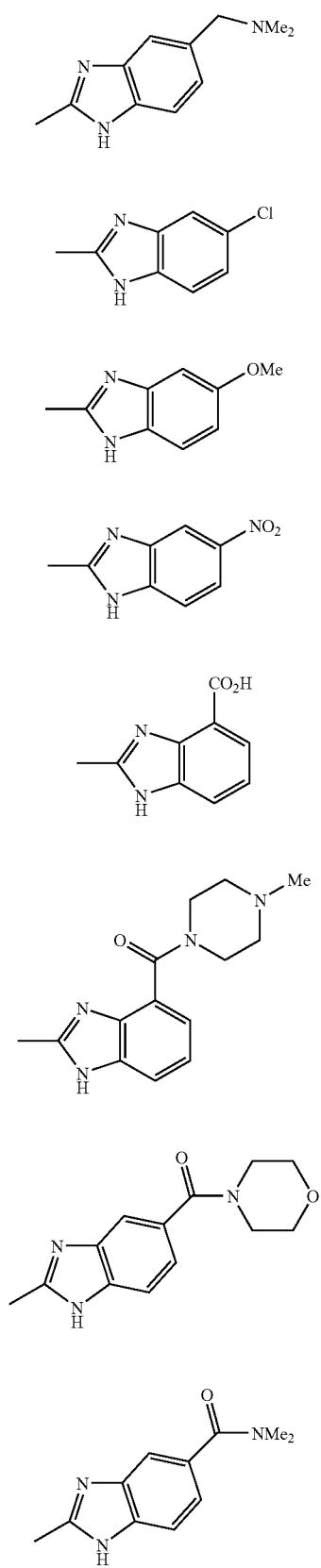
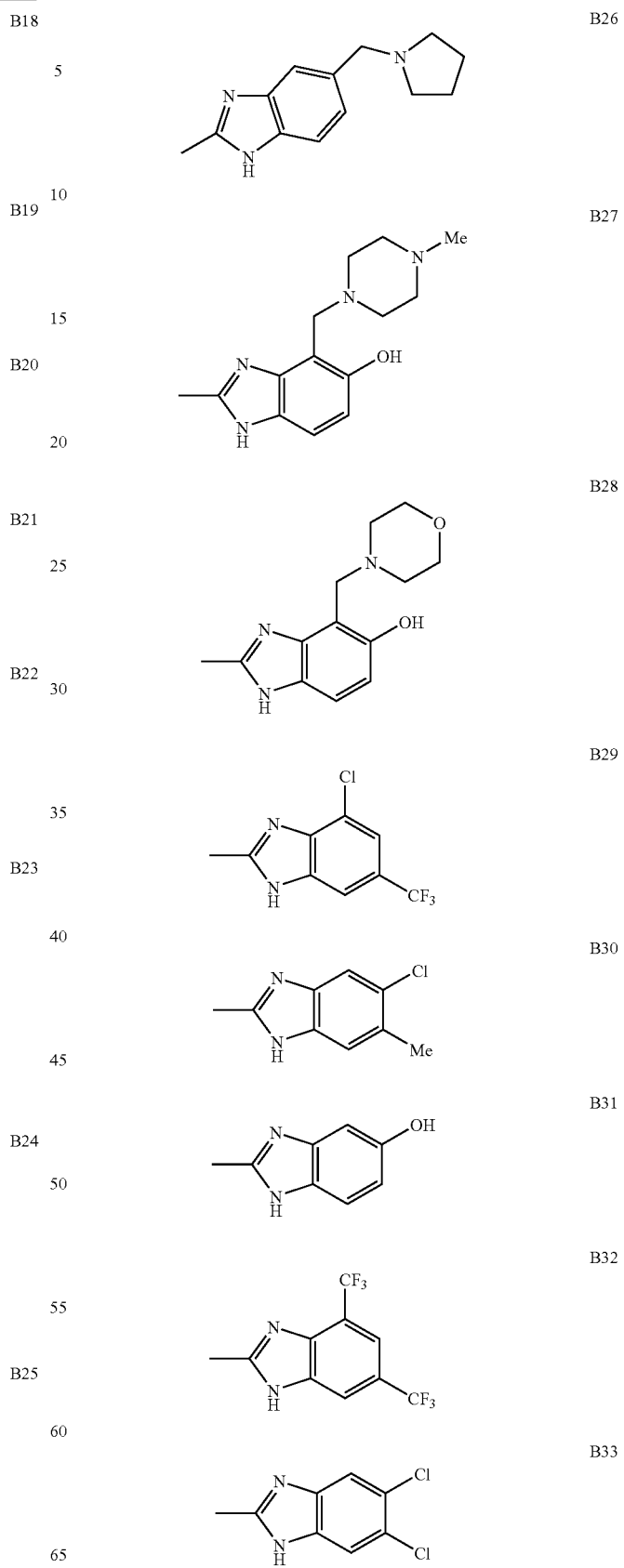

TABLE 2-continued
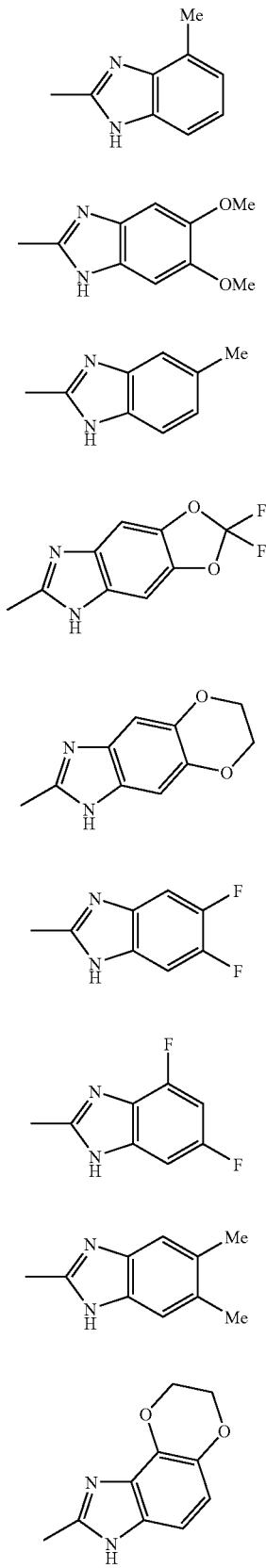
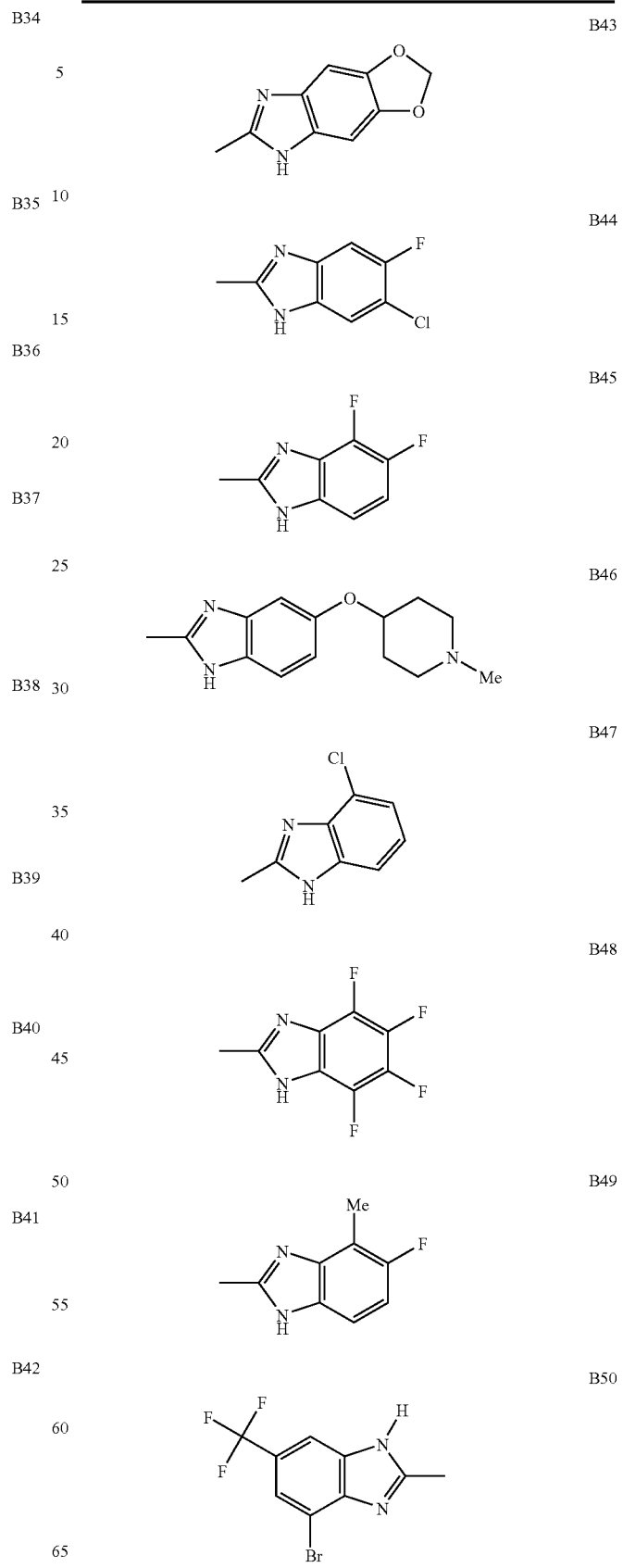

TABLE 2-continued
B51 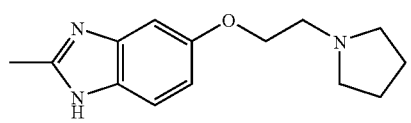
B52 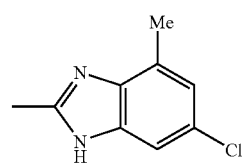
B53 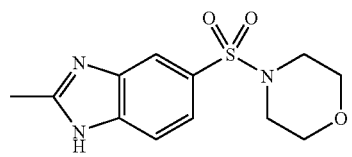
B54 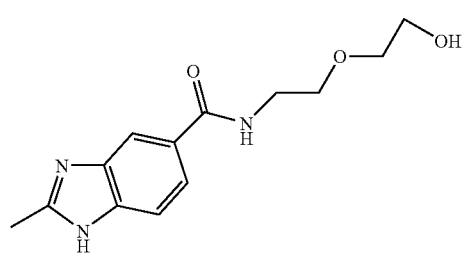
B55 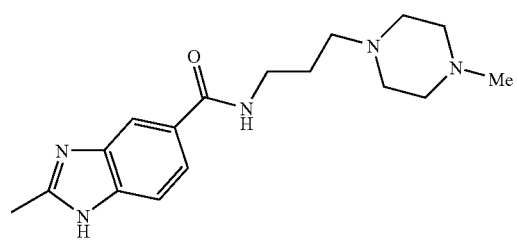
B56 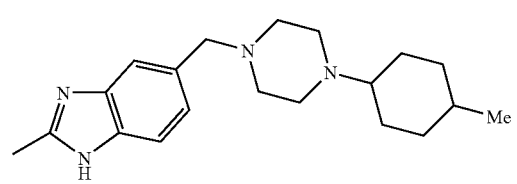
B57 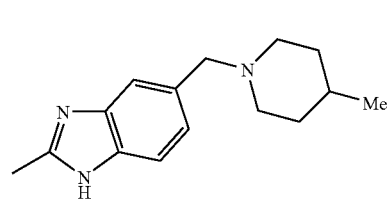
B58 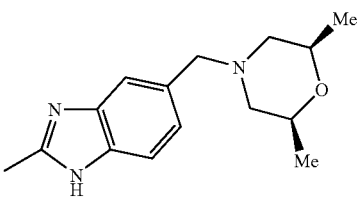
B59 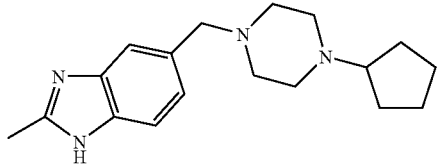
B60 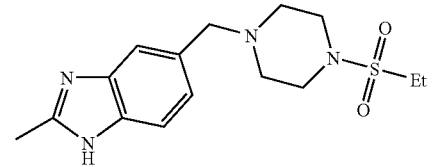
B61 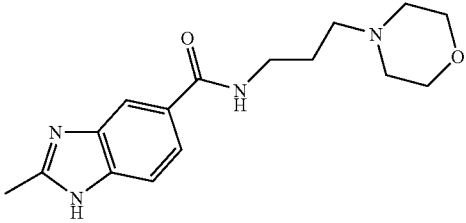
B62 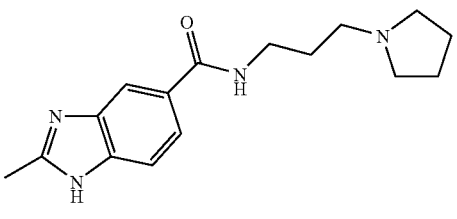
B63 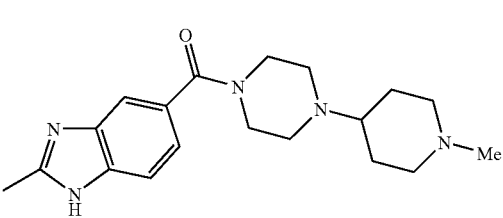
B64 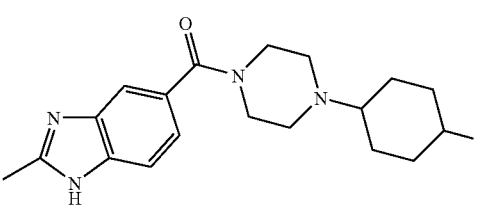

TABLE 2-continued

B65 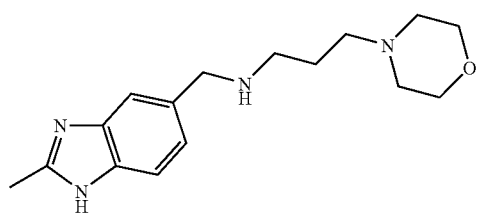

B66 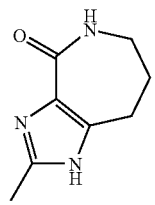

B67 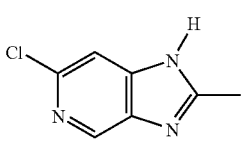

B68 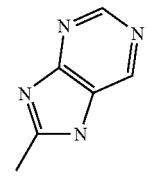

B69 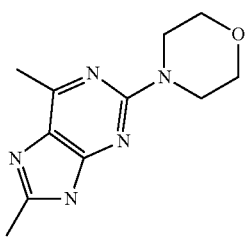

B70 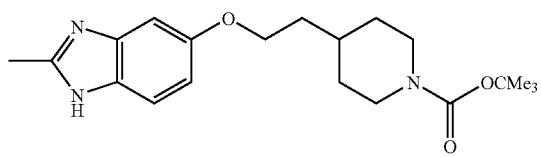

B71 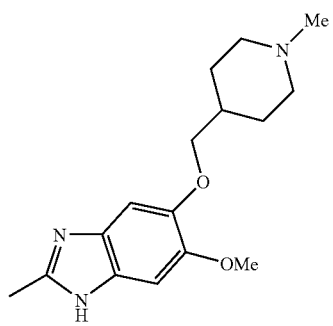

Of the benzimidazole groups set out in Table 2 above, particular groups include groups B1, B3, B5-B8, B11-B20, B23-B30 and B32-B47.

One sub-set of preferred compounds is the group of compounds wherein the benzimidazole moiety is selected from groups B1, B3, B5-B8, B11-B20, B24, B25, B27-B30 and B32-B47.

Particularly preferred benzimidazole moieties are groups B8, B15 and B35, and more particularly group B15.

One group of novel compounds of the invention can be represented by the formula (IV):

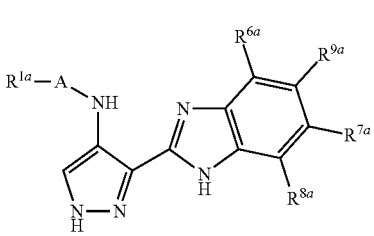

(IV)

A is NH(C=O), O(C=O) or C=O;

$R^{6a}$, $R^{7a}$, $R^{8a}$ and $R^{9a}$ are the same or different and each is selected from hydrogen, halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; or two adjacent groups $R^{6a}$, $R^{7a}$, $R^{8a}$ or $R^{9a}$ together with the carbon atoms to which they are attached may form a 5-membered heteroaryl ring or a 5- or 6-membered non-aromatic heterocyclic ring, wherein the said heteroaryl and heterocyclic groups contain up to 3 heteroatom ring members selected from N, O and S;

$R^c$ is selected from hydrogen and $C_{1-4}$ hydrocarbyl; and $X^1$ is O, S or $NR^c$ and $X^2$ is =O, =S or =$NR^c$;

or an adjacent pair of substituents selected from $R^{6a}$, $R^{7a}$, $R^{8a}$ and $R^{9a}$ together with the carbon atoms to which they are attached may form a non-aromatic five or six membered ring containing up to three heteroatoms selected from O, N and S;

$R^{1a}$ is selected from:

6-membered monocyclic aryl groups substituted by one to three substituents $R^{10c}$ provided that when the aryl group is substituted by a methyl group, at least one substituent other than methyl is present;

6-membered monocyclic heteroaryl groups containing a single heteroatom ring member which is nitrogen, the heteroaryl groups being substituted by one to three substituents $R^{10c}$;

5-membered monocyclic heteroaryl groups containing up to three heteroatom ring members selected from nitrogen and sulphur, and being optionally substituted by one to three substituents $R^{10c}$;

5-membered monocyclic heteroaryl groups containing a single oxygen heteroatom ring member and optionally a nitrogen heteroatom ring member, and being substituted by one to three substituents $R^{10c}$ provided that when the heteroaryl group contains a nitrogen ring member and is substituted by a methyl group, at least one substituent other than methyl is present;

bicyclic aryl and heteroaryl groups having up to four heteroatom ring members and wherein either one ring is aromatic and the other ring is non-aromatic, or wherein both rings are aromatic, the bicyclic groups being optionally substituted by one to three substituents $R^{10c}$;

four-membered, six-membered and seven-membered monocyclic C-linked saturated heterocyclic groups containing up to three heteroatoms selected from nitrogen, oxygen and sulphur, the heterocyclic groups being optionally substituted by one to three substituents $R^{10c}$ provided that when the heterocyclic group has six ring members and contains only one heteroatom which is oxygen, at least one substituent $R^{10c}$ is present;

five membered monocyclic C-linked saturated heterocyclic groups containing up to three heteroatoms selected from nitrogen, oxygen and sulphur, the heterocyclic groups being optionally substituted by one to three substituents $R^{10c}$ provided that when the heterocyclic group has five ring members and contains only one heteroatom which is nitrogen, at least one substituent $R^{10c}$ other than hydroxy is present;

four and six membered cycloalkyl groups optionally substituted by one to three substituents $R^{10c}$;

three and five membered cycloalkyl groups substituted by one to three substituents $R^{10c}$; and a group Ph'$CR^{17}R^{18}$— where Ph' is a phenyl group substituted by one to three substituents $R^{10c}$; $R^{17}$ and $R^{18}$ are the same or different and each is selected from hydrogen and methyl; or $R^{17}$ and $R^{18}$ together with the carbon atom to which they are attached form a cyclopropyl group; or one of $R^{17}$ and $R^{18}$ is hydrogen and the other is selected from amino, methylamino, $C_{1-4}$ acylamino, and $C_{1-4}$ alkoxycarbonylamino;

and where one of $R^{6a}$, $R^{7a}$, $R^{8a}$ and $R^{9a}$ is a morpholinomethyl group, then $R^{1a}$ is additionally selected from:

unsubstituted phenyl and phenyl substituted with one or more methyl groups;

unsubstituted 6-membered monocyclic heteroaryl groups containing a single heteroatom ring member which is nitrogen;

unsubstituted furyl;

5-membered monocyclic heteroaryl groups containing a single oxygen heteroatom ring member and a nitrogen heteroatom ring member, and being unsubstituted or substituted by one or more methyl groups;

unsubstituted six membered monocyclic C-linked saturated heterocyclic groups containing only one heteroatom which is oxygen; and unsubstituted three and five membered cycloalkyl groups; and $R^{10c}$ is selected from:

halogen (e.g. F and Cl);

hydroxyl;

$C_{1-4}$ hydrocarbyloxy optionally substituted by one or more substituents selected from hydroxyl and halogen;

$C_{1-4}$ hydrocarbyl substituted by one or more substituents selected from hydroxyl, halogen and five and six-membered saturated heterocyclic rings containing one or two heteroatom ring members selected from nitrogen, oxygen and sulphur;

S—$C_{1-4}$ hydrocarbyl;

phenyl optionally substituted with one to three substituents selected from $C_{1-4}$ alkyl, trifluoromethyl, fluoro and chloro;

heteroaryl groups having 5 or 6 ring members (e.g. oxazole, pyridyl, pyrimidinyl) and containing up to 3 heteroatoms selected from N, O and S, the heteroaryl groups being optionally substituted with one to three substituents selected from $C_{1-4}$ alkyl, trifluoromethyl, fluoro and chloro;

5- and 6-membered non-aromatic heterocyclic groups (e.g. pyrrolidino, piperidino, piperazine, N-methylpiperazino, morpholino) containing up to 3 heteroatoms selected from N, O and S and being optionally substituted with one to three substituents selected from $C_{1-4}$ alkyl, trifluoromethyl, fluoro and chloro;

cyano, nitro, amino, $C_{1-4}$ alkylamino, di-$C_{1-4}$alkylamino, $C_{1-4}$ acylamino, $C_{1-4}$ alkoxycarbonylamino;

a group $R^{19}$—S(O)$_n$— where n is 0, 1 or 2 and $R^{19}$ is selected from amino; $C_{1-4}$ alkylamino; di-$C_{1-4}$alkylamino; $C_{1-4}$ hydrocarbyl; phenyl optionally substituted with one to three substituents selected from $C_{1-4}$ alkyl, trifluoromethyl, fluoro and chloro; and 5- and 6-membered non-aromatic heterocyclic groups containing up to 3 heteroatoms selected from N, O and S and being optionally substituted with one to three $C_{1-4}$ alkyl group substituents; and a group $R^{20}$-Q- where $R^{20}$ is phenyl optionally substituted with one to three substituents selected from $C_{1-4}$ alkyl, trifluoromethyl, fluoro and chloro; and Q is a linker group selected from OCH$_2$, CH$_2$O, NH, CH$_2$NH, NCH$_2$, CH$_2$, NHCO and CONH.

In one preferred sub-group of compounds, $R^{1a}$ is selected from heteroaryl groups having 5 or 6 ring members (e.g. oxazole, thiazole, pyridyl, pyrimidinyl) and containing up to 3 heteroatoms selected from N, O and S, the heteroaryl groups being optionally substituted with one to three substituents selected from $C_{1-4}$ alkyl, trifluoromethyl, fluoro and chloro. A substituted thiazole group, for example, 2-methyl-4-trifluoromethyl-2-thiazolyl, represents one preferred embodiment.

In another preferred sub-group of compounds, $R^{1a}$ is selected from 5-membered monocyclic heteroaryl groups containing a single oxygen heteroatom ring member and optionally a nitrogen heteroatom ring member, and being substituted by one to three substituents $R^{10c}$ provided that when the heteroaryl group contains a nitrogen ring member and is substituted by a methyl group, at least one substituent other than methyl is present. One such group is isoxazole substituted by a $C_{2-4}$ alkyl group such as a propyl or butyl group, e.g. isobutyl. In another preferred sub-group of compounds, $R^{1a}$ is selected from three and five membered cycloalkyl groups substituted by one to three substituents $R^{10c}$. Substituted cyclopropyl groups are particularly preferred, for example cyclopropyl group substituted by phenyl or cyano, e.g. 1-cyanocyclopropyl and 1-phenylcyclopropyl.

In a further sub-group of compounds, $R^{1a}$ is selected from a group Ph'$CR^{17}R^{18}$— where Ph' is a phenyl group substituted by one to three substituents $R^{10c}$; $R^{17}$ and $R^{18}$ are the same or different and each is selected from hydrogen and methyl; or $R^{17}$ and $R^{18}$ together with the carbon atom to which they are attached form a cyclopropyl group; or one of $R^{17}$ and $R^{18}$ is hydrogen and the other is selected from amino, methylamino, $C_{1-4}$ acylamino, and $C_{1-4}$ alkoxycarbonylamino.

Another group of novel compounds of the invention can be represented by the formula (V):

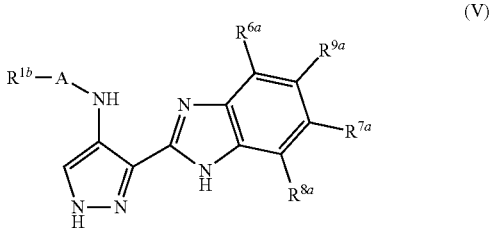

(V)

wherein

A is NH(C=O) or C=O;

$R^{1b}$ is a substituted phenyl group having from 1 to 4 substituents whereby:

(i) when $R^{1b}$ bears a single substituent it is selected from halogen, hydroxyl, $C_{1-4}$ hydrocarbyloxy optionally substituted by one or more substituents selected from hydroxyl and halogen; $C_{1-4}$ hydrocarbyl substituted by one or more substituents selected from hydroxyl and halogen; heteroaryl groups having 5 ring members; and 5- and 6-membered non-aromatic heterocyclic groups, wherein the heteroaryl and heterocyclic groups contain up to 3 heteroatoms selected from N, O and S;

(ii) when $R^{1b}$ bears 2, 3 or 4 substituents, each is selected from halogen, hydroxyl, $C_{1-4}$ hydrocarbyloxy optionally substituted by one or more substituents selected from hydroxyl and halogen; $C_{1-4}$ hydrocarbyl optionally substituted by one or more substituents selected from hydroxyl and halogen; heteroaryl groups having 5 ring members; amino; and 5- and 6-membered non-aromatic heterocyclic groups; or two adjacent substituents together with the carbon atoms to which they are attached form a 5-membered heteroaryl ring or a 5- or 6-membered non-aromatic heterocyclic ring; wherein the said heteroaryl and heterocyclic groups contain up to 3 heteroatoms selected from N, O and S; and $R^{6a}$, $R^{7a}$, $R^{8a}$ and $R^{9a}$ are as hereinbefore defined.

The group $R^{1a}$-A-NH or $R^{1b}$-A-NH linked to the 4-position of the pyrazole ring can take the form of an amide $R^{1a/1b}$—C(=O)NH, urea $R^{1a/1b}$—NHC(=O) or carbamate $R^{1a/1b}$—OC(=O). Amides and ureas are preferred. In one embodiment, the compound is an amide. In another embodiment, the compound is a urea.

In formula (V), the substituted phenyl group $R^{1b}$ is substituted by a single substituent as hereinbefore defined, or by more than one substituent. Thus, there may be 1 or 2 or 3 or 4 substituents, more preferably 1, 2 or 3 substituents. In one embodiment, there may be two or three substituents and these may be located at the 2-, 3-, 4-, 5- or 6-positions around the ring.

By way of example, a phenyl group $R^{1b}$ may be 2,6-disubstituted, 2,3-disubstituted, 2,4-disubstituted 2,5-disubstituted, 2,3,6-trisubstituted or 2,4,6-trisubstituted. In one group of preferred compounds, the phenyl group $R^{1b}$ is 2,6-disubstituted, 2,3-disubstituted or 2,4,6-trisubstituted. More particularly, a phenyl group $R^{1b}$ may be disubstituted at positions 2- and 6- with substituents selected from fluorine, chlorine and $R^a$-$R^b$, where $R^a$ is O and $R^b$ is $C_{1-4}$ alkyl, with fluorine being a particular substituent. Alternatively, two adjacent substituents (preferably in the 2- and 3-positions), together with the phenyl ring to which they are attached, may form a 2,3-dihydro-benzo[1,4]dioxine group, or an indolyl group or a 2,3-dihydrobenzofuranyl group.

In another group of preferred compounds, the phenyl group $R^{1b}$ is 2,4-disubstituted or 2,5-disubstituted. The 2-substituent may be, for example, a halogen (e.g. F or Cl) or a methoxy group. In one particular group of compounds, the 2-substituent is methoxy. The 5-substituent, when present, can be selected from, for example, halogen (e.g. Cl or F), $C_{1-4}$ alkyl (e.g. tert-butyl or isopropyl), methoxy, trifluoromethoxy, trifluoromethyl, or a group HetN-$SO_2$— where "HetN" is a nitrogen-containing saturated monocyclic heterocycle such as piperazino, N—$C_{1-4}$ alkylpiperazino, morpholino, piperidino or pyrrolidino. One preferred 5-subsitutent is Cl, and a preferred 2,5-combination is 2-methoxy-5-chlorophenyl.

In a further group of compounds, the phenyl group $R^{1b}$ has a single substituent at the 4-position of the phenyl ring. The substituent can be, for example, a halogen atom (preferably fluorine or chlorine, most preferably fluorine) or a trifluoromethyl group.

In another group of compounds, the phenyl group $R^{1b}$ is 2,4-disubstituted.

When two adjacent substituents together with the phenyl ring to which they are attached form an indolyl group or a 2,3-dihydrobenzofuranyl group, it is preferred that the said groups are the 4-indolyl and 7-(2,3-dihydrobenzofuranyl) groups respectively.

Where $R^{1b}$ is mono-substituted, and the substituent is located at the 4-position of the phenyl ring, it is preferably other than a difluoromethoxy group or a 2-chloroethyl group (although the 4-(2-chloroethyl)-phenyl group may serve as an intermediate to other compounds of the formula (V)).

In one embodiment, where $R^{1b}$ is disubstituted, the substituted phenyl group may be other than a dimethoxyphenyl group, and may be other than a 2-fluoro-5-methoxyphenyl group.

In another embodiment, the sub-group $R^{1b}$ may include the 2-fluoro-5-methoxyphenyl group. Such compounds have good activity against Aurora kinase.

Where two adjacent substituents combine to form a ring so that $R^{1b}$ is an indole group, the indole group is preferably other than an indol-7-yl group.

One preferred sub-group of compounds of the invention is the group wherein $R^{1b}$ is selected from the groups A1 to A8, A10, A12 and A14 to A24 set out in Table 1 above.

Particularly preferred groups $R^{1'}$ include 2,6-difluorophenyl, 2-fluoro-6-methoxyphenyl, 2-chloro-6-fluorophenyl, 2,6-dichlorophenyl, 2,4,6-trifluorophenyl and 2,3-dihydrobenzo[1,4]dioxine.

One currently preferred group $R^{1'}$ is 2,6-difluorophenyl.

The moieties $R^{6a}$, $R^{7a}$, $R^{8a}$ and $R^{9a}$ are typically selected from hydrogen, halogen, hydroxy, trifluoromethyl, cyano, nitro, carboxy, amino, monocyclic carbocyclic and heterocyclic groups having from 3 to 12 (preferably 3 to 7, and more typically 5 or 6) ring members, a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, a carbocyclic or heterocyclic group with 3-7 ring members and a $C_{1-8}$ hydrocarbyl group optionally substituted by one or more substituents selected from hydroxy, $C_{1-4}$ acyloxy, oxo, halogen, cyano, nitro, carboxy, amino, mono- or di-$C_{1-4}$ hydrocarbylamino, a carbocyclic or heterocyclic group with 3-7 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; and $R^c$, $X^1$ and $X^2$; or an adjacent pair of substituents selected from $R^{6a}$, $R^{7a}$, $R^{8a}$ and $R^{9a}$ together with the carbon atoms to which they are attached may form a non-aromatic five or six membered ring containing up to three heteroatoms selected from O, N and S.

In one embodiment, $R^{6a}$ to $R^{9a}$ are each hydrogen or are selected from halogen, cyano, hydroxy, trifluoromethyl, nitro, a group $R^a$-$R^b$ wherein $R^a$ is a bond, O, CO or $C(X^2)X^1$ and $R^b$ is selected from hydrogen, heterocyclic groups having from 3 to 12 ring members (preferably 4 to 7 ring members), and a $C_{1-8}$ hydrocarbyl group (preferably a $C_{1-4}$ hydrocarbyl group), optionally substituted by one or more substituents selected from hydroxy, $C_{1-4}$ acyloxy, mono- or di-$C_{1-4}$ hydrocarbylamino, heterocyclic groups having from 3 to 12 ring members, more preferably 4 to 7 ring members; where $R^c$ is selected from hydrogen and $C_{1-4}$ hydrocarbyl, $X^1$ is O or $NR^c$ and $X^2$ is =O.

In another embodiment, $R^{6a}$, $R^{7a}$, $R^{8a}$ and $R^{9a}$ are selected from hydrogen, fluorine, chlorine, bromine, nitro, trifluoromethyl, carboxy, a group $R^a$-$R^b$ wherein $R^a$ is a bond, O, CO, $C(X^2)X^1$, and $R^b$ is selected from hydrogen, heterocyclic groups having 3-7 (preferably 5 or 6) ring members (e.g. pyrrolidine, N-methyl piperazine or morpholine) and a $C_{1-4}$ hydrocarbyl group optionally substituted by one or more substituents selected from hydroxy, carboxy, $C_{1-4}$ acyloxy, amino, mono- or di-$C_{1-4}$ hydrocarbylamino, heterocyclic groups with 3-7 (preferably 5 or 6) ring members (e.g. pyrrolidine, N-methyl piperazine or morpholine); or an adjacent pair of substituents selected from $R^{6a}$, $R^{7a}$, $R^{8a}$ and $R^{9a}$ together with the carbon atoms to which they are attached may form a non-aromatic five or six membered ring containing one or two oxygen atoms as ring members.

In a more preferred embodiment, $R^{6a}$, $R^{7a}$, $R^{8a}$ and $R^{9a}$ are selected from hydrogen, fluorine, chlorine, trifluoromethyl, a group $R^a$-$R^b$ wherein $R^a$ is a bond, O, CO, $C(X^2)X^1$, and $R^b$ is selected from hydrogen, saturated heterocyclic groups having 5-6 ring members and a $C_{1-2}$ hydrocarbyl group (e.g. alkyl) optionally substituted by one or more substituents selected from hydroxy, carboxy, $C_{1-2}$ acyloxy, amino, mono- or di-$C_{1-4}$ hydrocarbylamino (e.g. mono- or dialkylamino), heterocyclic groups with 5-6 ring members; or an adjacent pair of substituents selected from $R^{6a}$, $R^{7a}$, $R^{8a}$ and $R^{9a}$ may form a methylenedioxy or ethylenedioxy group each optionally substituted by one or more fluorine atoms.

In another embodiment, particular substituent groups $R^{6a}$ to $R^{9a}$ include halogen, nitro, carboxy, a group $R^a$-$R^b$ wherein $R^a$ is a bond, O, CO, $C(X^2)X^1$, and $R^b$ is selected from hydrogen, heterocyclic group having 3-7 ring members (preferably 5 or 6 ring members) and a $C_{1-4}$ hydrocarbyl group (e.g. alkyl or cycloalkyl) optionally substituted by one or more substituents selected from hydroxy, carboxy, amino, mono- or di-$C_{1-4}$ hydrocarbylamino (e.g. mono- or di-alkylamino), heterocyclic group with 3-7 ring members (preferably 5 or 6 ring members).

Whereas each of $R^{6a}$ to $R^{9a}$ can be hydrogen or a substituent other than hydrogen as hereinbefore defined, it is preferred that at least one, more preferably at least two, of $R^{6a}$ to $R^{9a}$ are hydrogen.

In one particular embodiment, one of $R^{6a}$ to $R^{9a}$ is a substituent other than hydrogen and the others each are hydrogen. For example, $R^{6a}$ can be a substituent group other than hydrogen and $R^{7a}$ to $R^{9a}$ can each be hydrogen, or $R^{9a}$ can be a substituent other than hydrogen and $R^{6a}$, $R^{7a}$ and $R^{8a}$ can each be hydrogen.

In another particular embodiment, two of $R^{6a}$ to $R^{9a}$ are substituents other than hydrogen and the other two are both hydrogen. For example, $R^{6a}$ and $R^{9a}$ can both be substituents other than hydrogen when $R^{7a}$ and $R^{8a}$ are both hydrogen; or $R^{6a}$ and $R^{7a}$ can both be substituents other than hydrogen when $R^{9a}$ and $R^{8a}$ are both hydrogen; or $R^{9a}$ and $R^{7a}$ can both be substituents other than hydrogen when $R^{6a}$ and $R^{8a}$ are both hydrogen.

$R^{6a}$ is preferably selected from:
hydrogen;
halogen (preferably fluorine or chlorine);
methyl optionally substituted by a substituent selected from hydroxy, halogen (e.g. fluorine, preferably difluoro or trifluoro, and more preferably trifluoro) and
$NR^{11}R^{12}$; and
$C(=O)NR^{11}R^{12}$;
wherein $R^{11}$ and $R^{12}$ are the same or different and each is selected from hydrogen and $C_{1-4}$ alkyl or $R^{11}$ and $R^{12}$ together with the nitrogen atom form a five or six membered heterocyclic ring having 1 or 2 heteroatom ring members selected from O, N and S (preferably O and N).

$R^{9a}$ is preferably selected from:
hydrogen;
halogen (preferably fluorine or chlorine);
$C_{1-4}$ alkoxy (for example methoxy);
methyl optionally substituted by a substituent selected from hydroxy, halogen (e.g. fluorine, preferably difluoro or trifluoro, and more preferably trifluoro) and
$NR^{11}R^{12}$; and
$C(=O)NR^{11}R^{12}$;
wherein $R^{11}$ and $R^{12}$ are the same or different and each is selected from hydrogen and $C_{1-4}$ alkyl or $R^{11}$ and $R^{12}$ together with the nitrogen atom form a five or six membered heterocyclic ring having 1 or 2 heteroatom ring members selected from O, N and S (preferably O and N).

$R^{7a}$ is preferably selected from:
hydrogen;
halogen (preferably fluorine or chlorine);
$C_{1-4}$ alkoxy (for example methoxy);
methyl optionally substituted by a substituent selected from hydroxy, halogen (e.g. fluorine, preferably difluoro or trifluoro, and more preferably trifluoro) and
$NR^{11}R^{12}$; and
$C(=O)NR^{11}R^{12}$;
wherein $R^{11}$ and $R^{12}$ are the same or different and each is selected from hydrogen and $C_{1-4}$ alkyl or $R^{11}$ and $R^{12}$ together with the nitrogen atom form a five or six membered heterocyclic ring having 1 or 2 heteroatom ring members selected from O, N and S (preferably O and N).

$R^{8a}$ is preferably selected from hydrogen, fluorine and methyl, most preferably hydrogen.

Alternatively, $R^{6a}$ and $R^{9a}$, or $R^{9a}$ and $R^{7a}$, together with the carbon atoms to which they are attached may form a cyclic group selected from:

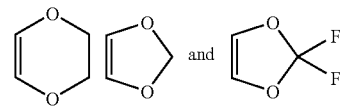

In the foregoing definitions, when $R^{11}$ and $R^{12}$ together with the nitrogen atom in the group $NR^{11}R^{12}$ form a five or six membered heterocyclic ring, the heteroatom ring members are preferably selected from O and N. The heterocyclic ring is typically non-aromatic and examples of such rings include morpholine, piperazine, N—$C_{1-4}$-alkylpiperazine, piperidine and pyrrolidine. Particular examples of N—$C_{1-4}$-alkylpiperazine groups include N-methylpiperazine and N-isopropylpiperazine.

Preferred groups $R^{6a}$ to $R^{9a}$ include those in which the benzimidazole group

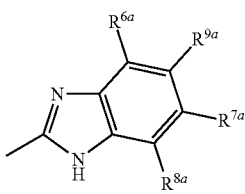

is as shown in Table 2 above.

Of the benzimidazole groups set out in Table 2 above, particular groups include groups B1, B3, B5-B8, B11-B20, B23-B30 and B32-B47.

Particularly preferred groups are groups B1, B3, B5-B8, B11-B20, B24, B25, B27-B30 and B32-B47.

One preferred group of compounds of the formula (V) can be represented by the formula (Va):

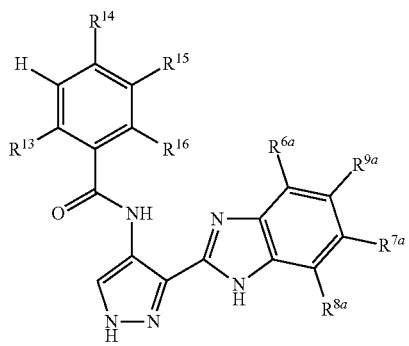

wherein $R^{6a}$ to $R^{9a}$ are as hereinbefore defined; and
(i) $R^{13}$ is methoxy and $R^{14}$ to $R^{16}$ each are hydrogen; or
(ii) $R^{14}$ is oxazolyl, imidazolyl or thiazolyl, preferably oxazolyl, and $R^{13}$, $R^{15}$ and $R^{16}$ each are hydrogen; or
(iii) $R^{13}$ is selected from fluorine, chlorine and methyl, $R^{16}$ is selected from fluorine, chlorine, methyl and methoxy, and $R^{14}$ and $R^{15}$ each are hydrogen; or
(iv) $R^{13}$ and $R^{16}$ each are selected from fluorine, chlorine and methyl; $R^{14}$ is selected from fluorine, chlorine, methyl and methoxy; and $R^{15}$ is hydrogen; or
(v) $R^{13}$ and $R^{14}$ each are hydrogen; $R^{15}$ is selected from fluorine, chlorine, methyl and methoxy (more preferably methyl and methoxy), and $R^{16}$ is selected from fluorine, chlorine and methyl (more preferably fluorine), or $R^{15}$ and $R^{16}$ together with the carbon atoms of the phenyl ring form a group selected from:

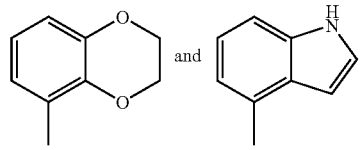

Particularly preferred substituents for the phenyl ring are the groups of substituents (i), (iii), (iv) and (v).

Within formula (Va), one particular sub-group of compounds is the group of compounds wherein:
(i) $R^{13}$ is methoxy and $R^{14}$ to $R^{16}$ each are hydrogen; or
(iii) $R^{13}$ is selected from fluorine, chlorine and methyl, $R^{16}$ is selected from fluorine, chlorine, methyl and methoxy, and $R^{14}$ and $R^{15}$ each are hydrogen; or (vi) $R^{13}$ and $R^{16}$ each are selected from fluorine, chlorine and methyl; $R^{14}$ is selected from fluorine, chlorine and methoxy; and $R^{15}$ is hydrogen; or
(vii) $R^{13}$ and $R^{14}$ each are hydrogen, $R^{15}$ is methoxy and $R^{16}$ is fluorine, or $R^{15}$ and $R^{16}$ together with the carbon atoms of the phenyl ring form a group selected from:

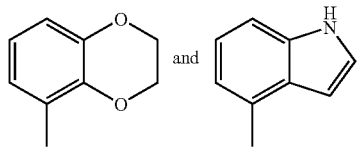

A particularly preferred sub-group of compounds within formula (Va) is the group of compounds wherein:
(iii) $R^{13}$ is selected from fluorine, chlorine and methyl, $R^{16}$ is selected from fluorine, chlorine, methyl and methoxy, and $R^{14}$ and $R^{15}$ each are hydrogen; or
(vi) $R^{13}$, $R^{14}$ and $R^{16}$ each are fluorine and $R^{15}$ is hydrogen; or
(vii) $R^{13}$ and $R^{14}$ each are hydrogen and $R^{15}$ and $R^{16}$ together with the carbon atoms of the phenyl ring form a group:

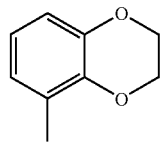

Compounds of the formulae (V) and (Va) are particularly preferred as inhibitors of CDK.

In a further embodiment, the invention provides a compound of the formula (VI):

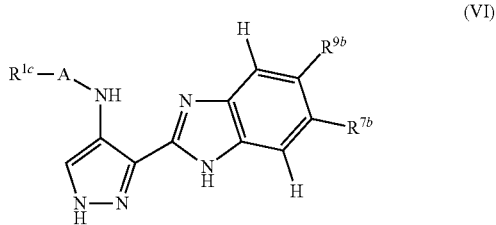

wherein:
when A is NH(C=O) or C=O;
$R^{1c}$ is selected from:
(a) a mono-substituted phenyl group wherein the substituent is selected from o-amino, o-methoxy; o-chloro; p-chloro; o-difluoromethoxy; o-trifluoromethoxy; o-tert-butyloxy; m-methylsulphonyl and p-fluoro;
(b) a 2,4- or 2,6-disubstituted phenyl group wherein one substituent is selected from o-methoxy, o-ethoxy, o-fluoro, p-morpholino and the other substituent is selected from o-fluoro, o-chloro, p-chloro, and p-amino;
(c) a 2,5-disubstituted phenyl group wherein one substituent is selected from o-fluoro and o-methoxy and the other substituent is selected from m-methoxy, m-isopropyl; m-fluoro, m-trifluoromethoxy, m-trifluoromethyl, m-methylsulphanyl, m-pyrrolidinosulphonyl, m-(4-methylpiperazin-1-yl)sulphonyl, m-morpholinosulphonyl, m-methyl, m-chloro and m-aminosulphonyl;
(d) a 2,4,6-tri-substituted phenyl group where the substituents are the same or different and are each selected from o-methoxy, o-fluoro, p-fluoro, p-methoxy provided that no more than one methoxy substituent is present;
(e) a 2,4,5-tri-substituted phenyl group where the substituents are the same or different and are each selected from o-methoxy, m-chloro and p-amino;
(f) unsubstituted benzyl; 2,6-difluorobenzyl; α,α-dimethylbenzyl; 1-phenylcycloprop-1-yl; and α-tert-butoxycarbonylaminobenzyl;
(g) an unsubstituted 2-furyl group or a 2-furyl group bearing a single substituent selected from 4-(morpholin-4-ylmethyl), piperidinylmethyl; and optionally a further substituent selected from methyl;
(h) an unsubstituted pyrazolo[1,5-a]pyridin-3-yl group;
(i) isoxazolyl substituted by one or two $C_{1-4}$ alkyl groups;
(j) 4,5,6,7-tetrahydro-benzo[d]isoxazol-3-yl;
(k) 3-tert-butyl-phenyl-1H-pyrazol-5-yl;
(l) quioxalinyl;
(m) benzo[c]isoxazol-3-yl;
(n) 2-methyl-4-trifluoromethyl-thiazol-5-yl;
(o) 3-phenylamino-2-pyridyl;
(p) 1-toluenesulphonylpyrrol-3-yl;
(q) 2,4-dimethoxy-3-pyridyl; and 6-chloro-2-methoxy-4-methyl-3-pyridyl;
(r) imidazo[2,1-b]thiazol-6-yl;
(s) 5-chloro-2-methylsulphanyl-pyrimidin-4-yl;
(t) 3-methoxy-naphth-2-yl;
(u) 2,3-dihydro-benzo[1,4]dioxin-5-yl;
(v) 2,3-dihydro-benzofuranyl group optionally substituted in the five membered ring by one or two methyl groups;
(w) 2-methyl-benzoxazol-7-yl;
(x) 4-aminocyclohex-1-yl;
(y) 1,2,3,4-tetrahydro-quinolin-6-yl;
(z) 2-methyl-4,5,6,7-tetrahydro-benzofuran3-yl;
(aa) 2-pyrimidinyl-1piperidin-4-yl; and 1-(5-trifluoromethyl-2-pyridyl)-piperidin-4-yl and 1-methylsulphonylpiperidin-4-yl;
(ab) 1-cyanocyclopropyl;
(ac) N-benzylmorpholin-2-yl;
and when A is NH(C=O), $R^{1'}$ is additionally selected from:
(ad) unsubstituted phenyl;
$R^{9b}$ is selected from hydrogen; chlorine; methoxy; methylsulphonyl; 4-methyl-piperazin-1-ylcarbonyl; morpholinocarbonyl; morpholinomethyl; pyrrolidinylcarbonyl; N-methyl-piperidinyloxy; pyrrolidinylethoxy; morpholinopropylaminomethyl; 4-cyclopentyl-piperazin-1-ylmethyl; 4-ethylsulphonyl-piperazin-1-ylmethyl; morpholinosulphonyl; 4-(4-methylcyclohexyl)-piperazin-1-ylmethyl; and
$R^{7b}$ is selected from hydrogen; methyl; methoxy and ethoxy.
Compounds of the formula (VI) have good activity against Aurora kinases.
Preferred compounds of the formula (VI) are those that have a mean $IC_{50}$ against Aurora kinase A of less than 0.03 μM, and more preferably 0.01 μM or less when determined by the methods described herein.
One particular sub-group of compounds of the formula (VI) is the group of compounds in which $R^{9b}$ is selected from morpholinomethyl and methoxy, and $R^{7b}$ is methoxy when $R^{9b}$ is methoxy, or $R^{7b}$ is hydrogen when $R^{9b}$ is morpholinomethyl.
A further group of novel compounds of the invention can be represented by the formula (VII):

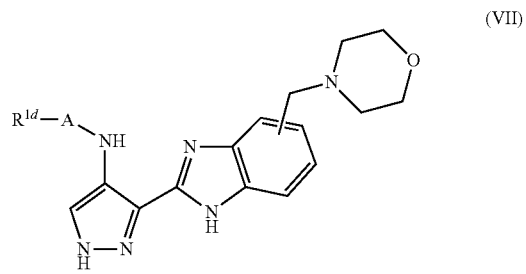

(VII)

wherein $R^{1d}$ is a group $R^1$, $R^{1a}$, $R^{1b}$ or $R^{1c}$ as hereinbefore defined.
Compounds of the formula (VII) show good CDK inhibitory activity and are also particularly active against Aurora kinases.
A particularly preferred sub-group of compounds within formula (VII) is represented by formula (VIIa):

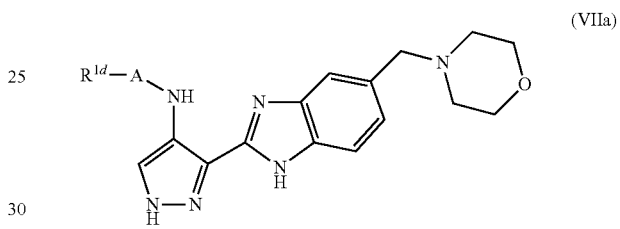

(VIIa)

where $R^{1d}$ is as hereinbefore defined.
Another sub-group of novel compounds of the invention is represented by formula (VIII):

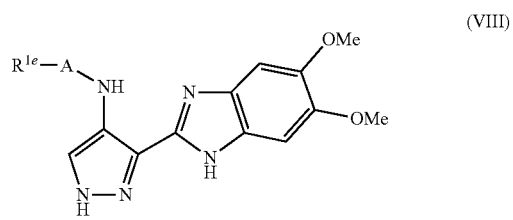

(VIII)

where $R^{1c}$ is a group $R^1a$ or a group $R^1b$ as hereinbefore defined.
A further group of novel compounds of the invention is represented by general formula (IX):

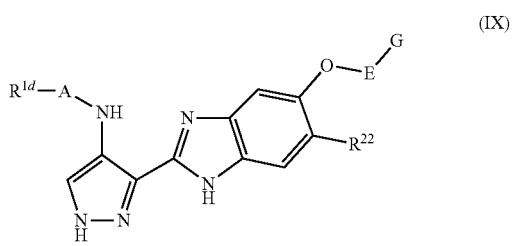

(IX)

wherein $R^{1d}$ is as defined herein, E is a bond, $CH_2$ or $CH_2CH_2$, $R^{22}$ is selected from hydrogen, halogen (e.g. fluorine or chlorine), and $C_{1-2}$ alkoxy (e.g methoxy), and G is a 4-7 membered saturated heterocyclic ring containing up to 3 heteroatom ring members selected from N, O and S, the heterocyclic ring being optionally substituted by 1 to 4 (preferably up to 2, e.g. 0 or 1) groups $R^{10}$ (or a sub group thereof as defined herein).

Within formula (IX), one particular group of compounds is represented by formula (IXa):

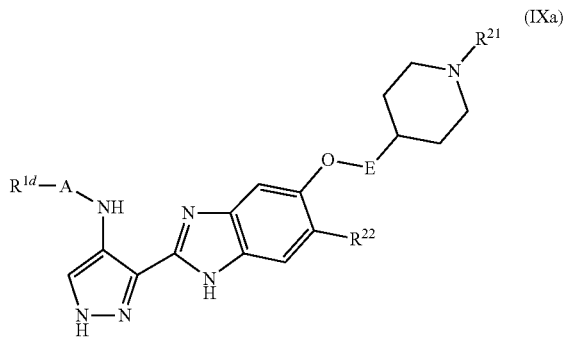

(IXa)

Wherein $R^{1d}$, E and $R^{22}$ are as defined herein and $R^{21}$ is selected from hydrogen, $C_{1-4}$ alkyl (e.g. methyl), $C_{1-4}$ acyl, and $C_{1-4}$ alkoxycarbonyl. A preferred combination is the combination in which E is $CH_2$, $R^{21}$ is methyl and $R^{22}$ is methoxy.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^5$ and/or $R^6$ and/or $R^7$ and/or $R^8$ and/or $R^9$ and/or $R^{10}$ and any sub-groups thereof and that all such combinations are embraced by this application.

For example, any one of the groups $R^1$ (e.g. as in $R^1$-A where A is C=O) shown in Table 1 may be combined with any one of the benzimidazole groups shown in Table 2.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular and specific compounds of the invention are as illustrated in the examples below.

Unless otherwise specified, a reference to a particular compound also includes ionic, salt, solvate, and protected forms thereof, for example, as discussed below.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds.

Acid addition salts may be formed with a wide variety of acids, both inorganic and organic. Examples of acid addition salts include salts formed with hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium salts are within the scope of formula (I).

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I) the benzimidazole group may take either of the following two tautomeric forms A and B. For simplicity, the general formula (I) illustrates form A but the formula is to be taken as embracing both tautomeric forms.

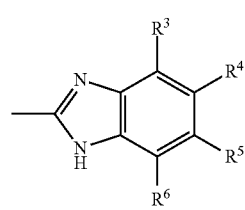

A

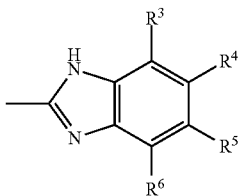

B

The pyrazole ring may also exhibit tautomerism and can exist in the two tautomeric forms C and D below.

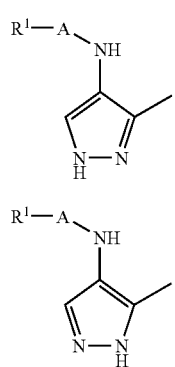

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

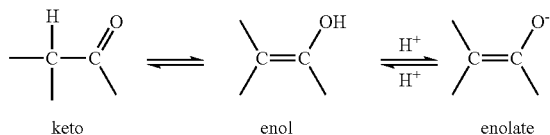

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures or two or more optical isomers, unless the context requires otherwise.

For example, the group A can include one or more chiral centres. Thus, when E and $R^1$ are both attached to the same carbon atom on the linker group A, the said carbon atom is typically chiral and hence the compound of the formula (I) will exist as a pair of enantiomers (or more than one pair of enantiomers where more than one chiral centre is present in the compound).

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I). Examples of esters are compounds containing the group —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —
C(═O)OR wherein R is:
$C_{1-7}$alkyl
(e.g., -Me, -Et, -nPr, -iPr, -nBu, -sBu, -iBu, -tBu);
$C_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;

acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Biological Activity

The compounds of the formula (I) are inhibitors of cyclin dependent kinases. For example, compounds of the invention have activity against CDK1, CDK2, CDK3, CDK5, CDK6 and CDK7 kinases.

In addition, CDK4, CDK8 and/or CDK9 may be of interest.

Compounds of the invention also have activity against glycogen synthase kinase-3 (GSK-3).

Compounds of the invention also have activity against Aurora kinases.

As a consequence of their activity in modulating or inhibiting CDK and Aurora kinases and glycogen synthase kinase, they are expected to be useful in providing a means of arresting, or recovering control of, the cell cycle in abnormally dividing cells. It is therefore anticipated that the compounds will prove useful in treating or preventing proliferative disorders such as cancers. It is also envisaged that the compounds of the invention will be useful in treating conditions such as viral infections, autoimmune diseases and neurodegenerative diseases for example.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB-ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, esophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; or Kaposi's sarcoma.

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atrophy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

It has also been discovered that some cyclin-dependent kinase inhibitors can be used in combination with other anti-cancer agents. For example, the cytotoxic activity of cyclin-dependent kinase inhibitor flavopiridol, has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include breast cancer, ovarian cancer, colon cancer, prostate cancer, oesophageal cancer, squamous cancer and non-small cell lung carcinomas.

In the case of compounds having activity against Aurora kinase, particular examples of cancers where it is envisaged that the Aurora kinase inhibiting compounds of the invention will be useful include:
human breast cancers (e.g. primary breast tumours, node-negative breast cancer, invasive duct adenocarcinomas of the breast, non-endometrioid breast cancers);
ovarian cancers (e.g. primary ovarian tumours);
pancreatic cancers;
human bladder cancers;
colorectal cancers (e.g. primary colorectal cancers);
gastric tumours;
renal cancers;
cervical cancers:
neuroblastomas;
melanomas;
lymphomas;
prostate cancers;
leukemia;
non-endometrioid endometrial carcinomas;
gliomas;
non-Hodgkin's lymphoma;

Cancers which may be particularly amenable to Aurora inhibitors include breast, bladder, colorectal, pancreatic, ovarian, non-Hodgkin's lymphoma, gliomas and nonendometrioid endometrial carcinomas.

The activity of the compounds of the invention as inhibitors of cyclin dependent kinases, Aurora kinases and glycogen synthase kinase-3 can be measured using the assays set forth in the examples below and the level of activity exhibited by a given compound can be defined in terms of the $IC_{50}$ value. Preferred compounds of the present invention are compounds having an $IC_{50}$ value of less than 1 micromole, more preferably less than 0.1 micromole.

Methods for the Preparation of Compounds of the Formula (I)

Compounds of the formula (I) can be prepared in accordance with synthetic methods well known to the skilled person.

Unless stated otherwise $R^1$, $R^2$, $R^3$ and $R^4$ are as herein defined.

Compounds of the formula (I) wherein $R^1$-A- forms an acyl group can be prepared as illustrated in Scheme 1 below.

As shown in Scheme 1, an amine of the formula (X) can be reacted with a carboxylic acid, or reactive derivative thereof, of the formula $R^1$—B—$CO_2H$ under standard amide formation conditions. Thus, for example, the coupling reaction between the carboxylic acid and the amine (X) can be carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (EDC) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) (L. A. Carpino, *J. Amer. Chem. Soc.*, 1993, 115, 4397) and phosphonium-based coupling agents such as 1-benzo-triazolyloxytris(pyrrolidino) phosphonium hexafluorophosphate (PyBOP) (Castro et al, *Tetrahedron Letters,* 1990, 31, 205). Carbodiimide-based cooling agents are advantageously used in combination with 1-hydroxyazabenzotriazole (HOAt) or 1-hydroxybenzotriazole (HOBt) (Konig et al, *Chem. Ber.,* 103, 708, 2024-2034). Preferred coupling reagents include EDC and DCC in combination with HOAt or HOBt.

Scheme 1

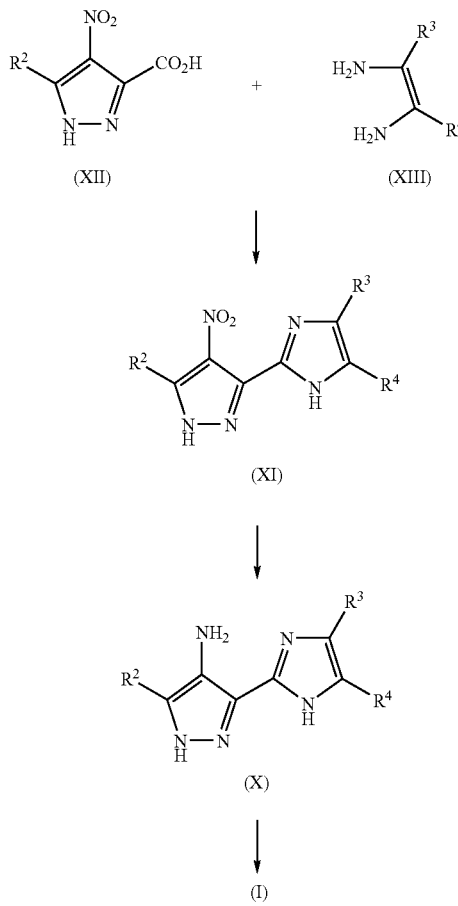

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

Amines of the formula (X) can be prepared by reduction of the corresponding nitro-compound of the formula (XI) under standard conditions. The reduction may be effected, for example by catalytic hydrogenation in the presence of a catalyst such as palladium on carbon in a polar solvent such as ethanol or dimethylformamide at room temperature.

When X is nitrogen, the compounds of the formula (XI) can be prepared by reaction of a nitro-pyrazole carboxylic acid of the formula (XII) with a diamine of the formula (XII). The reaction between the diamine (XIII) and carboxylic acid (XII) can be carried out in the presence of a reagent such as DCC or EDC in the presence of HOBt as described above, under amide coupling conditions as described previously, to give an intermediate ortho-aminophenylamide (not shown) which is then cyclised to form the benzimidazole ring. The final cyclisation step is typically carried out by heating under reflux in the presence of acetic acid.

Diamines of the formula (XIII) can be obtained commercially or can be prepared from appropriately substituted phenyl precursor compounds using standard chemistry and well known functional group interconversions, see for example, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8), 1995. Examples of methods of preparing diamines of the formula (XIII) are provided in the examples below.

The diamines of the formula (XIII) can also be reacted with carboxylic acids of the formula (XIV) to give compounds of the formula (I).

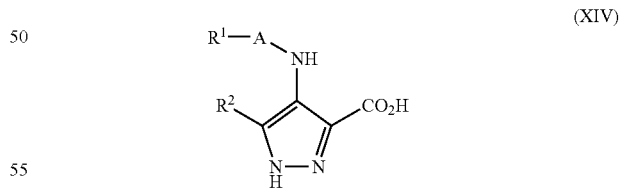

The reaction of the diamine (XIII) with the carboxylic acid (XIV) can be carried out under conditions analogous to those described above for preparing the nitro-compounds (XI). Carboxylic acids of the formula (XIV) can be prepared by the sequence of reactions shown in Scheme 2.

As shown in Scheme 2, a substituted or unsubstituted 4-nitro-3-pyrazole carboxylic acid (XV) can be esterified by reaction with thionyl chloride to give the acid chloride intermediate followed by reaction with ethanol to form the ethyl ester (XVI). Alternatively, the esterification can be carried out by reacting the alcohol and carboxylic acid in the presence of an acidic catalyst, one example of which is thionyl chloride. The reaction is typically carried out at room temperature using the esterifying alcohol (e.g. ethanol) as the solvent. The nitro group can then be reduced using palladium on carbon according to standard methods to give the amine (XVII). The amine (XVII) is coupled with an appropriate carboxylic acid $R^1$—$CO_2H$ under amide forming conditions the same as or analogous to those described above to give the amide (XVIII). The ester group of the amide (XVIII) can then be hydrolysed using an alkali metal hydroxide such as sodium hydroxide in a polar water miscible solvent such as methanol, typically at room temperature.

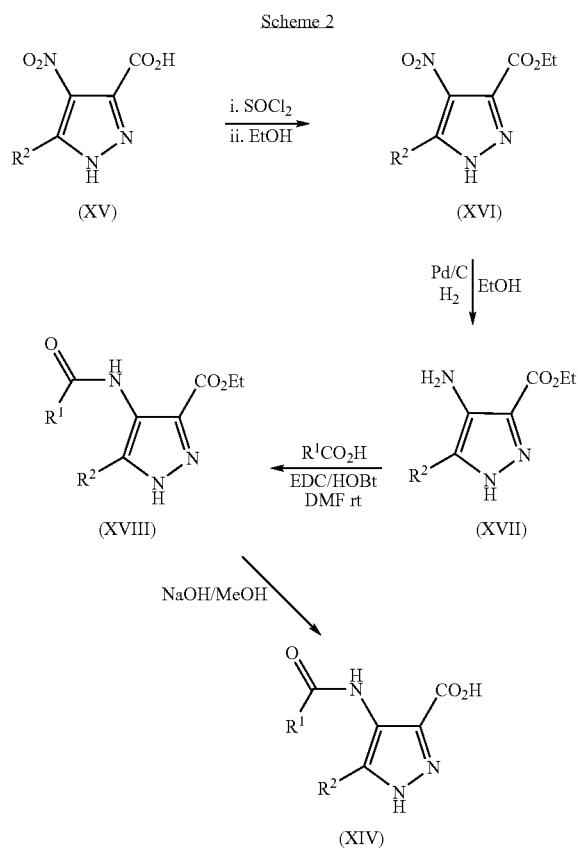

Compounds of the formula (I) in which A is NH(CO) can be prepared using standard methods for the synthesis of ureas. For example, such compounds can be prepared by reacting an aminopyrazole compound of the formula (X) with a suitably substituted phenylisocyanate in a polar solvent such as DMF. The reaction is conveniently carried out at room temperature.

A further route to compounds of the formula (I) is shown in Scheme 3 below.

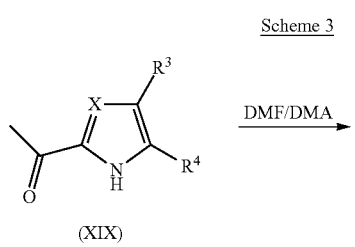

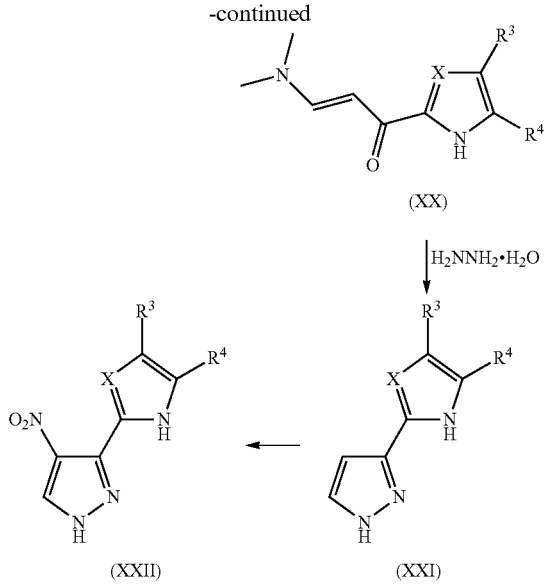

As illustrated in Scheme 3, the ketone (XIX) can be reacted with dimethylformamide-dimethylacetal at elevated temperature to give an $\alpha,\beta$-unsaturated ketone (XX) (Jachak et al, *Montash. Chem.*, 1993, 124(2), 199-207), which upon heating with hydrazine hydrate gives a pyrazole of formula (XXI). This can then be nitrated as discussed herein to give the nitropyrazole (XXII).

The procedure illustrated in Scheme 3 is of particular utility in the preparation of compounds when X is a group $CR^5$.

The starting materials for the synthetic routes shown in the Schemes above, pyrazoles of Formula (XII) and (XV), can either be obtained commercially or can be prepared by methods known to those skilled in the art. They can be obtained using known methods e.g. from ketones, such as in a process described in EP308020 (Merck), or the methods discussed by Schmidt in *Helv. Chim. Acta.*, 1956, 39, 986-991 and *Helv. Chim. Acta.*, 1958, 41, 306-309. Alternatively they can be obtained by conversion of a commercially available pyrazole, for example those containing halogen, nitro, ester, or amide functionalities, to pyrazoles containing the desired functionality by standard methods known to a person skilled in the art. For example, in 3-carboxy-4-nitropyrazole, the nitro group can be reduced to an amine by standard methods. 4-Nitropyrazole-3-carboxylic acid (XII) can either be obtained commercially or can be prepared by nitration of the corresponding 4-unsubstituted pyrazole carboxy compound, and pyrazoles containing a halogen, may be utilized in coupling reactions with tin or palladium chemistry. A substituted or unsubstituted 4-nitro-3-pyrazole carboxylic acid can be esterified by reaction with thionyl chloride to give the acid chloride intermediate followed by reaction with an alcohol to form the ester of formula (XVI). Alternatively, the esterification can be carried out by reacting the alcohol and carboxylic acid in the presence of an acidic catalyst, one example of which is thionyl chloride. The reaction is typically carried out at room temperature using the esterifying alcohol (e.g. ethanol) as the solvent.

In many of the reactions described above, it may be necessary to protect one or more groups to prevent reaction from taking place at an undesirable location on the molecule. Examples of protecting groups, and methods of protecting and deprotecting functional groups, can be found in Protective Groups in Organic Synthesis (T. Green and P. Wuts; 3rd Edition; John Wiley and Sons, 1999). A hydroxy group may be protected, for example, as an ether (—OR) or an ester (—OC(=O)R), for example, as: a t-butyl ether; a benzyl, benzhydryl(diphenylmethyl), or trityl(triphenylmethyl) ether; a trimethylsilyl or t-butyldimethylsilyl ether; or an acetyl ester (—OC(=O)CH$_3$, —OAc). An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Methods of Purification

The compounds may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

One such system for purifying compounds via preparative LC-MS is described in the experimental section below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Pharmaceutical Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The pharmaceutical compositions can be in any form suitable for oral, parenteral, topical, intranasal, ophthalmic, optic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Methods of Diagnosis and Treatment

It is envisaged that the compounds of the formula (I) will useful in the prophylaxis or treatment of a range of disease states or conditions mediated by cyclin dependent kinases, glycogen synthase kinase-3 and Aurora kinases. Examples of such disease states and conditions are set out above.

Compounds of the formula (I) are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound can be in the range from 100 picograms to 100 milligrams per kilogram of body weight, more typically 10 nanograms to 10 milligrams per kilogram of bodyweight although higher or lower doses may be administered where required. Ultimately, the quantity of compound administered and the type of composition used will be commensurate with the nature of the disease or physiological condition being treated and will be at the discretion of the physician.

The compounds of the formula (I) can be administered as the sole therapeutic agent or they can be administered in combination therapy with one of more other compounds for treatment of a particular disease state, for example a neoplastic disease such as a cancer as hereinbefore defined. Examples of other therapeutic agents that may be administered together (whether concurrently or at different time intervals) with the compounds of the formula (I) include but are not limited to topoisomerase inhibitors, alkylating agents, antimetabolites, DNA binders and microtubule inhibitors (tubulin targeting agents), such as cisplatin, cyclophosphamide, doxorubicin, irinotecan, fludarabine, 5FU, taxanes, mitomycin C, or radiotherapy. For the case of CDK or Aurora inhibitors combined with other therapies, the two or more treatments may be given in individually varying dose schedules and via different routes.

Where the compound of the formula (I) is administered in combination therapy with one, two, three, four or more other therapeutic agents (preferably one or two, preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through their common general knowledge the dosing regimes and combination therapies to use.

Prior to administration of a compound of the formula (I), a patient may be screened to determine whether a disease or condition from which the patient is or may be suffering is one which would be susceptible to treatment with a compound having activity against Aurora kinases. For example, a biological sample taken from a patient may be analysed to determine whether a condition or disease, such as cancer, that the patient is or may be suffering from is one which is characterised by upregulation of Aurora kinase, this includes elevated expression or over-expression of Aurora kinase, including gene amplification (i.e. multiple gene copies) and increased expression by a transcriptional effect, and hyperactivity and activation of Aurora kinase, including activation by mutations. Thus, the patient may be subjected to a diagnostic test to detect a marker characteristic of over-expression, up-regulation or activation of Aurora kinase. The term diagnosis includes screening. By marker we include genetic markers including, for example, the measurement of DNA composition to identify mutations of Aurora or CDC4. The term marker also includes markers which are characteristic of up regulation of Aurora or cyclin E, including enzyme activity, enzyme levels, enzyme state (e.g. phosphorylated or not) and mRNA levels of the aforementioned proteins.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, see Ewart-Toland et al., (Nat. Genet. 2003 August; 34(4):403-12), that individuals forming part of the sub-population possessing the Ile31 variant of the STK gene (the gene for Aurora kinase A) may have an increased susceptibility to certain forms of cancer. It is envisaged therefore that such individuals suffering from cancer will benefit from the administration of compounds having Aurora kinase inhibiting activity. A patient suffering from, or suspected of suffering from, a cancer may therefore be screened to determine whether he or she forms part of the Ile31 variant sub-population. The screening process will typically involve direct sequencing, oligonucleotide microarray analysis, or a mutant specific antibody.

Tumours with activating mutants of Aurora or up-regulation of Aurora including any of the isoforms thereof, may be particularly sensitive to Aurora inhibitors. Tumours may preferentially be screened for up-regulation of Aurora or for Aurora possessing the Ile31 variant prior to treatment (Ewart-Toland et al., Nat. Genet. 2003 August; 34(4):403-12). Ewart-Toland et al identified a common genetic variant in STK15 (resulting in the amino acid substitution F31I1) that is preferentially amplified and associated with the degree of aneuploidy in human colon tumors. These results are consistent with an important role for the Ile31 variant of STK15 in human cancer susceptibility.

The aurora A gene maps to the chromosome 20q13 region that is frequently amplified in many cancers e.g. breast, bladder, colon, ovarian, pancreatic. Patients with a tumour that has this gene amplification might be particularly sensitive to treatments targeting aurora kinase inhibition Methods of identification and analysis of Aurora mutations and up-regulation of Aurora isoforms and chromosome 20q13 amplification are known to a person skilled in the art. Screening methods could include, but are not limited to, standard methods such as reverse-transcriptase polymerase chain reaction (RT-PCR) or in-situ hybridisation.

In screening by RT-PCR, the level of Aurora mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing Aurora mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled artisan will recognize that all such well-known techniques for detection of Aurora up-regulation and mutants of Aurora could be applicable in the present case.

In addition, all of these techniques could also be used to identify tumours particularly suitable for treatment with CDK inhibitors. Tumours with mutants of CDC4 or up-regulation, in particular over-expression, of cyclin E or loss of p21 or p27 may be particularly sensitive to CDK inhibitors. Tumours may preferentially be screened for up-regulation, in particular over-expression, of cyclin E (Harwell R M, Mull B B, Porter D C, Keyomarsi K.; J Biol. Chem. 2004 Mar. 26; 279(13): 12695-705) or loss of p21 or p27 or for CDC4 variants prior to treatment (Rajagopalan H, Jallepalli P V, Rago C, Velculescu V E, Kinzler K W, Vogelstein B, Lengauer C.; Nature. 2004 Mar. 4; 428(6978):77-81).

Antifungal Use

In a further aspect, the invention provides the use of the compounds of the formula (I) as hereinbefore defined as antifungal agents.

The compounds of the formula (I) may be used in animal medicine (for example in the treatment of mammals such as humans), or in the treatment of plants (e.g. in agriculture and horticulture), or as general antifungal agents, for example as preservatives and disinfectants.

In one embodiment, the invention provides a compound of the formula (I) as hereinbefore defined for use in the prophylaxis or treatment of a fungal infection in a mammal such as a human.

Also provided is the use of a compound of the formula (I) for the manufacture of a medicament for use in the prophylaxis or treatment of a fungal infection in a mammal such as a human.

For example, compounds of the invention may be administered to human patients suffering from, or at risk of infection by, topical fungal infections caused by among other organisms, species of Candida, Trichophyton, Microsporum or Epidermophyton, or in mucosal infections caused by Candida albicans (e.g. thrush and vaginal candidiasis). The compounds of the invention can also be administered for the treatment or prophylaxis of systemic fungal infections caused by, for example, Candida albicans, Cryptococcus neoformans, Aspergillus flavus, Aspergillus fumigatus, Coccidiodies, Paracoccidioides, Histoplasma or Blastomyces.

In another aspect, the invention provides an antifungal composition for agricultural (including horticultural) use, comprising a compound of the formula (I) together with an agriculturally acceptable diluent or carrier.

The invention further provides a method of treating an animal (including a mammal such as a human), plant or seed having a fungal infection, which comprises treating said animal, plant or seed, or the locus of said plant or seed, with an effective amount of a compound of the formula (I).

The invention also provides a method of treating a fungal infection in a plant or seed which comprises treating the plant or seed with an antifungally effective amount of a fungicidal composition containing a compound of the formula (I) as hereinbefore defined.

Differential screening assays may be used to select for those compounds of the present invention with specificity for non-human CDK enzymes. Compounds which act specifically on the CDK enzymes of eukaryotic pathogens can be used as anti-fungal or anti-parasitic agents. Inhibitors of the Candida CDK kinase, CKSI, can be used in the treatment of candidiasis. Antifungal agents can be used against infections of the type hereinbefore defined, or opportunistic infections that commonly occur in debilitated and immunosuppressed patients such as patients with leukemias and lymphomas, people who are receiving immunosuppressive therapy, and patients with predisposing conditions such as diabetes mellitus or AIDS, as well as for non-immunosuppressed patients.

Assays described in the art can be used to screen for agents which may be useful for inhibiting at least one fungus implicated in mycosis such as candidiasis, aspergillosis, mucormycosis, blastomycosis, geotrichosis, cryptococcosis, chromoblastomycosis, coccidiodomycosis, conidiosporosis, histoplasmosis, maduromycosis, rhinosporidosis, nocaidiosis, para-actinomycosis, penicilliosis, monoliasis, or sporotrichosis. The differential screening assays can be used to identify anti-fungal agents which may have therapeutic value in the treatment of aspergillosis by making use of the CDK genes cloned from yeast such as Aspergillus fumigatus, Aspergillus flavus, Aspergillus niger, Aspergillus nidulans, or Aspergillus terreus, or where the mycotic infection is muconnycosis, the CDK assay can be derived from yeast such as Rhizopus arrhizus, Rhizopus oryzae, Absidia corymbifera, Absidia ramosa, or Mucorpusillus. Sources of other CDK enzymes include the pathogen Pneumocystis carinii.

By way of example, in vitro evaluation of the antifungal activity of the compounds can be performed by determining the minimum inhibitory concentration (M.I.C.) which is the lowest concentration of the test compounds, in a suitable medium, at which growth of the particular microorganism fails to occur. In practice, a series of agar plates, each having the test compound incorporated at a particular concentration is inoculated with a standard culture of, for example, Candida albicans and each plate is then incubated for an appropriate period at 37° C. The plates are then examined for the presence or absence of growth of the fungus and the appropriate M.I.C. value is noted. Alternatively, a turbidity assay in liquid cultures can be performed and a protocol outlining an example of this assay can be found in Example 314.

The in vivo evaluation of the compounds can be carried out at a series of dose levels by intraperitoneal or intravenous injection or by oral administration, to mice that have been inoculated with a fungus, e.g., a strain of Candida albicans or Aspergillus flavus. The activity of the compounds can be assessed by monitoring the growth of the fungal infection in groups of treated and untreated mice (by histology or by retrieving fungi from the infection). The activity may be measured in terms of the dose level at which the compound provides 50% protection against the lethal effect of the infection ($PD_{50}$).

For human antifungal use, the compounds of the formula (I) can be administered alone or in admixture with a pharmaceutical carrier selected in accordance with the intended route of administration and standard pharmaceutical practice. Thus, for example, they may be administered orally, parenterally, intravenously, intramuscularly or subcutaneously by means of the formulations described above in the section headed "Pharmaceutical Formulations".

For oral and parenteral administration to human patients, the daily dosage level of the antifungal compounds of the formula (I) can be from 0.01 to 10 mg/kg (in divided doses), depending on inter alia the potency of the compounds when administered by either the oral or parenteral route. Tablets or capsules of the compounds may contain, for example, from 5 mg to 0.5 g of active compound for administration singly or two or more at a time as appropriate. The physician in any event will determine the actual dosage (effective amount) which will be most suitable for an individual patient and it will vary with the age, weight and response of the particular patient.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

In addition to the therapeutic uses described above, antifungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms. In similar fashion, side by side comparison of inhibition of a mammalian CDK and an insect CDK, such as the Drosophilia CDK5 gene (Hellmich et al. (1994) FEBS Lett 356:317-21), will permit selection amongst the compounds herein of inhibitors which discriminate between the human/mammalian and insect enzymes. Accordingly, the present invention expressly contemplates the use and formulation of the compounds of the invention in insecticides, such as for use in management of insects like the fruit fly.

In yet another embodiment, certain of the subject CDK inhibitors can be selected on the basis of inhibitory specificity for plant CDK's relative to the mammalian enzyme. For example, a plant CDK can be disposed in a differential screen with one or more of the human enzymes to select those compounds of greatest selectivity for inhibiting the plant enzyme. Thus, the present invention specifically contemplates formulations of the subject CDK inhibitors for agricultural applications, such as in the form of a defoliant or the like.

For agricultural and horticultural purposes the compounds of the invention may be used in the form of a composition formulated as appropriate to the particular use and intended purpose. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they can be manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack. By way of example, the compositions may contain from 0.01 to 1 wt. % of the active ingredient. For field use, likely application rates of the active ingredient may be from 50 to 5000 g/hectare.

The invention also contemplates the use of the compounds of the formula (I) in the control of wood decaying fungi and in the treatment of soil where plants grow, paddy fields for seedlings, or water for perfusion. Also contemplated by the invention is the use of the compounds of the formula (I) to protect stored grain and other non-plant loci from fungal infestation.

EXAMPLES

The invention will now be illustrated, but not limited, by reference to the specific embodiments described in the following examples.

In the examples, the compounds prepared were characterised by liquid chromatography and mass spectroscopy using the systems and operating conditions set out below. Where chlorine is present, the mass quoted for the compound is for $^{35}Cl$. Several systems were used, as described below, and these were equipped with were set up to run under closely similar operating conditions. The operating conditions used are also described below.

Platform System 1
System: Waters 2790/Platform LC
Mass Spec Detector: Micromass Platform LC
PDA Detector: Waters 996 PDA
Analytical Conditions:
Eluent A: 5% $CH_3CN$ in 95% $H_2O$ (0.1% Formic Acid)
Eluent B: $CH_3CN$ (0.1% Formic Acid)
Gradient: 10-95% eluent B
Flow: 1.2 ml/min
Column: Synergi 4 μm Max-RP $C_{12}$, 80A, 50×4.6 mm (Phenomenex)
MS Conditions:
Capillary voltage: 3.5 kV
Cone voltage: 30 V
Source Temperature: 120° C.
FractionLynx System 1
System: Waters FractionLynx (dual analytical/prep)
Mass Spec Detector: Waters-Micromass ZQ
PDA Detector: Waters 2996 PDA
Analytical Conditions:
Eluent A: $H_2O$ (0.1% Formic Acid)
Eluent B: $CH_3CN$ (0.1% Formic Acid)
Gradient: 5-95% eluent B
Flow: 1.5 ml/min
Column: Synergi 4 μm Max-RP $C_{12}$, 80A, 50×4.6 mm (Phenomenex)
MS Conditions:
Capillary voltage: 3.5 kV
Cone voltage: 30 V
Source Temperature: 120° C.
Desolvation Temperature: 300° C.
Platform System 2
HPLC System: Waters 2795
Mass Spec Detector: Micromass Platform LC
PDA Detector: Waters 2996 PDA
Acidic Analytical Conditions:
Eluent A: $H_2O$ (0.1% Formic Acid)
Eluent B: $CH_3CN$ (0.1% Formic Acid)
Gradient: 5-95% eluent B over 3.5 minutes
Flow: 1.5 ml/min
Column: Phenomenex Synergi 41 Max-RP 80A, 50×4.6 mm
Basic Analytical Conditions:
Eluent A: $H_2O$ (10 mM $NH_4HCO_3$ buffer adjusted to pH=9.5 with $NH_4OH$)
Eluent B: $CH_3CN$
Gradient: 05-95% eluent B over 3.5 minutes
Flow: 1.5 ml/min
Column: Waters XTerra MS $C_{18}$ 5 μm 4.6×50 mm
Polar Analytical Conditions:
Eluent A: $H_2O$ (0.1% Formic Acid)
Eluent B: $CH_3CN$ (0.1% Formic Acid)
Gradient: 00-50% eluent B over 3 minutes
Flow: 1.5 ml/min
Column: Phenomenex Synergi 4μ Hydro 80A, 50×4.6 mm
MS Conditions:
Capillary voltage: 3.5 kV
Cone voltage: 30 V
Source Temperature: 120° C.
Scan Range: 165-700 amu
Ionisation Mode: ElectroSpray Negative, Positive or Positive & Negative
FractionLynx System 2
System: Waters FractionLynx (dual analytical/prep)
HPLC Pump: Waters 2525
Injector-Autosampler: Waters 2767
Mass Spec Detector: Waters-Micromass ZQ
PDA Detector: Waters 2996 PDA
Analytical Conditions:
Eluent A: $H_2O$ (0.1% Formic Acid)
Eluent B: $CH_3CN$ (0.1% Formic Acid)
Gradient: 5-95% eluent B over 5 minutes
Flow: 2.0 ml/min
Column: Phenomenex Synergi 4μ Max-RP 80A, 50×4.6 mm Polar Analytical Conditions:
Eluent A: $H_2O$ (0.1% Formic Acid)
Eluent B: $CH_3CN$ (0.1% Formic Acid)
Gradient: 00-50% eluent B over 5 minutes
Flow: 2.0 ml/min
Column: Phenomenex Synergi 4, Max-RP 80A, 50×4.6 mm
MS Conditions:
Capillary voltage: 3.5 kV
Cone voltage: 25 V
Source Temperature: 120° C.
Scan Range: 125-800 amu
Ionisation Mode: ElectroSpray Positive or ElectroSpray Positive & Negative
Mass Directed Purification LC-MS System The following preparative chromatography systems can be used to purify the compounds of the invention.
Hardware:
Waters Fractionlynx system:
2767 Dual Autosampler/Fraction Collector
2525 preparative pump
CFO (column fluidic organizer) for column selection
RMA (Waters reagent manager) as make up pump
Waters ZQ Mass Spectrometer
Waters 2996 Photo Diode Array detector
Software: Masslynx 4.0
Columns:
1. Low pH chromatography: Phenomenex Synergy MAX-RP, 10μ, 150×15 mm (alternatively used same column type with 100×21.2 mm dimensions).
2. High pH chromatography: Phenomenex Luna C18 (2), 10μ, 100×21.2 mm (alternatively used Thermo Hypersil Keystone BetaBasic C18, 5μ, 100×21.2 mm)
Eluents:
1. Low pH chromatography:
Solvent A: $H_2O$+0.1% Formic Acid, pH 1.5
Solvent B: $CH_3CN$+0.1% Formic Acid
2. High pH chromatography:
Solvent A: $H_2O$+10 mM $NH_4HCO_3$+$NH_4OH$, pH 9.5
Solvent B: $CH_3CN$
3. Make up solvent: MeOH+0.1% formic acid (for both chromatography type)
Methods:

Prior to using preparative chromatography to isolate and purify the product compounds, analytical LC-MS can first be used to determine the most appropriate conditions for preparative chromatography. A typical routine is to run an analytical LC-MS using the type of chromatography (low or high pH) most suited for compound structure. Once the analytical trace shows good chromatography, a suitable preparative method of the same type can be chosen. Typical running condition for both low and high pH chromatography methods are:
Flow rate: 24 ml/min
Gradient: Generally all gradients have an initial 0.4 min step with 95% A+5% B. Then according to analytical trace a 3.6 min gradient is chosen in order to achieve good separation (e.g. from 5% to 50% B for early retaining compounds; from 35% to 80% B for middle retaining compounds and so on)
Wash: 1 minute wash step is performed at the end of the gradient
Re-equilibration: A 2.1 minute re-equilibration step is carried out to prepare the system for the next run
Make Up flow rate: 1 ml/min
Solvent:
All compounds were usually dissolved in 100% MeOH or 100% DMSO MS running conditions:
Capillary voltage: 3.2 kV
Cone voltage: 25 V
Source Temperature: 120° C.
Multiplier: 500 V
Scan Range: 125-800 amu
Ionisation Mode: ElectroSpray Positive
Analytical LC-MS System
HPLC System: Waters 2795
Mass Spec Detector: Micromass Platform LC
PDA Detector: Waters 2996 PDA
Acidic Analytical Conditions:
Eluent A: $H_2O$ (0.1% Formic Acid)
Eluent B: $CH_3CN$ (0.1% Formic Acid)
Gradient: 5-95% eluent B over 3.5 minutes
Flow: 0.8 ml/min
Column: Phenomenex Synergi 4μ MAX-RP 80A, 2.0×50 mm
Basic Analytical Conditions:
Eluent A: $H_2O$ (10 mM $NH_4HCO_3$ buffer adjusted to pH=9.5 with $NH_4OH$)
Eluent B: $CH_3CN$
Gradient: 05-95% eluent B over 3.5 minutes
Flow: 0.8 ml/min
Column: Thermo Hypersil-Keystone BetaBasic-18 5 μm 2.1×50 mm or
Column: Phenomenex Luna C18(2) 5 μm 2.0×50 mm
Polar Analytical Conditions:
Eluent A: $H_2O$ (0.1% Formic Acid)
Eluent B: $CH_3CN$ (0.1% Formic Acid)
Gradient: 00-50% eluent B over 3 minutes
Flow: 0.8 ml/min
Column: Thermo Hypersil-Keystone HyPurity Aquastar, 51, 2.1×50 mm or
Column: Phenomenex Synergi 4μ MAX-RP 80A, 2.0×50 mm or
Longer Analytical Conditions:
Eluent A: $H_2O$ (0.1% Formic Acid)
Eluent B: $CH_3CN$ (0.1% Formic Acid)
Gradient: 05-95% eluent B over 15 minutes
Flow: 0.4 ml/min
Column: Phenomenex Synergi 4μ MAX-RP 80A, 2.0×150 mm
MS Conditions:
Capillary voltage: 3.6 kV
Cone voltage: 30 V
Source Temperature: 120° C.
Scan Range: 165-700 amu
ionisation Mode: ElectroSpray Positive or
ElectroSpray Negative or
ElectroSpray Positive & Negative The starting materials for each of the Examples are commercially available unless otherwise specified.

Example 1

Synthesis of 2-(4-Nitro-1H-pyrazol-3-yl)-1H-benzimidazole

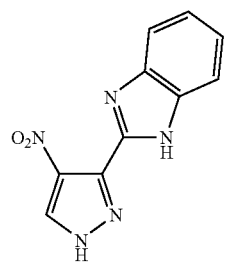

A mixture of o-phenylenediamine (1.51 g, 14.0 mmol), 4-amino-1H-pyrazole-3-carboxylic acid (2.00 g, 12.7 mmol), EDC (2.93 g, 15.3 mmol) and HOBt (2.08 g, 15.3 mmol) in DMF (70 ml) was stirred at ambient temperature for 24 h. The mixture was reduced in vacuo and the residue dissolved in AcOH (150 ml) and heated at reflux for 3 h. The solvent was removed in vacuo, water (100 ml) added and the resultant solid collected by filtration washing with water. The solid was dried through azeotrope with toluene (3×150 ml) yielding 2-(4-nitro-1H-pyrazol-3-yl)-1H-benzimidazole as a yellow solid (1.44 g, 50%). A 100 mg portion was purified by preparative LC/MS and following evaporation of product containing fractions gave 70 mg of the title compound. (LC/MS: $R_t$ 1.72, [M+H]$^+$ 229.61).

Example 2

Synthesis of 3-(1H-Benzimidazol-2-yl)-1H-pyrazol-4-ylamine

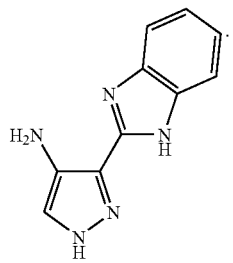

A mixture of 2-(4-nitro-1H-pyrazol-3-yl)-1H-benzimidazole (1.34 g, 5.85 mmol) and 10% Pd/C (0.13 g) in DMF (200 ml) was subjected to an atmosphere of hydrogen at room temperature for 36 h. The reaction mixture was filtered through a plug of Celite and reduced in vacuo. The residue was partitioned between EtOAc and water and the organic portion dried (MgSO$_4$), filtered and reduced in vacuo. The residue was azeotroped with toluene (3×150 ml) yielding 3-(1H-benzimidazol-2-yl)-1H-pyrazol-4-ylamine as a purple solid (0.32 g, 26%). (LC/MS: $R_t$ 0.97, [M+H]$^+$ 199.62).

Example 3

Synthesis of N-[3-(1H-Benzimidazol-2-yl)-1H-pyrazol-4-yl]-benzamide

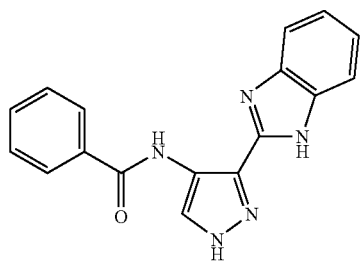

A mixture of benzoic acid (34 mg, 0.28 mmol), 3-(1H-benzimidazol-2-yl)-1H-pyrazol-4-ylamine (50 mg, 0.25 mmol), EDC (58 mg, 0.30 mmol) and HOBt (40.5 mg, 0.30 mmol) in DMF (5 ml) was stirred at room temperature for 24 h. The solvent was removed in vacuo, the crude product purified by preparative LC/MS and following reduction of the product-containing fractions N-[3-(1H-benzimidazol-2-yl)-1H-pyrazol-4-yl]-benzamide was obtained as a brown solid (23 mg, 30%). (LC/MS: $R_t$ 3.66, [M+H]$^+$ 303.67).

Example 4

Synthesis of N-[3-(1H-Benzimidazol-2-yl)-1H-pyrazol-4-yl]-acetamide

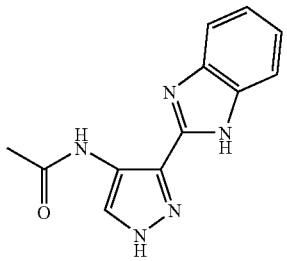

Acetic anhydride (27 μl, 0.28 mmol) was added to a solution of 3-(1H-benzimidazol-2-yl)-1H-pyrazol-4-ylamine (50 mg, 0.25 mmol) in pyridine (5 ml) and the reaction mixture stirred at ambient temperature for 24 h. The mixture was reduced in vacuo and the residue purified by flash column chromatography [SiO$_2$, EtOAc-petrol (1:2.5, 2:1)] to give N-[3-(1H-benzimidazol-2-yl)-1H-pyrazol-4-yl]-acetamide as a brown crystalline solid (29 mg, 48%). (LC/MS: $R_t$ 1.70, [M+H]$^+$ 241.64).

Example 5

Synthesis of N-[3-(1H-Benzimidazol-2-yl)-1H-pyrazol-4-yl]-2,2,2-trifluoro-acetamide

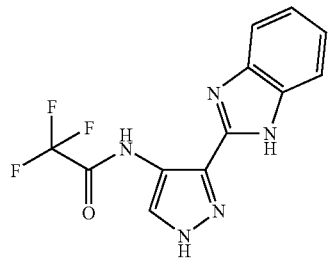

Trifluoroacetic anhydride (40 μl, 0.28 mmol) was added to a solution of 3-(1H-benzimidazol-2-yl)-1H-pyrazol-4-ylamine (50 mg, 0.25 mmol) in pyridine (5 ml) and the reaction mixture stirred at ambient temperature for 24 h. The mixture was reduced in vacuo and the residue purified by flash column chromatography [SiO$_2$, EtOAc-petrol (1:2)] to afford N-[3-(1H-benzimidazol-2-yl)-1H-pyrazol-4-yl]-2,2,2-trifluoro-acetamide as a cream solid (23 mg, 32%). (LC/MS: R$_t$ 3.67, [M+H]$^+$ 295.63).

Example 6

Synthesis of N-[3-(1H-Benzimidazol-2-yl)-1H-pyrazol-4-yl]-2,6-difluoro-benzamide

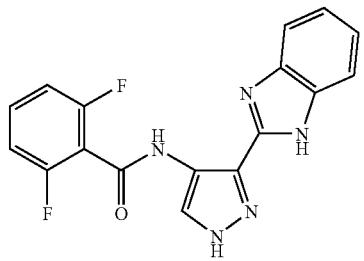

A mixture of 2,6-difluorobenzoic acid (43 mg, 0.28 mmol), 3-(1H-benzimidazol-2-yl)-1H-pyrazol-4-ylamine (50 mg, 0.25 mmol), EDC (58 mg, 0.30 mmol) and HOBt (40.5 mg, 0.30 mmol) in DMF (10 ml) was stirred at ambient temperature for 24 h. The mixture was reduced in vacuo, water (30 ml) added and the resultant solid collected by filtration, dried in the vacuum oven and purified by flash column chromatography [SiO$_2$, EtOAc-petrol (1:2, 1:1, 3:1)] affording N-[3-(1H-benzimidazol-2-yl)-1H-pyrazol-4-yl]-2,6-difluoro-benzamide (20 mg, 24%). (LC/MS: R$_t$ 3.29, [M+H]$^+$ 339.64).

Example 7

Synthesis of Cyclohexanecarboxylic Acid [3-(1H-benzimidazol-2-yl)-1H-pyrazol-4-yl]-amide

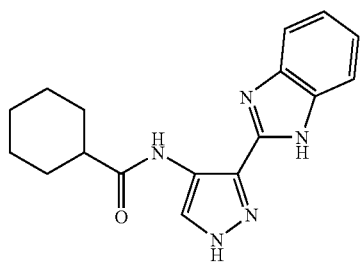

A mixture of cyclohexanecarboxylic acid (36 mg, 0.28 mmol), 3-(1H-benzimidazol-2-yl)-1H-pyrazol-4-ylamine (50 mg, 0.25 mmol), EDC (58 mg, 0.30 mmol) and HOBt (41 mg, 0.30 mmol) in DMSO (2 ml) was stirred at ambient temperature for 24 h. The reaction mixture was partitioned between EtOAc (40 ml) and water (40 ml) and the organic portion dried (MgSO$_4$), filtered and reduced in vacuo. The residue was purified by flash column chromatography [SiO$_2$, EtOAc-petrol (1:4, 1:3, 1:2, 1:1)] affording cyclohexanecarboxylic acid [3-(1H-benzimidazol-2-yl)-1H-pyrazol-4-yl]-amide as an off-white solid (25 mg, 32%). (LC/MS: R$_t$ 3.59, [M+H]$^+$ 310.16).

Example 8

Synthesis of N-[3-(1H-Benzimidazol-2-yl)-1H-pyrazol-4-yl]-2-phenyl-acetamide

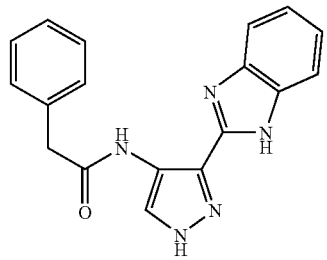

A mixture of phenylacetic acid (38 mg, 0.28 mmol), 3-(1H-benzimidazol-2-yl)-1H-pyrazol-4-ylamine (50 mg, 0.25 mmol), EDC (58 mg, 0.30 mmol) and HOBt (41 mg, 0.30 mmol) in DMSO (2 ml) was stirred at ambient temperature for 24 h. The reaction mixture was partitioned between EtOAc (40 ml) and water (40 ml) and the organic portion dried (MgSO$_4$), filtered and reduced in vacuo. The residue was purified by flash column chromatography [SiO$_2$, EtOAc-petrol (1:2, 1:1, 2:1)] to give N-[3-(1H-benzimidazol-2-yl)-1H-pyrazol-4-yl]-2-phenyl-acetamide as a brown solid (15 mg, 19%). (LC/MS: R$_t$ 3.26, [M+H]$^+$ 318.13).

Example 9

Synthesis of 5-Methyl-3-phenyl-isoxazole-4-carboxylic Acid [3-(1H-benzimidazol-2-yl)-1H-pyrazol-4-yl]-amide

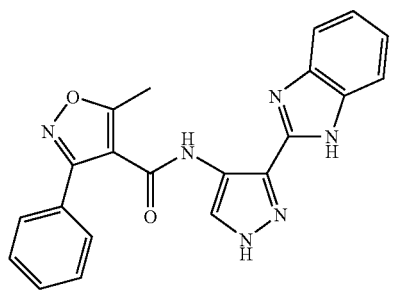

A mixture of 5-methyl-3-phenylisoxazole-4-carboxylic acid (57 mg, 0.28 mmol), 3-(1H-benzimidazol-2-yl)-1H-pyrazol-4-ylamine (50 mg, 0.25 mmol), EDC (58 mg, 0.30 mmol) and HOBt (41 mg, 0.30 mmol) in DMSO (2 ml) was stirred at ambient temperature for 24 h. The reaction mixture was partitioned between EtOAc and water and the organic portion dried (MgSO$_4$), filtered and reduced in vacuo. The residue was purified by flash column chromatography [SiO$_2$, EtOAc-petrol (1:2, 1:1, 2:1)] affording 5-methyl-3-phenyl-isoxazole-4-carboxylic acid [3-(1H-benzimidazol-2-yl)-1H-pyrazol-4-yl]-amide as a cream solid (15 mg, 16%). (LC/MS: R$_t$ 3.73, [M+H]$^+$ 385.14).

Example 10

Synthesis of 2-[4-(2,6-Difluoro-benzoylamino-1H-pyrazol-3-yl]-1H-benzimidazole-4-carboxylic Acid methyl ester

10A. Methyl-2-amino-3-nitrobenzoate

Sodium methoxide (1.50 g, 27.7 mmol) was added to a solution of methyl-2-(acetylamino)-3-nitrobenzoate (1.0 g, 4.2 mmol) in MeOH (30 ml) and the mixture stirred at ambient temperature under nitrogen for 16 h. The reaction was cautiously acidified with concentrated hydrochloric acid then heated at reflux overnight, followed by evaporation and re-evaporation by toluene (2×30 ml). The residue was treated with $CH_2Cl_2$ (50 ml), the insoluble material removed through filtration and the filtrate reduced in vacuo. The residue was purified by flash column chromatography [$SiO_2$, EtOAc-hexane (1:4, 1:0)] affording methyl-2-amino-3-nitrobenzoate (535 mg) as a bright yellow solid.

10B. Methyl 2,3-diaminobenzoate

A mixture of methyl-2-amino-3-nitrobenzoate (530 mg) and 10% Pd/C (55 mg) in EtOH (10 ml) was stirred under an atmosphere of hydrogen at ambient temperature for 16 h. The catalyst was removed by filtration through Celite and the filtrate reduced in vacuo to give methyl 2,3-diaminobenzoate (420 mg) as a yellow/brown oil which solidified on standing.

10C. 2-[4-(2,6-Difluoro-benzoylamino)-1H-pyrazol-3-yl]-1H-benzimidazole-4-carboxylic Acid methyl ester

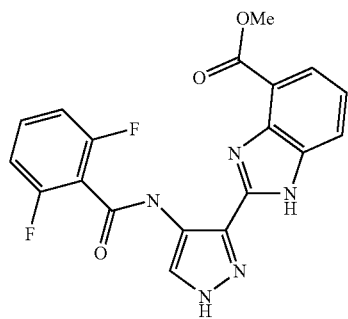

A mixture of 4-(2,6-difluorobenzylamino)-1H-pyrazole-3-carboxylic acid (690 mg, 2.6 mmol) Example 16D), methyl 2,3-diaminobenzoate (415 mg, 2.6 mmol), EDC (590 mg, 3.1 mmol) and HOBt (415 mg, 3.1 mmol) in DMF (10 ml) was stirred at ambient temperature for 16 h and then reduced in vacuo. The residue was partitioned between EtOAc and brine and the organic portion dried ($MgSO_4$), filtered, reduced then crystallised from hot EtOH. The amide intermediate (480 mg) was dissolved in AcOH (10 ml) then heated at reflux for 3 h. The reaction mixture was reduced in vacuo and then azeotroped with toluene (2×20 ml) to afford 2-[4-(2,6-difluoro-benzoylamino)-1H-pyrazol-3-yl]-1H-benzimidazole-4-carboxylic acid methyl ester (420 mg) as a fawn coloured solid. (LC/MS: $R_t$ 3.82, $[M+H]^+$ 398).

Example 11

Synthesis of 2,6-Difluoro-N-[3-(4-hydroxymethyl-1H-benzimidazol-2-yl)-1H-pyrazol-4-yl]-benzamide and Acetic Acid 2-[4-(2,6-difluoro-benzoylamino)-1H-pyrazol-3-yl]-1H-benzimidazol-4-ylmethyl ester

11A. 2-amino-3-nitrobenzoic Acid

A solution of methyl-2-(acetylamino)-3-nitrobenzoate (2.6 g) in EtOH (50 ml) was treated with concentrated hydrochloric acid (10 ml) then heated at reflux for 16 h. The reaction mixture was cooled, reduced in vacuo and azeotroped with toluene (2×50 ml) to give 2-amino-3-nitrobenzoic acid (1.83 g) as a bright yellow solid.

11B. 2-amino-3-nitrobenzyl Alcohol

To a solution of 2-amino-3-nitrobenzoic acid (1.82 g, 10.0 mmol) in anhydrous THF (50 ml) was added sodium borohydride (770 mg, 20.0 mmol) followed by boron trifluoride diethyl etherate (2.5 ml, 20 mmol) and the mixture stirred at ambient temperature under a nitrogen atmosphere for 2 h. MeOH was cautiously added until gas evolution had ceased and the mixture reduced in vacuo. The residue was partitioned between EtOAc and brine and the organic portion dried ($MgSO_4$) and reduced in vacuo to give 2-amino-3-nitrobenzyl alcohol (1.42 g) as a yellow solid.

11C. 2,3-diaminobenzyl Alcohol

A mixture of 2-amino-3-nitrobenzyl alcohol (1.4 g) and 10% Pd/C (140 mg) in EtOH (40 ml) and DMF (10 ml) was stirred under an atmosphere of hydrogen at ambient temperature for 18 h. The catalyst was removed by filtration through Celite, the filtrate reduced in vacuo and azeotroped with toluene (2×50 ml) to give 2,3-diaminobenzyl alcohol (1.15 g) as a dark brown solid.

11D. Synthesis of 4-(2,6-difluoro-benzoylamino)-1H-pyrazole-3-carboxylic Acid (2-amino-3-hydroxymethyl-phenyl)-amide

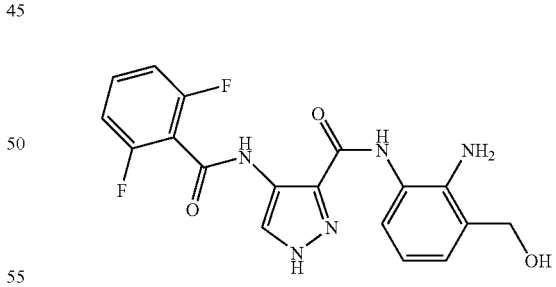

A mixture of 4-(2,6-difluorobenzylamino)-1H-pyrazole-3-carboxylic acid (1.0 g, 3.7 mmol) (Example 16D), 2,3-diaminobenzylalcohol (560 mg, 4.1 mmol), EDC (870 mg, 4.5 mmol) and HOBt (610 mg, 4.5 mmol) in DMF (20 ml) was stirred at ambient temperature for 18 h and then reduced in vacuo. The residue was partitioned between EtOAc and brine and the organic portion dried ($MgSO_4$) and reduced in vacuo. The residue was purified by flash column chromatography [$SiO_2$, EtOAc-hexane (1:1, 2:1)] to give 4-(2,6-difluoro-benzoylamino)-1H-pyrazole-3-carboxylic acid (2-amino-3-hydroxymethyl-phenyl)-amide (860 mg).

11E. Synthesis of 2,6-Difluoro-N-[3-(4-hydroxymethyl-1H-benzimidazol-2-yl)-1H-pyrazol-4-yl]-benzamide and Acetic acid 2-[4-(2,6-difluoro-benzoylamino)-1H-pyrazol-3-yl]-1H-benzimidazol-4-ylmethyl ester

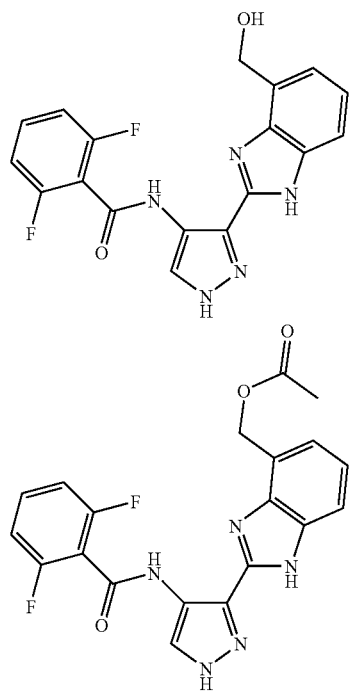

4-(2,6-Difluoro-benzoylamino)-1H-pyrazole-3-carboxylic acid (2-amino-3-hydroxymethyl-phenyl)-amide (100 mg, 0.26 mmol) was dissolved in acetic acid (10 ml) then heated for 10 min at 150° C. (100 W) in a CEM discover microwave synthesiser. The reaction mixture was reduced then azeotroped with toluene (2×20 ml). The residue was purified by flash column chromatography [SiO$_2$, EtOAc-hexane (1:1, 2:1, 3:1)] to give 2,6-difluoro-N-[3-(4-hydroxymethyl-1H-benzimidazol-2-yl)-1H-pyrazol-4-yl]-benzamide (25 mg) as an off white solid (LC/MS: R$_t$ 2.70, [M+H]$^+$ 370) and acetic acid 2-[4-(2,6-difluoro-benzoylamino)-1H-pyrazol-3-yl]-1H-benzimidazol-4-ylmethyl ester (20 mg) as an off white solid. (LC/MS: R$_t$ 3.60, [M+H]$^+$ 412).

Example 12

Synthesis of 2,6-Difluoro-N-[3-(4-morpholin-4-yl-methyl-1H-benzimidazol-2-yl)-1H-pyrazol-4-yl]-benzamide 12A. 2,6-difluoro-N-[3-(4-formyl-1H-benzimidazol-2-yl)-1H-pyrazol-4-yl]-benzamide

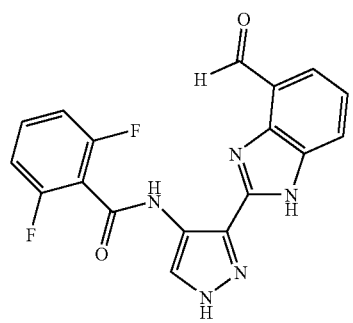

A mixture of 2,6-difluoro-N-[3-(4-hydroxymethyl-1H-benzimidazol-2-yl)-1H-pyrazol-4-yl]-benzamide (200 mg, 0.54 mmol) and MnO$_2$ (500 mg) in CH$_2$Cl$_2$/MeOH (5:1, 12 ml) was stirred at ambient temperature for 18 h, then filtered through Celite and reduced in vacuo. The residue was purified by flash column chromatography [SiO$_2$, EtOAc-hexane (1:3, 1:2)] to give 2,6-difluoro-N-[3-(4-formyl-1H-benzimidazol-2-yl)-1H-pyrazol-4-yl]-benzamide (30 mg) as a cream solid.

12B. 2,6-Difluoro-N-[3-(4-morpholin-4-yl-methyl-1H-benzimidazol-2-yl)-1H-pyrazol-4-yl]-benzamide

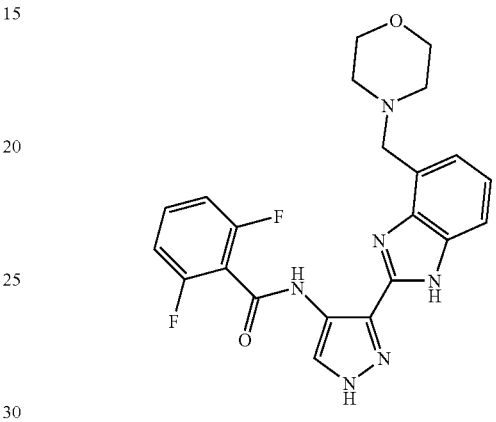

To a solution of 2,6-difluoro-N-[3-(4-formyl-1H-benzimidazol-2-yl)-1H-pyrazol-4-yl]-benzamide (30 mg, 0.08 mmol) and morpholine (14 mg, 0.16 mmol) in CH$_2$Cl$_2$ (5 ml) and THF (2 ml) was added 3 Å molecular sieves (1 g) followed by sodium triacetoxyborohydride (50 mg, 0.24 mmol) and the mixture stirred at ambient temperature under a nitrogen atmosphere for 2 h. The reaction mixture was filtered through Celite, reduced in vacuo then purified by flash column chromatography [SiO$_2$, EtOAc-hexane (1:1, 1:0), then CH$_2$Cl$_2$-MeOH (95:5)] affording 2,6-difluoro-N-[3-(4-morpholin-4-yl-methyl-1H-benzimidazol-2-yl)-1H-pyrazol-4-yl]-benzamide (13 mg) as a cream solid. (LC/MS: R$_t$ 1.80, [M+H]$^+$ 439).

Example 13

Synthesis of 2,6-Difluoro-N-[3-(N-methyl-piperazinyl-4-ylmethyl-1H-benzimidazol-2-yl)-1H-pyrazol-4-yl]-benzamide

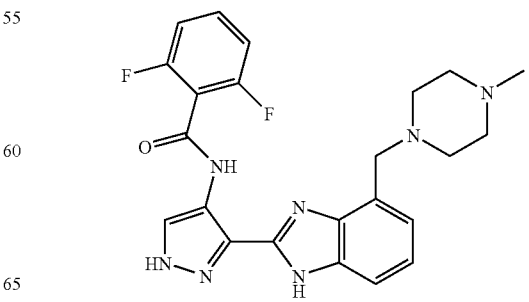

The compound was prepared in a manner analogous to Example 12B, but using N-methylpiperazine in place of morpholine. (LC/MS: $R_t$ 1.93, $[M+H]^+$ 452).

Example 14

Synthesis of N-{3-[4-(tert-Butylamino-methyl)-1H-benzimidazol-2-yl]-1H-pyrazol-4-yl}-2,6-difluoro-benzamide

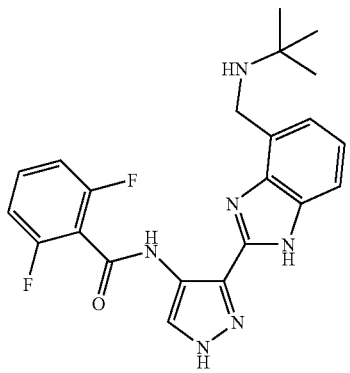

The compound was prepared in a manner analogous to Example 12B, but using tert-butylamine in place of morpholine. (LC/MS: $R_t$ 2.04, $[M+H]^+$ 425).

Example 15

Synthesis of N-[3-(4-Dimethylaminomethyl-1H-benzimidazol-2-yl)-1H-pyrazol-4-yl]-2,6-difluoro-benzamide

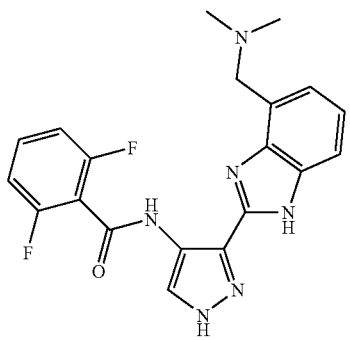

The compound was prepared in a manner analogous to Example 12B, but using 35% dimethylamine in EtOH in place of morpholine. (LC/MS: $R_t$ 1.85, $[M+H]^+$ 397).

Example 16

Synthesis of 2-[4-(2,6-Difluoro-benzoylamino)-1H-pyrazol-3-yl]-1H-benzimidazole-5-carboxylic Acid methyl ester 16A. Synthesis of 4-Nitro-1H-pyrazole-3-carboxylic acid ethyl ester

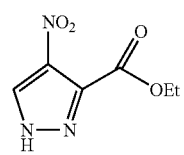

Thionyl chloride (2.90 ml, 39.8 mmol) was slowly added to a mixture of 4-nitro-3-pyrazolecarboxylic acid (5.68 g, 36.2 mmol) in EtOH (100 ml) at ambient temperature and the mixture stirred for 48 h. The mixture was reduced in vacuo and dried through azeotrope with toluene to afford 4-nitro-1H-pyrazole-3-carboxylic acid ethyl ester as a white solid (6.42 g, 96%). ($^1$H NMR (400 MHz, DMSO-$d_6$) δ 14.4 (s, 1H), 9.0 (s, 1H), 4.4 (q, 2H), 1.3 (t, 3H)).

16B. Synthesis of 4-Amino-1H-pyrazole-3-carboxylic acid ethyl ester

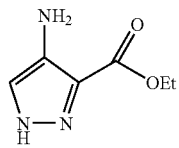

A mixture of 4-nitro-1H-pyrazole-3-carboxylic acid ethyl ester (6.40 g, 34.6 mmol) and 10% Pd/C (650 mg) in EtOH (150 ml) was stirred under an atmosphere of hydrogen for 20 h. The mixture was filtered through a plug of Celite, reduced in vacuo and dried through azeotrope with toluene to afford 4-amino-1H-pyrazole-3-carboxylic acid ethyl ester as a pink solid (5.28 g, 98%). ($^1$H NMR (400 MHz, DMSO-$d_6$) δ 12.7 (s, 1H), 7.1 (s, 1H), 4.8 (s, 2H), 4.3 (q, 2H), 1.3 (t, 3H)).

16C. Synthesis of 4-(2,6-Difluoro-benzoylamino)-1H-pyrazole-3-carboxylic acid ethyl ester

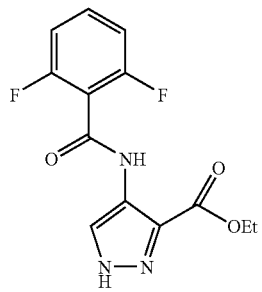

A mixture of 2,6-difluorobenzoic acid (6.32 g, 40.0 mmol), 4-amino-1H-pyrazole-3-carboxylic acid ethyl ester (5.96 g, 38.4 mmol), EDC (8.83 g, 46.1 mmol) and HOBt (6.23 g, 46.1 mmol) in DMF (100 ml) was stirred at ambient temperature for 6 h. The mixture was reduced in vacuo, water added and the solid formed collected by filtration and air-dried to give 4-(2,6-difluoro-benzoylamino)-1H-pyrazole-3-carboxylic acid ethyl ester as the major component of a mixture (15.3 g). (LC/MS: $R_t$ 3.11, $[M+H]^+$ 295.99).

16D. Synthesis of 4-(2,6-Difluoro-benzoylamino)-1H-pyrazole-3-carboxylic Acid

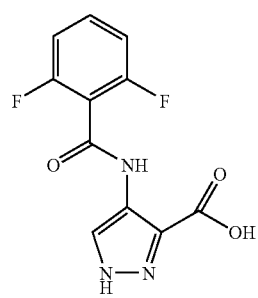

A mixture of 4-(2,6-difluoro-benzoylamino)-1H-pyrazole-3-carboxylic acid ethyl ester (10.2 g) in 2 M aqueous NaOH/MeOH (1:1, 250 ml) was stirred at ambient temperature for 14 h. Volatile materials were removed in vacuo, water (300 ml) added and the mixture taken to pH 5 using 1M aqueous HCl. The resultant precipitate was collected by filtration and dried through azeotrope with toluene to afford 4-(2,6-difluoro-benzoylamino)-1H-pyrazole-3-carboxylic acid as a pink solid (5.70 g). (LC/MS: $R_t$ 2.33, [M+H]$^+$ 267.96).

16E. Synthesis of 2-[4-(2,6-Difluoro-benzoylamino)-1H-pyrazol-3-yl]-1H-benzimidazole-5-carboxylic acid methyl ester

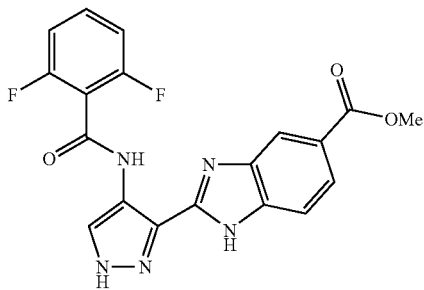

A mixture of 4-(2,6-difluoro-benzoylamino)-1H-pyrazole-3-carboxylic acid (500 mg, 1.87 mmol), methyl 3,4-diaminobenzoate (375 mg, 2.25 mmol), EDC (430 mg, 2.25 mmol) and HOBt (305 mg, 2.25 mmol) in DMF (5 ml) was stirred at ambient temperature for 12 h. The residue was reduced in vacuo and then dissolved in the minimum amount of methanol and petroleum ether added to give the intermediate amide as a pink solid which was collected by filtration (427 mg). (LC/MS: $R_t$ 3.24, [M+H]$^+$ 416.02).

A mixture of the amide (150 mg, 0.36 mmol) in glacial acetic acid (4 ml) was heated in the microwave (100 W) at 120° C. for 10 mins. The mixture was reduced in vacuo and petroleum ether (3 ml) and methanol (2 ml) added forming a precipitate, which was collected by filtration to give 2-[4-(2,6-difluoro-benzoylamino)-1H-pyrazol-3-yl]-1H-benzimidazole-5-carboxylic acid methyl ester (96 mg, 67%) as a pink solid. (LC/MS: $R_t$ 3.67, [M+H]$^+$ 397.99).

Example 17

Synthesis of 2-[4-(2,6-Difluoro-benzoylamino)-1H-pyrazol-3-yl]-1H-benzimidazole-5-carboxylic Acid

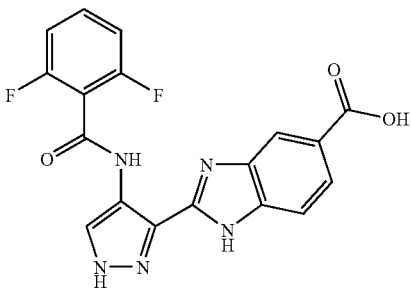

A mixture of 2-[4-(2,6-difluoro-benzoylamino)-1H-pyrazol-3-yl]-1H-benzimidazole-5-carboxylic acid methyl ester (12.0 mg, 0.03 mmol) in 2 M aqueous NaOH/MeOH (1:1, 4 ml) was stirred at ambient temperature for 14 h. The mixture was reduced in vacuo, water (5 ml) added and the mixture taken to pH 4 using 1 M aqueous HCl. The precipitate formed was collected by filtration and dried under vacuum to give 2-[4-(2,6-difluoro-benzoylamino)-1H-pyrazol-3-yl]-1H-benzimidazole-5-carboxylic acid as a pale coloured solid (6 mg, 52%). (LC/MS: $R_t$ 2.88, [M+H]$^+$ 383.97).

Example 18

Synthesis of 2-[4-(2,6-Difluoro-benzoylamino)-1H-pyrazol-3-yl]-1H-benzimidazole-5-carboxylic Acid amide

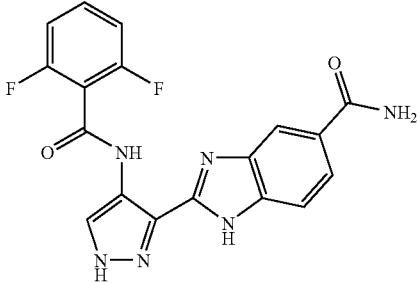

To a mixture of 2-[4-(2,6-difluoro-benzoylamino)-1H-pyrazol-3-yl]-1H-benzimidazole-5-carboxylic acid (100 mg, 0.26 mmol), EDC (75 mg, 0.39 mmol) and HOBt (53 mg, 0.39 mmol) in DMF (1.5 ml) was successively added diisopropylethylamine (0.15 ml, 1.04 mmol) and ammonium chloride (28 mg, 0.52 mmol). The mixture was stirred at ambient temperature for 48 h and then reduced in vacuo. Water was added and the precipitate formed collected by filtration and dried through azeotrope with toluene to afford 2-[4-(2,6-difluoro-benzoylamino)-1H-pyrazol-3-yl]-1H-benzimidazole-5-carboxylic acid amide (49 mg, 49%) as a beige solid. (LC/MS: $R_t$ 2.54, [M+H]$^+$ 382.99).

Example 19

Synthesis of 2,6-Difluoro-N-[3-(5-hydroxymethyl-1H-benzimidazol-2-yl)-1H-pyrazol-4-yl]-benzamide

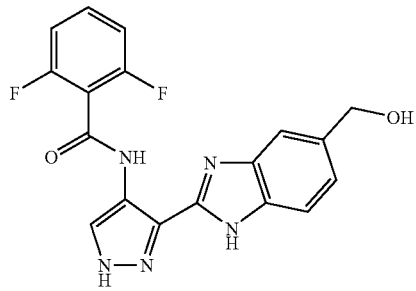

A mixture of 4-(2,6-difluoro-benzoylamino)-1H-pyrazole-3-carboxylic acid (584 mg, 2.19 mmol), (3,4-diaminophenyl)-methanol (332 mg, 2.40 mmol), EDC (504 mg, 2.63 mmol) and HOBt (355 mg, 2.63 mmol) in DMF (15 ml) was stirred at ambient temperature for 20 h. The mixture was reduced in vacuo and the residue taken up in EtOAc, washed with water and brine and the organic portion dried (MgSO$_4$) and reduced in vacuo to give the intermediate amide (591 mg) as a brown solid. (LC/MS: $R_t$ 2.34, [M+H]$^+$ 388.00).

A mixture of the amide (575 mg) in glacial AcOH (4 ml) was heated in the microwave (80 W) at 90° C. for 20 min. The mixture was poured into water and the solid formed collected by filtration. The residue was taken up in MeOH (10 ml) and stirred in the presence of NaOMe (320 mg, 5.90 mmol) for 30 min. The mixture was reduced in vacuo, taken up in EtOAc and washed with water and brine, dried (MgSO$_4$) and reduced in vacuo. The residue was purified by column chromatography [SiO$_2$, EtOAc] to give 2,6-difluoro-N-[3-(5-hydroxymethyl-1H-benzimidazol-2-yl)-1H-pyrazol-4-yl]-benzamide as a white solid (78 mg, 10% over two steps). (LC/MS: R$_t$ 2.45, [M+H]$^+$ 370.05).

Example 20

Synthesis of N-[3-(1H-Benzimidazol-2-yl)-1H-pyrazol-4-yl]-2-fluoro-3-methoxy-benzamide

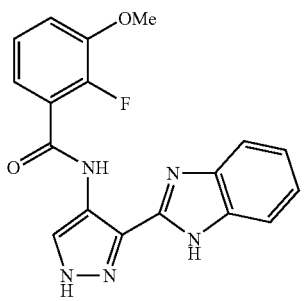

A mixture of 2-fluoro-3-methoxybenzoic acid (47 mg, 0.28 mmol), 3-(1H-benzimidazol-2-yl)-1H-pyrazol-4-ylamine (50 mg, 0.25 mmol), EDC (58 mg, 0.30 mmol) and HOBt (41 mg, 0.30 mmol) in DMF (1.5 ml) was stirred at ambient temperature for 20 h. The reaction mixture was poured into water (30 ml) and the resultant solid collected by filtration and purified by re-crystallisation from MeOH/petrol to yield N-[3-(1H-benzimidazol-2-yl)-1H-pyrazol-4-yl]-2-fluoro-3-methoxy-benzamide (7 mg, 8%) as a gray solid. (LC/MS: R$_t$ 3.63, [M+H]$^+$ 352.00).

Example 21

Synthesis of 2,6-Difluoro-N-{3-[5-(4-methyl-piperazine-1-carbonyl)-1H-benzimidazol-2-yl]-1H-pyrazol-4-yl}-benzamide

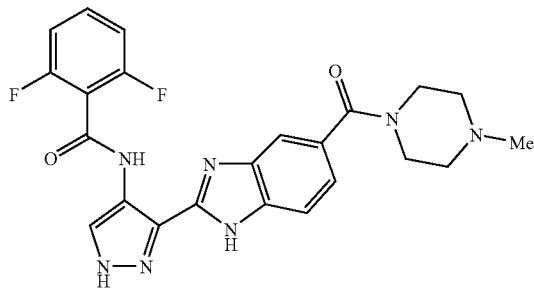

A mixture of 2-[4-(2,6-difluoro-benzoylamino)-1H-pyrazol-3-yl]-1H-benzimidazole-5-carboxylic acid (115 mg, 0.30 mmol), 1-methyl-piperazine (50.0 µL, 0.45 mmol), EDC (104 mg, 0.54 mmol) and HOBt (73.0 mg, 0.54 mmol) in DMF (5 ml) was stirred at ambient temperature for 14 h. The residue was reduced in vacuo, taken up in EtOAc and washed with water and brine, dried (MgSO$_4$) and reduced in vacuo to give 2,6-difluoro-N-{3-[5-(4-methyl-piperazine-1-carbonyl)-1H-benzimidazol-2-yl]-1H-pyrazol-4-yl}-benzamide (37 mg, 26%) as a pale yellow solid. (LC/MS: R$_t$ 1.78, [M+H]$^+$ 466.09).

Example 22

Synthesis of 2,6-Difluoro-N-[3-(5-morpholin-4-ylmethyl-1H-benzimidazol-2-yl)-1H-pyrazol-4-yl]-benzamide

22A. Synthesis of 2,6-Difluoro-N-[3-(5-formyl-1H-benzimidazol-2-yl)-1H-pyrazol-4-yl]-benzamide

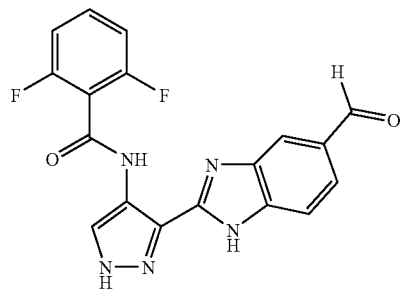

A mixture of 2,6-difluoro-N-[3-(5-hydroxymethyl-1H-benzimidazol-2-yl)-1H-pyrazol-4-yl]-benzamide (800 mg, 2.17 mmol) and MnO$_2$ (5.00 g, 57.5 mmol) in CH$_2$Cl$_2$/MeOH (10:1, 110 ml) was stirred at ambient temperature for 5 days. The mixture was filtered through a plug of Celite washing with MeOH and the filtrate reduced in vacuo to give 2,6-difluoro-N-[3-(5-formyl-1H-benzimidazol-2-yl)-1H-pyrazol-4-yl]-benzamide (380 mg, 48%) as a yellow solid. (LC/MS: R$_t$ 3.41, [M+H]$^+$ 368.04).

22B. Synthesis of 2,6-Difluoro-N-[3-(5-morpholin-4-ylmethyl-1H-benzimidazol-2-yl)-1H-pyrazol-4-yl]-benzamide

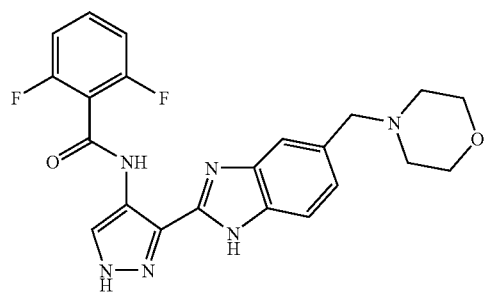

To a mixture of 2,6-difluoro-N-[3-(5-formyl-1H-benzimidazol-2-yl)-1H-pyrazol-4-yl]-benzamide (75.0 mg, 0.20 mmol) in anhydrous THF (5 ml) stirring at ambient temperature was successively added 3 Å molecular sieves, morpholine (35 µL, 0.40 mmol) and triacetoxy sodiumborohydride (127 mg, 0.60 mmol). The mixture was stirred for 4 h, MeOH (3 ml) added and then the mixture reduced in vacuo. The residue was taken up in EtOAc, washed with water and brine, dried (MgSO$_4$), reduced in vacuo and then purified through preparative LC/MS to give 2,6-difluoro-N-[3-(5-morpholin-4-ylmethyl-1H-benzimidazol-2-yl)-1H-pyrazol-4-yl]-benzamide (9 mg, 10%) as a white solid. (LC/MS: R$_t$ 1.90, [M+H]$^+$ 439.09).

Example 23

Synthesis of 2,6-Difluoro-N-{3-[5-(4-methyl-piperazin-1-ylmethyl)-1H-benzimidazol-2-yl]-1H-pyrazol-4-yl}-benzamide

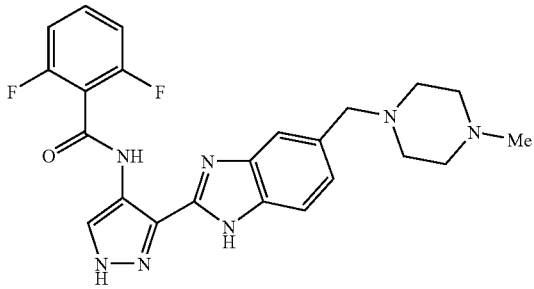

The compound was prepared in a manner analogous to Example 22B, however using 1-methyl piperazine (44.0 µL, 0.40 mmol) as the amine fragment to give 2,6-difluoro-N-{3-[5-(4-methyl-piperazin-1-ylmethyl)-1H-benzimidazol-2-yl]-1H-pyrazol-4-yl}-benzamide (4 mg, 5%) as a yellow solid. (LC/MS: $R_t$ 1.66, $[M+H]^+$ 452.11)

Example 24

Synthesis of N-{3-[5-(tert-Butylamino-methyl)-1H-benzimidazol-2-yl]-1H-pyrazol-4-yl}-2,6-difluoro-benzamide

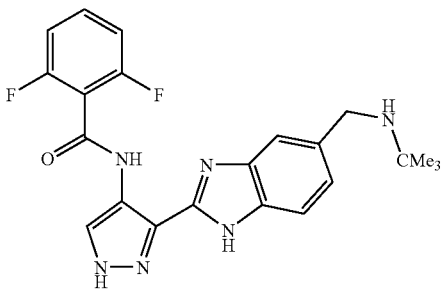

The compound was prepared in a manner analogous to Example 22B, however using tert-butylamine (42 µL, 0.40 mmol) as the amine fragment to give N-{3-[5-(tert-butylamino-methyl)-1H-benzimidazol-2-yl]-1H-pyrazol-4-yl}-2,6-difluoro-benzamide (5 mg, 6%) as a white solid. (LC/MS: $R_t$ 2.00, $[M+H]^+$ 425.11)

Example 25

Synthesis of N-[3-(5-Dimethylaminomethyl-1H-benzimidazol-2-yl)-1H-pyrazol-4-yl]-2,6-difluoro-benzamide

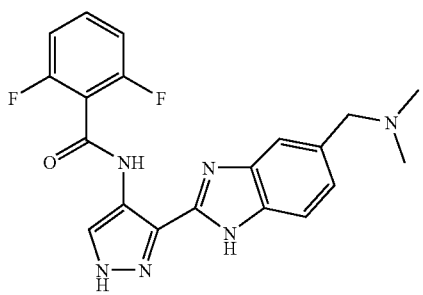

The compound was prepared in a manner analogous to Example 22B, however using 2,6-difluoro-N-[3-(5-formyl-1H-benzimidazol-2-yl)-1H-pyrazol-4-yl]-benzamide (57.4 mg, 0.16 mmol), dry THF (5 ml), 3 Å molecular sieves, dimethylamine (35% in EtOH) (55 µL, 0.31 mmol) and triacetoxy sodium borohydride (100 mg, 0.47 mmol) to give N-[3-(5-dimethylaminomethyl-1H-benzimidazol-2-yl)-1H-pyrazol-4-yl]-2,6-difluoro-benzamide (11 mg, 18%) as a yellow solid. (LC/MS: $R_t$ 2.85, $[M+H]^+$ 397.17).

Example 26

Synthesis of N-[3-(5-Chloro-1H-benzimidazol-2-yl)-1H-pyrazol-4-yl]-2,6-difluoro-benzamide

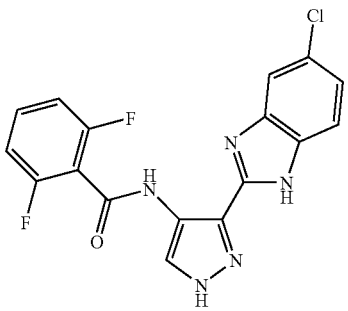

A mixture of 4-(2,6-difluoro-benzoylamino)-1H-pyrazole-3-carboxylic acid (50 mg, 0.18 mmol), 4-chlorophenylenediamine (30 mg, 0.21 mmol), EDC (45 mg, 0.22 mmol) and HOBt (30 mg, 0.22 mmol) in DMF (5 ml) was stirred at ambient temperature for 18 h. The reaction mixture was reduced in vacuo and the residue purified by column chromatography [SiO$_2$, EtOAc/hexane (1:1)] to give the intermediate amide. A mixture of the amide in AcOH (2 ml) was heated in a microwave (50 W) at 140° C. for 15 min and then reduced in vacuo. The residue was purified by column chromatography [SiO$_2$, EtOAc/petrol (1:1)] to give N-[3-(5-chloro-1H-benzimidazol-2-yl)-1H-pyrazol-4-yl]-2,6-difluoro-benzamide (20 mg) as a fawn solid. (LC/MS: $R_t$ 4.16, $[M+H]^+$ 374).

Example 27

Synthesis of 2,6-Difluoro-N-[3-(5-methoxy-1H-benzimidazol-2-yl)-1H-pyrazol-4-yl]-benzamide

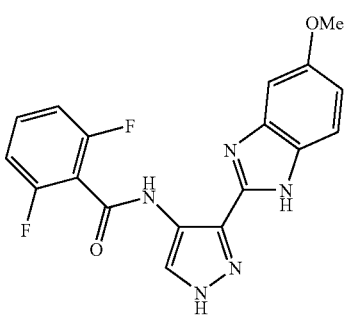

The compound was prepared in a manner analogous to Example 26, but using 4-methoxyphenylenediamine (28 mg, 0.21 mmol) as the amine fragment to give 2,6-difluoro-N-[3-(5-methoxy-1H-benzimidazol-2-yl)-1H-pyrazol-4-yl]-benzamide (25 mg) as a pale brown solid. (LC/MS: $R_t$ 3.26, $[M+H]^+$ 370).

Example 28

Synthesis of 2,6-Difluoro-N-[3-(5-nitro-1H-benzimidazol-2-yl)-1H-pyrazol-4-yl]-benzamide

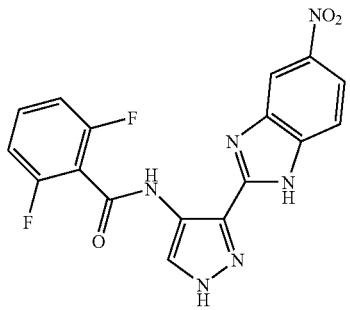

The compound was prepared in a manner analogous to Example 26, but using 4-nitrophenylenediamine (32 mg, 0.21 mmol) as the amine fragment to give 2,6-difluoro-N-[3-(5-nitro-1H-benzimidazol-2-yl)-1H-pyrazol-4-yl]-benzamide (18 mg). (LC/MS: $R_t$ 3.84, $[M+H]^+$ 385).

Example 29

Synthesis of 2,6-Difluoro-N-[3-(1H-imidazo[4,5-c]pyridin-2-yl)-1H-pyrazol-4-yl]-benzamide

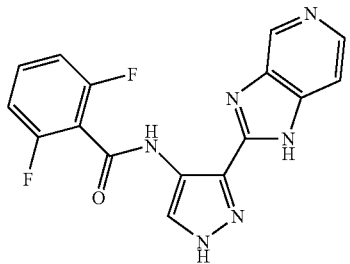

The compound was prepared in a manner analogous to Example 26, but using 3,4-diaminopyridine (22 mg, 0.21 mmol) as the amine fragment to give 2,6-difluoro-N-[3-(1H-imidazo[4,5-c]pyridin-2-yl)-1H-pyrazol-4-yl]-benzamide (13 mg) as a brown solid. (LC/MS: $R_t$ 4.16, $[M+H]^+$ 341).

Example 30

Synthesis of 2-[4-(2,6-Difluoro-benzoylamino-1H-pyrazol-3-yl]-1H-benzimidazole-4-carboxylic Acid

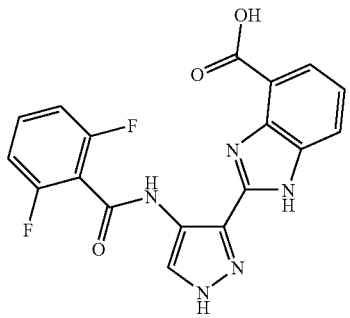

A solution of 2-[4-(2,6-difluoro-benzoylamino)-1H-pyrazol-3-yl]-1H-benzimidazole-4-carboxylic acid methyl ester (220 mg, 0.55 mmol) in THF/water (1:1, 10 ml) was treated with lithium hydroxide hydrate (70 mg, 1.66 mmol) and the mixture stirred at ambient temperature for 18 h. The volatiles were removed in vacuo, the mixture acidified to pH5 by the addition of 2M aqueous hydrochloric acid and the solid formed collected by filtration, washed with water then dried under vacuum to give 2-[4-(2,6-difluoro-benzoylamino)-1H-pyrazol-3-yl]-1H-benzimidazole-4-carboxylic acid (165 mg) as a brown solid. (LC/MS: $R_t$ 3.28, $[M+H]^+$ 384).

Example 31

Synthesis of 2,6-Difluoro-N-{3-[4-(4-methyl-piperazine-1-carbonyl)-1H-benzimidazol-2-yl]-1H-pyrazol-4-yl}-benzamide

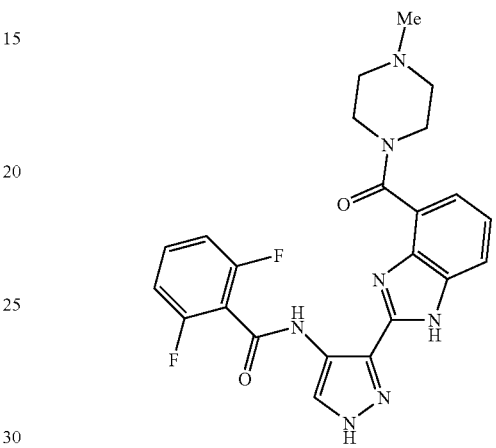

A mixture of 2-[4-(2,6-difluoro-benzoylamino)-1H-pyrazol-3-yl]-1H-benzimidazole-4-carboxylic acid (50 mg, 0.13 mmol), N-methylpiperazine (20 µl, 0.18 mmol), EDC (30 mg, 0.15 mmol) and HOBt (22 mg, 0.15 mmol) in DMF (5 ml) was stirred at ambient temperature for 18 h. The mixture was reduced in vacuo and the residue purified by flash column chromatography [SiO$_2$, CH$_2$Cl$_2$/MeOH (95:5, 90:10)] to give 2,6-difluoro-N-{3-[4-(4-methyl-piperazine-1-carbonyl)-1H-benzimidazol-2-yl]-1H-pyrazol-4-yl}-benzamide (14 mg) as a cream solid. (LC/MS: $R_t$ 2.21, $[M+H]^+$ 466).

Example 32

Synthesis of N-[3-(1H-Benzimidazol-2-yl)-1H-pyrazol-4-yl]-2-(2-pyrrolidin-1-yl-ethoxy)-benzamide

32A. Synthesis of 2-(2-Pyrrolidin-1-yl-ethoxy)-benzoic Acid methyl ester

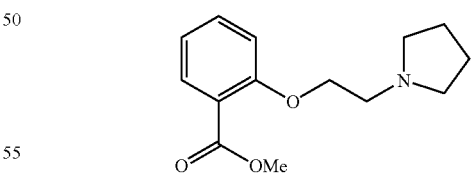

To a mixture of triphenylphosphine (0.79 g, 3.0 mmol) in THF (15 ml) was successively added diisopropylazodicarboxylate (0.61 g, 3.0 mmol) followed by methyl salicylate (0.46 g, 3.0 mmol) and the resultant mixture stirred at ambient temperature for 1 h. 1-(2-Hydroxyethyl)-pyrrolidine (0.35 g, 3.0 mmol) was then added drop-wise and the reaction mixture left stirring at ambient temperature for a further 5 h. The reaction mixture was reduced in vacuo and purified by flash column chromatography [SiO$_2$, EtOAc/MeOH (3:1, 1:1)] to give 2-(2-pyrrolidin-1-yl-ethoxy)-benzoic acid methyl ester as a clear yellow oil (446 mg, 60%). (LC/MS: $R_t$ 1.58, $[M+H]^+$ 250.05).

32B. Synthesis of N-[3-(1H-Benzimidazol-2-yl)-1H-pyrazol-4-yl]-2-(2-pyrrolidin-1-yl-ethoxy)-benzamide

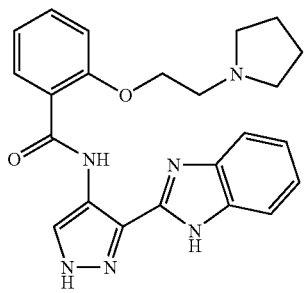

2-(2-Pyrrolidin-1-yl-ethoxy)-benzoic acid methyl ester (125 mg, 0.50 mmol) and lithium hydroxide (21 mg, 0.50 mmol) were dissolved in THF/H₂O (1:1, 2 ml) and the mixture stirred at ambient temperature for 20 h. The reaction mixture was reduced in vacuo and azeotroped with toluene (3×5 ml) to give a white solid, which was dissolved in water (1 ml) and acidified with 2 M aqueous HCl (1 ml). The resulting solution was reduced in vacuo and azeotroped with toluene (3×5 ml) to give a pale yellow gel, which was combined with 3-(1H-benzimidazol-2-yl)-1H-pyrazol-4-ylamine (100 mg, 0.50 mmol), EDC (116 mg, 0.60 mmol) and HOBt (81 mg, 0.60 mmol) and stirred at ambient temperature in DMF (3 ml) for 20 h. The reaction mixture was reduced in vacuo and purified by flash column chromatography [SiO₂, CH₂Cl₂/MeOH (95:5, 87.5:12.5) then 120 DMAW] to give N-[3-(1H-benzimidazol-2-yl)-1H-pyrazol-4-yl]-2-(2-pyrrolidin-1-yl-ethoxy)-benzamide (63 mg, 30%) as a pale pink solid. (LC/MS: $R_t$ 2.08, $[M+H]^+$ 417.11).

Example 33

Synthesis of N-[3-(1H-Benzimidazol-2-yl)-1H-pyrazol-4-yl]-3-methoxy-benzamide

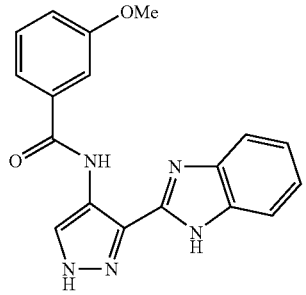

A mixture of 3-methoxybenzoic acid (84 mg, 0.55 mmol), 3-(1H-benzimidazol-2-yl)-1H-pyrazol-4-ylamine (100 mg, 0.50 mmol), EDC (116 mg, 0.60 mmol) and HOBt (81 mg, 0.60 mmol) was stirred at ambient temperature in DMSO (3 ml) for 20 h. The reaction mixture was poured into water (30 ml) and the resultant solid was collected by filtration and purified by flash column chromatography [SiO₂, (dichloromethane 120 ml, methanol 15, acetic acid 3 ml, water 2 ml (DMAW 120)] to yield N-[3-(1H-Benzimidazol-2-yl)-1H-pyrazol-4-yl]-3-methoxy-benzamide as a pale pink-gray solid (21 mg, 13%). (LC/MS: $R_t$ 3.81, $[M+H]^+$ 334.03).

Example 34

Synthesis of Quinoline-8-carboxylic Acid [3-(1H-benzimidazol-2-yl)-1H-pyrazol-4-yl]-amide

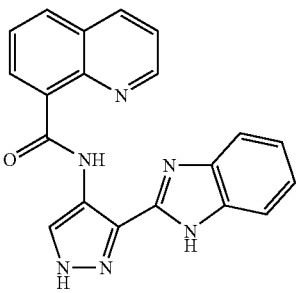

A mixture of quinoline-8-carboxylic acid (104 mg, 0.60 mmol), 3-(1H-benzimidazol-2-yl)-1H-pyrazol-4-ylamine (100 mg, 0.50 mmol), EDC (116 mg, 0.60 mmol) and HOBt (81 mg, 0.60 mmol) was stirred at room temperature in DMF (1.5 ml) for 20 h. The reaction mixture was purified by preparative LC/MS to give quinoline-8-carboxylic acid [3-(1H-benzimidazol-2-yl)-1H-pyrazol-4-yl]-amide (11 mg, 6%) as a brown solid. (LC/MS: $R_t$ 3.85, $[M+H]^+$ 355.11).

Examples 35-67

By following the procedure described in Example 34, but using the appropriate carboxylic acid in place of quinoline-8-carboxylic acid, the following compounds were prepared.

| Example | COMPOUND | $R_t$ | m/z $[M + H]^+$ |
|---|---|---|---|
| 35 | ![structure] | 3.28 | 343.07 |

-continued

| Example | COMPOUND | R$_t$ | m/z [M + H]$^+$ |
|---|---|---|---|
| 36 | | 3.54 | 362.07 |
| 37 | | 4.26 | 384.04 |
| 38 | | 3.51 | 334 |
| 39 | | 2.98 | 294 |
| 40 | | 3.09 | 357 |

-continued
| Example | COMPOUND | R$_t$ | m/z [M + H]$^+$ |
|---|---|---|---|
| 41 | 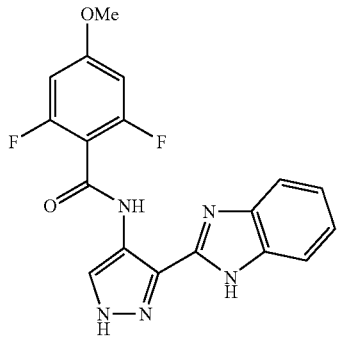 | 3.32 | 370 |
| 42 | 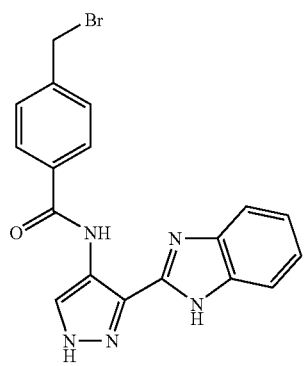 | 3.45 | 397 |
| 43 | 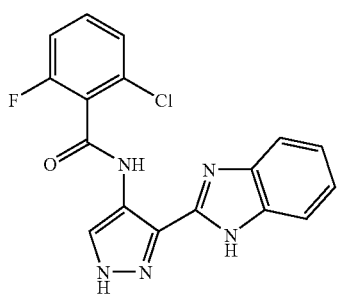 | 3.50 | 356 |
| 44 | 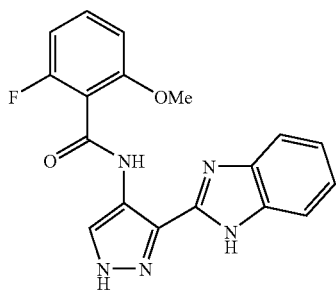 | 3.32 | 352 |

-continued

| Example | COMPOUND | R_t | m/z [M + H]+ |
|---------|----------|-----|--------------|
| 45 | | 3.88 | 352.03 |
| 46 | | 3.07 | 364.06 |
| 47 | | 4.06 | 336.01 |
| 48 | | 2.85 | 403.03 |
| 49 | | 3.58 | 364.11 |

-continued

| Example | COMPOUND | R_t | m/z [M + H]+ |
|---------|----------|-----|--------------|
| 50 | | 4.22 | 343.07 |
| 51 | | 3.91 | 370.07 |
| 52 | | 4.11 | 366.08 |
| 53 | | 3.53 | 346.06 |

-continued

| Example | COMPOUND | $R_t$ | m/z $[M + H]^+$ |
|---|---|---|---|
| 54 | | 3.82 | 384.09 |
| 55 | | 3.77 | 348.10 |
| 56 | | 3.62 | 358.07 |
| 57 | | 3.75 | 352.07 |

-continued

| Example | COMPOUND | R$_t$ | m/z [M + H]$^+$ |
|---|---|---|---|
| 58 | | 3.95 | 340.06 |
| 59 | | 2.96 | 372/374 |
| 60 | | 3.49 | 348.14 |
| 61 | | 4.46 | 406.00 |

-continued
| Example | COMPOUND | R$_t$ | m/z [M + H]$^+$ |
|---|---|---|---|
| 62 | 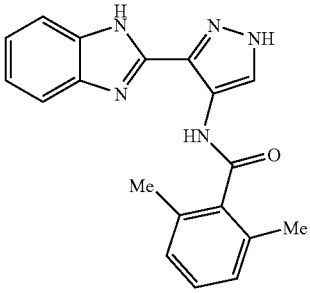 | 3.78 | 332.10 |
| 63 | 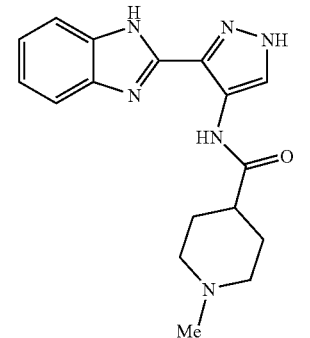 | 0.98 | 325.13 |
| 64 | 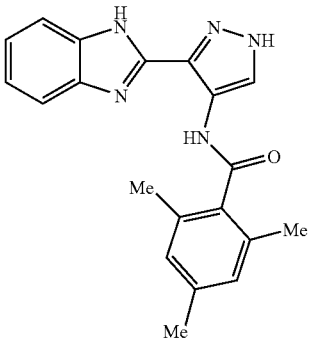 | 4.12 | 346.13 |
| 65 | 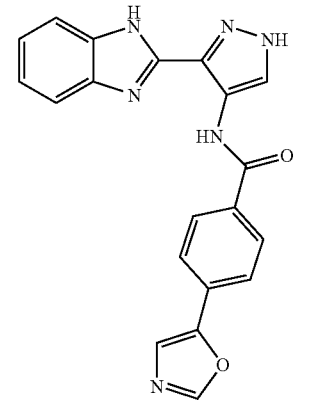 | 3.44 | 371.07 |

-continued
| Example | COMPOUND | $R_t$ | m/z [M + H]⁺ |
|---|---|---|---|
| 66 | 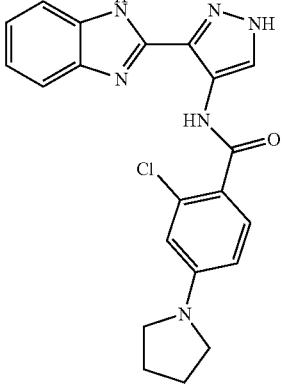 | 4.44 | 407.11 |
| 67 | 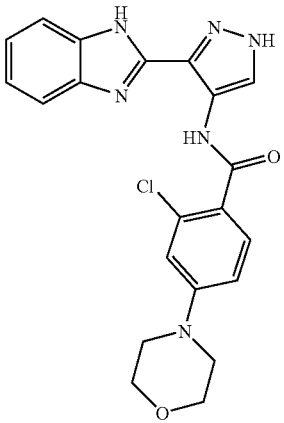 | 3.47 | 423.12 |
Examples 68-70
By following the methods described in Examples 21 and 22, the following compounds were prepared.
| Example | Method | COMPOUND | $R_t$ | m/z [M + H]⁺ |
|---|---|---|---|---|
| 68 | Example 21 | 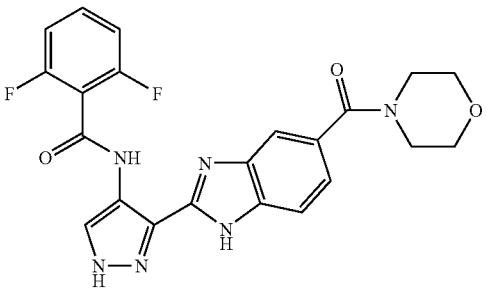 | 2.82 | 453.07 |

| Example | Method | COMPOUND | $R_t$ | m/z [M + H]$^+$ |
|---|---|---|---|---|
| 69 | Example 21 | (structure) | 2.84 | 411.08 |
| 70 | Example 22 | (structure) | 1.91 | 423.14 |

Examples 71-75

General Procedure A

A mixture of 4-(2,6-difluoro-benzoylamino)-1H-pyrazole-3-carboxylic acid (0.134 g, 050 mmol), appropriate benzene-1,2-diamine (0.60 mmol), EDC (0.116 g, 0.60 mmol) and HOBt (0.081 g, 0.60 mmol) in DMF (3 ml) was stirred at ambient temperature for 18 h. The reaction mixture was reduced in vacuo and the residue partioned between ethyl acetate (50 ml) and saturated aqueous sodium bicarbonate solution (50 ml). The organic layer was washed with brine, dried (MgSO$_4$) and reduced in vacuo to give the intermediate amide. Acetic acid (6 ml) was added to the crude amide and the mixture was heated in a microwave (120 W) at 110° C. for 10 min and then reduced in vacuo. The residue was purified by preparative LC/MS to give the desired product.

The following compounds were made using General Procedure A:

| Example | COMPOUND | $R_t$ | m/z [M + H]$^+$ |
|---|---|---|---|
| 71 | (structure) | 3.03 | 376.06 |
| 72 | (structure) | 3.03 | 376.05 |
| 73 | (structure) | 2.79 | 368.17 |

| Example | COMPOUND | R_t | m/z [M + H]+ |
|---|---|---|---|
| 74 | | 2.57 | 398.12 |
| 75 | | 2.52 | 384.09 |

Example 76

Synthesis of 2,6-Difluoro-N-{3-[5-(1-methyl-piperidin-4-yloxy)-1H-benzimidazol-2-yl]-1H-pyrazol-4-yl}-benzamide

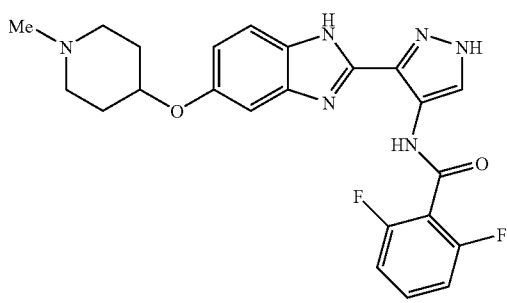

3,4-Dinitrofluorobenzene (1.86 g, 10 mmol) and 4-hydroxy-1-methylpiperidine (1.38 g, 12 mmol) were dissolved in THF (20 ml) and stirred at ambient temperature while sodium hydride (60% dispersion in mineral oil, 0.40 g, 10 mmol) was added in several small portions. The reaction mixture was stirred for one hour and then reduced in vacuo, partitioned between ethyl acetate and water, and the organic phase washed with brine, dried (MgSO$_4$) and reduced in vacuo. The resulting residue was subject to column chromatography, eluting with 5% MeOH/DCM to give a yellow solid (1.76 g, 2:1 ratio of desired 4-(3,4-dinitro-phenoxy)-1-methyl-piperidine and a side product, 4-(4-fluoro-2-nitro-phenoxy)-1-methyl-piperidine).

A sample of the mixture of products obtained (0.562 g) was dissolved in DMF (10 ml) under an atmosphere of nitrogen. The reaction mixture was then shaken under a hydrogen atmosphere for 40 hours, the solids were removed by filtration and the filtrate reduced in vacuo to give a black oil (1:1 mixture of desired 4-(1-methyl-piperidin-4-yloxy)-benzene-1,2-diamine and the reduced side product, 5-fluoro-2-(1-methyl-piperidin-4-yloxy)-phenylamine).

A sample of the black oil (0.221 g) was combined with 4-(2,6-difluoro-benzoylamino)-1H-pyrazole-3-carboxylic acid (0.134 g, 0.50 mmol), EDC (0.116 g, 0.60 mmol) and HOBt (0.081 g, 0.60 mmol) and DMF (3 ml) and the resulting reaction mixture was stirred at ambient temperature for 18 hours. One half of the reaction mixture was subjected to work up conditions: after reducing in vacuo the residue was partitioned between ethyl acetate (50 ml) and saturated aqueous sodium bicarbonate solution (50 ml). The organic layer was washed with brine, dried (MgSO$_4$) and reduced in vacuo to give the intermediate amide. Acetic acid (6 ml) was added to the crude amide and the mixture was heated at reflux for 3.5 hours and then reduced in vacuo. The residue was purified by preparative LC/MS to give the formate salt of 2,6-difluoro-N-{3-[5-(1-methyl-piperidin-4-yloxy)-1H-benzimidazol-2-yl]-1H-pyrazol-4-yl}-benzamide (0.035 g) as a brown solid. (LC/MS: R_t 1.82, [M+H]+ 453.30).

Example 77

Synthesis of N-[3-(4-Chloro-1H-benzimidazol-2-yl)-1H-pyrazol-4-yl]-2,6-difluoro-benzamide 77A. Synthesis of 3-Chloro-benzene-1,2-diamine

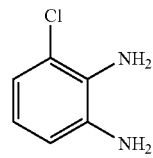

3-Chloro-2-nitro-aniline (0.345 g, 2 mmol) was dissolved in iso-propanol (10 ml) and water (2 ml). Catalytic acetic acid (0.1 ml) was added, followed by Raney nickel (0.02 g, as 50% slurry in H$_2$O) under a flow of nitrogen. The reaction mixture was then shaken under an atmosphere of hydrogen at ambient temperature for 5 hours and the catalyst was removed by filtration under a nitrogen atmosphere. The filtrate was reduced in vacuo, partitioned between ethyl acetate and water, and the organic layer reduced in vacuo to give 3-chloro-benzene-1,2-diamine as a brown oil (0.190 g, 67%). (LC/MS: R_t 1.84, [M+H]+ 143.07).

77B. Synthesis of N-[3-(4-Chloro-1H-benzimidazol-2-yl)-1H-pyrazol-4-yl]-2,6-difluoro-benzamide

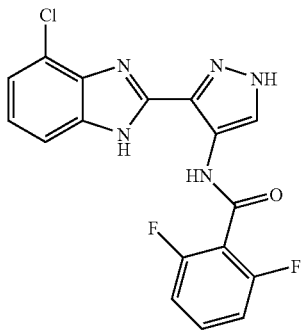

A mixture of 4-(2,6-difluoro-benzoylamino)-1H-pyrazole-3-carboxylic acid (0.134 g, 0.50 mmol), 3-chloro-benzene-1,2-diamine (0.085 g, 0.60 mmol), EDC (0.116 g, 0.60 mmol) and HOBt (0.081 g, 0.60 mmol) in DMF (3 ml) was stirred at ambient temperature for 18 hours. The reaction mixture was reduced in vacuo and the residue partitioned between ethyl acetate (50 ml) and saturated aqueous sodium bicarbonate solution (50 ml). The organic layer was washed with brine, dried (MgSO$_4$) and reduced in vacuo to give the intermediate amide. Acetic acid (5 ml) was added to the crude amide and the mixture was heated at reflux for 3 hours and then reduced in vacuo. The residue was purified by preparative LC/MS to give N-[3-(4-chloro-1H-benzimidazol-2-yl)-1H-pyrazol-4-yl]-2,6-difluoro-benzamide (0.052 g, 28%) as a brown solid. (LC/MS: R$_t$ 3.18, [M+H]$^+$ 374.09).

Examples 78-81

General Procedure B

A mixture of 4-(2,6-difluoro-benzoylamino)-1H-pyrazole-3-carboxylic acid (100 mg, 0.37 mmol), the relevant diamine (1.2 eq.), EDC (1.2 eq.) and HOAt (1.2 eq.) in DMF (1.2 ml) was stirred at ambient temperature for 16 hours. The reaction was worked up by pouring into water and extracting with EtOAc (×2). The combined organic layers were washed with water again, brine and dried over MgSO$_4$. The product was filtered and evaporated to dryness to leave the intermediate amide as a solid. A mixture of this amide in AcOH (2 ml) was heated in a microwave (50 W) at 110° C. until the reaction was complete. The suspension was reduced in vacuo and the residue was purified by prep HPLC.

The following compounds were prepared by General Procedure B:

| Example | Compound | m/z [M + H]$^+$ |
|---|---|---|
| 78 | 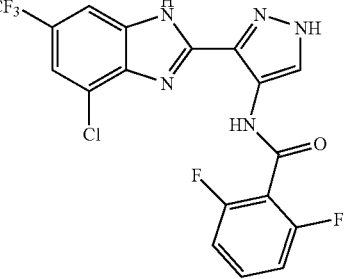 | 442, RT 3.51 min |
| 79 | 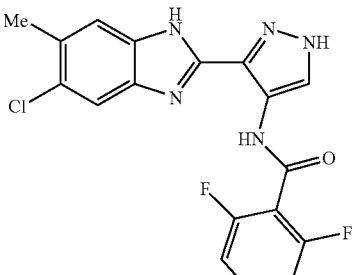 | 389, RT 3.33 min |
| 80 | 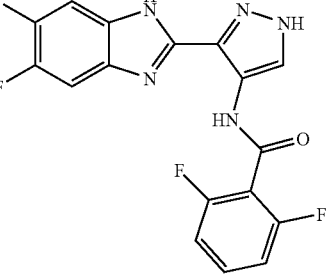 | 392/394, RT 3.24 min |
| 81 | 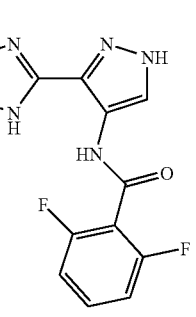 | 376, RT 3.09 min |

Examples 82-86

General Procedure C

A mixture of 4-(2,6-difluoro-benzoylamino)-1H-pyrazole-3-carboxylic acid (150 mg, 0.56 mmol), the relevant diamine (1.1 eq.), EDC (1.2 eq.) and HOBt (1.2 eq.) in DMF (4 ml) was stirred at ambient temperature for 16 hours and then reduced in vacuo. The residue was partitioned between EtOAc and saturated aqueous NaHCO$_3$ and the organic portion washed with water, dried (MgSO$_4$) and reduced in vacuo. The residue was taken up in AcOH (4 ml) and heated in a microwave (100 W) at 120° C. for 10 minutes. The mixture was reduced in vacuo and purified by preparative HPLC.

The following compounds were prepared by General Procedure C:

| Example | Compound | m/z [M + H]$^+$ |
|---|---|---|
| 82 | 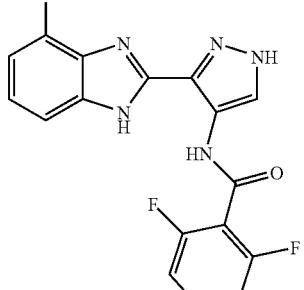 | 354, RT 2.88 min |

135
-continued

| Example | Compound | m/z [M + H]+ |
|---|---|---|
| 83 | | 400, RT 2.16 min |
| 84 | | 354, RT 2.78 min |
| 85 | | 420, RT 3.22 min |
| 86 | | 398, RT 2.42 min |

136

Example 87

Synthesis of 1-[3-(1H-Benzimidazol-2-yl)-1H-pyrazol-4-yl]-3-tert-butyl-urea

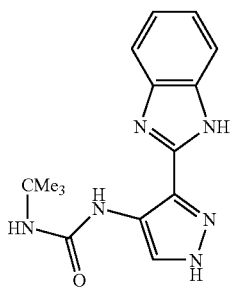

A mixture or 3-(1H-Benzimidazol-2-yl)-1H-pyrazol-4-ylamine (100 mg, 0.50 mmol), tert-butyl isocyanate (60 ul, 0.60 mmol) in DMF (5 ml) was stirred at ambient temperature for 4 h. The mixture was reduced in vacuo. The residue was purified by preparative LC/MS, and following evaporation, gave 52 mg of the title compound as a white solid (35%). (LC/MS: $R_t$ 2.61, [M+H]+ 299.15).

Example 88

Synthesis of 1-[3-(1H-Benzimidazol-2-yl)-1H-pyrazol-4-yl]-3-(2,6-difluoro-phenyl)-urea

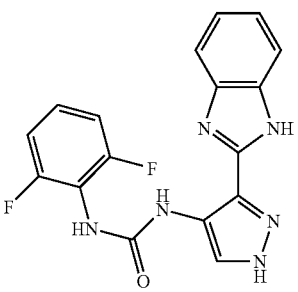

The compound was prepared in a manner analogous to Example 87, but using 2,6-difluorophenyl isocyanate to give the title compound as a white solid (15 mg). (LC/MS: $R_t$ 2.82, [M+H]+ 355).

Example 89

Synthesis of 2,6-Difluoro-N-{3-[5-(4-isopropyl-piperazine-1-carbonyl)-1H-benzimidazol-2-yl]-1H-pyrazol-4-yl}-benzamide

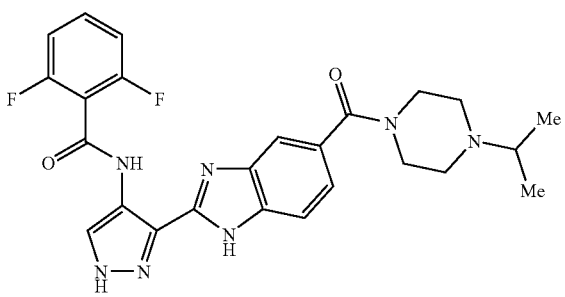

The compound was prepared in a manner analogous to Example 21 but using 1-isopropylpiperazine as the amine fragment to give 2,6-difluoro-N-{3-[5-(4-isopropyl-piperazine-1-carbonyl)-1H-benzimidazol-2-yl]-1H-pyrazol-4-yl}-benzamide as a yellow solid (63 mg). (LC/MS: $R_t$ 1.87, $[M+H]^+$ 494.18).

Example 90

Synthesis of 2,6-Difluoro-N-{3-[5-(pyrrolidine-1-carbonyl)-1H-benzimidazol-2-yl]-1H-pyrazol-4-yl}-benzamide

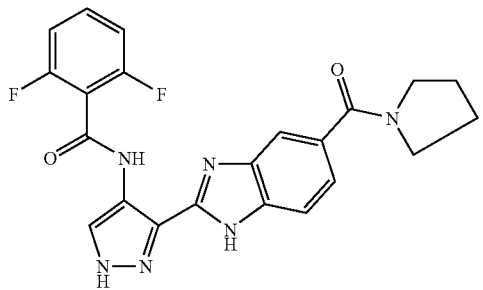

The compound was prepared in a manner analogous to Example 21 but using pyrrolidine as the amine fragment to give 2,6-difluoro-N-{3-[5-(pyrrolidine-1-carbonyl)-1H-benzimidazol-2-yl]-1H-pyrazol-4-yl}-benzamide as a white solid (17 mg). (LC/MS: $R_t$ 3.03, $[M+H]^+$ 437.16).

Example 91

Synthesis of 2,6-Difluoro-N-[3-(5-hydroxy-1H-benzimidazol-2-yl)-1H-pyrazol-4-yl]-benzamide

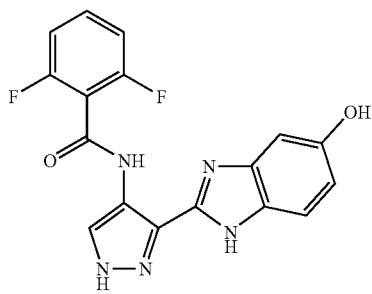

A mixture of 2,6-difluoro-N-[3-(5-methoxy-1H-benzimidazol-2-yl)-1H-pyrazol-4-yl]-benzamide (Example 27) (850 mg) and aluminium (III) chloride (220 mg) in toluene (4 ml) was heated at 80° C. for 3 hours, cooled to ambient temperature and saturated aqueous $NaHCO_3$ (4 ml) followed by 5% aqueous citric acid (4 ml) added. The mixture was extracted with EtOAc and organic extract washed with brine, dried ($MgSO_4$) and reduced in vacuo. Residue submitted for preparative LC/MS to give 2,6-difluoro-N-[3-(5-hydroxy-1H-benzimidazol-2-yl)-1H-pyrazol-4-yl]-benzamide (22 mg) as a beige solid. (LC/MS: $R_t$ 2.01, $[M+H]^+$ 356.09).

Example 92

Synthesis of 2,6-Difluoro-N-{3-[5-hydroxy-4-(4-methyl-piperazin-1-ylmethyl)-1H-benzimidazol-2-yl]-1H-pyrazol-4-yl}-benzamide

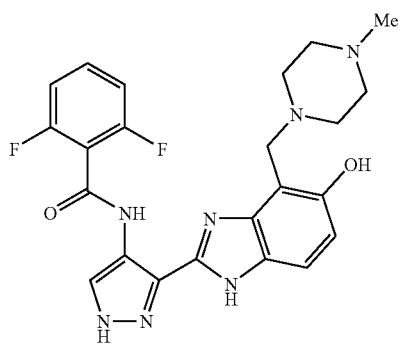

A mixture of 2,6-difluoro-N-[3-(5-hydroxy-1H-benzimidazol-2-yl)-1H-pyrazol-4-yl]-benzamide (50 mg), 37% aqueous formaldehyde (1 ml) and N-methylpiperazine (150 µL) in benzene (1 ml) was heated in a microwave at 100° C. and 50 W for 10 minutes, reduced in vacuo and submitted to preparative LC/MS for purification to give 2,6-difluoro-N-{3-[5-hydroxy-4-(4-methyl-piperazin-1-ylmethyl)-1H-benzimidazol-2-yl]-1H-pyrazol-4-yl}-benzamide (7 mg) as a yellow solid. (LC/MS: $R_t$ 1.98, $[M+H]^+$ 468.19).

Example 93

Synthesis of 2,6-Difluoro-N-[3-(5-hydroxy-4-morpholin-4-ylmethyl-1H-benzimidazol-2-yl)-1H-pyrazol-4-yl]-benzamide

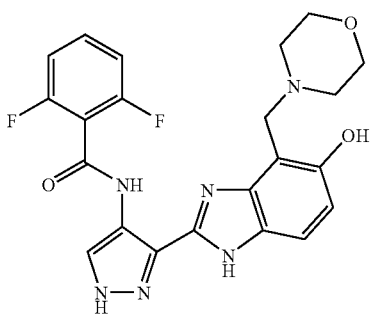

The compound was prepared in a manner analogous to Example 92, but using morpholine as the amine fragment to give 2,6-difluoro-N-[3-(5-hydroxy-4-morpholin-4-ylmethyl-1H-benzimidazol-2-yl)-1H-pyrazol-4-yl]-benzamide (14 mg) as a yellow solid. (LC/MS: $R_t$ 1.82, $[M+H]^+$ 455.13).

Example 94

Synthesis of 2,6-Dichloro-N-[3-(5-morpholin-4-ylmethyl-1H-benzimidazol-2-yl)-1H-pyrazol-4-yl]-benzamide

94A. Synthesis of (3,4-Dinitro-phenyl)-morpholin-4-yl-methanone

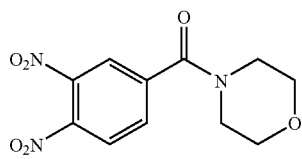

A mixture of 3,4-dinitrobenzoic acid (10.0 g) and thionyl chloride (30 ml) was heated at reflux for 2 hours, cooled to ambient temperature and excess thionyl chloride removed through azeotrope with toluene. The residue was taken up in THF (100 ml) and morpholine (4.1 ml) and Et$_3$N (7.2 ml) added concurrently to the mixture at 0° C. The mixture was stirred for 3 hours, water (100 ml) added and then extracted with EtOAc. The organic portion was washed with brine, dried (MgSO$_4$) and reduced in vacuo. Recrystallisation of the residue from MeOH gave (3,4-dinitro-phenyl)-morpholin-4-yl-methanone (8.23 g) as a yellow solid. ($^1$H NMR (300 MHz, DMSO-d$_6$) δ 8.3 (d, 1H), 8.3 (s, 1H), 8.0 (d, 1H), 3.7-3.5 (m, 8H)).

94B. Synthesis of (3,4-Diamino-phenyl)-morpholin-4-yl-methanone

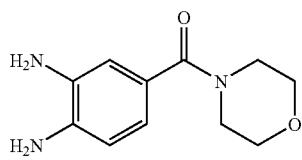

A mixture of (3,4-dinitro-phenyl)-morpholin-4-yl-methanone (1.0 g) and 10% Pd/C (150 mg) in MeOH (30 ml) was shaken under a hydrogen atmosphere at ambient temperature for 10 hours, then filtered through a plug of Celite and reduced in vacuo to give (3,4-diamino-phenyl)-morpholin-4-yl-methanone (900 mg). ($^1$H NMR (300 MHz, DMSO-d$_6$) δ 6.6 (s, 1H), 6.5 (s, 2H), 4.8 (s, 1.5H), 4.6 (s, 1.5H), 4.1 (s, 1H), 3.6 (m, 4H), 3.4 (m, 4H)).

94C. Synthesis of 4-Morpholin-4-ylmethyl-benzene-1,2-diamine

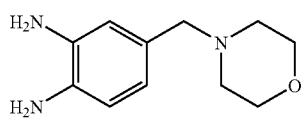

To a mixture of (3,4-dinitro-phenyl)-morpholin-4-yl-methanone (2.84 g) in dry THF (50 ml) was added NaBH$_4$ (954 mg) followed drop-wise by BF$_3$.Et$_2$O (3.2 ml). The mixture was stirred at ambient temperature for 3 hours and then quenched though addition of MeOH. The mixture was reduced in vacuo, partitioned between EtOAc and water and the organic portion washed with brine, dried (MgSO$_4$) and reduced in vacuo. The residue was purified via flash column chromatography eluting with EtOAc to give 4-(3,4-dinitro-benzyl)-morpholine (1.08 g).

A mixture of 4-(3,4-dinitro-benzyl)-morpholine (550 mg) and 10% Pd/C (75 mg) in MeOH (10 ml) was shaken under a hydrogen atmosphere at ambient temperature for 4 hours, then filtered through a plug of Celite and reduced in vacuo to give 4-morpholin-4-ylmethyl-benzene-1,2-diamine (483 mg) as the major component of a mixture.

94D. Synthesis of 4-(2,6-Dichloro-benzoylamino)-1H-pyrazole-3-carboxylic Acid

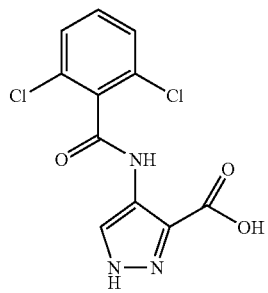

Thionyl chloride (0.65 ml) was added to 2,6-dichlorobenzoic acid (825 mg) and the mixture heated at 70° C. for 2 hours. The mixture was allowed to cool and excess thionyl chloride removed through azeotrope with toluene. The residue was taken up in THF (30 ml) and 4-amino-1H-pyrazole-3-carboxylic acid methyl ester (609 mg) and Et$_3$N (0.75 ml) added concurrently to the mixture at 0° C. The mixture was stirred for 4 hours, water (100 ml) added and then extracted with EtOAc. The organic portion was washed with brine, dried (MgSO$_4$) and reduced in vacuo to give 4-(2,6-dichloro-benzoylamino)-1H-pyrazole-3-carboxylic acid methyl ester (1.23 g) as a red solid. (LC/MS: R$_t$ 3.05, [M+H]$^+$ 313.96).

A mixture of 4-(2,6-dichloro-benzoylamino)-1H-pyrazole-3-carboxylic acid methyl ester (1.21 g) in 2 M aqueous NaOH/MeOH (1:1, 50 ml) was stirred at ambient temperature for 14 hours. Volatile materials were removed in vacuo, water (100 ml) added and the mixture taken to pH 5 using 1M aqueous HCl. The resultant precipitate was collected by filtration and dried through azeotrope with toluene to afford 4-(2,6-dichloro-benzoylamino)-1H-pyrazole-3-carboxylic acid as a beige solid (790 mg). (LC/MS: R$_t$ 2.53, [M+H]$^+$ 299.95).

94E. Synthesis of 2,6-Dichloro-N-[3-(5-morpholin-4-ylmethyl-1H-benzimidazol-2-yl)-1H-pyrazol-4-yl]-benzamide

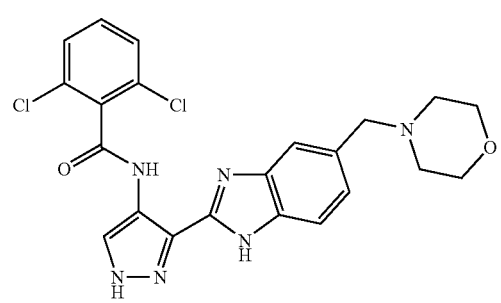

A mixture of 4-(2,6-dichloro-benzoylamino)-1H-pyrazole-3-carboxylic acid (75 mg, 0.25 mmol), 4-morpholin-4-ylmethyl-benzene-1,2-diamine (52 mg, 0.25 mmol), EDC (58 mg, 0.3 mmol) and HOBt (41 mg, 0.3 mmol) in DMF (4 ml) was stirred at ambient temperature for 48 hours. The mixture was partitioned between EtOAc and saturated aqueous NaHCO$_3$ and the organic portion washed with saturated aqueous NH$_4$Cl, dried (MgSO$_4$) and reduced in vacuo. The residue was taken up in AcOH and heated at 100° C. for 14 hours. cooled to ambient temperature and reduced in vacuo. The residue was purified via flash column chromatography eluting with CH$_2$Cl$_2$-MeOH (20:1-10:1) to give 2,6-dichloro-N-[3-(5-morpholin-4-ylmethyl-1H-benzimidazol-2-yl)-1H-pyrazol-4-yl]-benzamide (30 mg) as a pink solid. (LC/MS: R$_t$ 2.12, [M+H]$^+$ 471.14).

Example 95

Synthesis of 2-Chloro-6-fluoro-N-[3-(5-morpholin-4-ylmethyl-1H-benzimidazol-2-yl)-1H-pyrazol-4-yl]-benzamide 95A. Synthesis of 4-(2-Chloro-6-fluoro-benzoylamino)-1H-pyrazole-3-carboxylic Acid

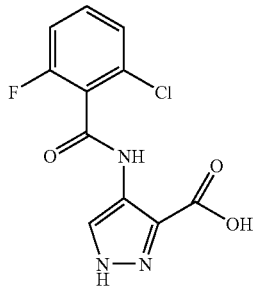

The compound was prepared in a manner analogous to 4-(2,6-difluoro-benzoylamino)-1H-pyrazole-3-carboxylic acid (Example 16D), but using 2-chloro-6-fluorobenzoic acid as the starting acid to give 4-(2-chloro-6-fluoro-benzoylamino)-1H-pyrazole-3-carboxylic acid (4.42 g) as a pale blue solid. (LC/MS: R$_t$ 2.35, [M+H]$^+$ 283.94).

95B. Synthesis of 2-Chloro-6-fluoro-N-[3-(5-morpholin-4-ylmethyl-1H-benzimidazol-2-yl)-1H-pyrazol-4-yl]-benzamide

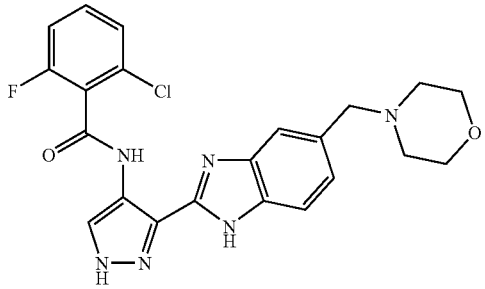

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using 4-(2-chloro-6-fluoro-benzoylamino)-1H-pyrazole-3-carboxylic acid, to give 2-chloro-6-fluoro-N-[3-(5-morpholin-4-ylmethyl-1H-benzimidazol-2-yl)-1H-pyrazol-4-yl]-benzamide (37 mg) as a pink solid. (LC/MS: R$_t$ 2.04, [M+H]$^+$ 455.18).

Example 96

Synthesis of 2,6-Difluoro-4-methoxy-N-[3-(5-morpholin-4-ylmethyl-1H-benzimidazol-2-yl)-1H-pyrazol-4-yl]-benzamide 96A. Synthesis of 4-(2,6-Difluoro-4-methoxy-benzoylamino)-1H-pyrazole-3-carboxylic Acid

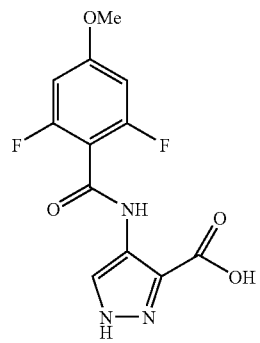

The compound was prepared in a manner analogous to 4-(2,6-difluoro-benzoylamino)-1H-pyrazole-3-carboxylic acid (Example 16D), but using 2,6-difluoro-4-methoxybenzoic acid as the starting acid, to give 4-(2,6-difluoro-4-methoxy-benzoylamino)-1H-pyrazole-3-carboxylic acid (1.58 g) as a white solid. ($^1$H NMR (300 MHz, DMSO-d$_6$) δ 13.0 (s, 2H), 10.7 (s, 1H), 8.0 (s, 1H), 6.9 (s, 1H), 6.8 (s, 1H), 3.7 (s, 3H)).

96B. Synthesis of 2,6-Difluoro-4-methoxy-N-[3-(5-morpholin-4-ylmethyl-1H-benzimidazol-2-yl)-1H-pyrazol-4-yl]-benzamide

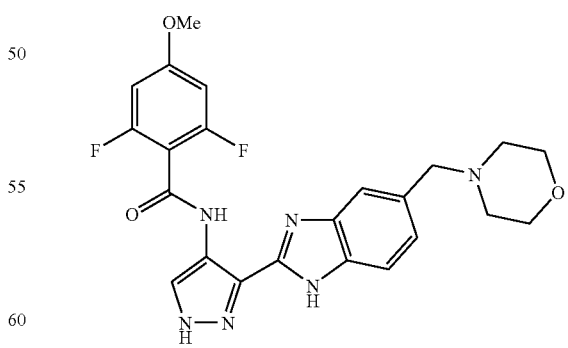

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using 4-(2,6-difluoro-4-methoxy-benzoylamino)-1H-pyrazole-3-carboxylic acid to give 2,6-difluoro-4-methoxy-N-[3-

(5-morpholin-4-ylmethyl-1H-benzimidazol-2-yl)-1H-pyrazol-4-yl]-benzamide (32 mg) as a pink solid. (LC/MS: R$_t$ 1.99, [M+H]$^+$ 469.21).

Example 97

Synthesis of 2,3-Dihydro-benzo[1,4]dioxine-5-carboxylic acid [3-(5-morpholin-4-ylmethyl-1H-benzimidazol-2-yl)-1H-pyrazol-4-yl]-amide

97A. Synthesis of 4-[(2,3-Dihydro-benzo[1,4]dioxine-5-carbonyl)-amino]-1H-pyrazole-3-carboxylic Acid

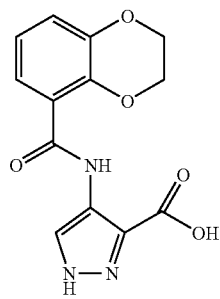

The compound was prepared in a manner analogous to 4-(2,6-difluoro-benzoylamino)-1H-pyrazole-3-carboxylic acid (Example 16D), but using 2,3-dihydro-benzo[1,4]dioxine-5-carboxylic acid as the starting acid to give 4-[(2,3-dihydro-benzo[1,4]dioxine-5-carbonyl)-amino]-1H-pyrazole-3-carboxylic acid (340 mg) as a white solid. ($^1$H NMR (300 MHz, DMSO-d$_6$) δ 13.5 (s, 2H), 11.2 (s, 1H), 8.4 (s, 1H), 7.7 (d, 1H), 7.1 (d, 1H), 7.0 (t, 1H), 4.5 (s, 2H), 4.4 (s, 2H)).

97B. Synthesis of 2,3-Dihydro-benzo[1,4]dioxine-5-carboxylic Acid [3-(5-morpholin-4-ylmethyl-1H-benzimidazol-2-yl)-1H-pyrazol-4-yl]-amide

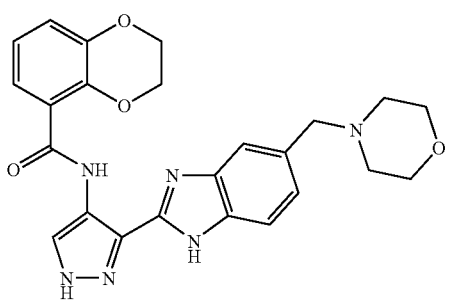

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using 4-[(2,3-dihydro-benzo[1,4]dioxine-5-carbonyl)-amino]-1H-pyrazole-3-carboxylic acid to give 2,3-dihydro-benzo[1,4]dioxine-5-carboxylic acid [3-(5-morpholin-4-ylmethyl-1H-benzimidazol-2-yl)-1H-pyrazol-4-yl]-amide (39 mg) as a pink solid. (LC/MS: R$_t$ 1.99, [M+H]$^+$ 461.23).

Example 98

Synthesis of 2,6-Dichloro-N-{3-[5-(morpholine-4-carbonyl)-1H-benzimidazol-2-yl]-1H-pyrazol-4-yl}-benzamide

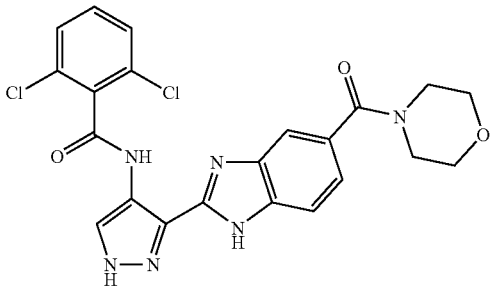

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using (3,4-diamino-phenyl)-morpholin-4-yl-methanone (Example 94B) to give 2,6-dichloro-N-{3-[5-(morpholine-4-carbonyl)-1H-benzimidazol-2-yl]-1H-pyrazol-4-yl}-benzamide (17 mg) as a beige solid. (LC/MS: R$_t$ 2.98, [M+H]$^+$ 485.13).

Example 99

Synthesis of 2-Chloro-6-fluoro-N-{3-[5-(morpholine-4-carbonyl)-1H-benzimidazol-2-yl]-1H-pyrazol-4-yl}-benzamide

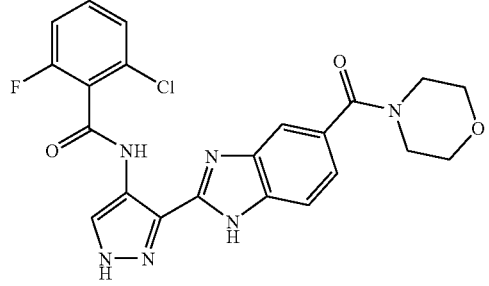

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using 4-(2-chloro-6-fluoro-benzoylamino)-1H-pyrazole-3-carboxylic acid (Example 95A) and (3,4-diamino-phenyl)-morpholin-4-yl-methanone (Example 94B) to give 2-chloro-6-fluoro-N-{3-[5-(morpholine-4-carbonyl)-1H-benzimidazol-2-yl]-1H-pyrazol-4-yl}-benzamide (18 mg) as a beige solid. (LC/MS: R$_t$ 2.89, [M+H]$^+$ 469.15).

Example 100

Synthesis of 2,6-Difluoro-4-methoxy-N-{3-[5-(morpholine-4-carbonyl)-1H-benzimidazol-2-yl]-1H-pyrazol-4-yl}-benzamide

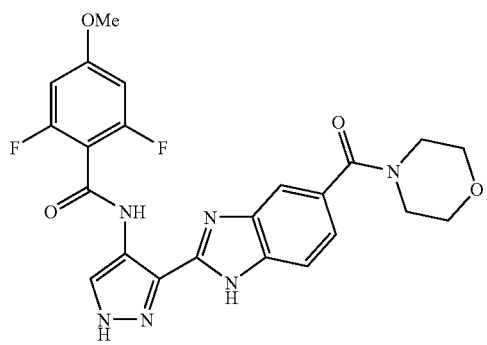

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), however using 4-(2,6-difluoro-4-methoxy-benzoylamino)-1H-pyrazole-3-carboxylic acid (Example 96A) and (3,4-diamino-phenyl)-morpholin-4-yl-methanone (Example 94B) to give 2,6-difluoro-4-methoxy-N-{3-[5-(morpholine-4-carbonyl)-1H-benzimidazol-2-yl]-1H-pyrazol-4-yl}-benzamide (24 mg) as a beige solid. (LC/MS: $R_t$ 2.94, [M+H]$^+$ 483.20).

Example 101

Synthesis of 2,3-Dihydro-benzo[1,4]dioxine-5-carboxylic Acid {3-[5-(morpholine-4-carbonyl)-1H-benzimidazol-2-yl]-1H-pyrazol-4-yl}-amide

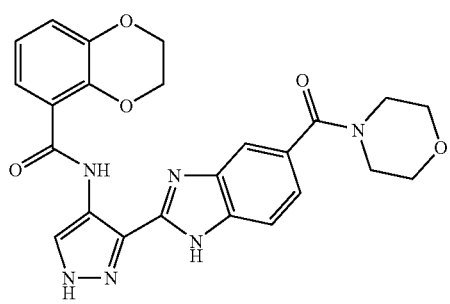

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using 4-[(2,3-dihydro-benzo[1,4]dioxine-5-carbonyl)-amino]-1H-pyrazole-3-carboxylic acid (Example 97A) and (3,4-diamino-phenyl)-morpholin-4-yl-methanone (Example 94B) to give 2,3-dihydro-benzo[1,4]dioxine-5-carboxylic acid {3-[5-(morpholine-4-carbonyl)-1H-benzimidazol-2-yl]-1H-pyrazol-4-yl]-1H-pyrazol-4-yl}-amide (15 mg) as a beige solid. (LC/MS: $R_t$ 2.89, [M+H]$^+$ 475.20).

Example 102

Synthesis of N-[3-(4,6-Bis-trifluoromethyl-1H-benzimidazol-2-yl)-1H-pyrazol-4-yl]-2,6-difluoro-benzamide

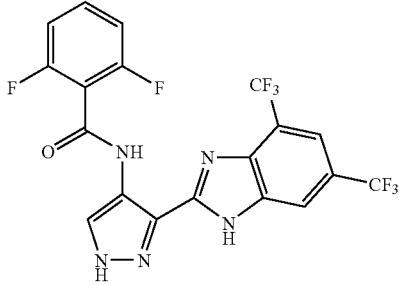

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using 4-(2,6-difluoro-benzoylamino)-1H-pyrazole-3-carboxylic acid (Example 16D) and 3,5-bis(trifluoromethyl)-1,2-diaminobenzene to give N-[3-(4,6-bis-trifluoromethyl-1H-benzimidazol-2-yl)-1H-pyrazol-4-yl]-2,6-difluoro-benzamide (51 mg) as a pink solid. (LC/MS: $R_t$ 3.64, [M+H]$^+$ 476.07).

Example 103

Synthesis of N-[3-(5,6-Dichloro-1H-benzimidazol-2-yl)-1H-pyrazol-4-yl]-2,6-difluoro-benzamide

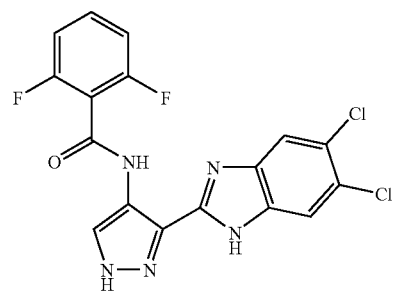

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), however using 4-(2,6-difluoro-benzoylamino)-1H-pyrazole-3-carboxylic acid (Example 16D) and 4,5-dichloro-1,2-phenylene diamine to give N-[3-(5,6-dichloro-1H-benzimidazol-2-yl)-1H-pyrazol-4-yl]-2,6-difluoro-benzamide (29 mg) as a beige solid. (LC/MS: $R_t$ 3.53, [M+H]$^+$ 408.02).

Example 104

Synthesis of N-[3-(4,5-Dimethyl-1H-benzimidazol-2-yl)-1H-pyrazol-4-yl]-2,6-difluoro-benzamide

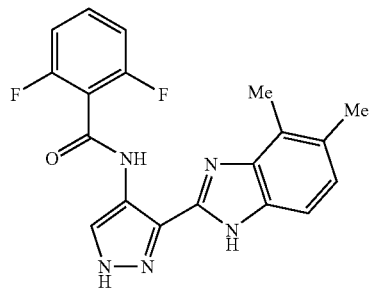

The compound was prepared in a manner analogous to 2,6-dichloro-N-[3-(5-morpholin-4-ylmethyl-1H-benzimidazol-2-yl)-1H-pyrazol-4-yl]-benzamide (Example 94E), but using 4-(2,6-difluoro-benzoylamino)-1H-pyrazole-3-carboxylic acid (Example 16D) and 3,4-dimethyl-1,2-phenylene diamine to give N-[3-(4,5-dimethyl-1H-benzimidazol-2-yl)-1H-pyrazol-4-yl]-2,6-difluoro-benzamide (89 mg) as a pale orange solid. (LC/MS: $R_t$ 2.98, $[M+H]^+$ 368.15).

Example 105

Synthesis of N-[3-(1H-Benzimidazol-2-yl)-1H-pyrazol-4-yl]-2-fluoro-3-pyrrolidin-1-ylmethyl-benzamide

105A. Synthesis of 3-Bromomethyl-2-fluoro-benzoic Acid

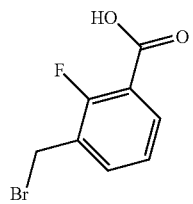

A mixture of 2-fluoro-3-methylbenzoic acid (0.462 g, 3 mmol), N-bromosuccinimide (0.560 g, 3.15 mmol), azobisisobutyronitrile (AIBN) (0.024 g, 0.15 mmol) and $CCl_4$ (10 ml) was heated at reflux for 18 h. The reaction mixture was then reduced in vacuo and partitioned between ethyl acetate and aqueous $K_2CO_3$. The aqueous layer was acidified (2M HCl) and cooled in ice. The precipitate obtained was collected by filtration and dried in vacuo to give 3-bromomethyl-2-fluoro-benzoic acid (0.1225 g, 13%) as a colourless solid. (LC/MS: $R_t$ 3.18, $[M-H]^-$ 232.91).

105B. Synthesis of N-[3-(1H-Benzimidazol-2-yl)-1H-pyrazol-4-yl]-2-fluoro-3-pyrrolidin-1-ylmethyl-benzamide

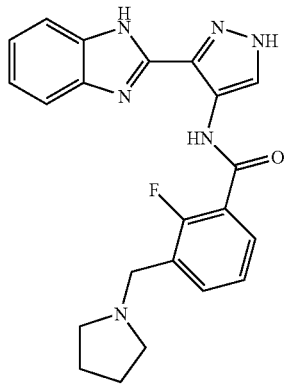

3-Bromomethyl-2-fluoro-benzoic acid (0.058 g, 0.25 mmol) and pyrrolidine (0.036 g, 0.5 mmol) were stirred at ambient temperature for 18 h. The reaction mixture was then azeotroped three times with toluene, acidified with 2M HCl and azeotroped a further three times with toluene to give 2-fluoro-3-pyrrolidin-1-ylmethyl-benzoic acid as its HCl salt. This was combined with 3-(1H-benzimidazol-2-yl)-1H-pyrazol-4-ylamine (0.050 g, 0.25 mmol), EDC (0.048 g, 0.25 mmol) and HOBt (0.032 g, 0.25 mmol) and the reaction mixture was stirred at ambient temperature in DMF (0.5 ml) for 20 h. The reaction mixture was purified by preparative LC/MS to give N-[3-(1H-benzimidazol-2-yl)-1H-pyrazol-4-yl]-2-fluoro-3-pyrrolidin-1-ylmethyl-benzamide (0.015 g, 15%) as a brown solid. (LC/MS: $R_t$ 1.79, $[M+H]^+$ 405.13).

Example 106

Synthesis of N-[3-(1H-Benzimidazol-2-yl)-1H-pyrazol-4-yl]-3-pyrrolidin-1-ylmethyl-benzamide

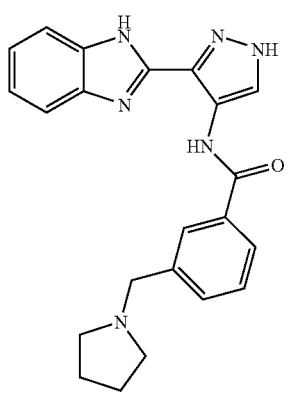

Methyl-3-(bromomethyl)benzoate (0.115 g, 0.5 mmol), pyrrolidine (0.036 g, 0.5 mmol) and $K_2CO_3$ (0.069 g, 0.5 mmol) were dissolved in DMF (2.5 ml) and stirred at reflux for 18 h. The reaction mixture was the reduced in vacuo and subject to column chromatography eluting with hexane ethyl acetate (1:1) to give the crude 3-pyrrolidin-1-ylmethyl-benzoic acid methyl ester, which was added to a solution of LiOH (0.014 g, 0.33 mmol) in 1:1 THF:H$_2$O (1 ml). The reaction mixture was stirred at ambient temperature for 18 h, reduced in vacuo and dried through azeotrope with toluene (×3). The resulting solid was dissolved in water (1 ml), acidified with 2M HCl (1 ml), reduced in vacuo and dried through azeotrope with toluene (×3) to give a clear, pale yellow gel. This was combined with 3-(1H-benzimidazol-2-yl)-1H-pyrazol-4-ylamine (0.050 g, 0.25 mmol), EDC (0.058 g, 0.30 mmol) and HOBt (0.041 g, 0.30 mmol) and the reaction mixture was stirred at ambient temperature in DMSO (0.75 ml) for 64 h. The reaction mixture was purified by preparative LC/MS to give the formate salt of N-[3-(1H-benzimidazol-2-yl)-1H-pyrazol-4-yl]-3-pyrrolidin-1-ylmethyl-benzamide (0.018 g, 9% over 3 steps) as a buff coloured solid. (LC/MS: R$_t$ 1.86, [M+H]$^+$ 387.16).

Examples 107-125

General Procedure D

A mixture of the relevant carboxylic acid (1.2 eq.), EDC (1.2 eq.), HOAt (1.2 eq.) in DMSO (1 ml) was added 3-(1H-benzimidazol-2-yl)-1H-pyrazol-4-ylamine (50 mg). The reaction was stirred at room temperature for 16 hours. The product was purified by prep HPLC.

The following compounds were prepared by General Procedure D:

| Example | Compound | m/z [M + H]$^+$ |
|---------|----------|-----------------|
| 107 | | 294, RT 3.11 min |
| 108 | | 310, RT 3.48 min |
| 109 | | 324, RT 3.96 min |
| 110 | | 308, RT 3.54 min |
| 111 | | 376, RT 4.25 min |
| 112 | | 309, RT 3.35 min |
| 113 | | 293, RT 2.40 min |

| Example | Compound | m/z [M+H]+ |
|---|---|---|
| 114 | | 364, RT 4.94 min |
| 115 | | 377, RT 4.15 min |
| 116 | | 340, RT 3.49 min |
| 117 | | 339, RT 3.35 min |
| 118 | | 323, RT 2.70 min |
| 119 | | 311, RT 2.55 min |
| 120 | | 308, RT 2.81 min |
| 121 | | 407, RT 1.67 min |
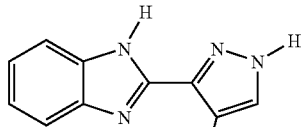

-continued

| Example | Compound | m/z [M + H]+ |
|---------|----------|--------------|
| 122 | | 344, RT 2.45 min |
| 123 | | 386, RT 3.47 min |
| 124 | | 393, RT 1.53 min |
| 125 | | 377, RT 1.57 min |

Example 126

126A. Synthesis of {2-[3-(1H-Benzimidazol-2-yl)-1H-pyrazol-4-ylamino}-carbamic Acid tert-butyl ester

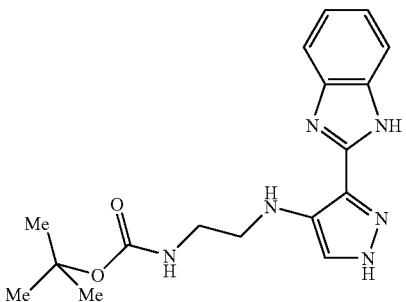

A mixture of 3-(1H-benzimidazol-2-yl)-1H-pyrazol-4-ylamine (250 mg, 1.3 mmol), acetic acid (108 ul, 1.9 mmol), sodium triacetoxy borohydride (401 mg, 1.9 mmol) and tert-butyl-N-(2-oxoethyl)carbamate (301 mg, 1.9 mmol) in dimethyl formamide (10 ml) was stirred at ambient temperature for 4 h. The mixture was reduced in vacuo. The residue was partitioned between ethyl acetate and sodium hydroxide solution (2N). The organic portion was dried ($MgSO_4$), filtered and reduced in vacuo to give 240 mg of the title compound as a colourless oil (56%). (LC/MS: $R_t$ 2.59, [M+H]+ 343.19).

126B Synthesis of N*1*-[3-(H-benzimidazol-2-yl)-1H-pyrazol-4-yl]-ethane-1,2-diamine

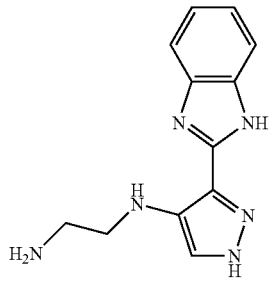

{2-[3-(1H-benzimidazol-2-yl)-1H-pyrazol-4-ylamino]-ethyl}-carbamic acid tert-butyl ester (240 mg, 0.70 mmol) was dissolved in a mixture of trifluoroacetic acid (5 ml) and dichloromethane (5 ml) and stirred at ambient temperature for 1 h. The solvent was reduced in vacuo. The residue was dissolved in a mixture of methanol (10 ml) and toluene (10 ml) and then reduced in vacuo to give 300 mg of the title compound as a di trifluoroacetate salt (91%). (LC/MS: $R_t$ 1.86, [M+H]+ 243.11).

126C. Synthesis of 1-[3-(1H-benzimidazol-2-yl)-1H-pyrazol-4-yl]-imidazolidin-2-one

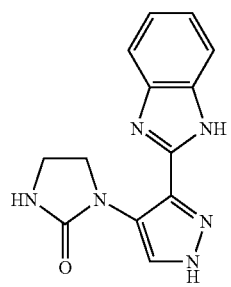

A mixture of N*-1*-[3-(1H-benzimidazol-2-yl)-1H-pyrazol-4-yl]-ethane-1,2-diamine (300 mg, 0.64 mmol), triethylamine (535 ul, 3.84 mmol) and N,N'-carbonyldiimidazole (156 mg, 0.96 mmol) in dichloromethane (10 ml) was stirred at ambient temperature for 1H. The mixture was the partitioned between ethyl acetate and sodium hydroxide solution (2N). The aqueous was saturated with sodium chloride and washed with ethyl acetate (×2). The organic portions were combined, dried (MgSO$_4$), filtered and reduced in vacuo. The residue was purified by preparative LC/MS and following evaporation of product containing fractions gave 8 mg of the title compound as a white solid (5%). (LC/MS: R$_t$ 1.86, [M+H]$^+$ 269.07).

Example 127

Synthesis of [3-(1H-Benzimidazol-2-yl)-1H-pyrazol-4-yl]-pyridin-2-yl-amine

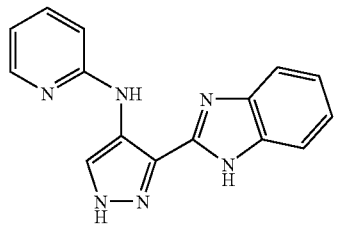

A mixture of 3-(1H-benzimidazol-2-yl)-1H-pyrazol-4-ylamine (150 mg, 0.75 mmol) and 2-fluoropyridine (0.26 ml, 3.0 mmol) was heated in the microwave at 150° C. and 100 W for 15 min. Petroleum ether was added and the solid formed collected by filtration. Recrystallisation from methanol gave [3-(1H-benzimidazol-2-yl)-1H-pyrazol-4-yl]-pyridin-2-yl-amine (12 mg). (LC/MS: R$_t$ 0.91, [M+H]$^+$ 277.00).

Example 128

Synthesis of N-[3-(5,6-Dimethyl-1H-benzimidazol-2-yl)-1H-pyrazol-4-yl]-4-methyl-benzamide 128A. Synthesis of 4-(4-Methyl-benzoylamino)-1H-pyrazole-3-carboxylic Acid

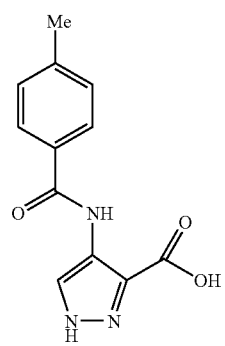

A mixture of p-toluic acid (272 mg), 4-amino-1H-pyrazole-3-carboxylic acid methyl ester (310 mg), EDC (460 mg) and HOBt (324 mg) in DMF (8 ml) was stirred at ambient temperature for 48 h. The mixture was reduced in vacuo, partitioned between EtOAc and saturated aqueous NaHCO$_3$ and then the organic portion washed with brine, dried (MgSO$_4$) and reduced in vacuo to give 4-(4-methyl-benzoylamino)-1H-pyrazole-3-carboxylic acid methyl ester (486 mg).

A mixture of 4-(4-methyl-benzoylamino)-1H-pyrazole-3-carboxylic acid methyl ester (486 mg) in 2 M aqueous NaOH/MeOH (1:1, 50 ml) was stirred at ambient temperature for 14 h. Volatile materials were removed in vacuo, water (100 ml) added and the mixture taken to pH 5 using 2M aqueous HCl. The resultant precipitate was collected by filtration and dried through azeotrope with toluene to afford 4-(4-methyl-benzoylamino)-1H-pyrazole-3-carboxylic acid as a gray solid (345 mg). (LC/MS: R$_t$ 2.35, [M+H]$^+$ 246.09).

128B. Synthesis of N-[3-(5,6-Dimethyl-1H-benzimidazol-2-yl)-1H-pyrazol-4-yl]-4-methyl-benzamide

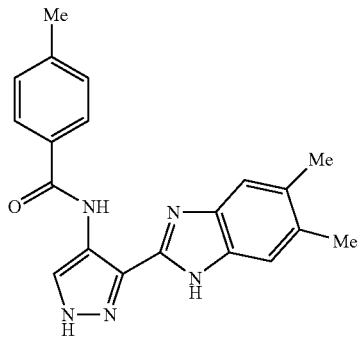

The compound was prepared in a manner analogous to 2,6-dichloro-N-[3-(5-morpholin-4-ylmethyl-1H-benzimidazol-2-yl)-1H-pyrazol-4-yl]-benzamide, however using 4-(4-methyl-benzoylamino)-1H-pyrazole-3-carboxylic acid and 4,5-dimethylbenzene-1,2-diamine to give N-[3-(5,6-dimethyl-1H-benzimidazol-2-yl)-1H-pyrazol-4-yl]-4-methyl-benzamide (32 mg) as a white solid. (LC/MS: R$_t$ 3.42, [M+H]$^+$ 346.26).

Example 129

Synthesis of 2,6-difluoro-N-[3-(5-methanesulphonyl-1H-benzimidazol-2-yl)-1H-pyrazol-4-yl]-benzamide

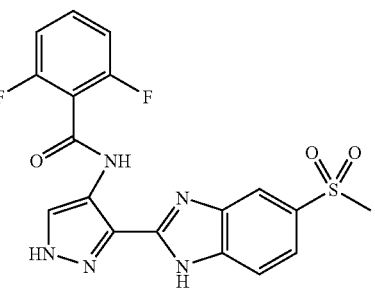

Pd/C (10%, 0.011 g) was added to a solution of 4-methoxysulphonyl-2-nitroaniline (0.108 g, 0.5 mmol) in DMF (5 ml). The reaction mixture was shaken under an atmosphere of hydrogen at ambient temperature for 4 h. Catalyst residues were removed by filtration through celite and the filtrate was reduced in vacuo, and then combined with 4-(2,6-difluoro-benzoylamino)-1H-pyrazole-3-carboxylic acid (0.112 g, 0.42 mmol), EDC (0.096 g, 0.50 mmol) and HOBt (0.068 g, 0.50 mmol) and DMF (4 ml). The reaction mixture was stirred at ambient temperature for 64 h, reduced in vacuo and the residue partitioned between ethyl acetate (50 ml) and saturated aqueous sodium bicarbonate solution (50 ml). The white precipitate formed was isolated by filtration, washed with water (3×25 ml) and dried by azeotrope with toluene to give the intermediate amide. Acetic acid (3 ml) was added to the crude amide and the mixture was heated in a microwave (120° C., 110 W, 40 min). The residue was purified by preparative LC/MS to give 2,6-difluoro-N-[3-(5-methanesulphonyl-1H-benzimidazol-2-yl)-1H-pyrazol-4-yl]-benzamide (0.016 g, 8% over 3 steps) as a colourless solid. (LC/MS: $R_t$ 2.61, $[M+H]^+$ 417.99).

Example 130

Synthesis of 2,6-difluoro-N-{3-[5-(2-piperidin-4-yl-ethoxy)-1H-benzimidazol-2-yl]-1H-pyrazol-4-yl}-benzamide 130A. Synthesis of 4-[2-(3,4-dinitro-phenoxy)-ethyl]-piperidine-1-carboxylic Acid tert-butyl ester Sodium hydride (60% dispersion in mineral oil, 0.096 g, 2.4 mmol) was added in several portions to a solution of N-Boc-4-piperidine ethanol (0.550 g, 2.4 mmol) in THF (20 ml). To this mixture was added a solution of 3,4-dinitrofluorobenzene (0.372 g, 2.0 mmol) and the resultant mixture was stirred at ambient temperature for 16 h. The reaction mixture was diluted with ethyl acetate (100 ml), washed with water (60 ml) and the aqueous phase back extracted with ethyl acetate (3×50 ml). The combined organics were washed with brine (50 ml), dried (MgSO$_4$) and reduced in vacuo. The resulting residue was subjected to column chromatography eluting with a 0-50% gradient of ethyl acetate in petroleum ether. 4-[2-(3,4-dinitro-phenoxy)-ethyl]-piperidine-1-carboxylic acid tert-butyl ester was obtained as a yellow oil (0.361 g, 46%).

130B. Synthesis of 4-[2-(3,4-diamino-phenoxy)-ethyl]-piperidine-1-carboxylic Acid tert-butyl ester 4-[2-(3,4-Dinitro-phenoxy)-ethyl]-piperidine-1-carboxylic acid tert-butyl ester (0.12 g, 0.3 mmol) was dissolved in DMF (3 ml) under an atmosphere of nitrogen. Pd/C (10%, 0.012 g) was added and the reaction mixture was shaken under a hydrogen atmosphere for 24 h. The reaction mixture was diluted with methanol (20 ml) and insoluble material was removed by filtration. The filtrate was reduced in vacuo to give 4-[2-(3,4-diamino-phenoxy)-ethyl]-piperidine-1-carboxylic acid tert-butyl ester as a brown oil (0.101 g, 100%). (LC/MS: $R_t$ 2.21, $[M+H]^+$ 336.16).

130C. Synthesis of 2,6-difluoro-N-{3-[5-(2-piperidin-4-yl-ethoxy)-1H-benzimidazol-2-yl]-1H-pyrazol-4-yl}-benzamide

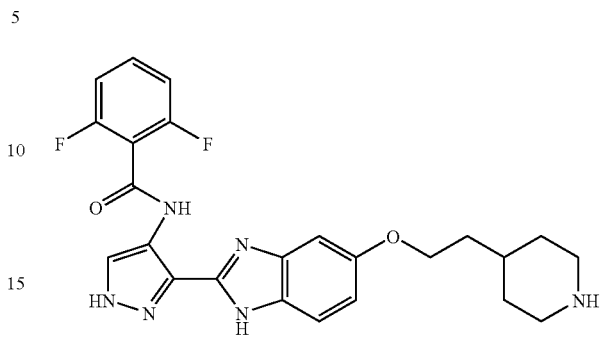

4-[2-(3,4-Diamino-phenoxy)-ethyl]-piperidine-1-carboxylic acid tert-butyl ester (0.101 g, 0.30 mmol), 4-(2,6-difluoro-benzoylamino)-1H-pyrazole-3-carboxylic acid (0.080 g, 0.30 mmol), EDC (0.057 g, 0.30 mmol) and HOBt (0.040 g, 0.30 mmol) were dissolved in DMF (2 ml) and stirred at ambient temperature for 18 hours. The reaction mixture was reduced in vacuo and the residue was partitioned between ethyl acetate (50 ml) and saturated aqueous sodium bicarbonate solution (50 ml). The organic layer was washed with brine, dried (MgSO$_4$) and reduced in vacuo to give the intermediate amide. Acetic acid (3 ml) was added to the crude amide and the mixture was heated in a microwave (120° C., 110 W, 30 min) then reduced in vacuo. Partial Boc-deprotection was observed in situ, and the desired deprotected amine was purified by preparative LC/MS to give the formate salt of 2,6-difluoro-N-{3-[5-(2-piperidin-4-yl-ethoxy)-1H-benzimidazol-2-yl]-1H-pyrazol-4-yl}-benzamide (0.017 g) as a brown oil. (LC/MS: $R_t$ 1.97, $[M+H]^+$ 467.05).

Example 131

Synthesis of N-[3-(6-chloro-4-hydroxymethyl-1H-benzimidazol-2-yl)-1H-pyrazol-4-yl]-2,6-difluoro-benzamide 131A. Synthesis of Acetic Acid 2-acetylamino-5-chloro-benzyl ester 2-Amino-5-chlorobenzyl alcohol (3.0 g, 19 mmol) in acetic anhydride (150 ml) was stirred at ambient temperature for 16 h. Water (50 ml) was added and the mixture stirred for a further 16 h. The reaction mixture was reduced in vacuo, dried by azeotrope with toluene (×2) and further acetic anhydride was added (100 ml). The resultant suspension was stirred for 16 h, then the solids collected by filtration, to give acetic acid 2-acetylamino-5-chloro-benzyl ester as a white solid (4.61 g). (LC/MS: $R_t$ 2.46, $[M-H]^-$ 240.10).

131B. Synthesis of Acetic Acid 2-acetylamino-5-chloro-3-nitro-benzyl ester

Potassium nitrate (1.01 g, 10 mmol) was added to conc. H$_2$SO$_4$ (10 ml) at 0° C. This mixture was stirred at 0° C. for 15 min, then acetic acid 2-acetylamino-5-chloro-benzyl ester (1.92 g, 8 mmol) was added in small portions over 15 min. The reaction mixture was stirred at 0° C. for a further 1 h, and then poured onto crushed ice. The precipitate formed was collected by filtration to give a mixture of isomers, which were separated by column chromatography eluting with a gradient of 0-60% ethyl acetate in petroleum ether to give the desired acetic acid 2-acetylamino-5-chloro-3-nitro-benzyl ester as a yellow solid (0.454 g, 20%).

131C. Synthesis of (2-amino-5-chloro-3-nitro-phenyl)-methanol

Acetic acid 2-acetylamino-5-chloro-3-nitro-benzyl ester (0.454 g, 0.45 mmol) and sodium hydroxide (0.436 g, 11 mmol) were dissolved in methanol-water (1:3, 40 ml) and the resulting solution heated at reflux for 5 h. After cooling the mixture was taken to pH 6 by the addition of conc. HCl. The precipitate formed was collected by filtration to give (2-amino-5-chloro-3-nitro-phenyl)-methanol as a dark orange solid (0.237 g, 73%). (LC/MS: $R_t$ 2.63, $[M–H]^-$ 200.96).

131 D. Synthesis of (2,3-diamino-5-chloro-phenyl)-methanol (2-Amino-5-chloro-3-nitro-phenyl)-methanol (0.202 g, 1 mmol) was suspended in a mixture of iso-propanol (5 ml), water (2 ml), methanol (3 ml) and acetic acid (0.05 ml). Raney Nickel (0.015 g, as a slurry in water) was added carefully under nitrogen. The reaction mixture was shaken under a hydrogen atmosphere for 4 h, then diluted with methanol-water (1:1, 50 ml) and filtered to removed catalyst residues. Volatiles were removed in vacuo, and the remaining aqueous layer extracted with ethyl acetate (4×30 ml). The combined organics were washed with brine, dried (MgSO$_4$) and reduced in vacuo to give (2,3-diamino-5-chloro-phenyl)-methanol as an orange solid (0.144 g, 84%). (LC/MS: $R_t$ 0.85, $[M+H]^+$ 173.03).

131 E. Synthesis of N-[3-(6-chloro-4-hydroxymethyl-1H-benzimidazol-2-yl)-1H-pyrazol-4-yl]-2,6-difluoro-benzamide

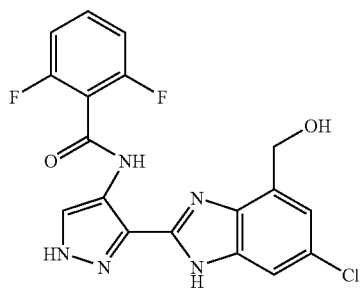

(2,3-Diamino-5-chloro-phenyl)-methanol (0.144 g, 0.84 mmol), 4-(2,6-difluoro-benzoylamino)-1H-pyrazole-3-carboxylic acid (0.187 g, 0.70 mmol), EDC (0.161 g, 0.84 mmol) and HOBt (0.113 g, 0.84 mmol) were dissolved in DMF (5 ml) and stirred at ambient temperature for 18 hours. The reaction mixture was reduced in vacuo and the residue was partitioned between ethyl acetate (50 ml) and saturated aqueous sodium bicarbonate solution (50 ml). The organic layer was washed with brine, dried (MgSO$_4$) and reduced in vacuo to give the intermediate amide. Acetic acid (5 ml) was added to the crude amide and the mixture was heated at reflux for 4 h then reduced in vacuo. The residue was partitioned between ethyl acetate (50 ml) and saturated aqueous sodium bicarbonate solution (50 ml). The organic layer was washed with brine, dried (MgSO$_4$) and reduced in vacuo. The orange solid formed (0.185 g) was taken up in methanol (3 ml) and NaOMe (0.090 g, 1.6 mmol) was added. The mixture was stirred at ambient temperature for 4 h, then reduced in vacuo and partitioned between ethyl acetate (50 ml) and water (50 ml). The organic layer was washed with brine, dried (MgSO$_4$) and reduced in vacuo to give an orange solid, which was purified by column chromatography eluting with a gradient of 0-100% ethyl acetate in petroleum ether. Product containing fractions were reduced in vacuo to give N-[3-(6-chloro-4-hydroxymethyl-1H-benzimidazol-2-yl)-1H-pyrazol-4-yl]-2,6-difluoro-benzamide as an orange-brown solid (0.061 g, 22%). (LC/MS: $R_t$ 2.79, $[M+H]^+$ 403.98).

Example 132

Synthesis of 2,6-Difluoro-N-{3-[5-(4-methyl-piperazine-1-sulphonyl)-1H-benzimidazol-2-yl]-1H-pyrazol-4-yl}-benzamide

132A. Synthesis of 1-(4-chloro-3-nitro-benzenesulphonyl)-4-methyl-piperazine 4-Chloro-3-nitro-benzenesulphonyl chloride (2.56 g, 10 mmol) was added in small portions to a solution of N-methyl piperazine (1.33 ml, 12 mmol) in DCM (25 ml) at 0° C. To this solution was added triethylamine (2.08 ml, 15 mmol) dropwise. The reaction mixture was stirred at ambient temperature for 2 h and then reduced in vacuo. The residue was partitioned between ethyl acetate and water, and the organic layer washed with brine, dried (MgSO$_4$) and reduced in vacuo. Purification with column chromatography eluting with 0-20% methanol in ethyl acetate gave 1-(4-chloro-3-nitro-benzenesulphonyl)-4-methyl-piperazine as an off-white solid (1.84 g, 58%). (LC/MS: $R_t$ 1.84, $[M+H]^+$ 319.97).

132B. Synthesis of benzyl-[4-(4-methyl-piperazine-1-sulphonyl)-2-nitro-phenyl]-amine 1-(4-Chloro-3-nitro-benzenesulphonyl)-4-methyl-piperazine (0.50 g, 1.57 mmol) and benzylamine (0.502 g, 4.70 mmol) were dissolved in THF (10 ml) and heated at reflux for 3 h. The reaction mixture was then reduced in vacuo and partitioned between ethyl acetate and water. The organics were washed with brine, dried (MgSO$_4$) and reduced in vacuo, and the resultant residue purified by column chromatography eluting with 0-10% methanol in ethyl acetate to give benzyl-[4-(4-methyl-piperazine-1-sulphonyl)-2-nitro-phenyl]-amine as a yellow solid (0.53 g, 86%). (LC/MS: $R_t$ 2.21, $[M+H]^+$ 391.05).

132C. Synthesis of 4-(4-methyl-piperazine-1-sulphonyl)-benzene-1,2-diamine

Benzyl-[4-(4-methyl-piperazine-1-sulphonyl)-2-nitro-phenyl]-amine (0.53 g, 1.35 mmol) was dissolved in DMF (15 ml) and Pd/C (10%, 0.05 g) added under nitrogen. The reaction mixture was shaken under a hydrogen atmosphere for 16 h, then diluted with ethyl acetate and filtered through celite. The filtrate was reduced in vacuo to give the partially reduced N-1-benzyl-4-(4-methyl-piperazine-1-sulphonyl)-benzene-1,2-diamine. This crude material was dissolved in ethanol (15 ml), and conc. HCl added (1 ml), followed by Pd/C (10%, 0.05 g). The resultant reaction mixture was shaken under a hydrogen atmosphere for 16 h, diluted with ethyl acetate and filtered through celite washing with methanol. The filtrate was reduced in vacuo and dried by azeotrope with toluene. The residue was partition between ethyl acetate and saturated sodium hydrogen carbonate solution. The organic layer was washed with brine, dried (MgSO$_4$) and reduced in vacuo to give 4-(4-methyl-piperazine-1-sulphonyl)-benzene-1,2-diamine as an off-white solid (0.114 g, 31%). (LC/MS: R$_t$ 0.37, [M+H]$^+$ 271.02).

132D. Synthesis of 2,6-difluoro-N-{3-[5-(4-methyl-piperazine-1-sulphonyl)-1H-benzimidazol-2-yl]-1H-pyrazol-4-yl}-benzamide

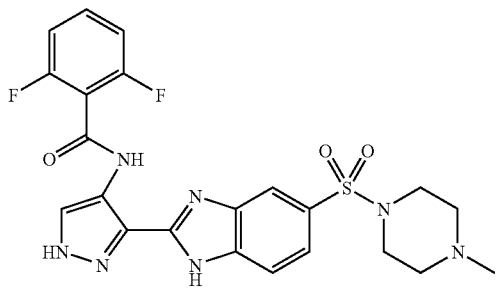

4-(4-Methyl-piperazine-1-sulphonyl)-benzene-1,2-diamine (0.083 g, 0.31 mmol), 4-(2,6-difluoro-benzoylamino)-1H-pyrazole-3-carboxylic acid (0.069 g, 0.26 mmol), EDC (0.060 g, 0.31 mmol) and HOBt (0.041 g, 0.31 mmol) were dissolved in DMF (2 ml) and stirred at ambient temperature for 18 hours. The reaction mixture was reduced in vacuo and the residue was partitioned between ethyl acetate (50 ml) and saturated aqueous sodium bicarbonate solution (50 ml). The organic layer was washed with brine, dried (MgSO$_4$) and reduced in vacuo to give the intermediate amide. Acetic acid (3 ml) was added to the crude amide and the mixture was heated in a microwave (120° C., 110 W, 20 min) then reduced in vacuo. The residue was partitioned between ethyl acetate (50 ml) and water (50 ml). The organic layer was washed with brine, dried (MgSO$_4$), reduced in vacuo and purified by preparative LC/MS to give the formate salt of 2,6-difluoro-N-{3-[5-(4-methyl-piperazine-1-sulphonyl)-1H-benzimidazol-2-yl]-1H-pyrazol-4-yl}-benzamide as a white solid (0.031 g, 20%). (LC/MS: R$_t$ 2.04, [M+H]$^+$ 502.06).

Example 133

Synthesis of 2,6-difluoro-N-{3-[5-(piperidin-4-ylmethoxy)-1H-benzimidazol-2-yl]-1H-pyrazol-4-yl}-benzamide

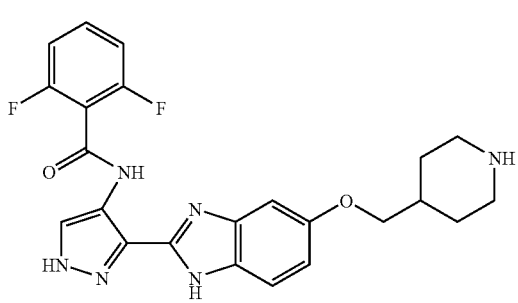

4-{2-[4-(2,6-Difluoro-benzoylamino)-1H-pyrazol-3-yl]-1H-benzimidazol-5-yloxymethyl}-piperidine-1-carboxylic acid tert-butyl ester (0.024 g, 0.043 mmol) (prepared in a manner analogous to Example 130) was treated with 1:1 TFA:DCM (2 ml) for 20 min. The solution was reduced in vacuo and azeotroped with toluene (×3). Purification by preparative LC/MS gave 2,6-difluoro-N-{3-[5-(piperidin-4-ylmethoxy)-1H-benzimidazol-2-yl]-1H-pyrazol-4-yl}-benzamide as a white solid (8 mg, 41%). (LC/MS: R$_t$ 1.99, [M+H]$^+$ 453.06).

Example 134

Synthesis of 2,6-difluoro-N-{3-[5-(1-methyl-piperidin-4-ylmethoxy)-1H-benzimidazol-2-yl]-1H-pyrazol-4-yl}-benzamide 134A: Synthesis of 1-methyl-piperidine-4-carboxylic Acid ethyl ester Thionyl chloride (0.80 ml, 11 mmol) was added dropwise to a suspension of the HCl salt of 1-methyl-piperidine-4-carboxylic acid (1.80 g, 10 mmol) in ethanol (25 ml). The reaction mixture was stirred at ambient temperature overnight, then reduced in vacuo and dried by azeotrope with toluene (×3) to give 1-methyl-piperidine-4-carboxylic acid ethyl ester as a colourless solid (1.7 g, 100%). (LC/MS: R$_t$ 0.41, [M+H]$^+$ 172.08).

134B: Synthesis of (1-Methyl-piperidin-4-yl)-methanol

To an ice-cooled solution of 1-methyl-piperidine-4-carboxylic acid ethyl ester (0.855 g, 5 mmol) in THF (30 ml) was added dropwise a 1M solution of LiAlH$_4$ in THF (20 ml, 20 mmol). The reaction mixture was then stirred for 18 h whilst warming to ambient temperature, and then quenched by careful addition of water (0.75 ml), 10% aqueous NaOH (0.75 ml) then water (3×0.75 ml) and stirred at ambient temperature for 2 h. The resultant mixture was reduced in vacuo, shaken with ethyl acetate and filtered to remove inorganic residues. The filtrate was reduced in vacuo to give (1-methyl-piperidin-4-yl)-methanol as a colourless oil (0.468 g, 73%). (LC/MS: R$_t$ 0.33, [M+H]$^+$ 130.20).

134C: Synthesis of 2,6-difluoro-N-{3-[5-(1-methyl-piperidin-4-ylmethoxy)-1H-benzimidazol-2-yl]-1H-pyrazol-4-yl}-benzamide

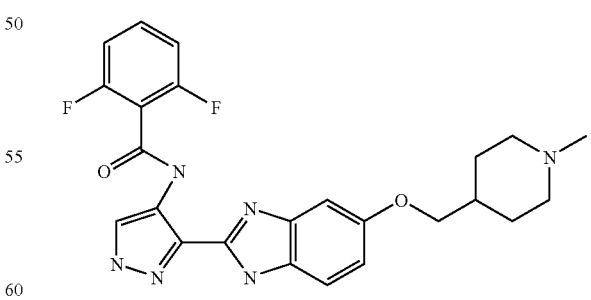

The synthesis of 2,6-difluoro-N-{3-[5-(1-methyl-piperidin-4-ylmethoxy)-1H-benzimidazol-2-yl]-1H-pyrazol-4-yl}-benzamide was carried out in a manner analogous to Example 130 using (1-methyl-piperidin-4-yl)-methanol as the starting alcohol to give the title compound (1.0 mg). (LC/MS: R$_t$ 1.99, [M+H]$^+$ 467.09).

Example 135

Synthesis of 2-[4-(2,6-difluoro-benzoylamino)-1H-pyrazol-3-yl]-6-ethoxy-1H-benzimidazole-5-carboxylic Acid methyl ester

135A. Synthesis of 4,5-dinitro-2-ethoxy-benzoic Acid

To a mixture of potassium nitrate (4.80 g, 47.4 mmol) in concentrated sulphuric acid (20 mL) was added portion-wise at 0° C. 2-ethoxy-4-nitrobenzoic acid (4.00 g, 19.0 mmol). The mixture was stirred at 0° C.-r.t. for 3 h, then poured onto ice (120 mL) and stirred for a further 1 h. The precipitate formed was collected by filtration, washing with water, and dried through azeotrope with toluene to give the title compound (4.28 g) as a white solid. $^1$H NMR (300 MHz, DMSO-$d_6$) δ 8.50 (s, 1H), 7.95 (s, 1H), 4.35 (q, 2H), 1.35 (t, 3H).

135B. Synthesis of 4,5-dinitro-2-ethoxy-benzoic Acid methyl ester

Thionyl chloride (315 μl, 4.30 mmol) was slowly added to a mixture of 4,5-dinitro-2-ethoxy-benzoic acid (1.00 g, 3.91 mmol) in methanol (10 mL) at r.t. The mixture was stirred for 16 h, then reduced in vacuo azeotroping with toluene. The residue was then purified by column chromatography using P.E.-EtOAc (1:0-1:1) to give the title compound (606 mg) as a white solid. $^1$H NMR (300 MHz, DMSO-$d_6$) δ 8.55 (s, 1H), 8.00 (s, 1H), 4.35 (q, 2H), 3.85 (s, 3H), 1.35 (t, 3H).

135C. Synthesis of 4,5-diamino-2-ethoxy-benzoic Acid methyl ester

A mixture of 4,5-dinitro-2-ethoxy-benzoic acid methyl ester (320 mg) and 10% Pd/C (40 mg) in MeOH (8 mL) was stirred under an atmosphere of hydrogen gas for 4 h at r.t., filtered through a plug of Celite and reduced in vacuo to give the title compound (234 mg) as a black gum. $^1$H NMR (300 MHz, MeOD) δ 7.30 (s, 1H), 6.40 (s, 1H), 4.00 (q, 2H), 3.80 (s, 3H), 1.35 (t, 3H).

135D. Synthesis of 2-[4-(2,6-difluoro-benzoylamino)-1H-pyrazol-3-yl]-6-ethoxy-1H-benzimidazole-5-carboxylic Acid methyl ester

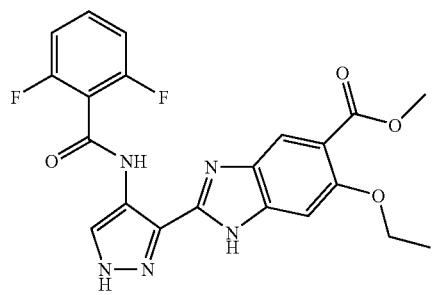

A mixture of 4-(2,6-difluoro-benzoylamino)-1H-pyrazole-3-carboxylic acid (254 mg, 0.95 mmol), 4,5-diamino-2-ethoxy-benzoic acid methyl ester (234 mg, 1.11 mmol), EDC (240 mg, 1.25 mmol) and HOBt (169 mg, 1.25 mmol) in DMF (10 mL) was stirred at r.t. for 14 h. The reaction mixture was reduced in vacuo and the residue partitioned between ethyl acetate and saturated aqueous sodium bicarbonate solution. The organic layer was washed with brine, dried (MgSO$_4$) and reduced in vacuo to give the intermediate amide. Acetic acid (10 mL) was added to the crude amide and the mixture was heated at reflux for 3 hours, allowed to cool to r.t. and then reduced in vacuo. The residue was partitioned between ethyl acetate and saturated aqueous sodium bicarbonate solution and the organic layer then washed with brine, dried (MgSO$_4$) and reduced in vacuo. Water was added to the residue and the solid formed collected by filtration and dried through azeotrope with toluene to give the title compound (182 mg) as a brown solid. (LC/MS: R$_t$ 2.94, [M+H]$^+$ 442.02).

Example 136

Synthesis of N-{3-[6-ethoxy-5-(morpholine-4-carbonyl)-1H-benzimidazol-2-yl]-1H-pyrazol-4-yl}-2,6-difluoro-benzamide

136A. Synthesis of 2-[4-(2,6-difluoro-benzoylamino)-1H-pyrazol-3-yl]-6-ethoxy-1H-benzimidazole-5-carboxylic Acid

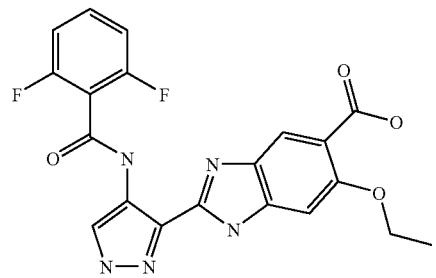

A mixture of 2-[4-(2,6-difluoro-benzoylamino)-1H-pyrazol-3-yl]-6-ethoxy-1H-benzimidazole-5-carboxylic acid methyl ester (90 mg) in MeOH-2M aqueous NaOH (1:1, 10 mL) was stirred at r.t. for 14 h. The MeOH was removed in vacuo and water (30 mL) added. The mixture was taken to pH=3 using 2M aqueous HCl and then extracted with EtOAc (×3). The combined organic extracts were reduced in vacuo and dried through azeotrope with toluene to give the title compound (72 mg) as a gray solid. (LC/MS: R$_t$ 2.70, [M+H]$^+$ 428.04).

136B. Synthesis of N-{3-[6-ethoxy-5-(morpholine-4-carbonyl)-1H-benzimidazol-2-yl]-1H-pyrazol-4-yl}-2,6-difluoro-benzamide

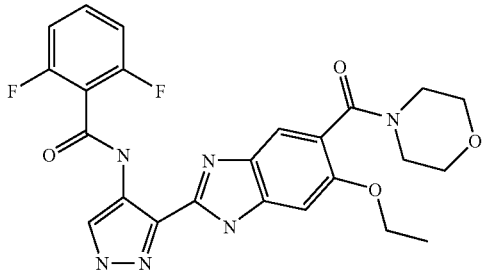

A mixture of 2-[4-(2,6-difluoro-benzoylamino)-1H-pyrazol-3-yl]-6-ethoxy-1H-benzimidazole-5-carboxylic acid (50 mg, 0.12 mmol), morpholine (13 μl, 0.14 mmol), EDC (29 mg, 0.15 mmol) and HOBt (21 mg, 0.15 mmol) in DMF (5 mL) was stirred at r.t. for 48 h. The reaction mixture was reduced in vacuo and the residue partitioned between ethyl acetate and saturated aqueous sodium bicarbonate solution. The organic layer was washed with brine, dried (MgSO$_4$) and reduced in vacuo to give the title compound (29 mg) as a gray solid. (LC/MS: R$_t$ 2.56, [M+H]$^+$ 497.03).

Example 137

Synthesis of 2,6-difluoro-N-[3-(5-piperazin-1-ylmethyl-1H-benzimidazol-2-yl)-1H-pyrazol-4-yl]-benzamide 137A. Synthesis of 4-{2-[4-(2,6-difluoro-benzoylamino)-1H-pyrazol-3-yl]-1H-benzimidazol-5-ylmethyl}-piperazine-1-carboxylic Acid tert-butyl ester

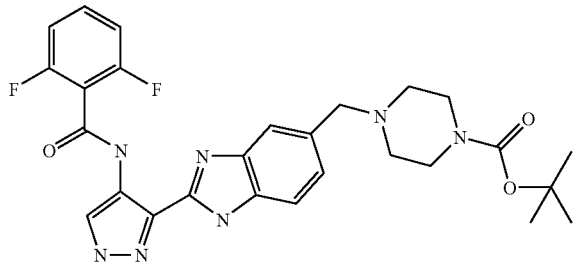

To a mixture of 2,6-difluoro-N-[3-(5-formyl-1H-benzimidazol-2-yl)-1H-pyrazol-4-yl]-benzamide (50 mg, 0.14 mmol) in anhydrous THF (1.5 mL) stirring at ambient temperature was successively added 3 Å molecular sieves, piperazine-1-carboxylic acid tert-butyl ester (52 mg, 0.28 mmol) and sodium triacetoxy borohydride (90 mg, 0.42 mmol). The mixture was stirred for 4 h, MeOH (3 ml) added and then the mixture was reduced in vacuo. The residue was taken up in EtOAc, washed with brine, dried (MgSO$_4$), reduced in vacuo and then purified through preparative LC/MS to give the title compound (84 mg) as a yellow oil. (LC/MS: R$_t$ 2.22, [M+H]$^+$ 538.15).

137B. Synthesis of 2,6-difluoro-N-[3-(5-piperazin-1-ylmethyl-1H-benzimidazol-2-yl)-1H-pyrazol-4-yl]-benzamide

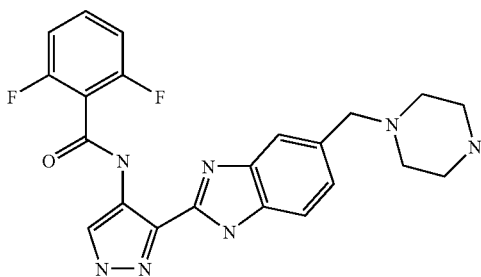

A mixture of 4-{2-[4-(2,6-difluoro-benzoylamino)-1H-pyrazol-3-yl]-1H-benzimidazol-5-ylmethyl}-piperazine-1-carboxylic acid tert-butyl ester (84 mg), MeOH (3 mL) and saturated HCl/EtOAc (3 mL) was stirred at r.t. for 16 h and then reduced in vacuo azeotroping with toluene to give the title compound (21 mg) as a yellow solid. (LC/MS: R$_t$ 1.60, [M+H]$^+$ 438.09).

Example 138

Synthesis of 2-fluoro-6-methoxy-N-[3-(5-morpholin-4-ylmethyl-1H-benzimidazol-2-yl)-1H-pyrazol-4-yl]-benzamide 138A. Synthesis of 4-Nitro-1H-pyrazole-3-carboxylic Acid ethyl ester

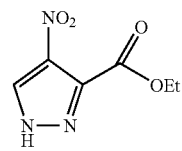

Thionyl chloride (3.8 ml, 52.5 mmol) was added cautiously to a stirred, ice-cold mixture of 4-nitropyrazole-3-carboxylic acid (7.5 g, 47.7 mmol) in EtOH (150 ml), the mixture stirred at ambient temperature for 1 hour then heated at reflux for 3 hours. The reaction mixture was cooled, evaporated in vacuo then azeotroped with toluene to give 4-nitro-1H-pyrazole-3-carboxylic acid ethyl ester (8.8 g).

138B. Synthesis of 1-(4-methoxy-benzyl)-4-nitro-1H-pyrazole-3-carboxylic Acid ethyl ester

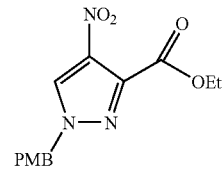

To a solution of 4-nitro-1H-pyrazole-3-carboxylic acid ethyl ester (8.8 g, 47.5 mmol) in MeCN (100 ml) was added K$_2$CO$_3$ (7.9 g, 57.0 mmol) followed by 4-methoxybenzyl chloride (7.1 ml, 52.3 mmol) and the mixture stirred at ambient temperature for 20 hours. The mixture was evaporated in vacuo, the residue partitioned between EtOAc and 2M aqueous hydrochloric acid and the organic portion washed with saturated aqueous sodium hydrogen carbonate, dried (MgSO$_4$) and evaporated in vacuo. The residue was purified by flash column chromatography [SiO$_2$, EtOAc-hexane (1:4)] to give 1-(4-methoxy-benzyl)-4-nitro-1H-pyrazole-3-carboxylic acid ethyl ester (11 g) as a colourless gum.

138C. Synthesis of 1-(4-methoxy-benzyl)-4-nitro-1H-pyrazole-3-carboxylic acid

A mixture of 1-(4-methoxy-benzyl)-4-nitro-1H-pyrazole-3-carboxylic acid ethyl ester (15.9 g, 52 mmol) in 2 M aqueous NaOH/MeOH (1:1, 400 ml) was stirred at ambient temperature for 14 h. Volatile materials were removed in vacuo, the residue dissolved in EtOAc (200 ml), water (100 ml) added and the mixture taken to pH 3 using 1M aqueous HCl. The layers were separated and the organic portion washed with saturated aqueous sodium hydrogen carbonate. EtOAc was added to the aqueous layer which was acidified to pH 3-4, and the combined organic portions dried (MgSO$_4$) and reduced in vacuo to give 1-(4-methoxy-benzyl)-4-nitro-1H-pyrazole-3-carboxylic acid (13 g, 86%) as a white solid. (LC/MS: R$_t$ 2.63, [M+H]$^+$ 292).

138D. Synthesis of 4-(3,4-dinitro-benzyl)-morpholine

To a solution of 3,4-dinitro-phenyl)-morpholin-4-yl-methanone (Example 94A) (4.5 g, 16 mmol) in anhydrous THF (50 ml) at 0° C. was added sodium borohydride (1.2 g, 32 mmol) followed by dropwise addition of boron trifluoride diethyl etherate (4 ml, 32 mmol) and the mixture stirred at 0° C. under a nitrogen atmosphere for 2.5 h. Dry MeOH was cautiously added until gas evolution had ceased and the mixture reduced in vacuo. The residue was partitioned between EtOAc and brine and the organic portion dried (MgSO$_4$) and reduced in vacuo to give a yellow-orange solid, which was recrystallized from MeOH to give 4-(3,4-dinitro-benzyl)-morpholine (3.5 g, 82%) as a yellow solid. (LC/MS: R$_t$ 1.52, [M+H]$^+$ 268).

138E. Synthesis of 4-morpholin-4-ylmethyl-benzene-1,2-diamine

To a mixture of 4-(3,4-dinitro-benzyl)-morpholine (2.5 g, 9.3 mmol), Fe powder (5.2 g, 93 mmol) and FeSO$_4$.7H$_2$O (1.3 g, 4.6 mmol) was added 1,4-dioxane:water (5:1, 60 ml). The mixture was refluxed for 3 h, filtered through celite, washing with MeOH, and reduced in vacuo azeotroping with toluene. EtOAc (100 ml) was added and insoluble material removed via filtration. The filtrate was reduced in vacuo to give 4-morpholin-4-ylmethyl-benzene-1,2-diamine as a dark brown solid (1.4 g, 73%). (LC/MS: R$_t$ 0.40, no ionization).

138F. Synthesis of 2-[1-(4-methoxy-benzyl)-4-nitro-1H-pyrazol-3-yl]-5-morpholin-4-ylmethyl-1H-benzimidazole A mixture of 4-morpholin-4-ylmethyl-benzene-1,2-diamine (2.5 g, 12 mmol), 1-(4-methoxy-benzyl)-4-nitro-1H-pyrazole-3-carboxylic acid (2.91 g, 10 mmol), EDC (2.3 g, 12 mmol) and HOBt (1.62 g, 12 mmol) in dry DMF (40 ml) was stirred at ambient temperature for 24 h. The mixture was reduced in vacuo, the residue partitioned between EtOAc (100 ml) and water (50 ml) and the organic portion washed with saturated aqueous sodium hydrogen carbonate, dried (MgSO$_4$) and reduced in vacuo. The residue was dissolved in AcOH (70 ml) and heated at reflux for 3 h. The solvent was removed in vacuo and the residue purified by flash column chromatography [SiO$_2$, MeOH:DCM (5:95)] to give 2-[1-(4-methoxy-benzyl)-4-nitro-1H-pyrazol-3-yl]-5-morpholin-4-ylmethyl-1H-benzimidazole (2 g, 37%) as a yellow foam. (LC/MS: R$_t$ 1.91, [M+H]$^+$ 449).

138G. Synthesis of 1-(4-methoxy-benzyl)-3-(5-morpholin-4-ylmethyl-1H-benzimidazol-2-yl)-1H-pyrazol-4-ylamine To a mixture of 2-[1-(4-methoxy-benzyl)-4-nitro-1H-pyrazol-3-yl]-5-morpholin-4-ylmethyl-1H-benzimidazole (1.6 g, 3.57 mmol), Fe powder (2 g, 35 mmol) and FeSO$_4$.7H$_2$O (0.496 g, 1.78 mmol) was added 1,4-dioxane:water (5:1, 120 ml). The mixture was refluxed for 3 h, filtered through celite, washing with MeOH, and reduced in vacuo azeotroping with toluene. EtOAc (100 ml) was added and insoluble material removed via filtration. The filtrate was reduced in vacuo to give 1-(4-methoxy-benzyl)-3-(5-morpholin-4-ylmethyl-1H-benzimidazol-2-yl)-1H-pyrazol-4-ylamine as a dark brown solid (1.4 g, 94%). (LC/MS: R$_t$ 1.72, [M+H]$^+$ 419).

138H. Synthesis of 2-fluoro-6-methoxy-N-[3-(5-morpholin-4-ylmethyl-1H-benzimidazol-2-yl)-1H-pyrazol-4-yl]-benzamide

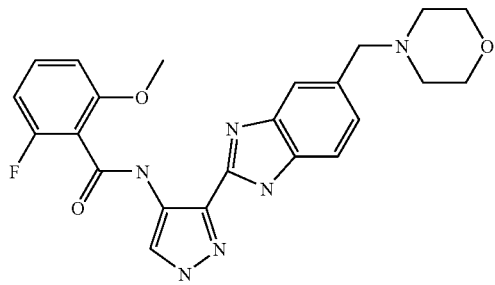

A mixture of 2-fluoro-6-methoxy-benzoic acid (20 mg, 0.12 mmol), 1-(4-methoxy-benzyl)-3-(5-morpholin-4-ylmethyl-1H-benzimidazol-2-yl)-1H-pyrazol-4-ylamine (50 mg, 0.12 mmol), EDC (116 mg, 0.14 mmol) and HOBt (81 mg, 0.14 mmol) was stirred at room temperature in DMF (2 ml) for 20 h. The mixture was reduced in vacuo and the residue partitioned between EtOAc (5 ml) and water (2 ml) and the organic portion washed with saturated aqueous sodium hydrogen carbonate, dried (MgSO$_4$) and reduced in vacuo. The residue was purified by flash column chromatography [SiO$_2$, EtOAc] to give 2-fluoro-6-methoxy-N-[1-(4-methoxy-benzyl)-3-(5-morpholin-4-ylmethyl-1H-benzimidazol-2-yl)-1H-pyrazol-4-yl]-benzamide as a white solid (80 mg, 61%).

A mixture of 2-fluoro-6-methoxy-N-[1-(4-methoxy-benzyl)-3-(5-morpholin-4-ylmethyl-1H-benzimidazol-2-yl)-1H-pyrazol-4-yl]-benzamide (80 mg) and anisole (25 µl) in trifluoroacetic acid (1 ml) was heated at 140° C. (100 W) for 20 min in a CEM Discover™ microwave synthesiser. The reaction mixture was evaporated and then azeotroped with toluene (2×10 ml). Diethyl ether (5 ml) was added to the crude material to give the trifluoroacetate salt of 2-fluoro-6-methoxy-N-[3-(5-morpholin-4-ylmethyl-1H-benzimidazol-2-yl)-1H-pyrazol-4-yl]-benzamide (30 mg, 32%) as a white solid. (LC/MS: R$_t$ 1.96, [M+H]$^+$ 451).

Example 139

Synthesis of N-[3-(5-morpholin-4-ylmethyl-1H-benzimidazol-2-yl)-1H-pyrazol-4-yl]-2-trifluoromethoxy-benzamide

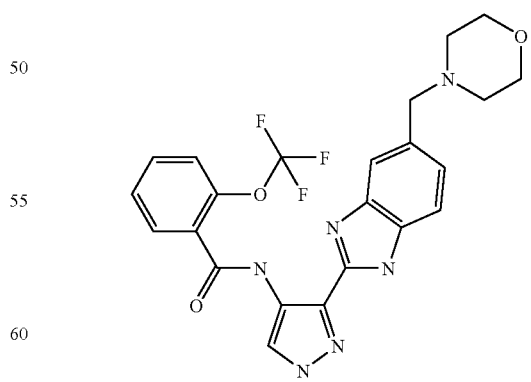

The compound was prepared in a manner analogous to Example 138F, but using 2-trifluoromethoxy-benzoic acid instead of 2-fluoro-6-methoxy-benzoic acid and using the procedure below for the deprotection of the para-methoxy benzyl substituent of the pyrazole ring.

A mixture of N-[1-(4-methoxy-benzyl)-3-(5-morpholin-4-ylmethyl-1H-benzimidazol-2-yl)-1H-pyrazol-4-yl]-2-trifluoromethoxy-benzamide (50 mg) and anisole (25 μl) in trifluoroacetic acid (1 ml) was heated at 140° C. (100 W) for 20 min in a CEM Discover™ microwave synthesiser. The reaction mixture was evaporated and then azeotroped with toluene (2×10 ml). To the crude material was added EtOAc (5 ml) and the mixture neutralised with saturated aqueous sodium hydrogen carbonate. The organic portion was washed with water, dried (MgSO₄) and reduced in vacuo. The residue was purified by flash column chromatography [SiO₂, CH₂Cl₂-MeOH (100:0-95:5)] to give N-[3-(5-morpholin-4-ylmethyl-1H-benzimidazol-2-yl)-1H-pyrazol-4-yl]-2-trifluoromethoxy-benzamide (12 mg) as a white solid. (LC/MS: R$_t$ 2.06, [M+H]⁺ 487).

Example 140

Synthesis of benzo[c]isoxazole-3-carboxylic Acid[3-(5-morpholin-4-ylmethyl-1H-benzimidazol-2-yl)-1-H-pyrazol-4-yl]-amide 140A. Synthesis of 5-morpholin-4-ylmethyl-2-(4-nitro-1H-pyrazol-3-yl)1H-benzimidazole A mixture of 4-morpholin-4-ylmethyl-benzene-1,2-diamine (2.30 g, 11.1 mmol), 4-nitro-1H-pyrazole-3-carboxylic acid (1.57 g, 10.0 mmol), EDC (2.13 g, 11.1 mmol) and HOBt (1.50 g, 11.1 mmol) in dry DMF (25 ml) was stirred at ambient temperature for 24 h. The mixture was reduced in vacuo and the crude residue dissolved in AcOH (40 ml) and heated at reflux for 3 h. The solvent was removed in vacuo and the residue was purified by flash column chromatography eluting with 0-20% MeOH in EtOAc to give 5-morpholin-4-ylmethyl-2-(4-nitro-1H-pyrazol-3-yl)1H-benzimidazole as a yellow solid. (1.0 g, 61%). (LC/MS: R$_t$ 1.83, [M+H]⁺ 329).

140B. Synthesis of 3-(5-morpholin-4-ylmethyl-1H-benzimidazol-2-yl)-1H-pyrazol-ylamine Palladium on carbon (10%, 0.08 g) was added to solution of 5-morpholin-4-ylmethyl-2-(4-nitro-1H-pyrazol-3-yl)1H-benzimidazole (0.82 g, 2.5 mmol) in DMF (30 ml) under an atmosphere of nitrogen. The mixture was shaken under a hydrogen atmosphere for 4 h then filtered through celite, washing with methanol. The filtrate was concentrated in vacuo to give 3-(5-morpholin-4-ylmethyl-1H-benzimidazol-2-yl)-1H-pyrazol-4-ylamine as a brown solid (530 mg, 71%). (LC/MS: R$_t$ 1.94, [M+H]⁺ 299).

140C. Synthesis of benzo[c]isoxazole-3-carboxylic Acid[3-(5-morpholin-4-ylmethyl-1H-benzimidazol-2-yl)-1-H-pyrazol-4-yl]-amide

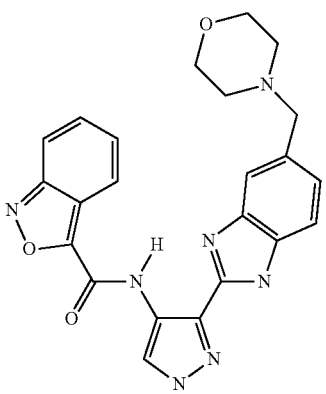

A mixture of benzo[c]isoxazole-3-carboxylic acid (46 mg, 0.28 mmol), 3-(5-morpholin-4-ylmethyl-1H-benzimidazol-2-yl)-1H-pyrazol-4-ylamine (100 mg, 0.33 mmol), EDC (64 mg, 0.33 mmol) and HOBt (45 mg, 0.33 mmol) was stirred at room temperature in DMF (2.5 ml) for 20 h. The mixture was reduced in vacuo and the residue partitioned between EtOAc (5 ml) and water (2 ml), the organic portion washed with saturated aqueous sodium hydrogen carbonate, dried (MgSO₄) and reduced in vacuo. The residue was purified by flash column chromatography [SiO₂, EtOAc-MeOH (100:0-90:10)] to give benzo[c]isoxazole-3-carboxylic acid[3-(5-morpholin-4-ylmethyl-1H-benzimidazol-2-yl)-1H-pyrazol-4-yl]-amide as a white solid (40 mg, 32%). (LC/MS: R$_t$ 2.13, [M+H]⁺ 444).

Example 141

Synthesis of N-[3-(4-bromo-6-trifluoromethyl-1H-benzimidazol-2-yl)-1H-pyrazol-4-yl]-2,6-difluoro-benzamide

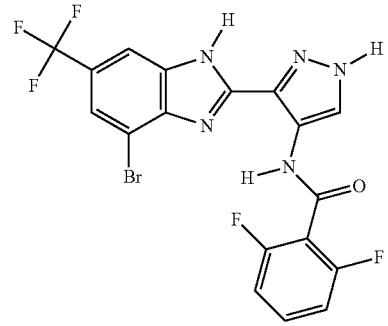

A mixture of 4-(2,6-difluorobenzylamino)-1H-pyrazole-3-carboxylic acid (520 mg, 1.96 mmol) (Example 16D), 3-bromo-5-trifluoromethyl-1,2-benzenediamine (500 mg, 1.96 mmol), EDC (413 mg, 2.15 mmol) and HOBt (290 mg, 2.15 mmol) in DMF (20 ml) was stirred at ambient temperature for 16 h and then reduced in vacuo. The residue was partitioned between EtOAc and brine and the organic portion dried (MgSO₄), filtered and evaporated. The amide intermediate was chromatographed using EtOAc-P.E. (1:4-1:0). The intermediate amide (271 mg), (LC/MS: R$_t$ 3.31, [M+H]⁺ 505), was dissolved in AcOH (3 ml) then heated at reflux for 1 h. The reaction mixture was allowed to cool at which time a solid crystallised out, that was filtered, washed with P.E. and dried to give the title compound (50 mg). (LC/MS: R$_t$ 3.42, [M+H]⁺ 486,488)

Example 142

Synthesis of N-[3-(5,6-dimethoxy-1H-benzimidazol-2-yl)-1H-pyrazol-4-yl]-5-fluoro-2-methoxy-benzamide 142A. Synthesis of 5,6-dimethoxy-2-(4-nitro-1H-pyrazol-3-yl)-1H-benzimidazole To a solution of EDC (4.81 g, 25 mmol), HOBt (3.40 g, 25 mmol) and triethylamine (4.67 g, 46 mmol) in DMF (100 ml) was added 4-nitro-1H-pyrazole-3-carboxylic acid (3.63 g, 23.09 mmol) and 4,5-dimethoxy-benzene-1,2-diamine, dihydrochloride (5.06 g, 20.99 mmol) and the mixture stirred at room temperature overnight. The solvent was removed in vacuo and the resulting solid partitioned between ethyl acetate (50 ml) and sodium bicarbonate (50 ml). A precipitate was formed and removed by filtration. This was washed with water followed by diethyl ether and then azeotroped with methanol and toluene to yield 4-nitro-1H-pyrazole-3-carboxylic acid (2-amino-4,5-dimethoxy-phenyl)-amide (2.35 g, 36%).

4-Nitro-1H-pyrazole-3-carboxylic acid (2-amino-4,5-dimethoxy-phenyl)-amide (2.35 g, 7.65 mmol) was dissolved in acetic acid (150 ml) and refluxed at 140° C. for 5 hours. The solution was left to cool and the solvent removed in vacuo. The resulting solid was partitioned between ethyl acetate (25 ml) and brine (25 ml). The organic layer was separated, dried (MgSO$_4$), filtered and the solvent removed in vacuo to yield 5,6-dimethoxy-2-(4-nitro-1H-pyrazol-3-yl)-1H-benzimidazole (2.08 g, 94%).

142B. Synthesis of 3-(5,6-dimethoxy-1H-benzimidazol-2-yl)-1H-pyrazol-4-ylamine A mixture of 5,6-dimethoxy-2-(4-nitro-1H-pyrazol-3-yl)-1H-benzimidazole (2.08 g, 7.2 mmol) and 10% palladium on carbon (200 mg) in ethanol (150 ml) and DMF (50 ml) was hydrogenated at room temperature and pressure overnight. The reaction mixture was filtered through celite and the solvent removed in vacuo. The resulting solid was azeotroped with methanol and toluene and the solvent removed in vacuo. The crude material was columned in DCM, methanol, acetic acid, water (120:18:3:2)[DMAW120] followed by dichloromethane 90 ml, methanol 18 ml, acetic acid 3 ml, water 2 ml (90:18:3:2) (DMAW90). Product fractions were combined and the solvent removed in vacuo to yield 3-(5,6-dimethoxy-1H-benzimidazol-2-yl)-1H-pyrazol-4-ylamine (~1 g, ~53%).

142C. Synthesis of N-[3-(5,6-dimethoxy-1H-benzimidazol-2-yl)-1H-pyrazol-4-yl]-5-fluoro-2-methoxy-benzamide

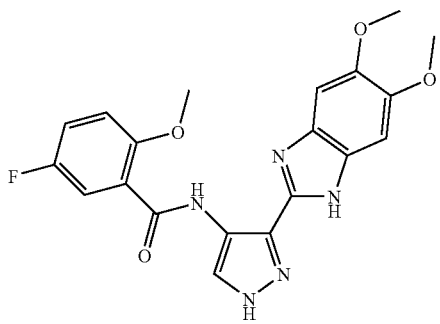

To a solution of EDC (44 mg, 0.23 mmol) and HOBt (31 mg, 0.23 mmol) in DMF (5 ml) was added 3-(5,6-dimethoxy-1H-benzimidazol-2-yl)-1H-pyrazol-4-ylamine (50 mg, 0.19 mmol) and 5-fluoro-2-methoxy-benzoic acid (36 mg, 0.21 mmol) and the mixture stirred at room temperature overnight. The solvent was removed in vacuo and the resulting solid partitioned between DCM (20 ml) and saturated aqueous sodium bicarbonate (20 ml). A precipitate was formed which was removed by filtration and oven dried to yield N-[3-(5,6-dimethoxy-1H-benzimidazol-2-yl)-1H-pyrazol-4-yl]-5-fluoro-2-methoxy-benzamide (64 mg, 81%). (LC/MS: R$_t$ 2.64, [M+H]$^+$ 412).

Example 143

Synthesis of 1-(2,6-difluoro-phenyl)-3-[3-(5,6-dimethoxy-1H-benzimidazol-2-yl)-1H-pyrazol-4-yl]-urea

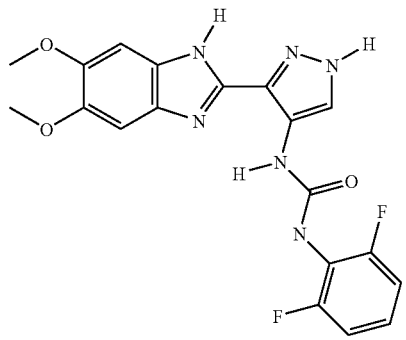

A mixture of 3-(5,6-dimethoxy-1H-benzimidazol-2-yl)-1H-pyrazol-4-ylamine (50 mg, 0.19 mmol), 2,4 difluorophenyl isocyanate (31.4 mg, 0.20 mmol) and Et$_3$N (0.027 ml) suspended in a mixture of DMF and EtOH (5 ml) was stirred at 70° C. for 1 h and then reduced in vacuo. The residue was purified by prep HPLC to give 1-(2,6-difluoro-phenyl)-3-[3-(5,6-dimethoxy-1H-benzimidazol-2-yl)-1H-pyrazol-4-yl]-urea as a white solid (11 mg) (LC/MS: R$_t$ 2.10, [M+H]$^+$ 415).

Example 144

Synthesis of 4-amino-N-[3-(5,6-dimethoxy-1H-benzimidazol-2-yl)-1H-pyrazol-4-yl]-2-ethoxy-benzamide

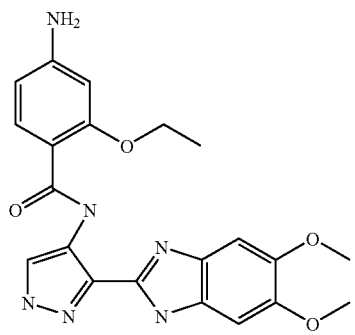

A mixture of 4-nitro-N-[3-(5,6-dimethoxy-1H-benzimidazol-2-yl)-1H-pyrazol-4-yl]-2-ethoxy-benzamide (115 mg) and 10% Pd/C (20 mg) in EtOH (10 mL) was stirred under a hydrogen atmosphere for 2 h at r.t. The mixture was filtered through Celite and reduced in vacuo to give the title compound (95 mg). (LC/MS: R$_t$ 2.11, [M+H]$^+$ 423).

Examples 145-239

By following the procedures described in the foregoing examples, modified where necessary, the compounds set out in Table 3 were prepared. In the column headed "Method", the general procedure used to prepare the compound is given with reference to an earlier example or procedure. In the column headed "Differences" are listed the key differences between the general procedure described in the referenced example and the specific procedure used to prepare the compound in question.

TABLE 3

| Ex. No. | Structure | Method | Differences | LCMS |
|---|---|---|---|---|
| 145 | 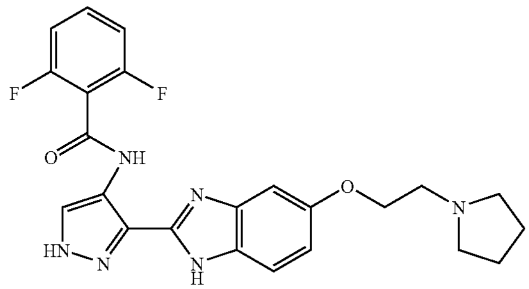 | Ex. 76 | — | [M + H]+ 453.36<br>R_t 1.98 |
| 146 | 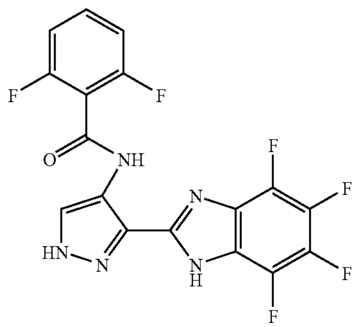 | Gen. Proc. A | Refluxed in AcOH for 6 h | [M + H]+ 412.06<br>R_t 3.36 |
| 147 | 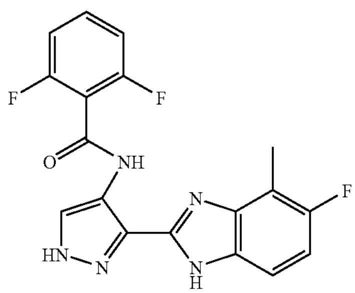 | Gen. Proc. A | Refluxed in AcOH for 3 h | [M + H]+ 372.09<br>R_t 3.22 |
| 148 | 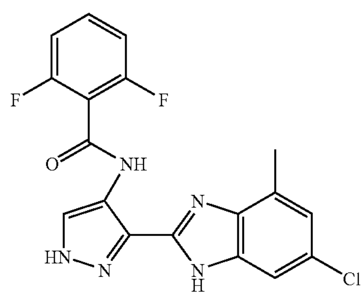 | Gen. Proc. A | Refluxed in AcOH for 3 h | [M + H]+ 388.10<br>R_t 3.47 |
| 149 | 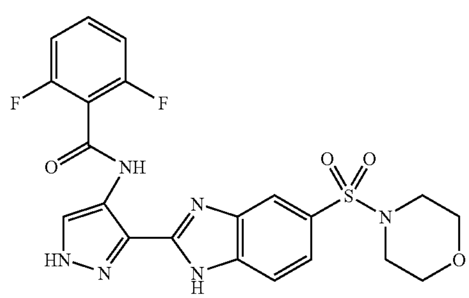 | Ex. 132 | | [M + H]+ 489.01<br>R_t 2.76 |

TABLE 3-continued

| Ex. No. | Structure | Method | Differences | LCMS |
|---|---|---|---|---|
| 150 | 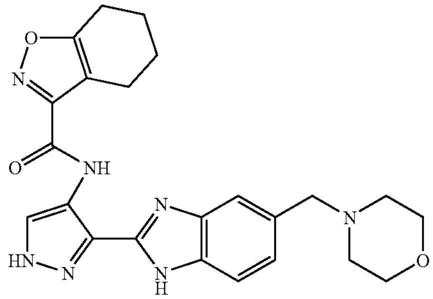 | Ex. 140C | | [M + H]+ 448.13<br>R, 2.17 |
| 151 | 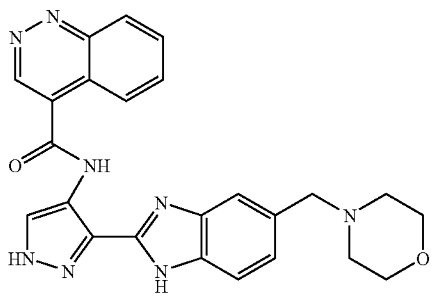 | Ex. 140C | | [M + H]+ 453.10<br>R, 1.84 |
| 152 | 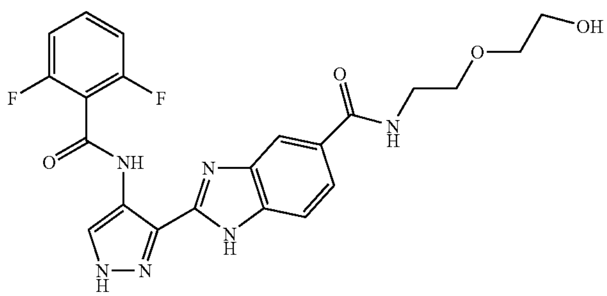 | Ex. 21 | Mixture stirred at ambient temperature for 48 h. | 2.20 min<br>471.04 |
| 153 | 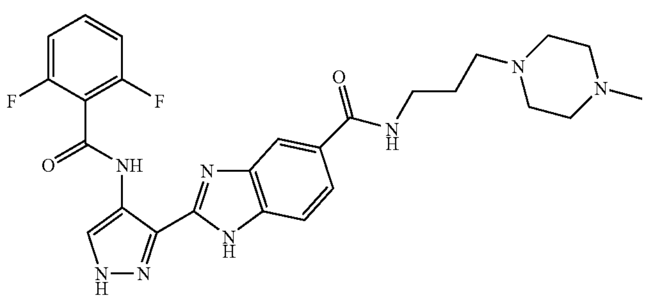 | Ex. 21 | Mixture stirred at ambient temperature for 48 h. | 2.42 min<br>523.14 |
| 154 | 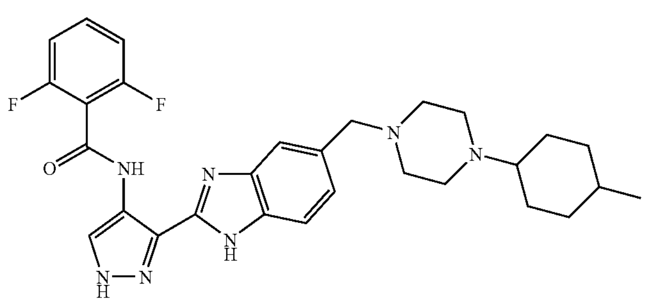 | Ex. 22 | | 2.06 min<br>534.11 |

TABLE 3-continued

| Ex. No. | Structure | Method | Differences | LCMS |
|---|---|---|---|---|
| 155 | 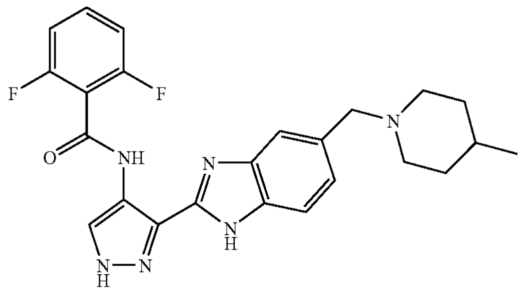 | Ex. 22 | | 2.13 min 451.12 |
| 156 | 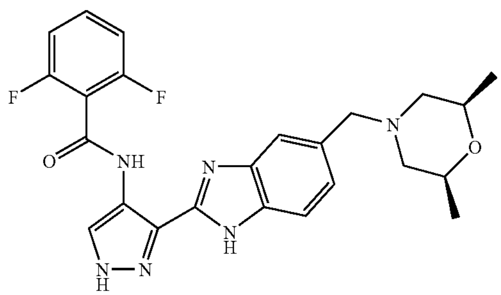 | Ex. 22 | | 2.04 min 467.14 |
| 157 | 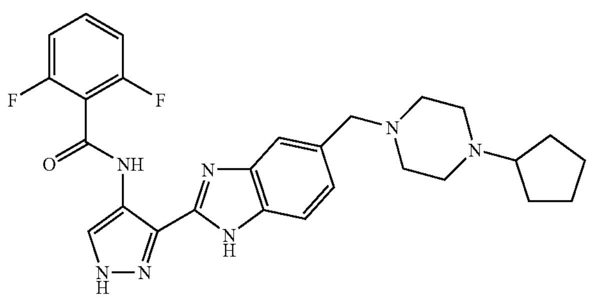 | Ex. 22 | | 1.80 min 506.14 |
| 158 | 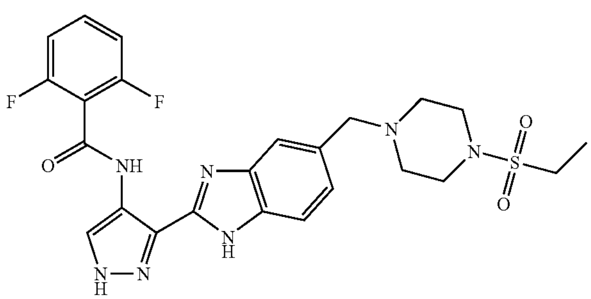 | Ex. 22 | | 2.01 min 530.04 |
| 159 | 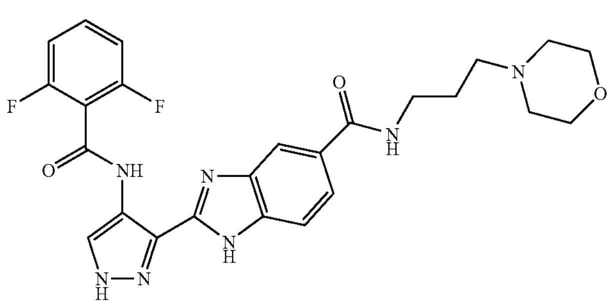 | Ex. 21 | Mixture stirred at ambient temperature for 48 h. | 1.95 min 510.10 |

TABLE 3-continued

| Ex. No. | Structure | Method | Differences | LCMS |
|---|---|---|---|---|
| 160 | 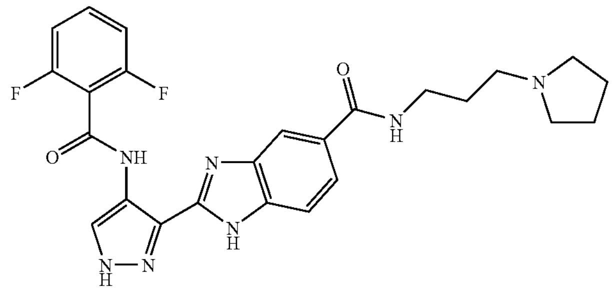 | Ex. 21 | Mixture stirred at ambient temperature for 48 h. | 1.99 min 494.11 |
| 161 | 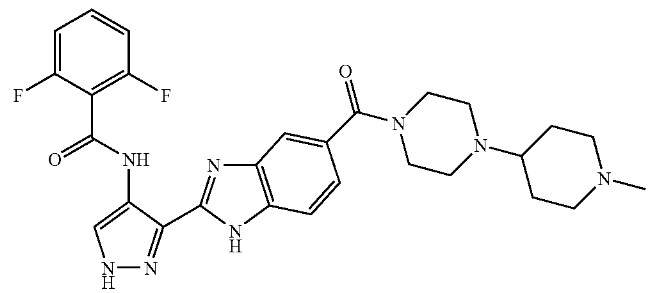 | Ex. 21 | Mixture stirred at ambient temperature for 48 h. | 2.61 min 549.16 |
| 162 | 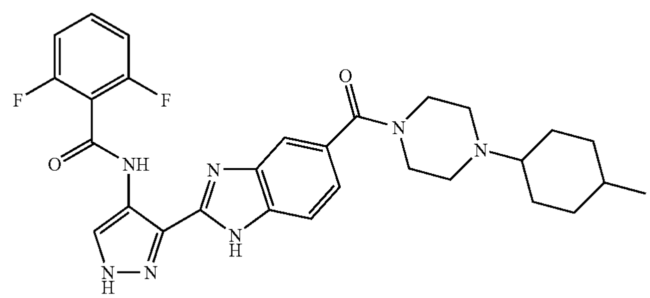 | Ex. 21 | Purified by column chromatography (EtOAc-MeOH (1:0-9:1)). | 2.15 min 548.11 |
| 163 | 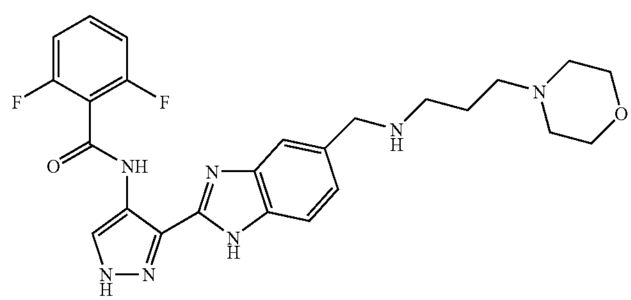 | Ex. 22 | | 1.63 min 496.11 |
| 164 | 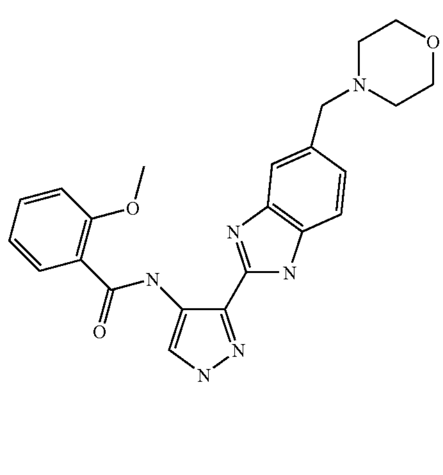 | Ex. 138F, then Ex. 139 | | [M + H]+ 433 Rt 2.01 |

TABLE 3-continued

| Ex. No. | Structure | Method | Differences | LCMS |
|---|---|---|---|---|
| 165 | 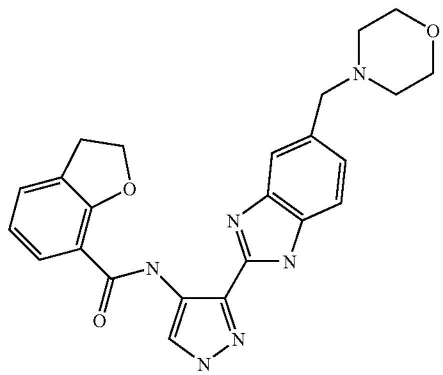 | Ex. 138F, then Ex. 139 | | [M + H]+ 455 Rt 2.05 |
| 166 | 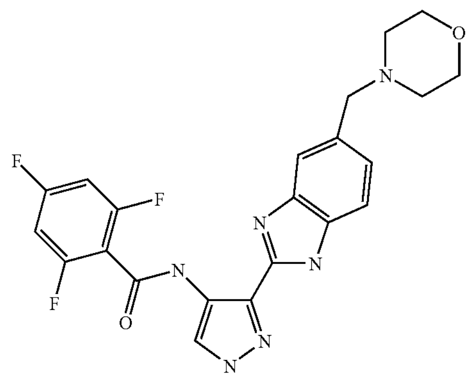 | Ex. 138F, then Ex. 139 | | [M + H]+ 457 Rt 1.98 |
| 167 | 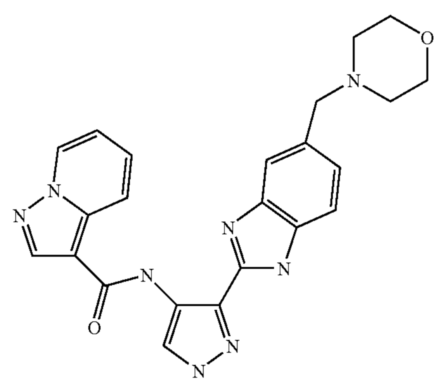 | Ex. 138F, then Ex. 139 | | [M + H]+ 443 Rt 1.91 |
| 168 | 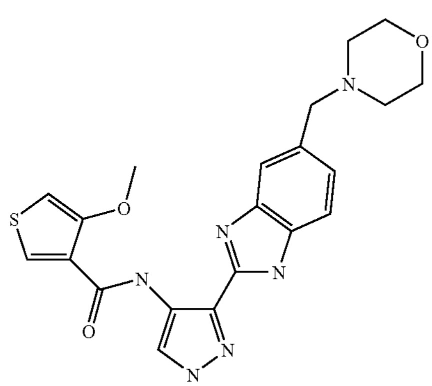 | Ex. 138F, then Ex. 139 | | [M + H]+ 439 Rt 2.58 |

TABLE 3-continued

| Ex. No. | Structure | Method | Differences | LCMS |
|---|---|---|---|---|
| 169 | 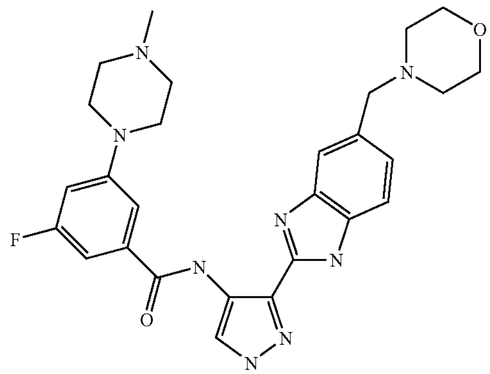 | Ex. 140C | | [M + H]+ 519 Rt 1.75 |
| 170 | 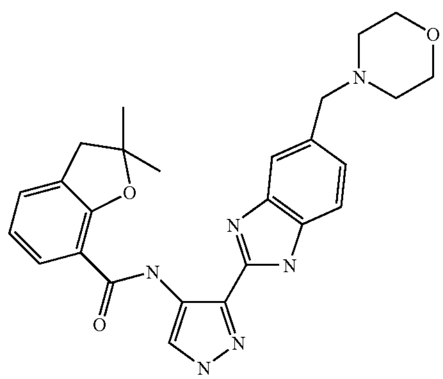 | Ex. 140C | | [M + H]+ 473 Rt 2.18 |
| 171 | 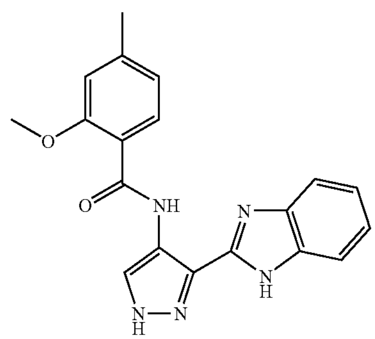 | Ex. 34 | Purified by trituration with ether | 348.07 3.12 |
| 172 | 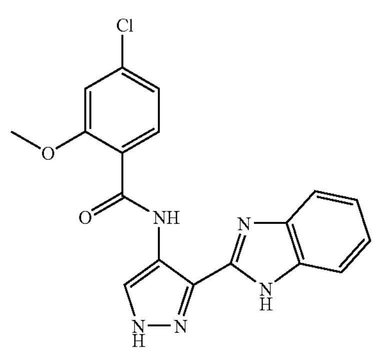 | Ex. 34 | Purified by trituration with ether | 368.02 3.29 |

TABLE 3-continued

| Ex. No. | Structure | Method | Differences | LCMS |
|---|---|---|---|---|
| 173 | 2-chlorobenzamide linked to 4-amino-3-(1H-benzimidazol-2-yl)-1H-pyrazole | Ex. 34 | None | 338.01 3.00 |
| 174 | 2-fluorobenzamide linked to 4-amino-3-(1H-benzimidazol-2-yl)-1H-pyrazole | Ex. 34 | None | 322.05 3.03 |
| 175 | 2-(trifluoromethoxy)benzamide linked to 4-amino-3-(1H-benzimidazol-2-yl)-1H-pyrazole | Ex. 34 | None | 338.03 3.23 |
| 176 | 2-(difluoromethoxy)benzamide linked to 4-amino-3-(1H-benzimidazol-2-yl)-1H-pyrazole | Ex. 34 | None | 370.06 3.11 |
| 177 | 2-ethoxybenzamide linked to 4-amino-3-(1H-benzimidazol-2-yl)-1H-pyrazole | Ex. 34 | None | 348.07 3.07 |

TABLE 3-continued

| Ex. No. | Structure | Method | Differences | LCMS |
|---|---|---|---|---|
| 178 | 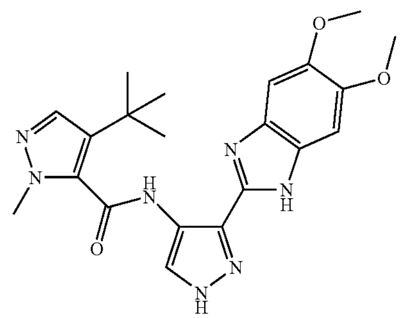 | Ex. 142C | Starting from 5-methyl-2-phenyl-2H-pyrazole-3-carboxylic acid | Rt = 2.63 min, m/z 424.14 |
| 179 | 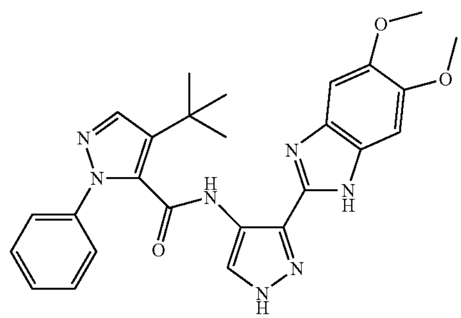 | Ex. 142C | Starting from 5-tert-butyl-2-phenyl-2H-pyrazole-3-carboxylic acid | [M + H]+ = 486 Rt = 3.05 |
| 180 | 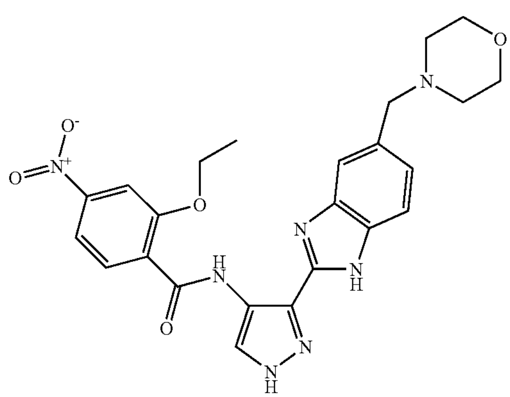 | Ex. 142C | | [M + H]+ = 453 Rt = 2.79 |
| 181 | 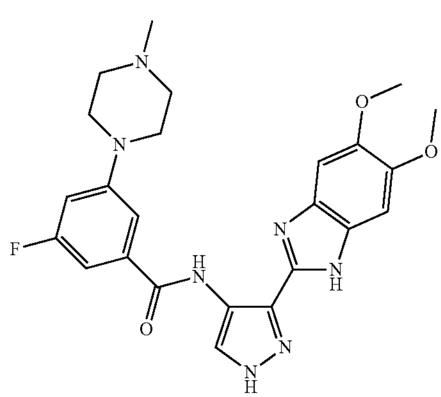 | Ex. 142C | | [M + H]+ = 480 Rt = 1.93 |

TABLE 3-continued

| Ex. No. | Structure | Method | Differences | LCMS |
|---|---|---|---|---|
| 182 | 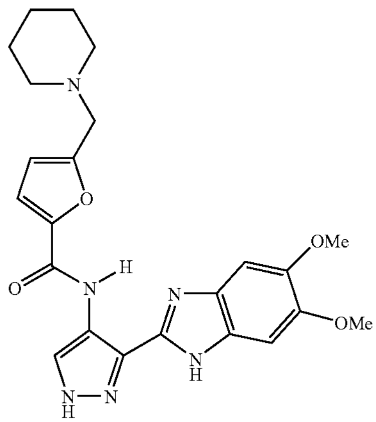 | Ex. 142C | Used HOAt instead of HOBt Worked up using EtOAc and NAHCO₃ aq. Recrystallized from MeOH | [M + H]+ 451 Rt 2.73 (basic method) |
| 183 | 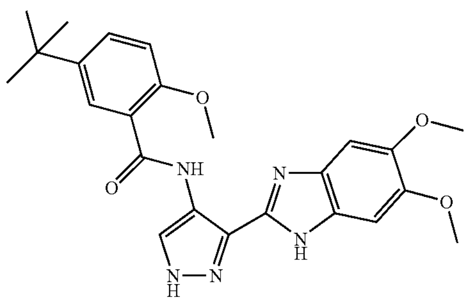 | Ex. 140C | — | [M + H]+ 450 Rt 3.07 (Acidic method) |
| 184 | 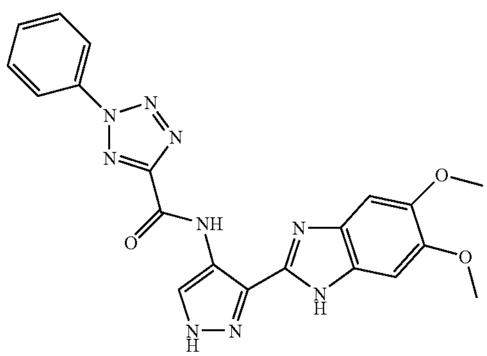 | Ex. 142C | DCM-containing layer separated and purified by column chromatography | [M + H]+ 432 Rt 2.69 (Acidic method) |
| 185 | 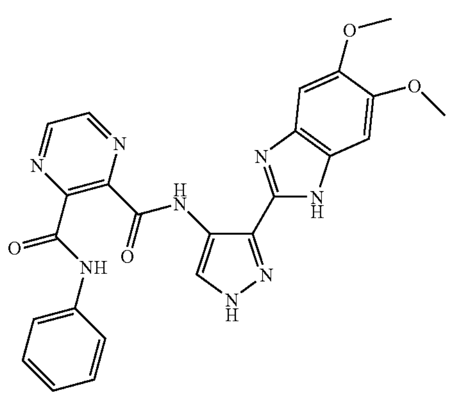 | Ex. 142C | — | [M + H]+ 485 Rt 2.15 (Acidic method) |

TABLE 3-continued

| Ex. No. | Structure | Method | Differences | LCMS |
|---|---|---|---|---|
| 186 | 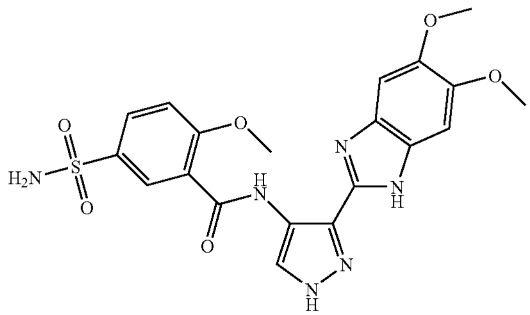 | Ex. 142C | Purified by LCMS | [M + H]+ 473 Rt 2.21 (Acidic method) |
| 187 | 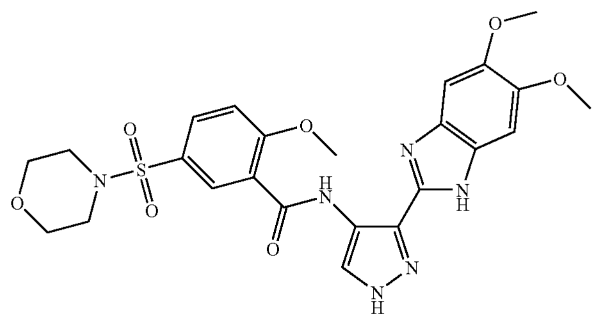 | Ex. 142C | DCM-containing layer separated and purified by column chromatography | [M + H]+ 543 Rt 2.51 (Acidic method) |
| 188 | 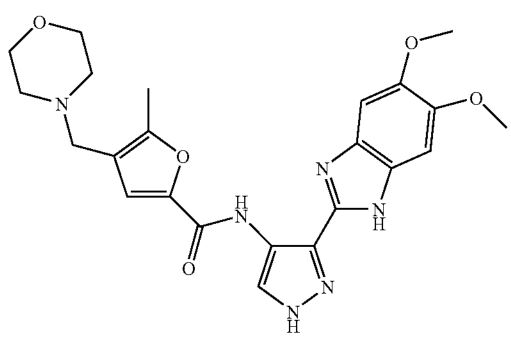 | Ex. 140C | — | [M + H]+ 467 Rt 1.74 (Acidic method) |
| 189 | 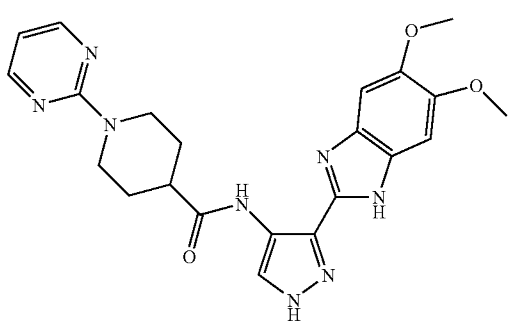 | Ex. 140C | Purified by LCMS | [M + H]+ 449 Rt 2.08 (Acidic method) |

TABLE 3-continued

| Ex. No. | Structure | Method | Differences | LCMS |
|---|---|---|---|---|
| 190 | 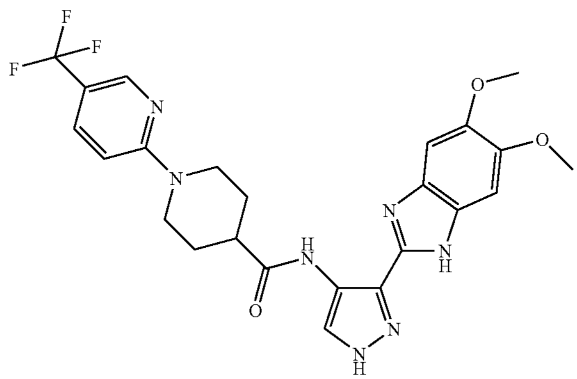 | Ex. 142C | Reaction mixture added dropwise to saturated aqueous NaHCO₃. Precipitate purified by column chromatography | [M + H]+ 516 Rt 2.71 (Acidic method) |
| 191 | 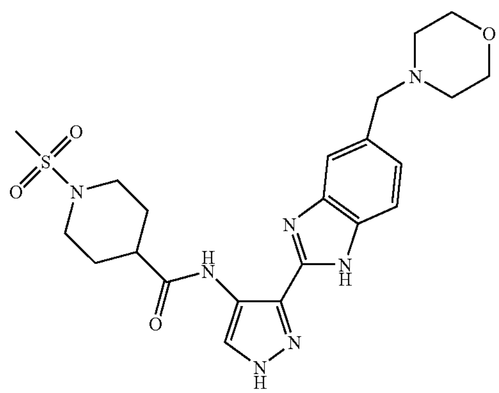 | Ex. 140C | No aqueous workup. Purified by column chromatography followed by LCMS | [M + H]+ 488 Rt 1.77 (Acidic method) |
| 192 | 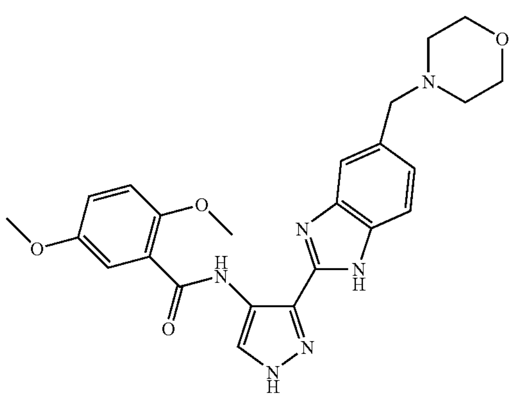 | Ex. 142C | Reaction mixture added dropwise to saturated aqueous NaHCO3. Precipitate purified by column chromatography | [M + H]+ 463 Rt 2.05 (Acidic method) |
| 193 | 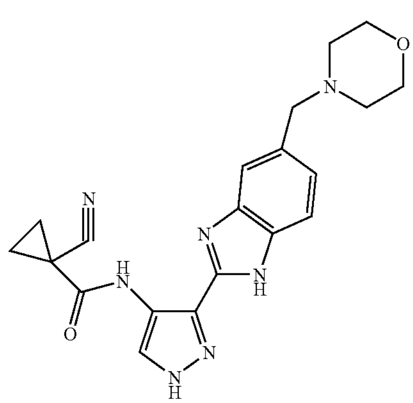 | Ex. 140C | No aqueous workup. Purified by column chromatography | [M + H]+ 392 Rt 1.83 (Acidic method) |

TABLE 3-continued

| Ex. No. | Structure | Method | Differences | LCMS |
|---|---|---|---|---|
| 194 | 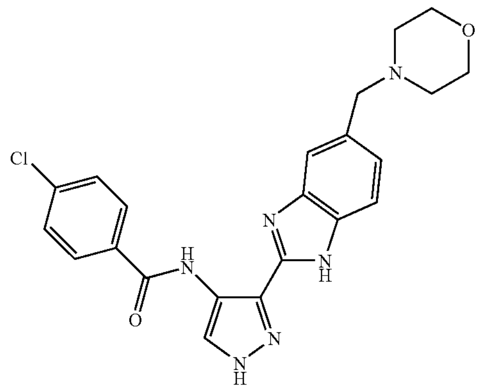 | Ex. 142C | Reaction mixture added dropwise to saturated aqueous NaHCO₃. Precipitate purified by column chromatography | [M + H]+ 437 Rt 2.19 (Acidic method) |
| 195 | 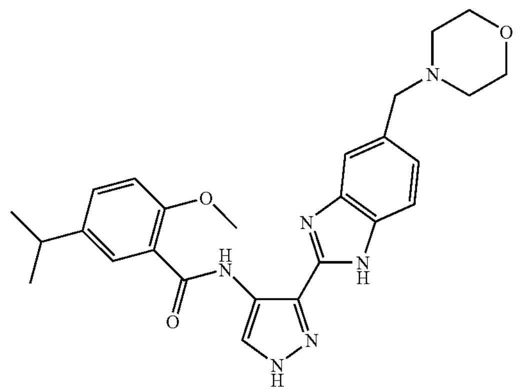 | Ex. 142C | Reaction mixture added dropwise to saturated aqueous NaHCO3. Precipitate purified by column chromatography | [M + H]+ 475 Rt 2.28 (Acidic method) |
| 196 | 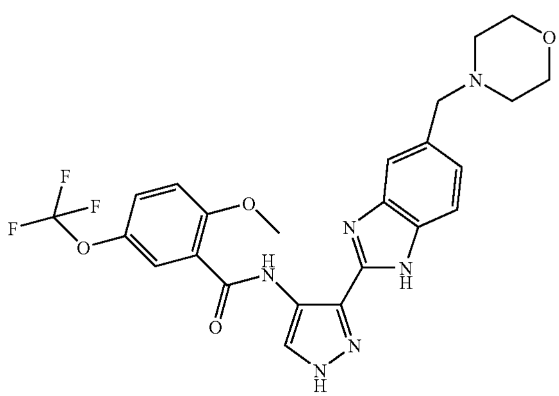 | Ex. 142C | Reaction mixture added dropwise to saturated aqueous NaHCO3. Precipitate purified by column chromatography | [M + H]+ 517 Rt 2.35 (Acidic method) |
| 197 | 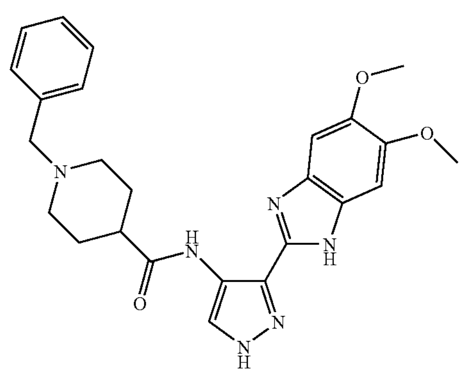 | Ex. 142C | Reaction mixture added dropwise to saturated aqueous NaHCO3. Precipitate purified by column chromatography followed by LCMS | [M + H]+ 461 Rt 1.87 (Acidic method) |

TABLE 3-continued

| Ex. No. | Structure | Method | Differences | LCMS |
|---|---|---|---|---|
| 198 | (structure) | Ex. 142C | Reaction mixture added dropwise to saturated aqueous NaHCO3. Precipitate purified by column chromatography | [M + H]+ 476 Rt 2.15 (Acidic method) |
| 199 | (structure) | Ex. 140C | Partitioned between EtOAc and sat. NaHCO₃, then organics washed with brine Purified by prep LC/MS | [M + H]+ 366.06 Rt 1.93 (Acidic method) |
| 200 | (structure) | Ex. 140C | Partitioned between EtOAc and sat. NaHCO₃, then organics washed with brine Purified by prep LC/MS | [M + H]+ 358.07 Rt 2.13 (Acidic method) |
| 201 | (structure) | Ex. 140C | Partitioned between EtOAc and sat. NaHCO3, then organics washed with brine. Purified by column chromatography [SiO2 eluting EtOAc-MeOH (100:0-80:20)] | [M + H]+ 471.04 Rt 1.95 (Acidic method) |

TABLE 3-continued

| Ex. No. | Structure | Method | Differences | LCMS |
|---|---|---|---|---|
| 202 | 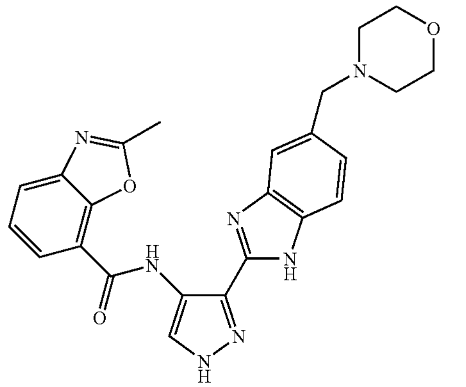 | Ex. 140C | Partitioned between EtOAc and sat. NaHCO₃, then organics washed with brine. Purified by column chromatography [SiO₂ eluting EtOAc-MeOH (100:0-80:20)] | [M + H]+ 458.08 Rt 1.91 (Acidic method) |
| 203 | 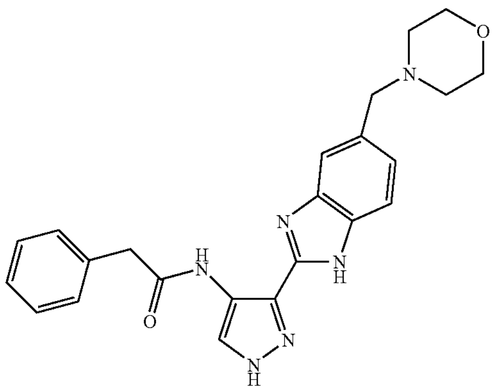 | Ex. 140C | Partitioned between DCM and sat. NaHCO₃, organics reduced in vacuo. Purified by column chromatography [SiO₂ eluting EtOAc-MeOH (100:0-80:20)] | [M + H]+ 417.09 Rt 1.92 (Acidic method) |
| 204 | 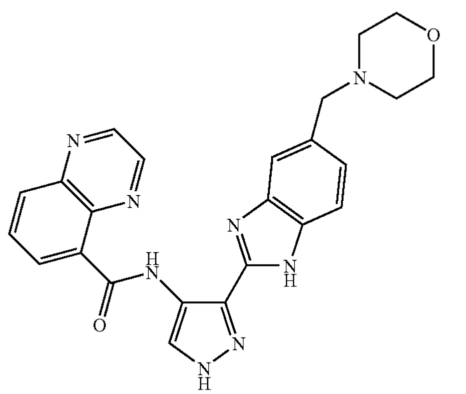 | Ex. 140C | Partitioned between DCM and sat. NaHCO₃, organics reduced in vacuo. Purified by column chromatography [SiO₂ eluting EtOAc-MeOH (100:0-80:20)] | [M + H]+ 455.07 Rt 1.88 (Acidic method) |
| 205 | 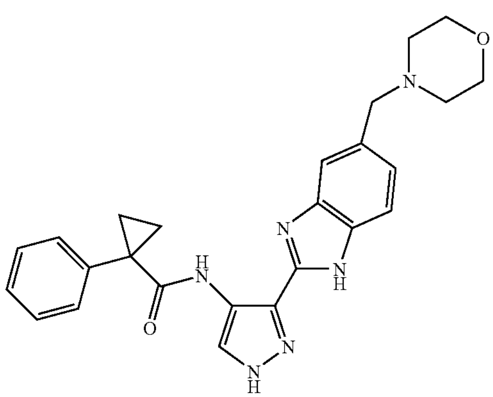 | Ex. 140C | Reaction mixture reduced in vacuo and water (2 ml) added. Precipitate formed collected under suction and purified by column chromatography [SiO₂ eluting EtOAc-MeOH (100:0-80:20)] | [M + H]+ 443.10 Rt 2.06 (Acidic method) |

TABLE 3-continued

| Ex. No. | Structure | Method | Differences | LCMS |
|---|---|---|---|---|
| 206 | 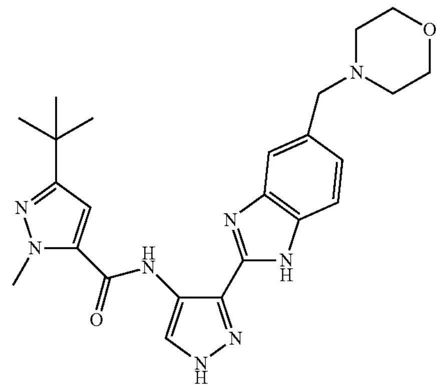 | Ex. 140C | Reaction mixture reduced in vacuo and water (2 ml) added. Precipitate formed collected under suction and purified by column chromatography [SiO₂ eluting EtOAc-MeOH (100:0-80:20)] | [M + H]+ 463.13 Rt 2.13 (Acidic method) |
| 207 | 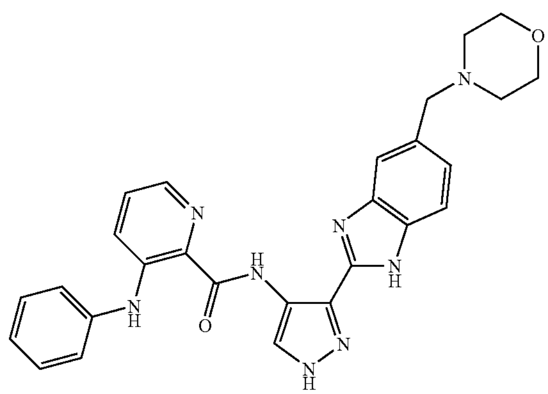 | Ex. 140C | Reaction mixture reduced in vacuo and water (2 ml) added. Precipitate formed collected under suction and purified by column chromatography [SiO₂ eluting EtOAc-MeOH (100:0-80:20) then NH₂-column(EtOAc-MeOH 100:0, 90:10, 80:20)] | [M + H]+ 495.11 Rt 2.25 (Acidic method) |
| 208 | 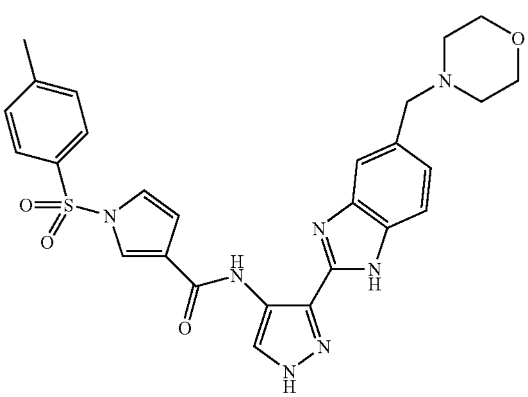 | Ex. 140C | Reaction mixture reduced in vacuo and water (2 ml) added. Precipitate formed collected under suction and subject to column chromatography [SiO₂ eluting EtOAc-MeOH (100:0-80:20)] then partitioned between EtOAc and sat. NaHCO₃. Organics washed (brine) dried (MgSO₄) and reduced in vacuo. | [M + H]+ 546.03 Rt 2.24 (Acidic method) |
| 209 | 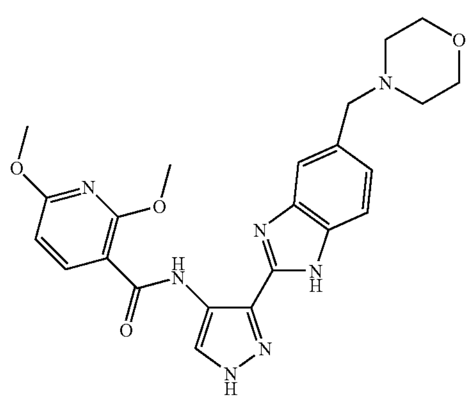 | Ex. 140C | Reaction mixture reduced in vacuo and water (2 ml) added. Precipitate formed collected under suction and subject to column chromatography [SiO₂ eluting EtOAc-MeOH (100:0-80:20)] then partitioned between EtOAc and sat. NaHCO₃. Organics washed (brine) dried (MgSO₄) and reduced in vacuo. | [M + H]+ 467.01 Rt 2.17 (Acidic method) |

TABLE 3-continued

| Ex. No. | Structure | Method | Differences | LCMS |
|---|---|---|---|---|
| 210 | 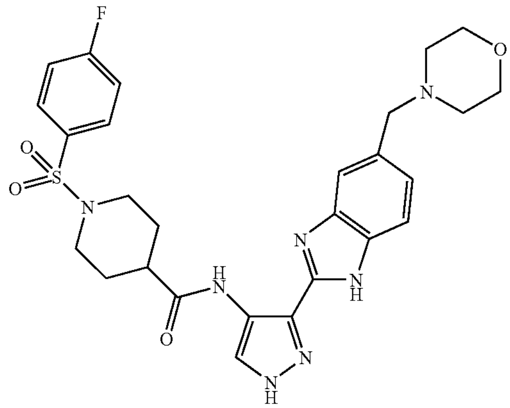 | Ex. 140C | Reaction mixture reduced in vacuo and water (2 ml) added. Precipitate formed collected under suction and purified by column chromatography [SiO$_2$ eluting EtOAc-MeOH (100:0-80:20) then NH$_2$-column (EtOAc-MeOH 90:10)] | [M + H]+ 568.06 Rt 2.10 (Acidic method) |
| 211 | 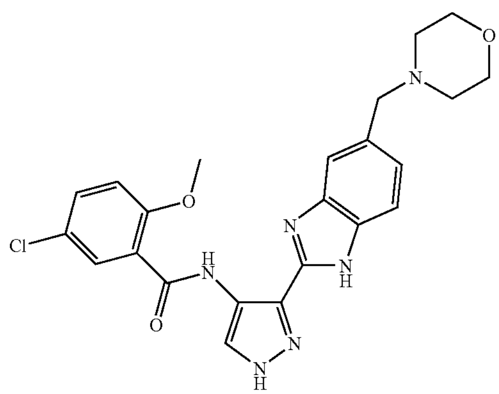 | Ex. 140C | Partitioned between DCM and water, organics reduced in vacuo. Subject to column chromatography [SiO$_2$ eluting EtOAc-MeOH (100:0-80:20)] then partitioned between EtOAc and sat. NaHCO$_3$. Organics washed (brine) dried (MgSO$_4$) and reduced in vacuo. | [M + H]+ 464.04 Rt 2.14 (Acidic method) |
| 212 | 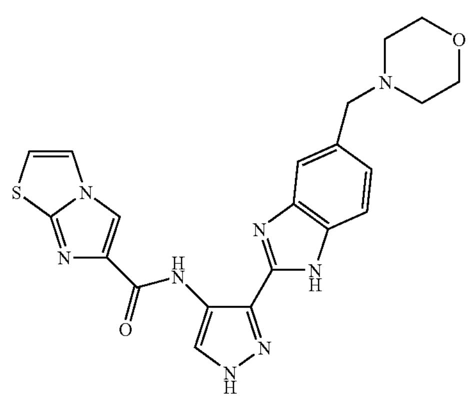 | Ex. 140C | Reaction mixture reduced in vacuo, and purified by column chromatography [SiO$_2$, eluting EtOAc-MeOH (100:0-80:20) then NH$_2$-column(EtOAc-MeOH 100:0, 90:10, 80:20)] | [M + H]+ 448.99 Rt 1.86 (Acidic method) |
| 213 | 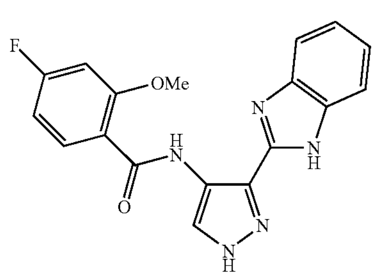 | Ex. 6 | Made using 4-fluoro-2-methoxybenzoic acid in place of 2,6-difluorobenzoic acid. Purified by trituration with diethylether | [M + H]+ 352.05 Rt 3.05 (Acidic method) |

TABLE 3-continued

| Ex. No. | Structure | Method | Differences | LCMS |
|---|---|---|---|---|
| 214 | 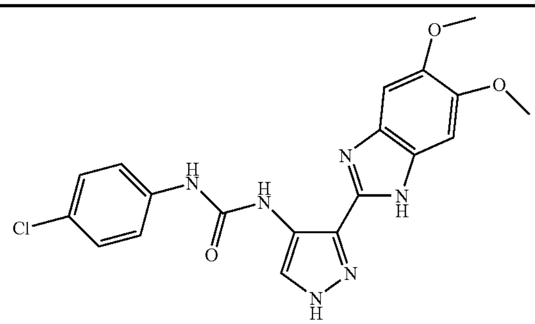 | Ex. 143 | | [M + H]+ 413 Rt 2.45 (Acidic method) |
| 215 | 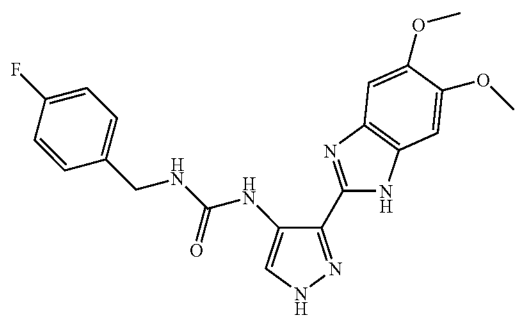 | Ex. 143 | | [M + H]+ 411 Rt 2.08 (Acidic method) |
| 216 | 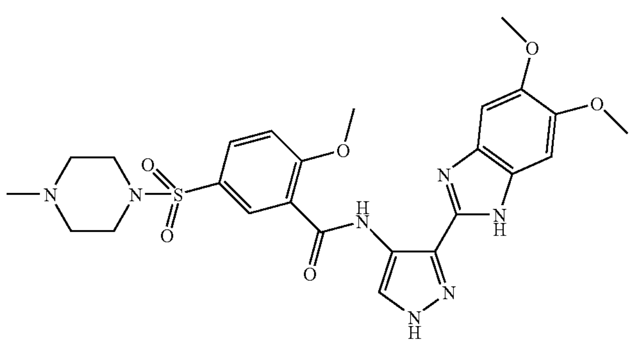 | Ex. 142C | Et$_3$N 2 eq (*Preparation of starting material given at foot of Table 3) | [M + H]+ 556 Rt 2.02 (Acidic method) |
| 217 | 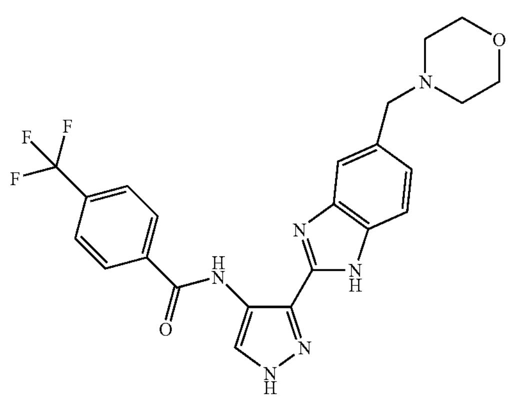 | Ex. 140C | | [M + H]+ 471 Rt 2.26 (Acidic method) |

TABLE 3-continued
| Ex. No. | Structure | Method | Differences | LCMS |
|---|---|---|---|---|
| 218 | 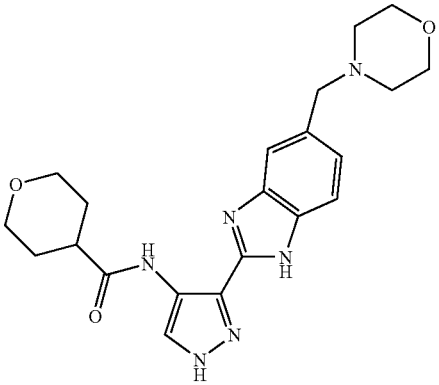 | Ex. 140C | | [M + H]+ 411 Rt 1.70 (Acidic method) |
| 219 | 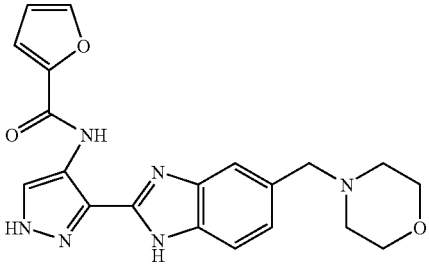 | Ex. 138F, then Ex. 139 | | [M + H]+ 393 Rt 1.86 (Acidic method) |
| 220 | 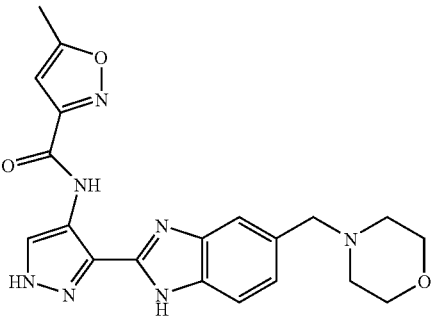 | Ex. 138F, then Ex. 139 | | [M + H]+ 407 Rt 2.40 (Acidic method) |
| 221 | 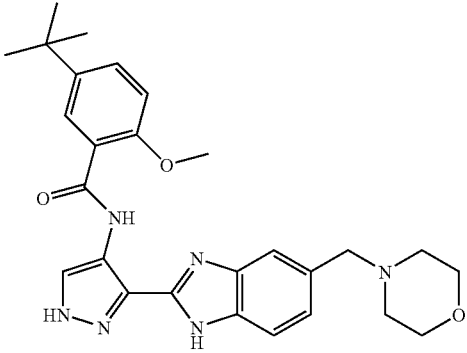 | Ex. 140C | | [M + H]+ 489 Rt 2.31 (Acidic method) |

TABLE 3-continued

| Ex. No. | Structure | Method | Differences | LCMS |
|---|---|---|---|---|
| 222 | 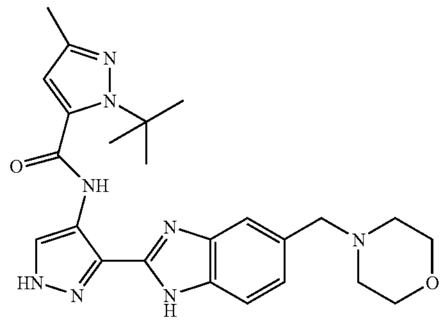 | Ex. 140C | | [M + H]+ 463<br>Rt 2.10<br>(Acidic method) |
| 223 | 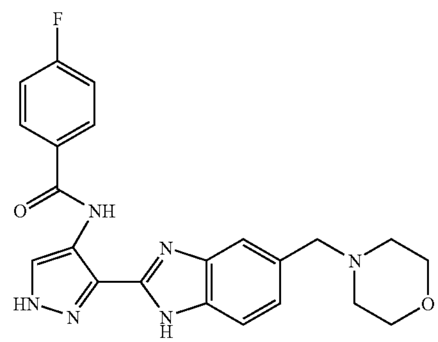 | Ex. 140C | | [M + H]+ 487<br>Rt 2.03<br>(Acidic method) |
| 224 | 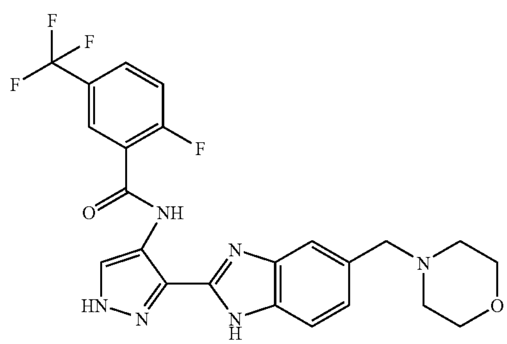 | Ex. 140C | | [M + H]+ 489<br>Rt 2.23<br>(Acidic method) |
| 225 | 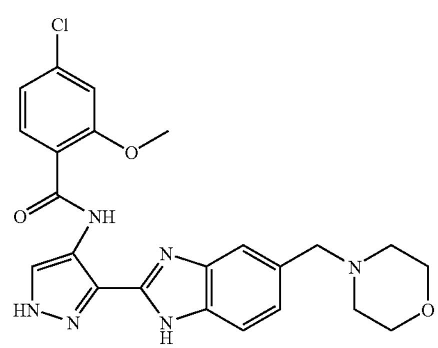 | Ex. 140C | | [M + H]+ 467<br>Rt 2.19<br>(Acidic method) |

TABLE 3-continued

| Ex. No. | Structure | Method | Differences | LCMS |
|---|---|---|---|---|
| 226 | 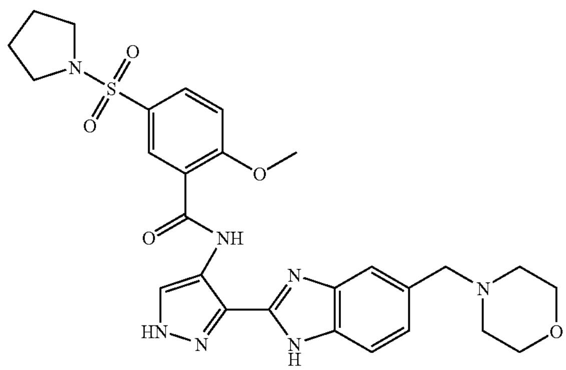 | Ex. 140C | | [M + H]+ 566 Rt 2.12 (Acidic method) |
| 227 | 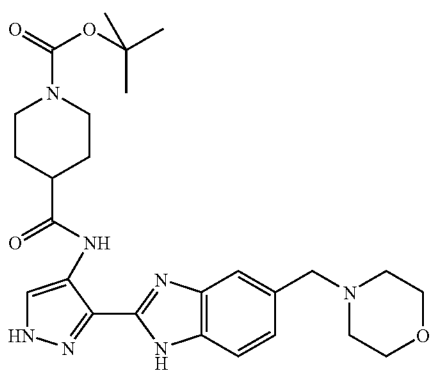 | Ex. 140C | | [M + H]+ 510 Rt 2.07 (Acidic method) |
| 228 | 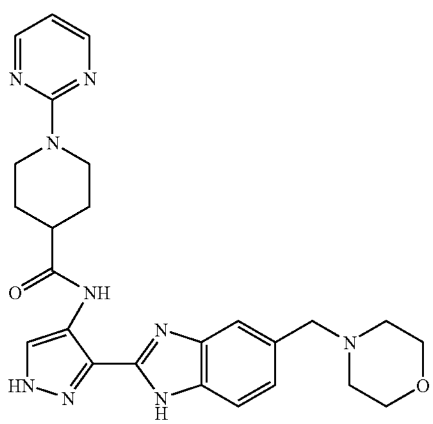 | Ex. 140C | | [M + H]+ 488 Rt 1.83 (Acidic method) |
| 229 | 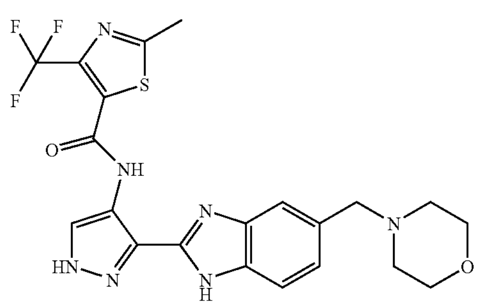 | Ex. 140C | | [M + H]+ 492 Rt 2.01 (Acidic method) |

TABLE 3-continued

| Ex. No. | Structure | Method | Differences | LCMS |
|---|---|---|---|---|
| 230 | 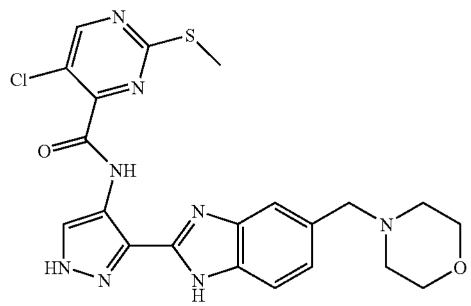 | Ex. 140C | | [M + H]+ 485 Rt 2.93 (Acidic method) |
| 231 | 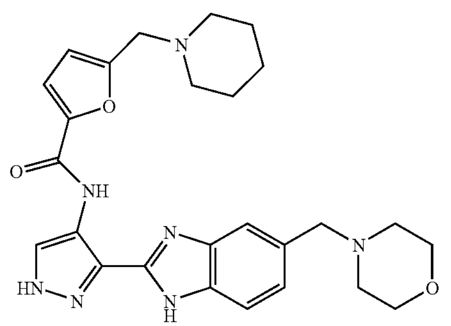 | Ex. 140C | | [M + H]+ 490 Rt 2.73 (Acidic method) |
| 232 | 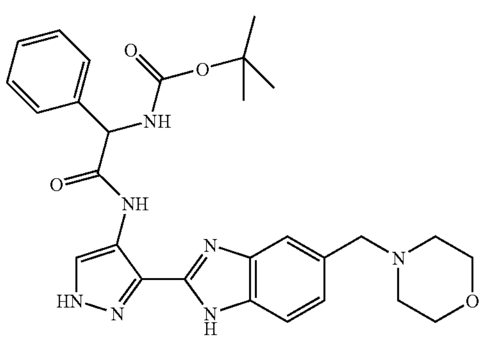 | Ex. 140C | Used racemic N-Boc-phenyl glycine as starting material | [M + H]+ 532 Rt 2.13 (Acidic method) |
| 233 | 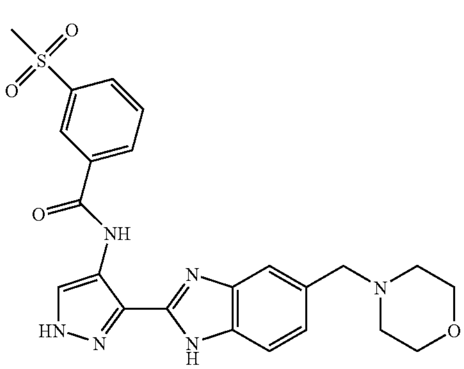 | Ex. 140C | | [M + H]+ 480 Rt 1.91 (Acidic method) |

TABLE 3-continued

| Ex. No. | Structure | Method | Differences | LCMS |
|---|---|---|---|---|
| 234 | 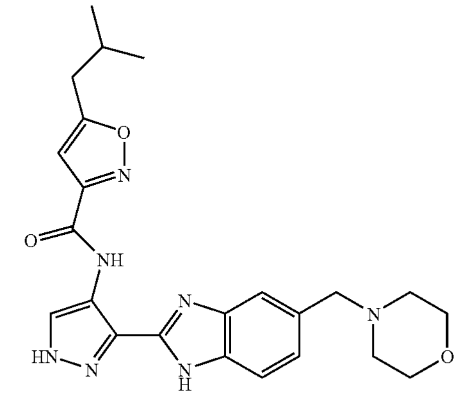 | Ex. 140C | | [M + H]+ 450 Rt 2.12 (Acidic method) |
| 235 | 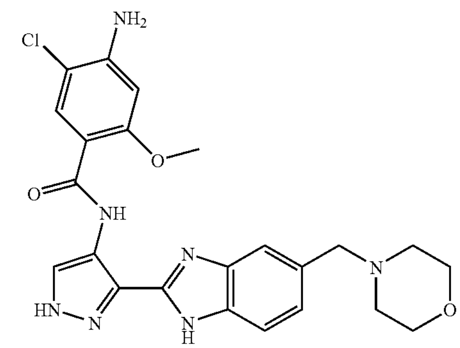 | Ex. 140C | | [M + H]+ 482 Rt 2.59 (Basic method) |
| 236 | 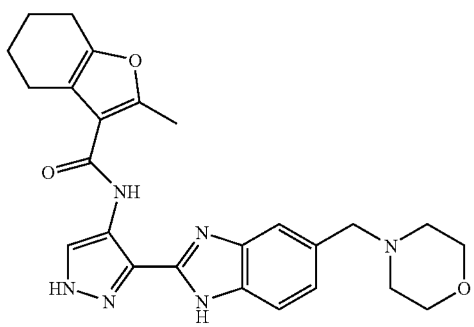 | Ex. 140C | | [M + H]+ 459 Rt 2.27 (Acidic method) |
| 237 | 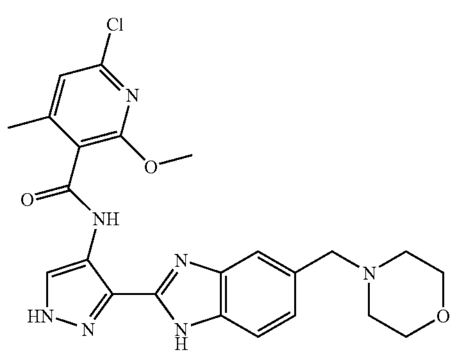 | Ex. 140C | | [M + H]+ 480 Rt 2.13 (Acidic method) |

TABLE 3-continued

| Ex. No. | Structure | Method | Differences | LCMS |
|---|---|---|---|---|
| 238 | 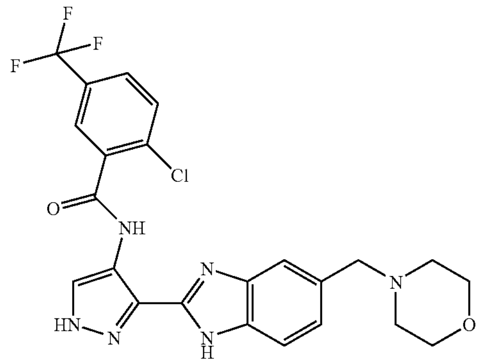 | Ex. 140C | | [M + H]+ 505 Rt 2.26 (Acidic method) |
| 239 | 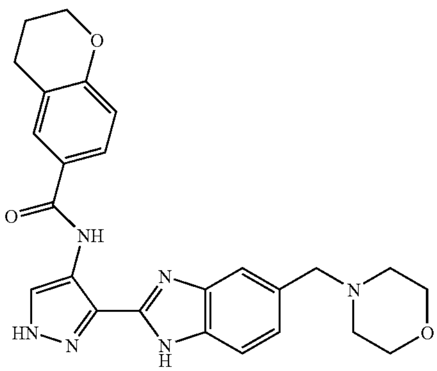 | Ex. 140C | | [M + H]+ 445 Rt 2.07 (Acidic method) |
| 240 | 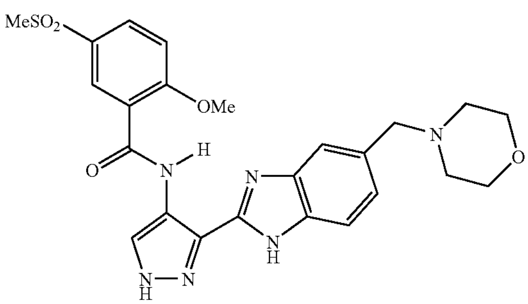 | Ex. 140C | Used HOAt instead of HOBt Crude product purified directly through preparative LC/MS | [M + H]+ 511 Rt 2.51 (basic method) |
| 241 | 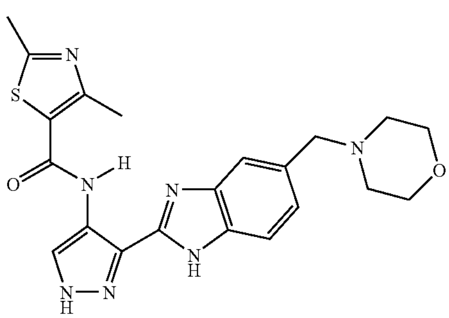 | Ex. 140C | Crude product purified directly through preparative LC/MS | [M − H+]− 436 Rt 2.57 (basic method) |

TABLE 3-continued

| Ex. No. | Structure | Method | Differences | LCMS |
|---|---|---|---|---|
| 242 | 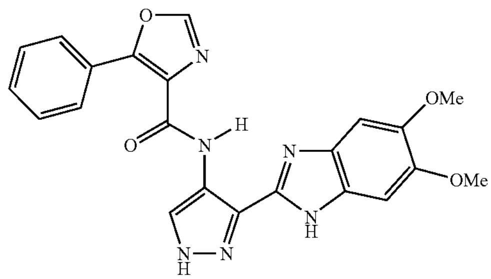 | Ex. 142C | Concentrated reaction mixture purified directly on SiO₂ (EtOAc/hexanes, 2:1) | [M + H]+ 431 Rt 2.69 (acidic method) |
| 243 | 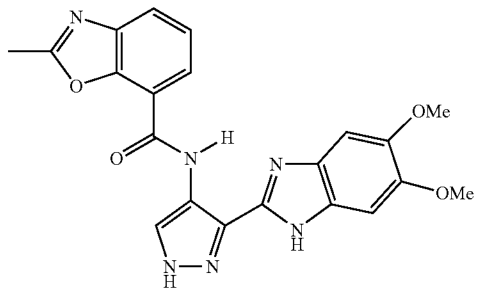 | Ex. 142C | Concentrated reaction mixture purified directly on SiO2 (CH2Cl2/MeOH, 98:2) | [M + H]+ 419 Rt 2.18 (acidic method) |
| 244 | 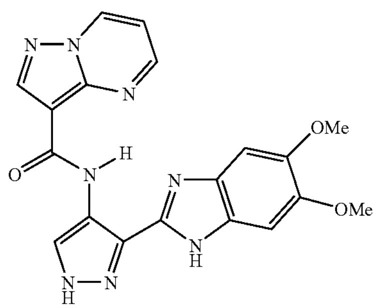 | E. 142C | Product collected as a precipitate after partitioning reaction mixture between CH₂Cl₂ and sat. aq. NaHCO₃ | [M + H]+ 405 Rt 1.96 (acidic method) |
| 245 | 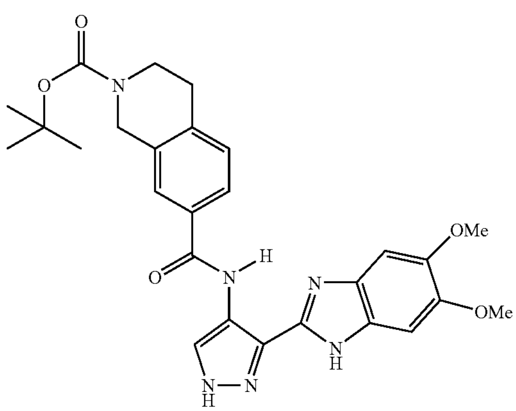 | Ex. 142C | Purified on SiO₂ eluting with(CH₂Cl₂/MeOH, 98:2-95:5) | [M + H]+ 519 Rt 3.00 (acidic method) |
| 246 | 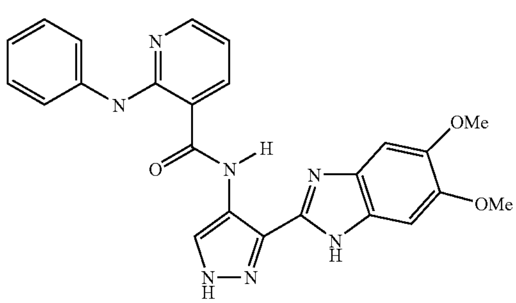 | Ex. 142C | Purified on SiO₂ eluting with(CH₂Cl₂/MeOH, 99:1-96:4) | [M + H]+ 456 Rt 2.89 (acidic method) |

TABLE 3-continued

| Ex. No. | Structure | Method | Differences | LCMS |
|---|---|---|---|---|
| 247 | 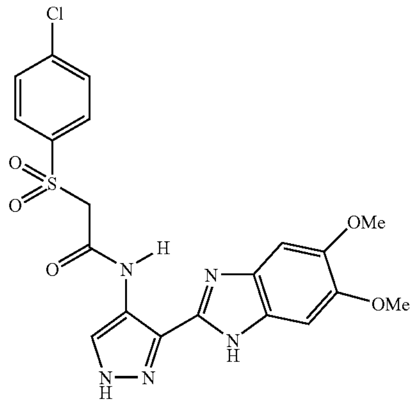 | Ex. 142C | Work up employed EtOAc instead of CH$_2$Cl$_2$. Purified on SiO$_2$ eluting with (CH$_2$Cl$_2$/MeOH, 95:5) | [M + H]+ 476 Rt 2.12 (acidic method) |
| 248 | 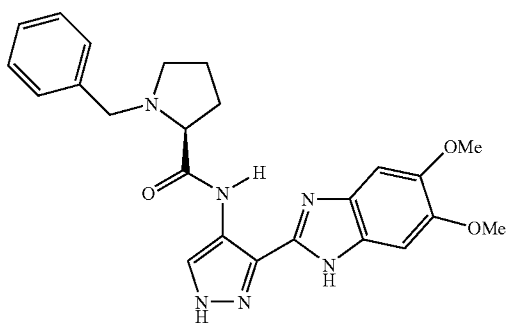 | Ex. 142C | Reaction mixture added to sat. aq. NaHCO$_3$. Product collected as a precipitate | [M + H]+ 447 Rt 1.78 (acidic method) |
| 249 | 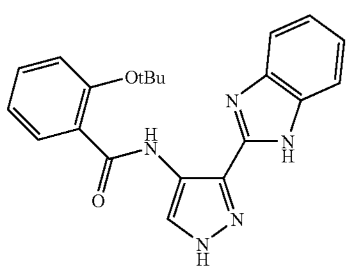 | Ex. 6 | Made using 2-t-butoxybenzoic acid in place of 2,6-difluorobenzoic acid. Purified by flash chromatography (SiO$_2$, 3:5 EtOAc:Petrol) | [[M + H]+ 376 Rt 3.25 (acidic method) |
| 250 | 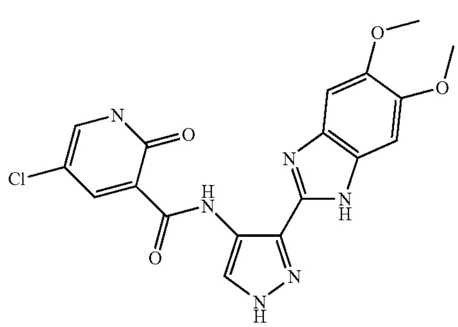 | Ex. 142C | Used EtOAc for work up. Purified through preparative LC/MS. | [M + H]+ 415 Rt = 1.9 (acidic method) |

TABLE 3-continued

| Ex. No. | Structure | Method | Differences | LCMS |
|---|---|---|---|---|
| 251 | 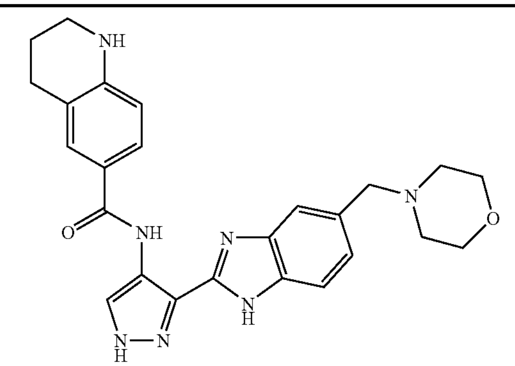 | Ex. 140C | Purified on SiO₂ eluting with DMAw 120 | [M + H]+ 458 Rt = 2.02 (acidic method) |
| 252 | 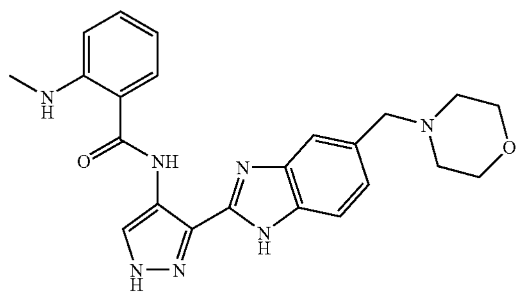 | Ex. 140C | Purified on SiO₂ eluting with DMAw 120 | [M + H]+ 432 Rt = 2.23 (acidic method) |
| 253 | 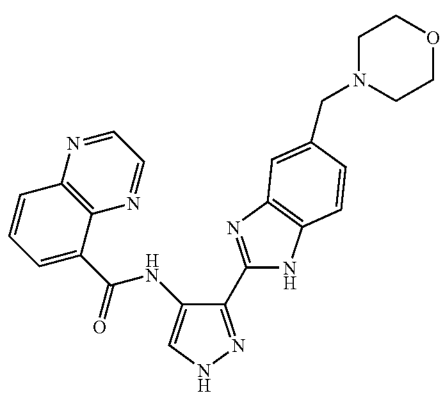 | Ex. 140C | Partitioned between DCM and sat. NaHCO₃, organics reduced in vacuo. Purified by column chromatography [SiO₂ eluting EtOAc-MeOH (100:0-80:20)] | [M + H]+ 455.07 Rt 1.88 (Acidic method) |
| 254 | 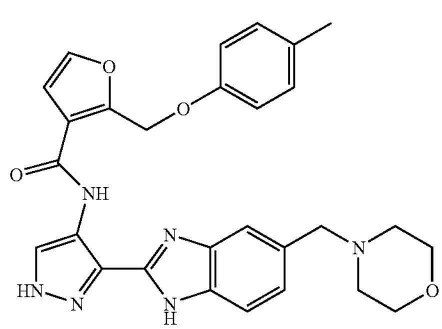 | Ex. 140C | Reaction mixture reduced in vacuo and water (3 ml) added. Precipitate formed collected under suction and purified by column chromatography [SiO₂ eluting EtOAc-MeOH (100:0-80:20)] | [M + H]+ 513.11 Rt 2.24 (Acidic method) |

TABLE 3-continued

| Ex. No. | Structure | Method | Differences | LCMS |
|---|---|---|---|---|
| 255 | 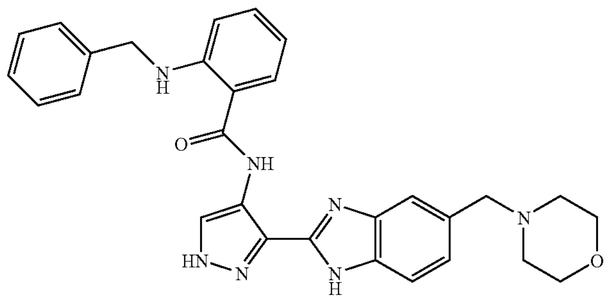 | Ex. 140C | Reaction mixture reduced in vacuo and water (2 ml) added. Precipitate formed collected under suction and purified by column chromatography [SiO$_2$ eluting EtOAc-MeOH (100:0-80:20)] | [M + H]+ 508.16 Rt 2.43 (Acidic method) |
| 256 | 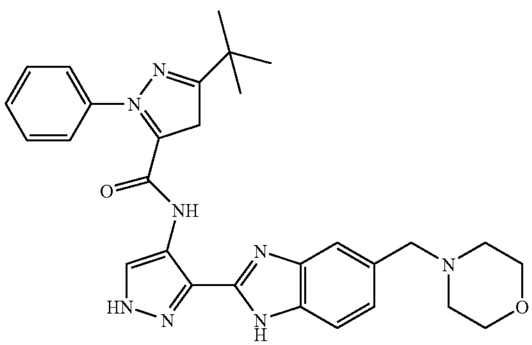 | Ex. 140C | Reaction mixture reduced in vacuo and water (2 ml) added. Precipitate formed collected under suction and purified by column chromatography [SiO$_2$ eluting EtOAc-MeOH (100:0-80:20)] | [M + H]+ 525.15 Rt 2.32 (Acidic method) |
| 257 | 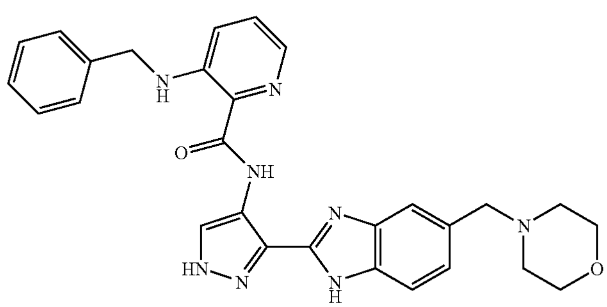 | Ex. 140C | Partitioned between DCM and sat. NaHCO$_3$, organics reduced in vacuo. Purified by column chromatography [SiO$_2$ eluting EtOAc-MeOH (100:0-80:20)] | [M + H]+ 509.12 Rt 2.10 (Acidic method) |
| 258 | 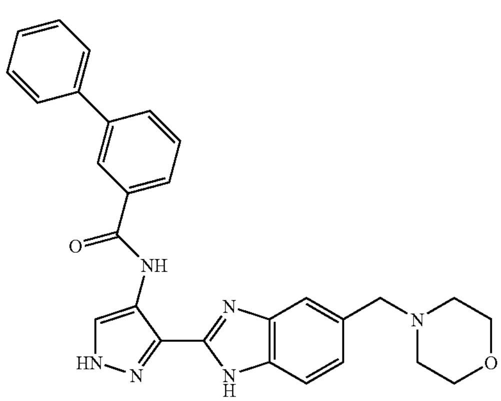 | Ex. 140C | Partitioned between DCM and sat. NaHCO$_3$, organics reduced in vacuo. Purified by column chromatography [SiO$_2$ eluting EtOAc-MeOH (100:0-80:20)] | [M + H]+ 479.12 Rt 2.28 (Acidic method) |

TABLE 3-continued

| Ex. No. | Structure | Method | Differences | LCMS |
|---|---|---|---|---|
| 259 | 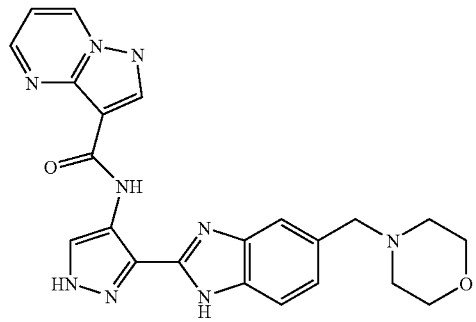 | Ex. 139 | Using pyrazolo[1,5-a] Pyrimidine-3-carboxylic acid as starting material | [M + H]+ 444 Rt 1.75 (Acidic method) |
| 260 | 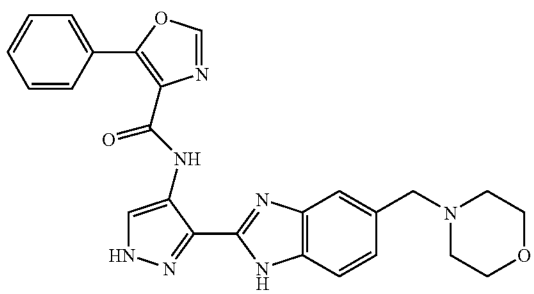 | Ex. 140C | Partitioned between DCM and sat. NaHCO$_3$, organics reduced in vacuo. Purified by column chromatography [SiO$_2$ eluting EtOAc-MeOH (100:0-90:10)] | [M + H]+ 470 Rt 1.93 (Acidic method) |
| 261 | 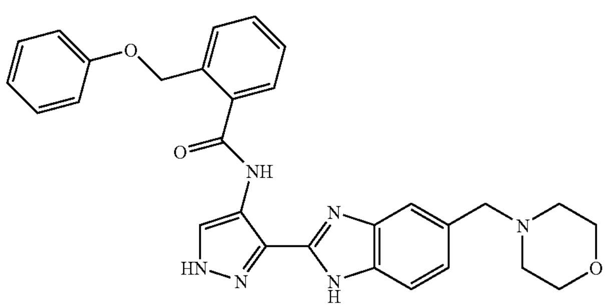 | Ex. 140C | Partitioned between DCM and sat. NaHCO$_3$, organics reduced in vacuo. Purified by column chromatography [SiO$_2$ eluting EtOAc-MeOH (100:0-90:10)] | [M + H]+ 509 Rt 2.22 (Acidic method) |
| 262 | 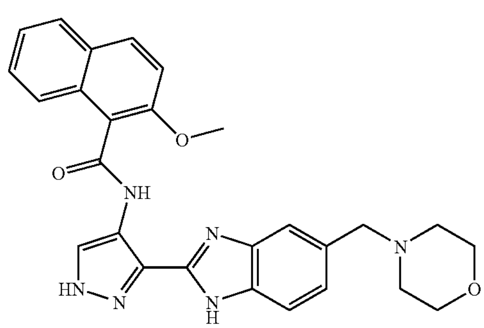 | Ex. 140C | Partitioned between DCM and sat. NaHCO$_3$, organics reduced in vacuo. Purified by column chromatography [SiO$_2$ eluting EtOAc-MeOH (100:0-80:20)] Repurified by column chromatography [SiO$_2$ eluting DMAW 120/90] | [M + H]+ 451 Rt 2.23 (Acidic method) |

TABLE 3-continued

| Ex. No. | Structure | Method | Differences | LCMS |
|---|---|---|---|---|
| 263 | 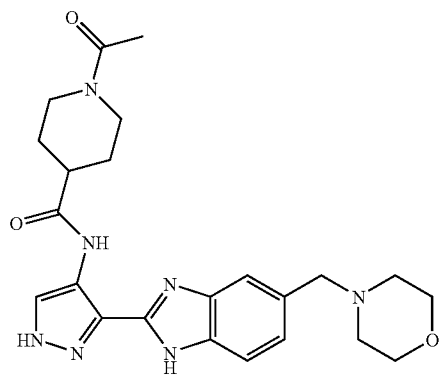 | Ex. 140C | Partitioned between DCM and sat. NaHCO$_3$, organics reduced in vacuo. Purified by column chromatography [SiO$_2$ eluting EtOAc-MeOH (100:0-90:10)] | [M + H]+ 452 Rt 2.17 (Basic method) |
| 264 | 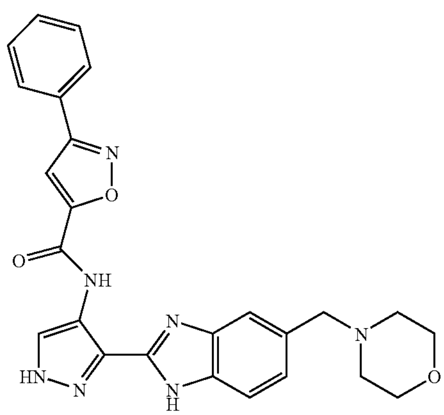 | Ex. 140C | Partitioned between DCM and sat. NaHCO$_3$, organics reduced in vacuo. Purified by column chromatography [SiO$_2$ eluting EtOAc-MeOH (100:0-80:20)] | [M + H]+ 470 Rt 2.26 (Acidic method) |
| 265 | 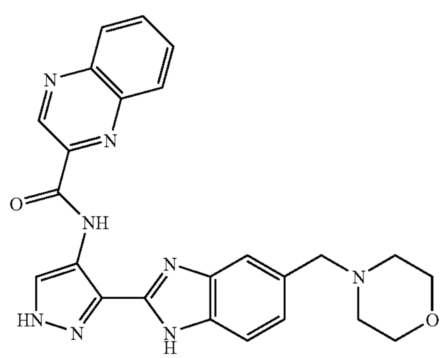 | Ex. 140C | Partitioned between DCM and sat. NaHCO$_3$, organics reduced in vacuo. Purified by column chromatography [SiO$_2$ eluting EtOAc-MeOH (100:0-90:10)] | [M + H]+ 455 Rt 2.09 (Basic method) |
| 266 | 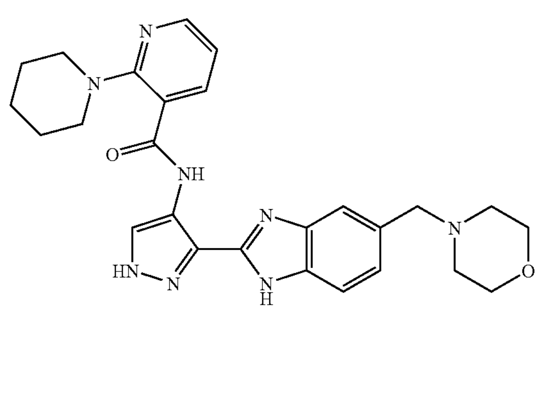 | Ex. 140C | Partitioned between DCM and sat. NaHCO$_3$, organics reduced in vacuo. Purified by column chromatography [SiO$_2$ eluting EtOAc-MeOH (100:0-80:20)] Repurified by column chromatography [SiO$_2$ eluting with DMAW 240/120] [DMAW 240 is: dichloromethane 240 ml, methanol 20 ml, acetic acid 3 ml, water 2 ml.] | [M + H]+ 487 Rt 2.59 (Basic method) |

TABLE 3-continued

| Ex. No. | Structure | Method | Differences | LCMS |
|---|---|---|---|---|
| 267 | 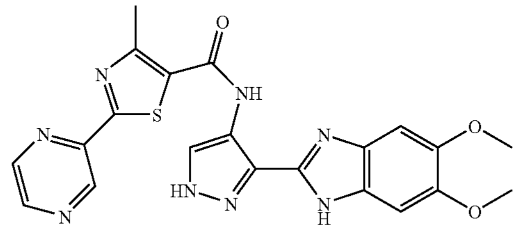 | Ex. 142C | Purified by preparative LCMS | [M + H]+ 463 Rt 3.72 (polar method) |
| 268 | 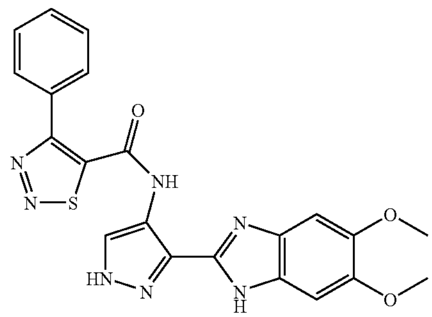 | Ex. 142C | Purified by preparative LCMS | [M + H]+ 448 Rt 3.36 (polar method) |
| 269 | 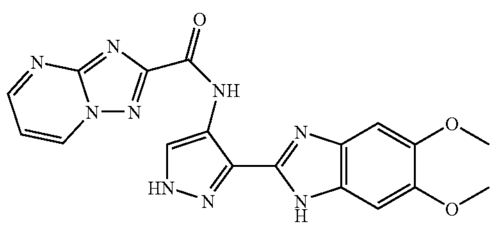 | Ex. 142C | Purified by preparative LCMS | [M + H]+ 406 Rt 2.3 (polar method) |

Preparation of Starting Material for Example 216: 2-Methoxy-5-(4-methyl-piperazine-1-sulphonyl)-benzoic Acid To solution of 5-chlorosulphonyl-2-methoxy-benzoic acid (0.5 g, 1.99 mmol) in acetone (5 ml) was added N-methylpiperazine (0.219 g, 2.19 mmol) and triethylamine (0.33 ml, 2.3 mmol) and the mixture stirred at RT. After 2 hours the reaction mixture was filtered and the collected solid washed with acetone, water and then diethylether to yield 2-methoxy-5-(4-methyl-piperazine-1-sulphonyl)-benzoic acid (150 mg, 24%). (LC/MS (acidic method): $R_t$ 0.34, [M+H]+ 315).

Example 270

Synthesis of 1-(2,6-Difluorophenyl)-N-[3-(5-Morpholin-4-ylmethyl-1H-benzimidazol-2-yl)-1H-pyrazol-4-yl]-urea

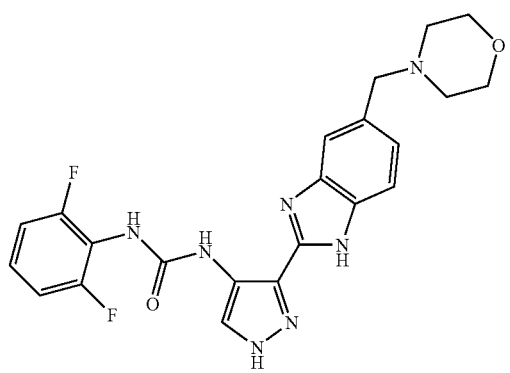

A mixture of 3-(5-morpholin-4-ylmethyl-1H-benzimidazol-2-yl)-1H-pyrazol-4-ylamine (50 mg, 0.16 mmol), 2,4 difluorophenyl isocyanate (26 mg, 0.16 mmol) and Et$_3$N (0.024 ml) suspended in a mixture of toluene (2 ml) and IPA (1 ml) was stirred at 80° C. for 1 h and then diluted with EtOAc. The reaction mixture was washed with water then brine, organics dried (MgSO$_4$) and reduced in vacuo The residue was purified by flash column chromatography [SiO$_2$, CH$_2$Cl$_2$-MeOH (90:10)] to give 1-(2,6-Difluorophenyl)-N-[3-(5-morpholin-4-ylmethyl-1H-benzimidazol-2-yl)-1H-pyrazol-4-yl]-urea (AT7787) as a colourless solid (30 mg, 39%). (LC/MS (acidic method): $R_t$ 1.80, [M+H]+ 454).

Examples 271-278

By following the procedure described in Example 270, the compounds set out in Table 4 were prepared.

TABLE 4

| Ex. No. | Structure | Method | Differences w.r.t. Ex. 240 | LCMS |
|---|---|---|---|---|
| 271 | 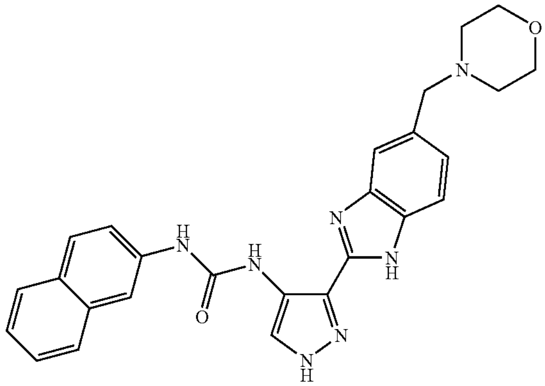 | Ex. 270 | | [M + H]+ 466 Rt 2.10 (Acidic method) |
| 272 | 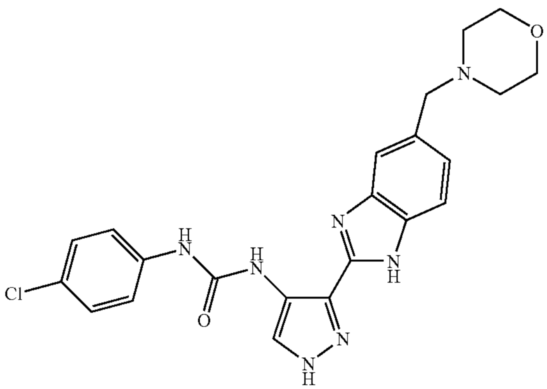 | Ex. 270 | | [M + H]+ 452 Rt 2.06 (Acidic method) |
| 273 | 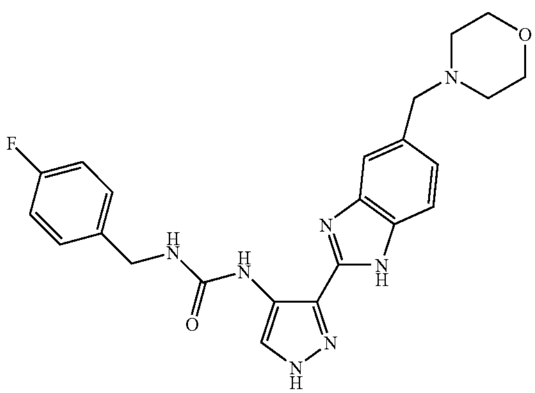 | Ex. 270 | | [M + H]+ 450 Rt 1.84 (Acidic method) |
| 274 | 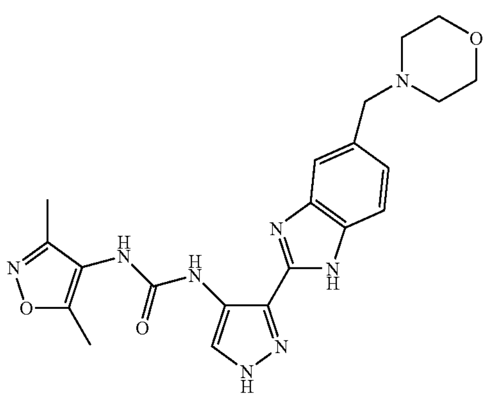 | Ex. 270 | | [M + H]+ 437 Rt 1.73 (Acidic method) |

TABLE 4-continued

| Ex. No. | Structure | Method | Differences w.r.t. Ex. 240 | LCMS |
|---|---|---|---|---|
| 275 | 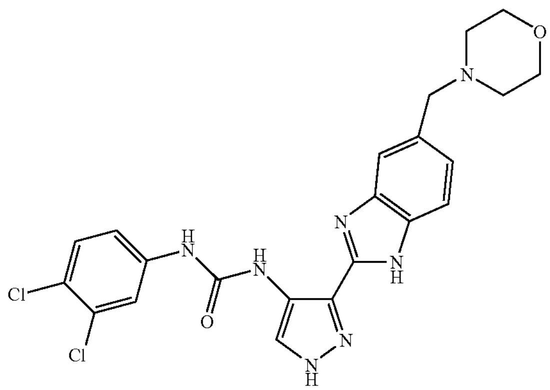 | Ex. 270 | | [M + H]+ 486 Rt 2.25 (Acidic method) |
| 276 | 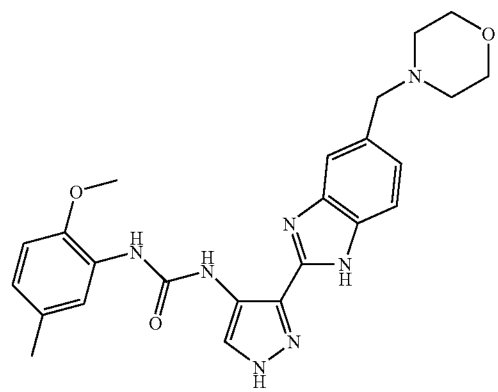 | Ex. 270 | | [M + H]+ 462 Rt 2.04 (Acidic method) |
| 277 | 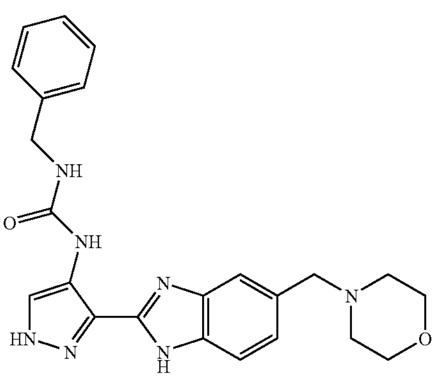 | Ex. 270 | THF was used as solvent and reaction was carried out at room temperature for 1 hour | [M + H]+ 432 Rt 2.16 (Acidic method) |
| 278 | 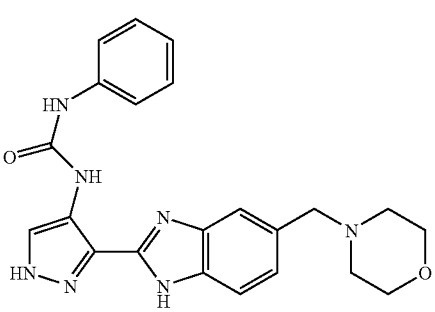 | Ex. 270 | THF was used as solvent and reaction was carried out at room temperature for 1 hour | [M + H]+ 418 Rt 1.93 (Acidic method) |

Example 279

Synthesis of N-[3-(5,6-dimethoxy-1H-benzimidazol-2-yl)-1H-pyrazol-4-yl]-trans-1,4-aminocyclohexanecarboxamide

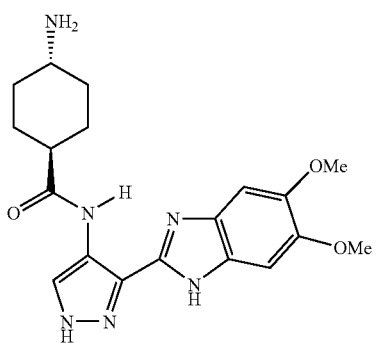

279A: Synthesis of N-[3-(5,6-dimethoxy-1H-benzimidazol-2-yl)-1H-pyrazol-4-yl]-N-BOC-trans-1,4-aminocyclohexanecarboxamide To a suspension of BOC-trans-1,4-carboxylic acid-caesium salt (95 mg, 0.25 mmol) in THF (2 ml) was added DMF (1.9 µl, 0.025 mmol) followed by oxalyl chloride (30 ul, 0.3 mmol). After stirring at room temperature for 20 min. the mixture was evaporated to dryness and then re-suspended in THF (2 ml). A solution of 3-(5,6-dimethoxy-1H-benzimidazol-2-yl)-1H-pyrazol-4-ylamine (50 mg, 0.17 mmol) and diisopropylethylamine (62 µl, 0.5 mmol) in THF (1 ml) was then added and the reaction stirred for at room temperature for 1 h. After 1 h, MeOH (1 ml) was added and the mixture was partitioned between chloroform and saturated aqueous sodium hydrogen carbonate, dried (MgSO$_4$) and reduced in vacuo. The residue was purified by flash column chromatography [SiO$_2$, EtOAc] to give N-[3-(5,6-dimethoxy-1H-benzimidazol-2-yl)-1H-pyrazol-4-yl]-N-BOC-trans-1,4-aminocyclohexane carboxamide as a white solid (45 mg, 55%). (LC/MS (basic method): R$_t$ 2.79 min, [M+H]$^+$ 485).

279B: Synthesis of N-[3-(5,6-dimethoxy-1H-benzimidazol-2-yl)-1H-pyrazol-4-yl]-trans-1,4-aminocyclohexane carboxamide N-[3-(5,6-dimethoxy-1H-benzimidazol-2-yl)-1H-pyrazol-4-yl]-N-BOC-trans-1,4-aminocyclohexane carboxamide (45 mg, 0.093 mmol) and anisole (40 µl, 0.28 mmol) were dissolved in a mixture of trifluoroacetic acid and dichloromethane (1:2; 3 ml). After 3 h at room temperature, the mixture was evaporated to dryness to give N-[3-(5,6-dimethoxy-1H-benzimidazol-2-yl)-1H-pyrazol-4-yl]-trans-1,4-aminocyclohexanecarboxamide (AT8241) as a white solid (49 mg). (LC/MS (basic method): R$_t$ 2.03 min, [M+H]$^+$ 385).

Example 280

Pyrrolidine-2-carboxylic Acid [3-(5,6-dimethoxy-1H-benzimidazol-2-yl)-1H-pyrazol-4-yl]-amide

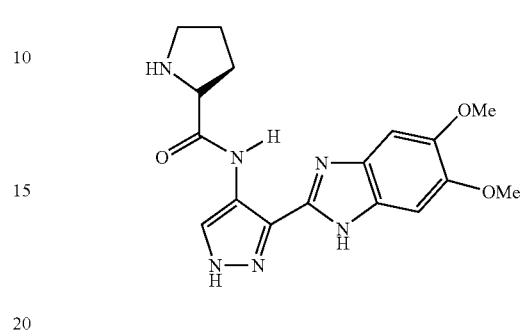

Following the procedure set out in Example 279 gave the title compound. [M+H]$^+$ 357 Rt 2.23 (basic method).

Example 281

Synthesis of N-[3-(5,6-dimethoxy-1H-benzimidazol-2-yl)-1H-pyrazol-4-yl]-rac-4-benzyl-2-morpholine carboxamide

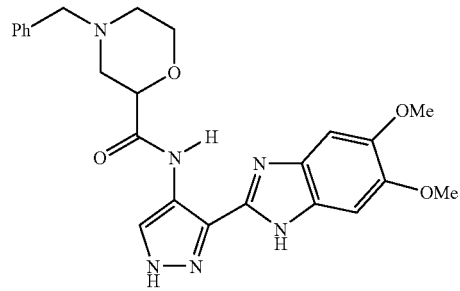

To a suspension of rac-4-benzyl-2-morpholinecarboxylic acid hydrochloride (77 mg, 0.30 mmol) in THF (2 ml) was added DMF (2.0 µl, 0.025 mmol) followed by oxalyl chloride (36 ul, 0.41 mmol). After stirring at room temperature for 20 min. the mixture was evaporated to dryness and then re-suspended in THF (2 ml). A solution of 3-(5,6-dimethoxy-1H-benzimidazol-2-yl)-1H-pyrazol-4-ylamine (60 mg, 0.2 mmol) and diisopropylethylamine (110 µl, 0.9 mmol) in THF (1 ml) was then added and the reaction stirred for at room temperature for 1 h. After 1 h, MeOH (1 ml) was added, the mixture concentrated and the residue purified through preparative LC/MS to give N-[3-(5,6-dimethoxy-1H-benzimidazol-2-yl)-1H-pyrazol-4-yl]-rac-4-benzyl-2-morpholinecarboxamide (AT8769) as a white solid (10 mg, 9%). (LC/MS (basic method): R$_t$ 2.86 min, [M+H]$^+$ 463).

Example 282

Synthesis of N-[3-(5,6-dimethoxy-1H-benzimidazol-2-yl)-1H-pyrazol-4-yl]-N-methyl-D-phenylglycine amide

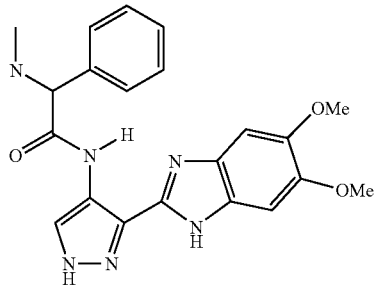

The compound was prepared in a manner analogous to N-[3-(5,6-dimethoxy-1H-benzimidazol-2-yl)-1H-pyrazol-4-yl]-5-fluoro-2-methoxy-benzamide (Example 142C), but using N-BOC-N-methyl-D-phenylglycine instead of 5-fluoro-2-methoxy-benzoic acid and HOAt instead of HOBt. The crude reaction mixture was partitioned between EtOAc and H$_2$O. The EtOAc layer was washed with saturated aqueous sodium hydrogen carbonate, brine, dried (MgSO$_4$) and reduced in vacuo. The residue was purified through preparative LC/MS, instead of flash chromatography, to give N-[3-(5,6-dimethoxy-1H-benzimidazol-2-yl)-1H-pyrazol-4-yl]-N-BOC-N-methyl-D-phenylglycine amide (10 mg, 10%) as a white solid. (LC/MS (basic): R$_t$ 3.07 min, [M+H]$^+$ 507).

Deprotection was performed in a manner analogous to Example 279B to give N-[3-(5,6-dimethoxy-1H-benzimidazol-2-yl)-1H-pyrazol-4-yl]-N-methyl-D-phenylglycine- (AT8768) as a white solid (10 mg). (LC/MS (basic method): R$_t$ 2.54 min, [M+H]$^+$ 407).

Example 283

Synthesis of 4-Morpholinyl-N-[3-(5-morpholin-4-ylmethyl-1H-benzimidazol-2-yl)-1-H-pyrazol-4-yl]-urea

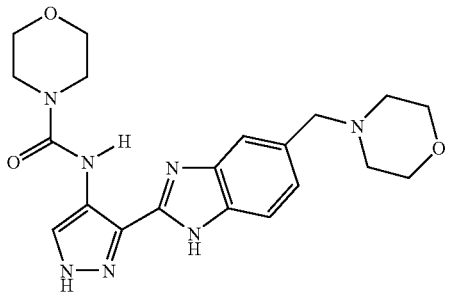

A mixture of 3-(5-morpholin-4-ylmethyl-1H-benzimidazol-2-yl)-1H-pyrazol-4-ylamine (70 mg, 0.23 mmol), morpholine-4-carbonyl chloride (80 µl, 0.7 mmol) and diisopropylethylamine (170 µl, 0.92 mmol) in THF (2 ml) was stirred at 0° C. and then allowed to warm to room temperature over 16 h. The reaction was quenched by the addition of conc. aq. NH$_3$ and then concentrated in vacuo. The residue was purified through preparative LC/MS to give 4-morpholinyl-N-[3-(5-morpholin-4-ylmethyl-1H-benzimidazol-2-yl)-1-H-pyrazol-4-yl]-urea as a white solid (35 mg). (LC/MS (basic method): R$_t$ 2.28 min, [M−H$^+$]$^-$ 415).

Example 284

Synthesis of 2,6-difluoro-N-[3-(4-oxo-1,4,5,6,7,8-hexahydro-1,3,5-triaza-azulen-2-yl)-1H-pyrazol-4-yl]-benzamide 284A. Synthesis of [7-ethoxy-4,6-dioxo-5-(triphenyl-lamda*5*-phosphanylidene)-heptyl]carbamic Acid tert-butyl ester

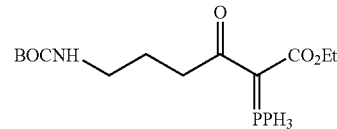

A solution of (ethoxycarbonylmethylene)triphenyl phosphorane (5.2 g, 14.91 mmoles), 4-tert-butoxycarbonylamino-butyric acid (3.3 g, 16.26 mmoles), EDC (3.4 g, 17.89 mmoles) and DMAP (0.182 g, 1.49 mmoles) in dichloromethane was stirred at ambient temperature for 48 hours. The reaction mixture was partitioned between EtOAc and water. The organic portion was dried (MgSO$_4$), filtered and evaporated in vacuo. The residue was purified [Biotage SP4, 40M, flow rate 40 ml/min, gradient 3:2 EtOAc/Petrol to EtOAc] to give [7-ethoxy-4,6-dioxo-5-(triphenyl-lamda*5*-phosphanylidene)-heptyl]carbamic acid tert-butyl ester as a light brown solid (4.7 g, 59%).

284B. Synthesis of (7-ethoxy-4,5,6-trioxo-heptyl)-carbamic Acid tert-butyl ester

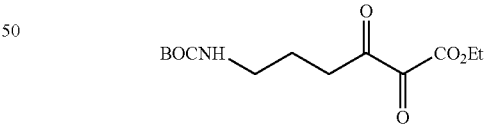

To a solution of give [7-ethoxy-4,6-dioxo-5-(triphenyl-lamda*5*-phosphanylidene)-heptyl]carbamic acid tert-butyl ester (4.7 g, 8.82 mmoles) in THF (75 ml) and water (20 ml) was added Oxone™ (6.5 g, 10.58 mmoles). The suspension was stirred at ambient temperature for 3 hours. The reaction mixture was partitioned between EtOAc and water. The organic portion was dried (MgSO$_4$), filtered and evaporated in vacuo. The residue was purified by flash column chromatography [silica, EtOAc:Petrol (1:2)] to give (7-ethoxy-4,5,6-trioxo-heptyl)-carbamic acid tert-butyl ester as a colourless oil (1.7 g, 67%).

284C. Synthesis of 5-(3-tert-butoxycarbonylamino-propyl)-2-[4-(2,6-difluoro benzoylamino-1-(tetrahydro-pyran-2-yl)-1H-pyrazol-3-yl]-1H-imiadzole-4-carboxylic Acid methyl ester

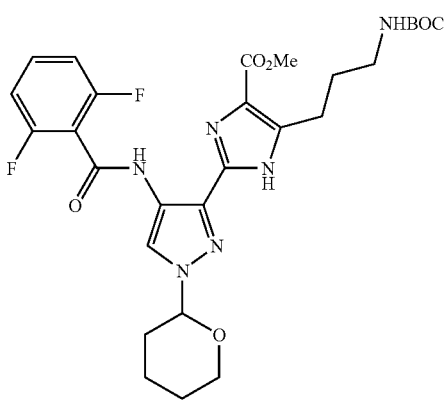

A solution of (7-ethoxy-4,5,6-trioxo-heptyl)-carbamic acid tert-butyl ester (1.7 g, 5.92 mmoles) and 2,6-difluoro-N-[3-formyl-1-(tetrahydro-pyran-2-yl)-1H-pyrazol-4-yl]-benzamide (0.99 g, 2.96 mmoles) in methanolic ammonia (2N, 20 ml) was stirred at ambient temperature for 2 hours. The solvent was removed in vacuo. The residue was purified [Biotage SP4, 40M, flow rate 40 ml/min, gradient 1:4 EtOAc/Petrol to 4:1 EtOAc/Petrol] to give 5-(3-tert-butoxycarbonylamino-propyl)-2-[4-(2,6-difluoro-benzoylamino-1-(tetrahydro-pyran-2-yl)-1H-pyrazol-3-yl]-1H-imiadzole-4-carboxylic acid methyl ester as a pale yellow solid (320 mg, 18%). (LC/MS: $R_t$ 3.36, [M+H]$^+$ 589.16).

284D. Synthesis of 5-(tert-butoxycarbonylamino-propyl)-2-[4-(2,6-difluoro-benzoylamino)-1-(tetrahydro-pyran-2-yl)-1H-pyrazol-3-yl]-1H-imidazole-4-carboxylic Acid

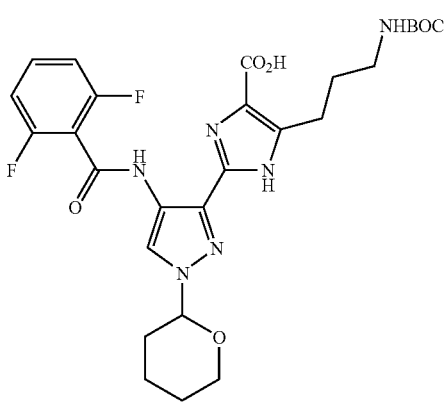

To a solution of 5-(3-tert-butoxycarbonylamino-propyl)-2-[4-(2,6-difluoro-benzoylamino)-1-(tetrahydro-pyran-2-yl)-1H-pyrazol-3-yl]-1H-imiadzole-4-carboxylic acid methyl ester (320 mg, 0.544 mmoles) in methanol (10 ml) was added a solution of NaOH (2N, 10 ml). The reaction mixture was stirred at ambient temperature for 24 hours. The methanol was removed in vacuo. The residue was partitioned between EtOAc and a 5% citric acid solution. The organic portion was dried (MgSO$_4$), filtered and evaporated in vacuo to give 5-(tert-butoxycarbonylamino-propyl)-2-[4-(2,6-difluoro-benzoylamino)-1-(tetrahydro-pyran-2-yl)-1H-pyrazol-3-yl]-1H-imidazole-4-carboxylic acid as a pale yellow solid (300 mg, 96%). (LC/MS: $R_t$ 3.03 [M+H]$^+$ 575.17).

284E. Synthesis of 5-(3-amino-propyl)-2-[4-(2,6-difluoro-benzoylamino)-1H-pyrazol-3-yl]-1H-imidazole carboxylic Acid

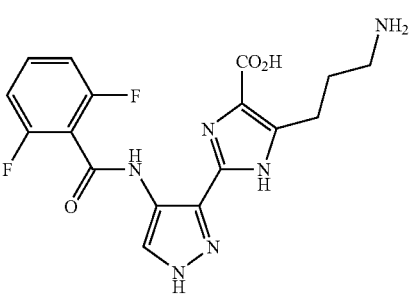

A solution of 5-(tert-butoxycarbonylamino-propyl)-2-[4-(2,6-difluoro benzoylamino)-1-(tetrahydro-pyran-2-yl)-1H-pyrazol-3-yl]-1H-imidazole-4-carboxylic acid (300 mg, 0.52 mmoles) and anisole (114 µl, 1.04 mmoles) in TFA (3 ml) was heated at 100° C. (80 W) in a CEM discover microwave synthesizer for 10 minutes. Toluene (10 ml) was added and the solvent removed in vacuo to give 5-(3-amino-propyl)-2-[4-(2,6-difluoro-benzoylamino)-1H-pyrazol-3-yl]-1H-imidazole carboxylic acid as a yellow/brown solid (200 mg, 99%). (LC/MS: $R_t$ 1.58, {M+H}$^+$ 391.00).

284F. Synthesis of 2,6-difluoro-N-[3-(4-oxo-1,4,5,6,7,8-hexahydro-1,3,5-triaza-azulen-2-yl)-1H-pyrazol-4-yl]-benzamide

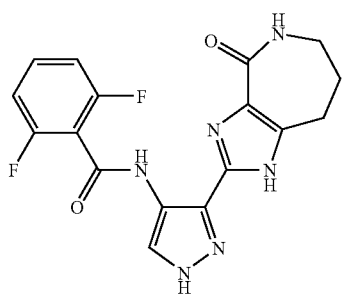

To a stirred solution of 5-(3-amino-propyl)-2-[4-(2,6-difluoro-benzoylamino)-1H-pyrazol-3-yl]-1H-imidazole carboxylic acid (200 mg, 0.51 mmoles) in DMF (10 ml) and dichloromethane (10 ml) was added EDC (118 mg, 0.62 mmoles), HOBt (84 mg, 0.62 mmoles) and NEM (260 µl, 2.04 mmoles). The solution was stirred at ambient temperature for 48 hours and then partitioned between EtOAc and water. The organic portion was dried (MgSO$_4$), filtered and evaporated in vacuo. The residue was purified by flash column chromatography [silica, 3% MeOH in DCM to 5% to 10%] to give 2,6-difluoro-N-[3-(4-oxo-1,4,5,6,7,8-hexahydro-1,3,5-triaza-azulen-2-yl)-1H-pyrazol-4-yl]-benzamide as a pale yellow solid (10 mg, 13%). (LC/MS: $R_t$ 1.93, [M+H]$^+$ 372.99).

Example 285

Synthesis of 2-amino-N-[3-(5-morpholin-4-yl-methyl-1H-benzimidazol-2-yl-)-1H-pyrazol-4-yl]-2-phenyl-acetamide

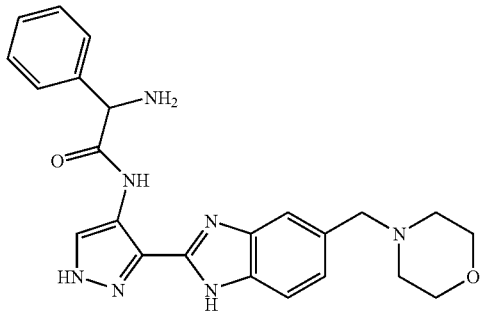

{[3-(5-Morpholin-4-yl-methyl-1H-benzimidazol-2-yl)-1H-pyrazol-4-yl-carbamoyl]-phenyl-methyl}-carbamic acid tert-butyl ester (Example 232) (30 mg) was dissolved in 4M HCl/dioxane, and 3 ml of methanol and stirred at room temperature overnight. The solvent was removed in vacuo and residue triturated with diethylether to give 2-amino-N-[3-(5-morpholin-4-yl-methyl-1H-benzimidazol-2-yl-)-1H-pyrazol-4-yl]-2-phenyl-acetamide (AT8162) as a white solid (20 mg, 83%). (LC/MS (acidic method): R$_t$ 2.39 min, [M+H]$^+$ 432).

Examples 286-287

By following the procedure described in Example 285, the compounds set out in Table 5 were prepared.

TABLE 5

| Ex. No. | Structure | Method | Differences w.r.t. Ex. 285 | LCMS |
|---|---|---|---|---|
| 286 | 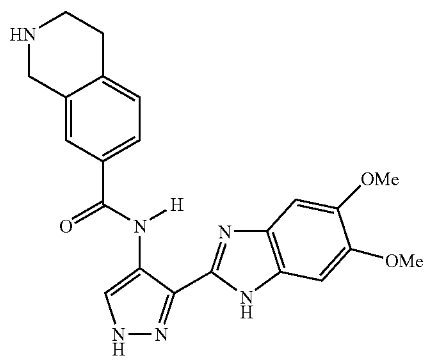 | Ex. 285 | Starting with product of Ex. 245. Sat. HCl in EtOAc used in place of HCl/dioxane | [M + H]+ 419 Rt 1.73 (acidic method) |
| 287 | 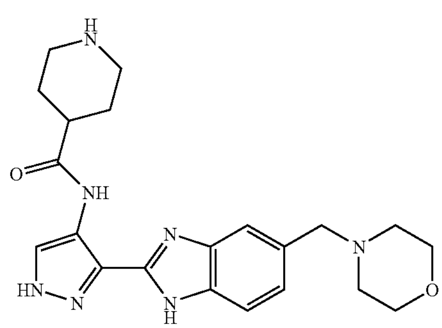 | Ex. 285 | 4-[3-(5-morpholin-4-ylmethyl-1H-benzimidazole-2-yl)-1H-pyrazol-4yl-carbamoyl]-piperidine-1-carboxylic acid tert-butyl ester used as starting material | [M + H]+ 410 Rt 2.03 (Basic method) |

Example 288

Synthesis of N-[3-(1H-benzimidazol-2-yl)-1H-pyrazol-4-yl]-5-tert-butyl-2-methoxy-benzamide

288A: Synthesis of 4-nitro-1H-pyrazole-3-carboxylic Acid methyl ester

The compound was prepared in a manner analogous to 4-nitro-1H-pyrazole-3-carboxylic acid ethyl ester (Example 16A) using 4-nitro-1H-pyrazole-3-carboxylic acid (100 g, 636 mmol), thionyl chloride (55.5 ml, 764 ml) and MeOH (750 ml), instead of EtOH. 4-Nitro-1H-pyrazole-3-carboxylic acid methyl ester was obtained as an off-white solid (109 g, 100%). (LC/MS (acidic method): $R_t$ 1.82 min, $[M+H]^+$ 172).

288B: Synthesis of 4-amino-1H-pyrazole-3-carboxylic Acid methyl ester

A mixture of 4-nitro-1H-pyrazole-3-carboxylic acid methyl ester (10 g, 58 mmol) and 10% palladium on carbon (500 mg) in ethanol (150 ml) and DMF (30 ml) stirred under an atmosphere of hydrogen overnight. The reaction mixture was filtered through celite reduced in vacuo and dried through azeotrope with toluene and methanol to afford 4-amino-1H-pyrazole-3-carboxylic acid methyl ester as a dark amber tar (9.35 g). (LC/MS (acidic): $R_t$ 0.39 min, $[M+H]^+$ 142).

288C: Synthesis of 4-(5-tert-butyl-2-methoxy-benzoylamino)-1H-pyrazole-3-carboxylic Acid methyl ester To a solution of EDC (11.59 g, 60.7 mmol), HOBt (8.19 g, 60.7 mmol) and 4-amino-1H-pyrazole-3-carboxylic acid methyl ester (7.84 g, 55.6 mmol) in DMF (100 ml) was added 5-tert-butyl-2-methoxy-benzoic acid (10.52 g, 50.6 mmol) and the mixture stirred at room temperature overnight. The mixture was reduced in vacuo and the residue partitioned between EtOAc (500 ml) and brine (200 ml), the organic portion was washed with saturated aqueous sodium hydrogen carbonate (200 ml), dried (MgSO$_4$) and reduced in vacuo to yield 4-(5-tert-butyl-2-methoxy-benzoylamino)-1H-pyrazole-3-carboxylic acid methyl ester as a pale yellow solid (17.07 g, 93%). (LC/MS (acidic method): $R_t$ 3.12 min, $[M+H]^+$ 332).

288D: Synthesis of 4-(5-tert-butyl-2-methoxy-benzoylamino)-1H-pyrazole-3-carboxylic Acid The compound was prepared in a manner analogous to Example 16D but using 4-(5-tert-butyl-2-methoxy-benzoylamino)-1H-pyrazole-3-carboxylic acid methyl ester (17.068 g) as starting material. 4-(5-tert-butyl-2-methoxy-benzoylamino)-1H-pyrazole-3-carboxylic acid was obtained as a brown solid (~15.6 g, 95%). (LC/MS (acidic method): $R_t$ 2.79 min, $[M+H]^+$ 318).

288E: Synthesis of 4-(5-tert-butyl-2-methoxy-benzoylamino)-1H-pyrazole-3-carboxylic Acid (2-amino-phenyl)-amide To a solution of EDC (720 mg, 3.8 mmol), HOBt (510 mg, 3.8 mmol) and 4-(5-tert-butyl-2-methoxy-benzoylamino)-1H-pyrazole-3-carboxylic acid (1 g, 3.16 mmol) in DMF (25 ml) was added benzene-1,2-diamine (375 mg, 3.5 mmol) and the mixture stirred at room temperature for 5 hours. The mixture was reduced in vacuo and the residue partitioned between EtOAc (50 ml) and brine (2×50 ml). Undissolved precipitate was removed by filtration, the organic portions washed with saturated aqueous sodium hydrogen carbonate (50 ml), dried (MgSO$_4$) and reduced in vacuo to yield 4-(5-tert-butyl-2-methoxy-benzoylamino)-1H-pyrazole-3-carboxylic acid (2-amino-phenyl)-amide as a pale yellow powder (848 mg, 66%). (LC/MS (acidic method): $R_t$ 3.21 min, $[M+H]^+$ 408).

288F: Synthesis of N-[3-(1H-benzimidazol-2-yl)-1H-pyrazol-4-yl]-5-tert-butyl-2-methoxy-benzamide

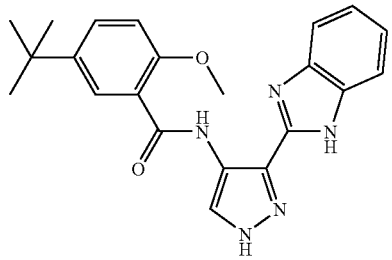

4-(5-tert-Butyl-2-methoxy-benzoylamino)-1H-pyrazole-3-carboxylic acid (2-amino-phenyl)-amide (848 mg, 2.08 mmol) was dissolved in acetic acid (150 ml) and refluxed at 140° C. for 3 hours. The solution was left to cool, the solvent removed in vacuo and the resulting solid dried through azeotrope with methanol and toluene. The crude product was purified by column chromatography [SiO$_2$, EtOAc/petrol (2:1)] to give N-[3-(1H-benzimidazol-2-yl)-1H-pyrazol-4-yl]-5-tert-butyl-2-methoxy-benzamide (500 mg, 62% yield) as a pale yellow powder. (LC/MS: $R_t$ 3.44, $[M+H]^+$ 390, acidic method.

Example 289

Synthesis of 4-(2-chloro-5-(methylthio)-N-[3-(5-morpholin-4-ylmethyl-1H-benzimidazol-2-yl)-1H-pyrazol-4-yl]-benzamide

289A: Synthesis of 4-(2-chloro-5-(methylthio)-benzoylamino)-1H-pyrazole-3-carboxylic Acid methyl ester The title compound was prepared in a manner analogous to Example 288C, but using 2-chloro-5-(methylthio)benzoic acid (15.34 g, 72.7 mmol) instead of 5-tert-butyl-2-methoxy-benzoic acid. The product was obtained as a beige solid containing 4-(2-chloro-5-(methylthio)-benzoylamino)-1H-pyrazole-3-carboxylic acid methyl ester as the major component (25 g). (LC/MS (acidic method): $R_t$ 2.78, $[M+H]^+$ 325.94).

289B: Synthesis of 4-(2-chloro-5-(methylthio)-benzoylamino)-1H-pyrazole-3-carboxylic Acid The compound was prepared in a manner analogous to Example 16D, but using 4-(2-chloro-5-(methylthio)-benzoylamino)-1H-pyrazole-3-carboxylic acid methyl ester (11.8 g) as the starting ester. This afforded 4-(2-chloro-5-(methylthio)-benzoylamino)-1H-pyrazole-3-carboxylic acid as a beige solid (5.82 g). (LC/MS (acidic method): $R_t$ 2.46, $[M+H]^+$ 311.99).

289C: Synthesis of 4-(2-chloro-5-(methylthio)-N-[3-(5-morpholin-4-ylmethyl-1H-benzimidazol-2-yl)-1H-pyrazol-4-yl]-benzamide

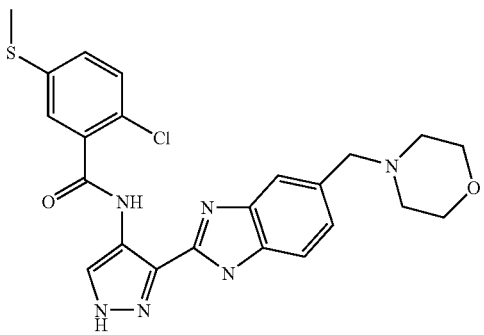

A mixture of 4-(2-chloro-5-(methylthio)-benzoylamino)-1H-pyrazole-3-carboxylic acid (2 g, 6.43 mmol), 4-morpholin-4-ylmethyl-benzene-1,2-diamine (1.33 g, 6.43 mmol) (Example 138C), EDC (1.36 g, 7.07 mmol) and HOBt (0.96 g, 7.07 mmol) in DMF (20 ml) was stirred at ambient temperature for 18 h. The residue was reduced in vacuo and then partitioned between saturated NaHCO$_3$ solution (150 ml) and EtOAc (3×150 ml). The combined organics were dried (Na$_2$SO$_4$), filtered and evaporated in vacuo to give a crude oil. This was purified by flash chromatography [SiO$_2$; eluting with CH$_2$Cl$_2$: MeOH (100:0-95:5)] to afford the product as a beige solid (1.23 g). (LC/MS (acidic method): R$_t$ 2.10, [M+H]$^+$ 501.09).

A mixture of this product (1.23 g, 2.46 mmol) in glacial AcOH (20 ml) was heated at 120° C. for 1.5 h. The mixture was reduced in vacuo and partitioned between saturated NaHCO$_3$ solution (150 ml) and EtOAc (2×150 ml). The combined organics were dried (Na$_2$SO$_4$), filtered and evaporated in vacuo to give a crude oil. This was purified by flash chromatography [SiO$_2$; eluting with CH$_2$Cl$_2$: MeOH (100:0-95:5)] to afford 4-(2-chloro-5-(methylthio)-N-[3-(5-morpholin-4-ylmethyl-1H-benzimidazol-2-yl)-1H-pyrazol-4-yl]-benzamide (AT8608) as a beige solid (0.9 g, 29%). (LC/MS (acidic method): R$_t$ 2.14, [M+H]$^+$ 483.13).

Example 290

Synthesis of: [3-(5-Morpholin-4-ylmethyl-1H-benzimidazol-2-yl)-1H-pyrazol-4-yl]-carbamic Acid, 4-fluoro-phenyl ester

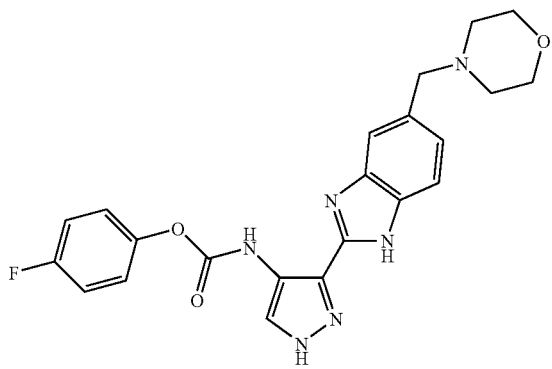

A mixture of 3-(5-morpholin-4-ylmethyl-1H-benzimidazol-2-yl)-1H-pyrazol-4-ylamine (50 mg, 0.16 mmol) and pyridine (0.02 ml, 0.24 mmol) dissolved in a mixture of CH$_2$Cl$_2$ (1 ml) and THF (1 ml) was stirred at 0° C. and then treated with 4-fluorophenylchloroformate (30.7 mgs, 0.168 mmol). The reaction mixture was stirred at RT until complete and then diluted with CH$_2$Cl$_2$. The CH$_2$Cl$_2$ fraction was washed with sat. bicarbonate, brine, dried (MgSO$_4$) and reduced in vacuo. The residue was purified by flash column chromatography [SiO$_2$, CH$_2$Cl$_2$-MeOH (90:10)] to give [3-(5-morpholin-4-ylmethyl-1H-benzimidazol-2-yl)-1H-pyrazol-4-yl]-carbamic acid 4-fluoro-phenyl ester (AT8428) as a colourless solid (5 mg, 7%). (LC/MS (acidic method): R$_t$ 2.08, [M+H]$^+$ 437).

Example 291

Synthesis of N-[3-(6-Chloro-1H-imidazo[4,5-c]pyridin-2-yl)-1H-pyrazol-4-yl]-2,6-difluoro-benzamide

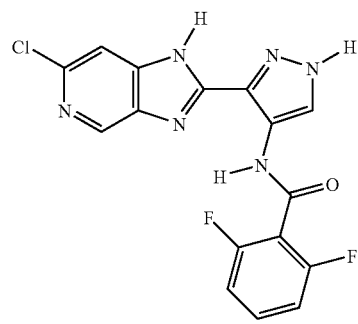

A mixture of 4-(2,6-difluorobenzylamino)-1H-pyrazole-3-carboxylic acid (100 mg, 0.37 mmol) (Example 16D), 6-chloro-pyridine-3,4-diamine (54 mg, 0.37 mmol), EDC (72 mg, 0.40 mmol), HOBt (57.3 mg, 0.40 mmol) and Et$_3$N (0.075 ml, 0.55 mmol) in DMF (20 ml) was stirred at ambient temperature for 48 h and then partitioned between EtOAc and saturated aqueous sodium bicarbonate and the organic portion dried (MgSO$_4$), filtered and evaporated. The amide intermediate was dissolved in AcOH (3 ml), heated at reflux for 1 h, and then heated in the microwave (150 W) at 160° C. until the reaction was complete. The reaction mixture was allowed to cool, a solid crystallised out, which was filtered and then washed with petroleum ether and dried to give the required product (9 mg). (LC/MS: R$_t$ 2.74, [M+H]$^+$ 375)

Examples 292-293

The following compounds were prepared using General Procedure A modified as shown in Table 6.

TABLE 6

| Ex. No. | Structure | Method | Differences | LCMS |
|---|---|---|---|---|
| 292 | 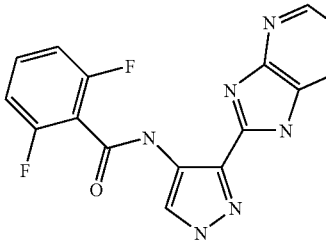 | Gen. Proc. A P032-GP B | Coupling heated at 85° C., cyclisation carried out at 180° C. | [M + H]+ 360 R$_t$ 1.74 |
| 293 | 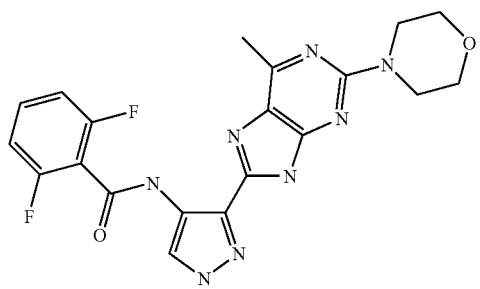 | Gen. Proc. A | Coupling heated at 85° C., cyclisation carried out at 180° C. | [M + H]+ 441 R$_t$ 2.66 |

Examples 294-303

The compounds of Examples 294 to 303 were prepared by the methods of the preceding Examples.

Example 294

4-(2-{2-[4-(2,6-Difluoro-benzoylamino)-1H-pyrazol-3-yl]-1H-benzimidazol-5-yloxy}-ethyl)-piperidine-1-carboxylic Acid tert-butyl ester

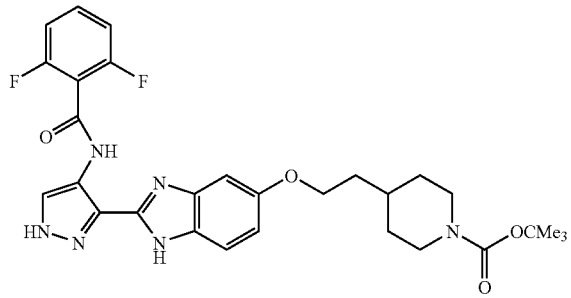

Example 295

5-Methyl-2-trifluoromethyl-furan-3-carboxylic Acid [3-(5-morpholin-4-ylmethyl-1H-benzimidazol-2-yl)-1H-pyrazol-4-yl]-amide

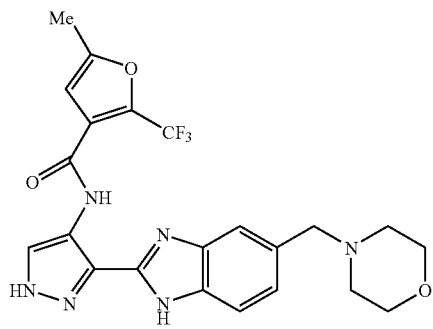

Example 296

Isobenzofuran-1-carboxylic Acid [3-(5-morpholin-4-ylmethyl-1H-benzimidazol-2-yl)-1H-pyrazol-4-yl]-amide

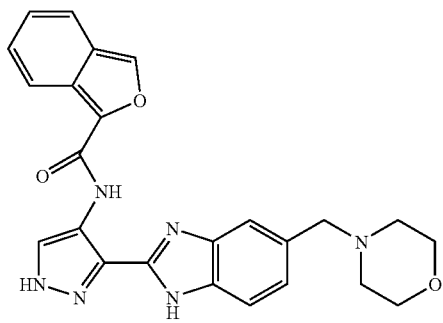

Example 297

2-(4-Chloro-phenyl)-4-methyl-thiazole-5-carboxylic Acid [3-(5,6-dimethoxy-1H-benzimidazol-2-yl)-1H-pyrazol-4-yl]-amide

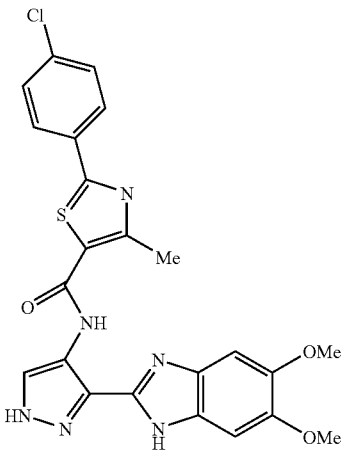

Example 298

2-(4-Fluoro-phenyl)-5-methyl-2H-[1,2,3]triazole-4-carboxylic Acid [3-(5,6-dimethoxy-1H-benzimidazol-2-yl)-1H-pyrazol-4-yl]-amide

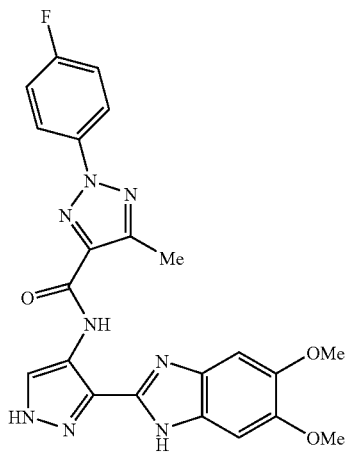

Example 299

Biphenyl-2-carboxylic Acid [3-(5-morpholin-4-ylmethyl-1H-benzimidazol-2-yl)-1H-pyrazol-4-yl]-amide

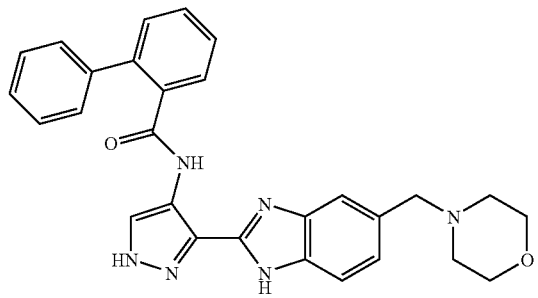

Example 300

4,6-Dimethyl-2-oxo-1,2-dihydro-pyridine-3-carboxylic Acid [3-(5-morpholin-4-ylmethyl-1H-benzimidazol-2-yl)-1H-pyrazol-4-yl]-amide

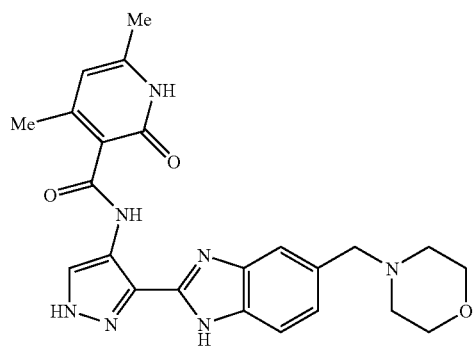

Example 301

2-Oxo-1,2-dihydro-pyridine-3-carboxylic Acid [3-(5-morpholin-4-ylmethyl-1H-benzimidazol-2-yl)-1H-pyrazol-4-yl]-amide

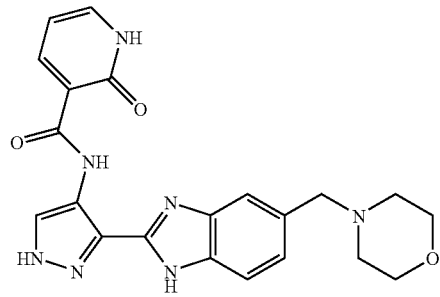

Example 302

3-(4-Fluoro-phenyl)-5-methyl-isoxazole-4-carboxylic Acid [3-(5-morpholin-4-ylmethyl-1H-benzimidazol-2-yl)-1H-pyrazol-4-yl]-amide

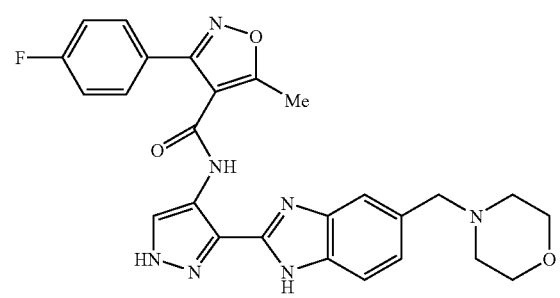

Example 303

2-(4-Chloro-phenylsulphanyl)-N-[3-(5-morpholin-4-ylmethyl-1H-benzimidazol-2-yl)-1H-pyrazol-4-yl]-nicotinamide

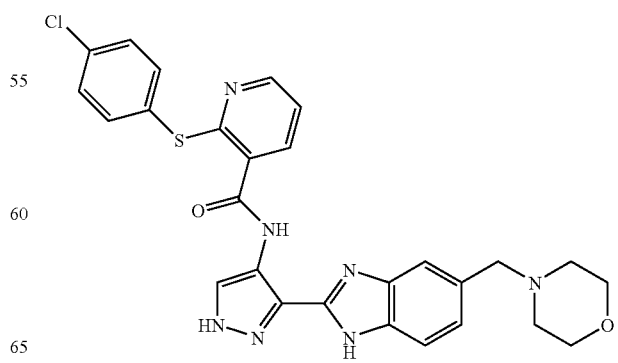

Example 304

Synthesis of N-[3-(5,6-dimethoxy-1H-benzimidazol-2-yl)-1H-pyrazol-4-yl]-2-methoxy-5-morpholin-4-yl-benzamide

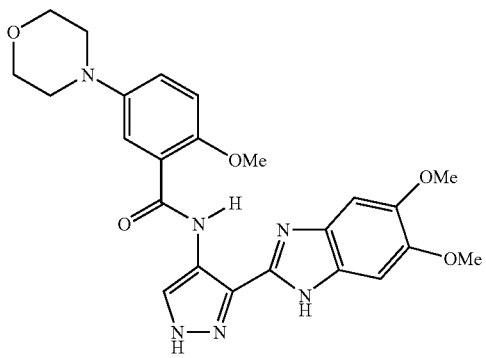

304A: Synthesis of 2-methoxy-5-morpholin-4-yl-benzoic Acid methyl ester

5-Iodo-2-methoxy-benzoic acid methyl ester (500 mg, 1.7 mmol), morpholine (223 µl, 2.5 mmol), cesium carbonate (850 mg, 2.7 mmol), xantphos (60 mg, 0.1 mmol) and bis(dibenzylideneacetone)dipalladium (35 mg, 0.04 mmol) were suspended in dioxane (5 ml) and heated at 100° C. for 5 h. The mixture was then cooled, filtered and the residue was purified by flash column chromatography [SiO$_2$, EtOAc] to give 2-methoxy-5-morpholin-4-yl-benzoic acid methyl ester (170 mg) as a colourless solid. (LC/MS (basic method): R$_t$ 2.35 min, [M+H]$^+$ 252).

304B: Synthesis of 2-methoxy-5-morpholin-4-yl-benzoic Acid 2-methoxy-5-morpholin-4-yl-benzoic acid methyl ester (170 mg) was dissolved in MeOH (5 ml) and H$_2$O (5 ml) and treated with 1 M aq. sodium hydroxide (2 ml). After stirring at r.t. for 16 h the mixture was concentrated and partitioned between EtOAc and H$_2$O. the aqueous layer was acidified (pH 2.0) and then extracted further with EtOAc (×3). The combined organic fraction was washed with brine, dried (MgSO$_4$) and reduced in vacuo to give 2-methoxy-5-morpholin-4-yl-benzoic acid (90 mg) as a yellow oil. (LC/MS (basic method): R$_t$ 0.91 min., [M+H]$^+$ 238).

304C: Synthesis of N-[3-(5,6-dimethoxy-1H-benzimidazol-2-yl)-1H-pyrazol-4-yl]-2-methoxy-5-morpholin-4-yl-benzamide The compound was prepared in a manner analogous to Example 142C but using EtOAc, instead of CH$_2$Cl$_2$, during the work up. The crude product was purified directly through preparative LC/MS to give N-[3-(5,6-dimethoxy-1H-benzimidazol-2-yl)-1H-pyrazol-4-yl]-2-methoxy-5-morpholin-4-yl-benzamide (AT8659) (20 mg) as a colourless solid. (LC/MS (acidic method): R$_t$ 2.34 min., [M+H]$^+$ 479).

Example 305

5-Chloro-2-methoxy-N-{3-[6-methoxy-5-(1-methyl-piperidin-4-ylmethoxy)-1H-benzimidazol-2-yl]-1H-pyrazol-4-yl}-benzamide

305A. N-[4-Methoxy-5-(4-methyl-piperidin-1-yl-methoxy)-2-nitro-phenyl]-acetamide

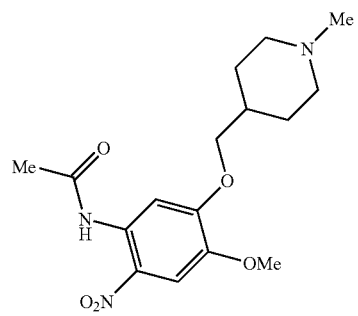

To a solution of 1-methyl-4-piperidinemethanol (0.566 g, 4.3 mmol) in THF (25 ml) at 0° C. was added, portion wise, 60% NaH (0.63 g, 15.48 mmol) and the mixture stirred for 15 mins. N-(5-Fluoro-4-methoxy-2-nitro-phenyl)-acetamide [U.S. Pat. No. 4,431,807] (1 g, 4.38 mmol) in THF (40 ml) was added to reaction, which was stirred at RT for 30 mins followed by heating at 50° C. for 1 hour. The reaction was quenched with water and then extracted with EtOAc twice, the organic portion was washed with brine, dried over MgSO$_4$, filtered and reduced in vacuo to yield N-[4-methoxy-5-(4-methyl-piperidin-1-ylmethoxy)-2-nitro-phenyl]-acetamide (1.34 g), (LC/MS (acidic method): R$_t$ 1.84, [M+H]$^+$ 338)

305B. 4-Methoxy-5-(4-methyl-piperidin-1-yl-methoxy)-2-nitro-phenylamine

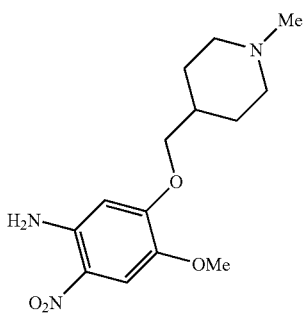

To a solution of N-[4-methoxy-5-(4-methyl-piperidin-1-ylmethoxy)-2-nitro-phenyl]-acetamide (1.34 g, 3.97 mmol) in MeOH (40 ml) was added sodium methoxide (1 g, 18.5 mmol) reaction stirred RT for 48 hours then reduced in vacuo. The residue was triturated with water and the solid filtered and washed with further water. Solid dried to yield 4-Methoxy-5-(4-methyl-piperidin-1-ylmethoxy)-2-nitro-phenylamine (0.9 g), (LC/MS (acidic method): R$_t$ 1.72, [M+H]$^+$ 296)

305C. 4-Methoxy-5-(4-methyl-piperidin-1-yl-methoxy)-benzene-1,2-diamine

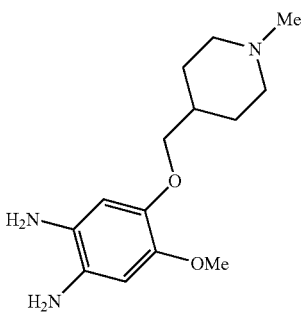

A mixture of 4-Methoxy-5-(4-methyl-piperidin-1-yl-methoxy)-2-nitro-phenylamine (0.9 g, 3.0 mmol) and 10% palladium on carbon (90 mg) in MeOH (20 ml) was shaken under an atmosphere of hydrogen for 4 hours. The reaction mixture was filtered through GF/A paper directly into saturated EtOAc/HCl to give a purple solution, which was reduced in vacuo to yield 4-Methoxy-5-(4-methyl-piperidin-1-ylmethoxy)-benzene-1,2-diamine as a purple foam (0.8 g), (LC/MS (acidic method): $R_t$ 0.34, $[M+H]^+$ 266)

305D. Synthesis of 4-(5-chloro-2-methoxy-benzoylamino)-1H-pyrazole-3-carboxylic Acid

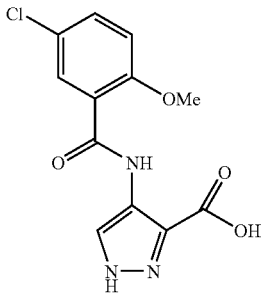

The compound was prepared in a manner analogous to 4-(2,6-difluoro-benzoylamino)-1H-pyrazole-3-carboxylic acid (Example 16D), but using 5-chloro-2-methoxy-benzoic acid as the starting acid to give 4-(5-chloro-2-methoxy-benzoylamino)-1H-pyrazole-3-carboxylic acid (12 g) as a colourless solid. (LC/MS: $R_t$ 2.48, $[M-H^+]^-$ 294)

305E. 5-Chloro-2-methoxy-N-{3-[6-methoxy-5-(1-methyl-piperidin-4-ylmethoxy)-1H-benzimidazol-2-yl]-1H-pyrazol-4-yl}-benzamide

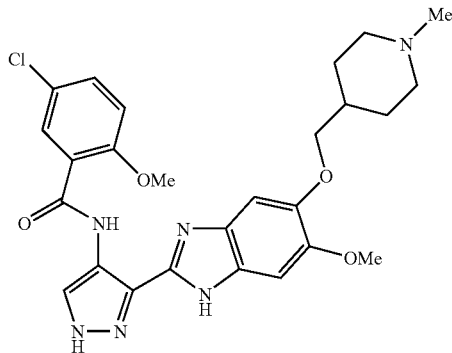

A mixture of 4-(5-Chloro-2-methoxy-benzoylamino)-1H-pyrazole-3-carboxylic acid (0.22 g, 0.745 mmol), 4-Methoxy-5-(4-methyl-piperidin-1-ylmethoxy)-benzene-1,2-diamine (0.2 g, 0.745 mmol), EDC (0.173 g, 0.89 mmol) and HOBt (0.122 g, 0.89 mmol) in DMF (20 ml) was stirred at 80° C. for 1 hour then at ambient temperature for 16 hours and then reduced in vacuo. The residue was partitioned between EtOAc and saturated bicarbonate, the organic portion was washed with brine and dried (MgSO$_4$), filtered and evaporated. The amide intermediate (150 mg), (LC/MS (acidic method): $R_t$ 2.13, $[M+H]^+$ 543) was dissolved in AcOH (5 ml) then heated at reflux for 4 hours. The reaction mixture was allowed to cool, reduced in vacuo, residue purified by preparative TLC to yield 5-Chloro-2-methoxy-N-{3-[6-methoxy-5-(1-methyl-piperidin-4-ylmethoxy)-1H-benzimidazol-2-yl-]1H-pyrazol-4-yl}-benzamide (2 mg). (LC/MS (acidic method): $R_t$ 2.25, $[M+H]^+$ 525)

Biological Activity

Example 306

Measurement of CDK2 Kinase Inhibitory Activity (IC$_{50}$)

Compounds of the invention were tested for kinase inhibitory activity using either Protocol A or Protocol B.

Protocol A 1.7 µl of active CDK2/CyclinA (Upstate Biotechnology, 10 U/µl) is diluted in assay buffer (250 µl of 10× strength assay buffer (200 mM MOPS pH 7.2, 250 mM β-glycerophosphate, 50 mM EDTA, 150 mM MgCl$_2$), 11.27 µl 10 mM ATP, 2.5 µl 1M DTT, 25 µl 100 mM sodium orthovanadate, 708.53 µl H$_2$O), and 10 µl mixed with 10 µl of histone substrate mix (60 µl bovine histone H1 (Upstate Biotechnology, 5 mg/ml), 940 µl H$_2$O, 35 µCi γ$^{33}$P-ATP) and added to 96 well plates along with 5 µl of various dilutions of the test compound in DMSO (up to 2.5%). The reaction is allowed to proceed for 5 hours before being stopped with an excess of ortho-phosphoric acid (30 µl at 2%).

γ$^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 µl of 0.5% orthophosphoric acid. Once the filters have dried, 25 µl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity (IC$_{50}$).

The compounds of Examples 3 to 128 each have IC$_{50}$ values of less than 20 µM or provide at least 50% inhibition of the CDK2 activity at a concentration of 10 µM. Preferred compounds have IC$_{50}$ values of less than 1 µM.

Protocol B

Activated CDK2/CyclinA (Brown et al, Nat. Cell Biol., 1, pp 438-443, 1999; Lowe, E. D., et al Biochemistry, 41, pp 15625-15634, 2002) is diluted to 125 pM in 2.5× strength assay buffer (50 mM MOPS pH 7.2, 62.5 mM O-glycerophosphate, 12.5 mM EDTA, 37.5 mM MgCl$_2$, 112.5 mM ATP, 2.5 mM DTT, 2.5 mM sodium orthovanadate, 0.25 mg/ml bovine serum albumin), and 10 fi mixed with 10 A1 of histone substrate mix (60 µl bovine histone H1 (Upstate Biotechnology, 5 mg/ml), 940 µl H$_2$O, 35 µCi γ$^{33}$P-ATP) and added to 96 well plates along with 5 µl of various dilutions of the test compound in DMSO (up to 2.5%). The reaction is allowed to proceed for 2 to 4 hours before being stopped with an excess of ortho-phosphoric acid (5 µl at 2%).

γ$^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 µl of 0.5% orthophosphoric acid. Once the filters have dried, 20 µl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity (IC$_{50}$).

CDK1/CyclinB Assay.

CDK1/CyclinB assay is identical to the CDK2/CyclinA above except that CDK1/CyclinB (Upstate Discovery) is used and the enzyme is diluted to 6.25 nM.

Example 307

GSK3-B/Aurora Kinase Inhibitory Activity Assay

AuroraA (Upstate Discovery) or GSK3-β (Upstate Discovery) are diluted to 10 nM and 7.5 nM respectively in 25 mM MOPS, pH 7.00, 25 mg/ml BSA, 0.0025% Brij-35, 1.25% glycerol, 0.5 mM EDTA, 25 mM MgCl$_2$, 0.025% β-mercaptoethanol, 37.5 mM ATP and 10 µl mixed with 10 µl of substrate mix. The substrate mix for Aurora is 500 µM Kemptide peptide (LRRASLG, Upstate Discovery) in 1 ml of water with 35 µCi γ$^{33}$P-ATP. The substrate mix for GSK3-β is 12.5 µM phospho-glycogen synthase peptide-2 (Upstate Discovery) in 1 ml of water with 35 µCi γ$^{33}$P-ATP. Enzyme and substrate are added to 96 well plates along with 5 µl of various dilutions of the test compound in DMSO (up to 2.5%). The reaction is allowed to proceed for 30 minutes (Aurora) or 3 hours (GSK3-β) before being stopped with an excess of ortho-phosphoric acid (5 µl at 2%). The filtration procedure is as for Activated CDK2/CyclinA assay above.

Example 309

Comparative Tests

The activities of novel compounds of the invention as CDK inhibitors have been compared with the activities of compounds disclosed in WO 03/035065 (Aventis). Amongst the large number of compounds disclosed in WO 03/035065 are compounds containing a 4-benzoylamino-3-(2-benzimidazolyl)-pyrazole ring skeleton.

The following comparative examples illustrate the effect on CDK inhibitory activity of differences in the substitution pattern on the phenyl ring of the benzoylamino group.

Comparative Example A

Compound A below is disclosed as combination A1-B32 on page 110, column 2 table 2 of WO 03/035065.

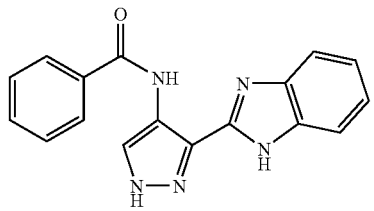

This compound can be prepared by the general methods set out in WO 03/035065. Alternatively, it can be prepared by the method set out in Example 3 herein.

In the Table below, the CDK inhibitory activity of Compound A (determined using the protocol set out in Example 306 above) is compared with the CDK inhibitory activities of novel compounds of the invention having a similarly unsubstituted benzimidazole group but having substituents on the phenyl ring.

| Compound/<br>Example No. | Phenyl ring substitution | IC$_{50}$ (µM)<br>or % inhibition |
|---|---|---|
| Compound A | unsubstituted | 0.0967 µM |
| Example 6 | 2,6-difluorophenyl | 0.0048 µM |
| Example 43 | 2-chloro-6-fluorophenyl | 52%@ 0.003 µM |
| Example 44 | 2-fluoro-6-methoxyphenyl | 57%@ 0.003 µM |
| Example 56 | 2,4,6-trifluorophenyl | 58%@0.003 µM |
| Example 57 | 2-chloro-6-methylphenyl | 41%@0.003 µM |
| Example 59 | 2,6-dichlorophenyl | 67%@0.003 µM |

Comparative Example B

Compound B below is disclosed as combination A9-B101 in column 1 of the table on page 117 of WO 03/035065 and is exemplified as Example (y) on page 428 of WO 03/035065. Compound B can be prepared by the method described in WO 03/035065 or by the method of Example 128 herein.

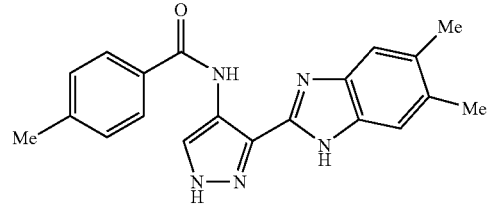

Compound B has an IC$_{50}$ of 3 µM in the CDK inhibitory assay described in Example 306. By contrast, the compound of Example 73, which is the 2,6-difluorophenyl analogue of Compound B, has an IC$_{50}$ of 0.0046 µM.

The anti-proliferative activity of the compounds of the invention has been determined by measuring inhibition of cell growth in the HCT-116 cell line. Example 73 has an IC$_{50}$ of 0.49 µM in HCT-116 cell line (determined using the protocol set out in Example 310 below) compared with Compound B which has an IC$_{50}$ of 5.7 µM in HCT-116 cell line.

Example 310

CDK Selectivity Assays

Compounds of the invention were tested for kinase inhibitory activity against a number of different kinases using the general protocol described in Example 129, but modified as set out below.

Kinases are diluted to a 10× working stock in 20 mM MOPS pH 7.0, 1 mM EDTA, 0.1% γ-mercaptoethanol, 0.01% Brij-35, 5% glycerol, 1 mg/ml BSA. One unit equals the incorporation of 1 nmol of phosphate per minute into 0.1 mg/ml histone H1, or CDK7 substrate peptide at 3.0° C. with a final ATP concentration of 100 uM.

The substrate for all the CDK assays (except CDK7) is histone H1, diluted to 10× working stock in 20 mM MOPS pH 7.4 prior to use. The substrate for CDK7 is a specific peptide diluted to 10× working stock in deionised water.

Assay Procedure for CDK1/cyclinB, CDK2/cyclinA. CDK2/cyclinE, CDK3/cyclinE, CDK5/p35. CDK6/cyclinD3:

In a final reaction volume of 25 μl, the enzyme (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx 500 cpm/pmol, concentration as required). The reaction is initiated by the addition of Mg$^{2+}$[γ-$^{33}$P-ATP]. After incubation for 40 minutes at room temperature the reaction is stopped by the addition of 5 μl of a 3% phosphoric acid solution. 10 ml of the reaction is spotted onto a P30 filter mat and washed 3 times for 5 minutes in 75 mM phosphoric acid and once in methanol prior to drying and counting.

Assay Procedure for CDK7/cyclinH/MAT1

In a final reaction volume of 25 μl, the enzyme (5-10 mU) is incubated with 8 mM MOPS pH 7.0, 0.2 mM EDTA, 500 μM peptide, 10 mM MgAcetate and [γ-$^{33}$P-ATP] (specific activity approx 500 cpm/pmol, concentration as required). The reaction is initiated by the addition of Mg$^{2+}$+[γ-$^{33}$P-ATP]. After incubation for 40 minutes at room temperature the reaction is stopped by the addition of 5 μl of a 3% phosphoric acid solution. 10 ml of the reaction is spotted onto a P30 filtermat and washed 3 times for 5 minutes in 75 mM phosphoric acid and once in methanol prior to drying and counting.

The compounds of Examples 6, 12, 13, 14, 21 and 41 have IC50 values of <1 μM against CDK 1, 3 and 5.

Example 311

Anti-Proliferative Activity

The anti-proliferative activities of compounds of the invention were determined by measuring the ability of the compounds to inhibition of cell growth in a number of cell lines. Inhibition of cell growth was measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells were plated onto 96 well plates and allowed to recover for 16 hours prior to the addition of inhibitor compounds for a further 72 hours. At the end of the incubation period 10% (v/v) Alamar Blue was added and incubated for a further 6 hours prior to determination of fluorescent product at 535 nM ex/590 nM em. In the case of the non-proliferating cell assay cells were maintained at confluence for 96 hour prior to the addition of inhibitor compounds for a further 72 hours. The number of viable cells was determined by Alamar Blue assay as before. All cell lines were obtained from ECACC (European Collection of cell Cultures).

By following the protocol set out above, compounds of the invention were found to inhibit cell growth in a number of cell lines.

Example 312

Measurement of Inhibitors Activity Against Glycogen Synthase Kinase-3 (GSK-3)

GSK3β (human) is diluted to a 10× working stock in 50 mM Tris pH 7.5, 0.1 mM EGTA, 0.1 mM sodium vanadate, 0.1% β-mercaptoethanol, 1 mg/ml BSA. One unit equals the incorporation of 1 nmol of phosphate per minute phosphoglycogen synthase peptide 2 per minute.

In a final reaction volume of 25 μl, GSK3β (5-10 mU) is incubated with 8 mM MOPS 7.0, 0.2 mM EDTA, 20 μM YRRAAVPPSPSLSRHSSPHQS(p)EDEEE (phospho GS2 peptide), 10 mM MgAcetate and [γ-$^{33}$P-ATP] (specific activity approx 500 cpm/pmol, concentration as required). The reaction is initiated by the addition of Mg$^{2+}$+[γ-$^{33}$P-ATP]. After incubation for 40 minutes at room temperature the reaction is stopped by the addition of 5 μl of a 3% phosphoric acid solution. 10 μl of the reaction is spotted onto a P30 filter mat and washed 3 times for 5 minutes in 50 mM phosphoric acid and once in methanol prior to drying and counting.

The compounds of Examples 6 and 12 have IC50 values of <1 uM against GSK30.

Pharmaceutical Formulations

Example 313

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

Example 314

Determination of Antifungal Activity

The antifungal activity of the compounds of the formula (I) is determined using the following protocol.

The compounds are tested against a panel of fungi including *Candida parpsilosis, Candida tropicalis, Candida albicans*-ATCC 36082 and *Cryptococcus neoformans*. The test organisms are maintained on Sabourahd Dextrose Agar slants at 4° C. Singlet suspensions of each organism are prepared by growing the yeast overnight at 27° C. on a rotating drum in yeast-nitrogen base broth (YNB) with amino acids (Difco, Detroit, Mich.), pH 7.0 with 0.05 M morpholine propanesulphonic acid (MOPS). The suspension is then centrifuged and washed twice with 0.85% NaCl before sonicating the washed cell suspension for 4 seconds (Branson Sonifier, model 350, Danbury, Conn.). The singlet blastospores are counted in a haemocytometer and adjusted to the desired concentration in 0.85% NaCl.

The activity of the test compounds is determined using a modification of a broth microdilution technique. Test compounds are diluted in DMSO to a 1.0 mg/ml ratio then diluted to 64 μg/ml in YNB broth, pH 7.0 with MOPS (Fluconazole is used as the control) to provide a working solution of each compound. Using a 96-well plate, wells 1 and 3 through 12 are prepared with YNB broth, ten fold dilutions of the compound solution are made in wells 2 to 11 (concentration ranges are 64 to 0.125 μg/ml). Well 1 serves as a sterility control and blank for the spectrophotometric assays. Well 12 serves as a growth control. The microtitre plates are inoculated with 10 μl in each of well 2 to 11 (final inoculum size is 10$^4$ organisms/ml). Inoculated plates are incubated for 48 hours at 35° C. The IC50 values are determined spectrophotometrically by measuring the absorbance at 420 nm (Automatic Microplate Reader, DuPont Instruments, Wilmington, Del.) after agitation of the plates for 2 minutes with a vortexmixer (Vorte-Genie 2 Mixer, Scientific Industries, Inc., Bolemia, N.Y.). The IC50 endpoint is defined as the lowest drug concentration exhibiting approximately 50% (or more) reduction of the growth compared with the control well. With the turbidity assay this is defined as the lowest drug concentration at which turbidity in the well is <50% of the control (IC50). Minimal Cytolytic Concentrations (MCC) are determined by sub-culturing all wells from the 96-well plate onto a Sabourahd Dextrose Agar (SDA) plate, incubating for 1 to 2 days at 35° C. and then checking viability.

Example 315

Protocol for the Biological Evaluation of Control of In Vivo Whole Plant Fungal Infection Compounds of the formula (I) are dissolved in acetone, with subsequent serial dilutions in acetone to obtain a range of desired concentrations. Final treatment volumes are obtained by adding 9 volumes of 0.05% aqueous Tween-20™ or 0.01% Triton X-100™, depending upon the pathogen.

The compositions are then used to test the activity of the compounds of the invention against tomato blight (*Phytophthora infestans*) using the following protocol. Tomatoes (cultivar Rutgers) are grown from seed in a soil-less peat-based potting mixture until the seedlings are 10-20 cm tall. The plants are then sprayed to run-off with the test compound at a rate of 100 ppm. After 24 hours the test plants are inoculated by spraying with an aqueous sporangia suspension of *Phytophthora infestans*, and kept in a dew chamber overnight. The plants are then transferred to the greenhouse until disease develops on the untreated control plants.

Similar protocols are also used to test the activity of the compounds of the invention in combating Brown Rust of Wheat (*Puccinia*), Powdery Mildew of Wheat (*Ervsiphe vraminis*), Wheat (cultivar Monon), Leaf Blotch of Wheat (*Septoria tritici*), and Glume Blotch of Wheat (*Leptosphaeria nodorum*).

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

What is claimed is:

1. A compound of the formula (VII):

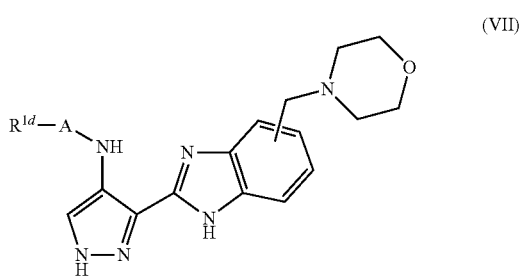

(VII)

or a salt or N-oxide thereof;
wherein A is —$(CH_2)_m$—$(B)_n$—; where m is 0 or 1, n is 1 and B is C=O or $NR^g$(C=O); and
$R^g$ is hydrogen; and $R^{1d}$ is a group $R^1$ where $R^1$ is hydrogen, an optionally substituted carbocyclic or heterocyclic group having from 3 to 12 ring members, or an optionally substituted $C_{1-8}$ hydrocarbyl group, wherein the optional substituents for the $C_{1-8}$ hydrocarbyl group are selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 ring members;

and, wherein the carbocyclic and heterocyclic groups in each instance are unsubstituted or substituted by one or more substituent groups $R^{10}$ selected from:

halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1$C $(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; or two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S;

$R^c$ is selected from hydrogen and $C_{1-4}$ hydrocarbyl; and $X^1$ is O, S or $NR^c$ and $X^2$ is =O, =S or =$NR^c$;

and provided that where the substituent group $R^{10}$ comprises or includes a carbocyclic or heterocyclic group, the said carbocyclic or heterocyclic group may be unsubstituted or may itself be substituted with one or more further substituent groups selected from halogen, hydroxy, trifluoromethyl, cyano, nitro, carboxy, amino, mono- or di-$C_{1-4}$ hydrocarbylamino, unsubstituted carbocyclic and unsubstituted heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, unsubstituted carbocyclic and unsubstituted heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, unsubstituted carbocyclic and unsubstituted heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)$ $X^1$; or two adjacent groups of the further substituent group, together with the carbon atoms or heteroatoms to which they are attached may form a 5-membered unsubstituted heteroaryl ring or a 5- or 6-membered non-aromatic unsubstituted carbocyclic or unsubstituted heterocyclic ring, wherein the said heteroaryl and heterocyclic groups contain up to 3 heteroatom ring members selected from N, O and S.

2. A compound according to claim 1, or a salt or N-oxide thereof, of the formula (VIIa):

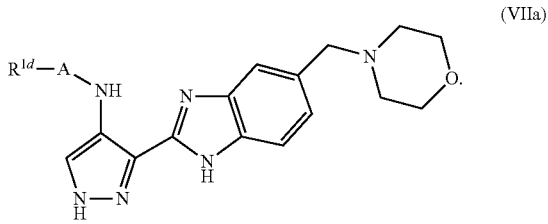

(VIIa)

3. A pharmaceutical composition comprising a compound as defined in claim 1, or a salt or N-oxide thereof, and a pharmaceutically acceptable carrier.

4. A compound according to claim 1, or a salt or N-oxide thereof, wherein $R^1$ is an optionally substituted monocyclic or bicyclic carbocyclic or heterocyclic group having from 3 to 12 ring members.

5. A compound according to claim 4, or a salt or N-oxide thereof, wherein $R^1$ is an optionally substituted monocyclic or bicyclic carbocyclic or heterocyclic group having from 3 to 10 ring members.

6. A compound according to claim 4, or a salt or N-oxide thereof, wherein $R^1$ is unsubstituted.

7. A compound according to claim 4, or a salt or N-oxide thereof, wherein $R^1$ is substituted by 1 or 2 or 3 or 4 substituents $R^{10}$.

8. A compound according to claim 4, or a salt or N-oxide thereof, wherein $R^1$ is a substituted group and the substituents on $R^1$ are selected from the group $R^{10a}$ consisting of halogen, hydroxy, trifluoromethyl, cyano, nitro, carboxy, heterocyclic groups having 5 or 6 ring members and up to 2 heteroatoms selected from O, N and S, a group $R^a$-$R^b$ wherein $R^a$ is a bond, O, CO, $X^3C(X^4)$, $C(X^4)X^3$, $X^3C(X^4)X^3$, S, SO, or $SO_2$, and $R^b$ is selected from hydrogen, a heterocyclic group having 5 or 6 ring members and up to 2 heteroatoms selected from O, N and S, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having 5 or 6 ring members and up to 2 heteroatoms selected from O, N and S; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is =O or =S.

9. A compound according to claim 4, or a salt or N-oxide thereof, wherein $R^1$ is a substituted group and the substituents on $R^1$ are selected from the group $R^{10b}$ consisting of halogen, hydroxy, trifluoromethyl, cyano, nitro, carboxy, and a group $R^a$-$R^b$ wherein $R^a$ is a bond, O, CO, $X^3C(X^4)$, $C(X^4)X^3$, $X^3C(X^4)X^3$, S, SO, or $SO_2$, and $R^b$ is selected from hydrogen and a $C_{1-8}$ hydrocarbyl group optionally substituted by one or more substituents selected from hydroxy, oxo, halogen, cyano, nitro, and carboxy; wherein one or more carbon atoms of the $C_{1-8}$ hydrocarbyl group may optionally be replaced by O, S, SO, $SO_2$, $X^3C(X^4)$, $C(X^4)X^3$ or $X^3C(X^4)X^3$; $X^3$ is O or S; and $X^4$ is =O or =S.

10. A compound according to claim 4, or a salt or N-oxide thereof, wherein the substituents on $R^1$ are selected from halogen, hydroxy, trifluoromethyl, and a group $R^a$-$R^b$ wherein $R^a$ is a bond or O, and $R^b$ is selected from hydrogen and a $C_{1-4}$ hydrocarbyl group optionally substituted by one or more substituents selected from hydroxyl and halogen.

11. A compound according to claim 4, or a salt or N-oxide thereof, wherein $R^1$ is a phenyl group which is 2,6-disubstituted, 2,3-disubstituted, 2,4-disubstituted 2,5-disubstituted, 2,3,6-trisubstituted or 2,4,6-trisubstituted.

12. A compound according to claim 4, or a salt or N-oxide thereof, wherein $R^1$ is a phenyl group which is disubstituted at positions 2- and 6- with substituents selected from fluorine, chlorine and $R^a$-$R^b$, where $R^a$ is O and $R^b$ is $C_{1-4}$ alkyl.

13. A compound according to claim 4, or a salt or N-oxide thereof, wherein $R^1$ is a substituted or unsubstituted non-aromatic carbocyclic group having from 3 to 7 ring members.

14. A compound according to claim 4, or a salt or N-oxide thereof, wherein $R^1$ is a substituted or unsubstituted non-aromatic carbocyclic group having from 3 to 6 ring members.

15. A compound according to claim 4, or a salt or N-oxide thereof, wherein the substituted or unsubstituted non-aromatic carbocyclic group $R^1$ is a cycloalkyl group.

16. A compound according to claim 1, or a salt or N-oxide thereof, wherein A is NH(C=O) or CO=O and $R^{1d}$ is a group $R^{1a}$
wherein $R^{1a}$ is selected from:
 a 6-membered monocyclic aryl group substituted by one to three substituents $R^{10c}$ provided that when the aryl group is substituted by a methyl group, at least one substituent other than methyl is present;
 a 6-membered monocyclic heteroaryl group containing a single heteroatom ring member which is nitrogen, the heteroaryl group being substituted by one to three substituents $R^{10c}$;
 a 5-membered monocyclic heteroaryl group containing up to three heteroatom ring members selected from nitrogen and sulphur, and being optionally substituted by one to three substituents $R^{10c}$;
 a 5-membered monocyclic heteroaryl group containing a single oxygen heteroatom ring member and optionally a nitrogen heteroatom ring member, and being substituted by one to three substituents $R^{10c}$ provided that when the heteroaryl group contains a nitrogen ring member and is substituted by a methyl group, at least one substituent other than methyl is present;
 bicyclic aryl and heteroaryl groups containing up to four heteroatom ring members and wherein either one ring is aromatic and the other ring is non-aromatic, or wherein both rings are aromatic, the bicyclic groups being optionally substituted by one to three substituents $R^{10c}$;
four-membered, six-membered and seven-membered monocyclic C-linked saturated heterocyclic groups containing up to three heteroatoms selected from nitrogen, oxygen and sulphur, the heterocyclic groups being optionally substituted by one to three substituents $R^{10c}$ provided that when the heterocyclic group has six ring members and contains only one heteroatom which is oxygen, at least one substituent $R^{10c}$ is present;
 a five membered monocyclic C-linked saturated heterocyclic group containing up to three heteroatoms selected from nitrogen, oxygen and sulphur, the heterocyclic group being optionally substituted by one to three substituents $R^{10c}$ provided that when the heterocyclic group has five ring members and contains only one heteroatom which is nitrogen, at least one substituent $R^{10c}$ other than hydroxy is present;
 four and six membered cycloalkyl groups optionally substituted by one to three substituents $R^{10c}$;
 three and five membered cycloalkyl groups substituted by one to three substituents $R^{10c}$; and
 a group Ph'CR$^{17}$R$^{18}$— where Ph' is a phenyl group substituted by one to three substituents $R^{10c}$; $R^{17}$ and $R^{18}$ are the same or different and each is selected from hydrogen and methyl; or $R^{17}$ and $R^{18}$ together with the carbon atom to which they are attached form a cyclopropyl group; or one of $R^{17}$ and $R^{18}$ is hydrogen and the other is selected from amino, methylamino, $C_{1-4}$ acylamino, and $C_{1-4}$ alkoxycarbonylamino;

unsubstituted phenyl and phenyl substituted with one or more methyl groups;

an unsubstituted 6-membered monocyclic heteroaryl group containing a single heteroatom ring member which is nitrogen;

unsubstituted furyl;

a 5-membered monocyclic heteroaryl group containing a single oxygen heteroatom ring member and a nitrogen heteroatom ring member, and being unsubstituted or substituted by one or more methyl groups;

an unsubstituted six membered monocyclic C-linked saturated heterocyclic group containing only one heteroatom which is oxygen; and unsubstituted three and five membered cycloalkyl groups;

and $R^{10c}$ is selected from:

halogen;

hydroxyl;

$C_{1-4}$ hydrocarbyloxy optionally substituted by one or more substituents selected from hydroxyl and halogen;

$C_{1-4}$ hydrocarbyl substituted by one or more substituents selected from hydroxyl, halogen and five and six-membered saturated heterocyclic rings containing one or two heteroatom ring members selected from nitrogen, oxygen and sulphur;

S—$C_{1-4}$ hydrocarbyl;

phenyl optionally substituted with one to three substituents selected from $C_{1-4}$ alkyl, trifluoromethyl, fluoro and chloro;

heteroaryl groups containing 5 or 6 ring members and containing up to 3 heteroatoms selected from N, O and S, the heteroaryl groups being optionally substituted with one to three substituents selected from $C_{1-4}$ alkyl, trifluoromethyl, fluoro and chloro;

5- and 6-membered non-aromatic heterocyclic groups containing up to 3 heteroatoms selected from N, O and S and being optionally substituted with one to three substituents selected from $C_{1-4}$ alkyl, trifluoromethyl, fluoro and chloro;

cyano, nitro, amino, $C_{1-4}$ alkylamino, di-$C_{1-4}$ alkylamino, $C_{1-4}$ acylamino, and $C_{1-4}$ alkoxycarbonylamino;

a group $R^{19}$—S(O)$_n$— where n is 0, 1 or 2 and $R^{19}$ is selected from amino; $C_{1-4}$ alkylamino; di-$C_{1-4}$ alkylamino; $C_{1-4}$ hydrocarbyl; phenyl optionally substituted with one to three substituents selected from $C_{1-4}$ alkyl, trifluoromethyl, fluoro and chloro; and 5- and 6-membered non-aromatic heterocyclic groups containing up to 3 heteroatoms selected from N, O and S and being optionally substituted with one to three $C_{1-4}$ alkyl group substituents; and a group $R^{20}$-Q- where $R^{20}$ is phenyl optionally substituted with one to three substituents selected from $C_{1-4}$ alkyl, trifluoromethyl, fluoro and chloro; and Q is a linker group selected from OCH$_2$, CH$_2$O, NH, CH$_2$NH, NCH$_2$, CH$_2$, NHCO and CONH.

17. A compound according to claim 1, or a salt or N-oxide thereof, wherein A is NH(C=O) or (C=O), and $R^{1d}$ is a group $R^{1b}$, wherein $R^{1b}$ is a substituted phenyl group having from 1 to 4 substituents whereby:

(i) when $R^{1b}$ bears a single substituent it is selected from halogen, hydroxyl, $C_{1-4}$ hydrocarbyloxy optionally substituted by one or more substituents selected from hydroxyl and halogen; $C_{1-4}$ hydrocarbyl substituted by one or more substituents selected from hydroxyl and halogen; heteroaryl group having 5 ring members; and 5- and 6-membered non-aromatic heterocyclic groups, wherein the heteroaryl and heterocyclic groups contain up to 3 heteroatoms selected from N, O and S; or (ii) when $R^{1b}$ bears 2, 3 or 4 substituents, each is selected from halogen, hydroxyl, $C_{1-4}$ hydrocarbyloxy optionally substituted by one or more substituents selected from hydroxyl and halogen; $C_{1-4}$ hydrocarbyl optionally substituted by one or more substituents selected from hydroxyl and halogen; heteroaryl groups having 5 ring members; amino; and 5- and 6-membered non-aromatic heterocyclic groups; or two adjacent substituents together with the carbon atoms to which they are attached form a 5-membered heteroaryl ring or a 5- or 6-membered non-aromatic heterocyclic ring; wherein the said heteroaryl and heterocyclic groups contain up to 3 heteroatoms selected from N, O and S.

18. A compound according to claim 1, or a salt or N-oxide thereof, wherein $R^{1d}$ is a group $R^{1c}$, wherein $R^{1c}$ is selected from:

(a) a mono-substituted phenyl group wherein the substituent is selected from o-amino, o-methoxy; o-chloro; p-chloro; o-difluoromethoxy; o-trifluoromethoxy; o-tert-butyloxy; m-methylsulphonyl and p-fluoro;

(b) a 2,4- or 2,6-disubstituted phenyl group wherein one substituent is selected from o-methoxy, o-ethoxy, o-fluoro, and p-morpholino and the other substituent is selected from o-fluoro, o-chloro, p-chloro, and p-amino;

(c) a 2,5-disubstituted phenyl group wherein one substituent is selected from o-fluoro and o-methoxy and the other substituent is selected from m-methoxy, m-isopropyl; m-fluoro, m-trifluoromethoxy, m-trifluoromethyl, m-methylsulphanyl, m-pyrrolidinosulphonyl, m-(4-methylpiperazin-1-yl)sulphonyl, m-morpholinosulphonyl, m-methyl, m-chloro and m-aminosulphonyl;

(d) a 2,4,6-tri-substituted phenyl group where the substituents are the same or different and are each selected from o-methoxy, o-fluoro, p-fluoro, and p-methoxy provided that no more than one methoxy substituent is present;

(e) a 2,4,5-tri-substituted phenyl group where the substituents are the same or different and are each selected from o-methoxy, m-chloro and p-amino;

(f) unsubstituted benzyl; 2,6-difluorobenzyl; α,α-dimethylbenzyl; 1-phenylcycloprop-1-yl; and α-tert-butoxycarbonylaminobenzyl;

(g) an unsubstituted 2-furyl group or a 2-furyl group bearing a single substituent selected from 4-(morpholin-4-ylmethyl) and piperidinylmethyl; and optionally a further substituent selected from methyl;

(h) an unsubstituted pyrazolo[1,5-a]pyridin-3-yl group;

(i) isoxazolyl substituted by one or two $C_{1-4}$ alkyl groups;

(j) 4,5,6,7-tetrahydro-benz[d]isoxazol-3-yl;

(k) 3-tert-butyl-phenyl-1H-pyrazol-5-yl;

(l) quinoxalinyl;

(m) benz[c]isoxazol-3-yl;

(n) 2-methyl-4-trifluoromethyl-thiazol-5-yl;

(o) 3-phenylamino-2-pyridyl;

(p) 1-toluenesulphonylpyrrol-3-yl;

(q) 2,4-dimethoxy-3-pyridyl; and 6-chloro-2-methoxy-4-methyl-3-pyridyl;

(r) imidazo[2,1-b]thiazol-6-yl;

(s) 5-chloro-2-methylsulphanyl-pyrimidin-4-yl;

(t) 3-methoxy-naphth-2-yl;

(u) 2,3-dihydro-benz[1,4]dioxin-5-yl;

(v) 2,3-dihydro-benzfuranyl group optionally substituted in the five membered ring by one or two methyl groups;

(w) 2-methyl-benzoxazol-7-yl;

(x) 4-aminocyclohex-1-yl;
(y) 1,2,3,4-tetrahydro-quinolin-6-yl;
(z) 2-methyl-4,5,6,7-tetrahydro-benzfuran-3-yl;
(aa) 2-pyrimidinyl-1-piperidin-4-yl; and 1-(5-trifluoromethyl-2-pyridyl)-piperidin-4-yl and 1-methylsulphonylpiperidin-4-yl;
(ab) 1-cyanocyclopropyl; and
(ac) N-benzylmorpholin-2-yl;
and when A is NH(C=O), $R^{1c}$ is additionally selected from:
(ad) unsubstituted phenyl.

19. A compound according to claim 2, or a salt or N-oxide thereof, wherein A is NH(C=O).

20. A compound according to claim 2, or a salt or N-oxide thereof, wherein A is C=O.

21. A compound according to claim 5, or a salt or N-oxide thereof, wherein $R^1$ is unsubstituted.

22. A compound according to claim 5, or a salt or N-oxide thereof, wherein $R^1$ is substituted by 1 or 2 or 3 or 4 substituents $R^{10}$.

23. A compound according to claim 1, wherein the compound is in the form of a salt.

* * * * *